US011807881B2

(12) United States Patent
Myung et al.

(10) Patent No.: US 11,807,881 B2
(45) Date of Patent: Nov. 7, 2023

(54) POLYPEPTIDE, FUSION POLYPEPTIDE, AND ANTIBIOTIC AGAINST GRAM-NEGATIVE BACTERIA COMPRISING SAME

(71) Applicant: LyseNTech Co., Ltd., Seongnam-si (KR)

(72) Inventors: Heejoon Myung, Yongin-si (KR); Min Soo Kim, Yongin-si (KR); Hye-Won Hong, Yongin-si (KR); Jione Pyeon, Seoul (KR); Jaeyeon Jang, Seongnam-si (KR)

(73) Assignee: LYSENTECH CO., LTD., Seongnam-si (KR)

( * ) Notice: Subject to any disclaimer, the term of this patent is extended or adjusted under 35 U.S.C. 154(b) by 0 days.

(21) Appl. No.: 17/853,027

(22) Filed: Jun. 29, 2022

(65) Prior Publication Data

US 2022/0348895 A1 Nov. 3, 2022

Related U.S. Application Data

(63) Continuation of application No. PCT/KR2021/006302, filed on May 20, 2021.

(30) Foreign Application Priority Data

May 22, 2020 (KR) ........................ 10-2020-0061906
Aug. 27, 2020 (KR) ........................ 10-2020-0108498
Feb. 10, 2021 (KR) ........................ 10-2021-0019108

(51) Int. Cl.

| | |
|---|---|
| ***C12N 9/36*** | (2006.01) |
| ***A61K 38/12*** | (2006.01) |
| ***A61K 38/47*** | (2006.01) |
| ***A61P 31/04*** | (2006.01) |
| ***C07K 14/435*** | (2006.01) |
| ***C12N 7/00*** | (2006.01) |
| ***A01N 65/40*** | (2009.01) |
| ***A01P 1/00*** | (2006.01) |
| ***A61K 31/7088*** | (2006.01) |
| ***A61K 45/06*** | (2006.01) |
| ***C12N 15/62*** | (2006.01) |
| ***A61K 38/00*** | (2006.01) |
| ***A23K 20/195*** | (2016.01) |
| ***C12N 9/24*** | (2006.01) |

(52) U.S. Cl.

CPC ............ *C12N 9/2462* (2013.01); *A61K 38/12* (2013.01); *A61K 38/47* (2013.01); *A61P 31/04* (2018.01); *C07K 14/43563* (2013.01); *C12N 7/00* (2013.01); *C12Y 302/01017* (2013.01); *C07K 2319/00* (2013.01)

(58) Field of Classification Search

CPC ...... A61K 45/06; A61K 38/00; C12N 9/2463; C12N 7/00; C12N 15/62; A61P 31/104; C07K 2313/00

See application file for complete search history.

(56) References Cited

FOREIGN PATENT DOCUMENTS

| | | |
|---|---|---|
| JP | 2013-541333 | 11/2013 |
| JP | 2020-500935 | 1/2020 |
| KR | 10-2012-0095345 | 8/2012 |
| KR | 10-2014-0093403 | 7/2014 |
| KR | 10-2017-0061544 | 6/2017 |
| KR | 10-2018-0064417 | 6/2018 |
| KR | 10-2019-0085549 | 7/2019 |
| KR | 10-2019-0110094 | 9/2019 |
| KR | 10-2020-0012844 | 2/2020 |
| KR | 10-2021-0014673 | 2/2021 |
| KR | 10-2224897 | 3/2021 |
| KR | 10-2228999 | 3/2021 |
| WO | 2018-100516 | 6/2018 |
| WO | 2019-229185 | 12/2019 |

OTHER PUBLICATIONS

KIPO, PCT Search Report & Written Opinion of PCT/KR2021/006302 dated Aug. 18, 2021.
NCBI Genbank, accession No. QBX32324.1 (Apr. 10, 2019).
Hang Yang et al., "Antibacterial Activity of a Novel Peptide-Modified Lysin Against Acinetobacter baumannii and Pseudomonas aeruginosa", Frontiers in Microbiology, vol. 6, Article 1471, Dec. 22, 2015.
Loraine Silvestro et al., "Antibacterial and Antimembrane Activities of Cecropin A in *Escherichia coli*", Antimicrobial Agents and Chemotherapy, vol. 44, No. 3, p. 602-607, Mar. 2000.
NCBI, Genbank Accession No. MK599315.1 (Apr. 10, 2019).
Samuel Karlin et al., "Applications and statistics for multiple high-scoring segments in molecular sequences", Natl. Acad. Sci. USA, 90, 5873, 1993.
William R. Pearson, "[5] Rapid and Sensitive Sequence Comparison with FASTP and FASTA", Enzymol., 183, 63, 1990.
"SubName: Full=Putative endolysin {ECO:0000313|EMBL:QBX32324.1};", UniProt, (Jul. 3, 2019), Database accession No. A0A4D6BG66, URL: EBI, XP002809590 [X] 7 * the whole document * [Y] 1-15.
Gerstmans Hans et al., "Synthetic biology of modular endolysins", Biotechnology Advances, vol. 36, No. 3, pp. 624-640, May 2018, doi: https://doi.org/10.1016/j.biotechadv.2017.12.009.
EPO, Search Report of EP 21809334.2 dated Jul. 10, 2023.

*Primary Examiner* — Suzanne M Noakes
*Assistant Examiner* — Jae W Lee
(74) *Attorney, Agent, or Firm* — LEX IP MEISTER, PLLC

(57) ABSTRACT

Provided are a novel polypeptide, a fusion polypeptide comprising the polypeptide, and a use thereof as an antibiotic. More specifically, provided are a novel polypeptide derived from a bacteriophage, a novel fusion polypeptide comprising cecropin A, and an antibiotic against Gram-negative bacteria comprising the polypeptide and/or the fusion polypeptide.

20 Claims, 17 Drawing Sheets

Specification includes a Sequence Listing.

【FIG. 1】
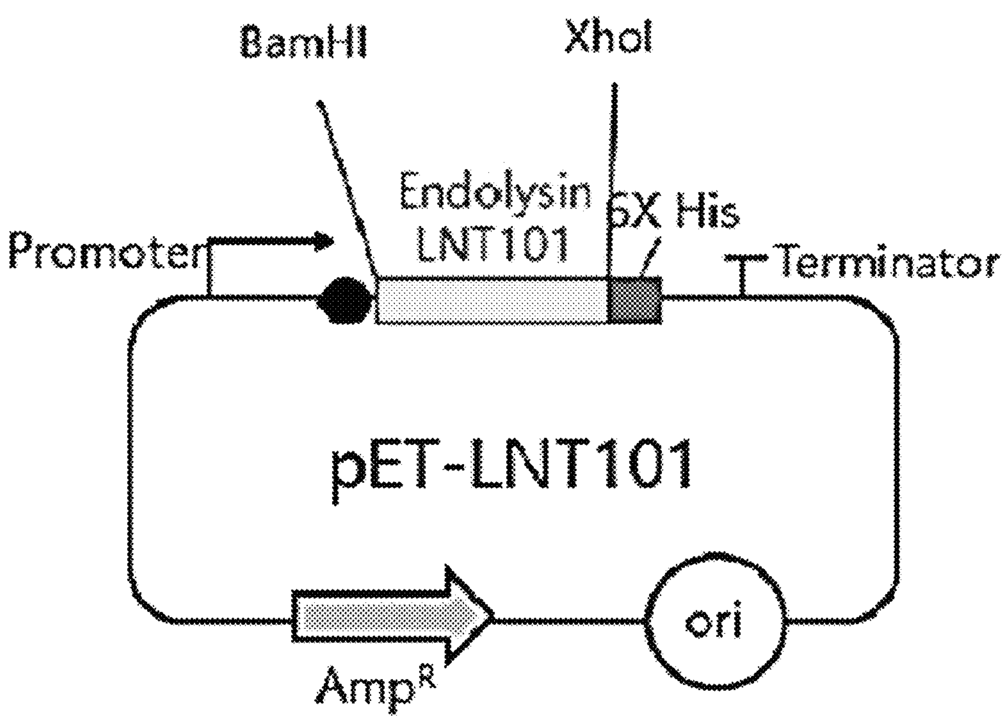

【FIG. 2】
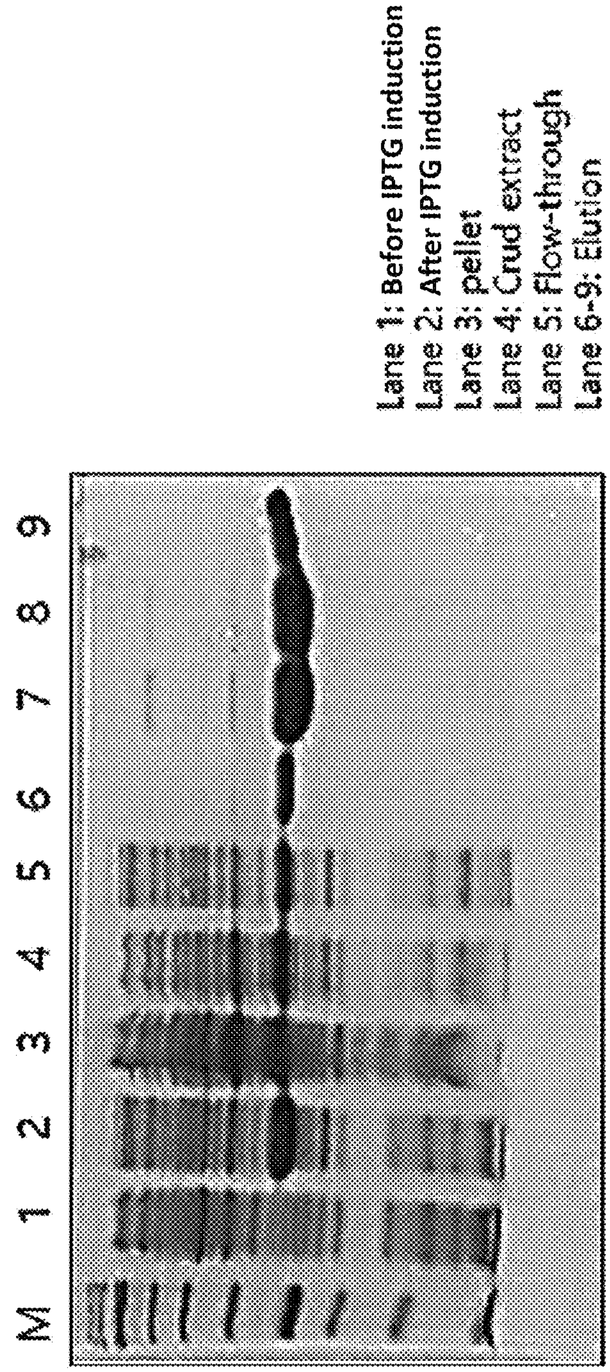

【FIG. 3】
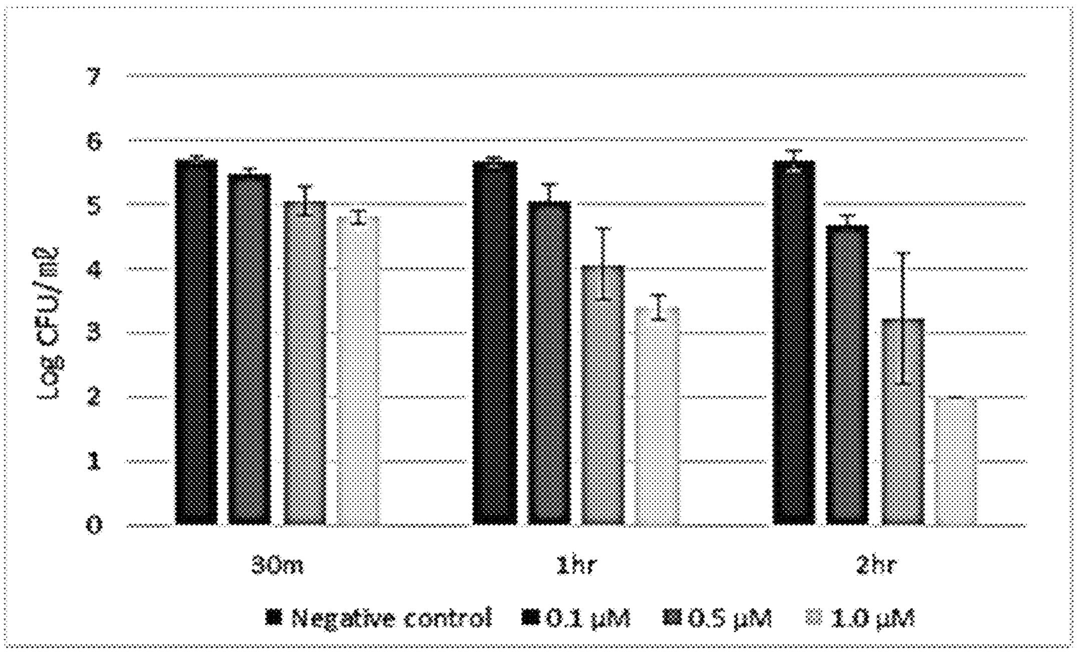

【FIG. 4】
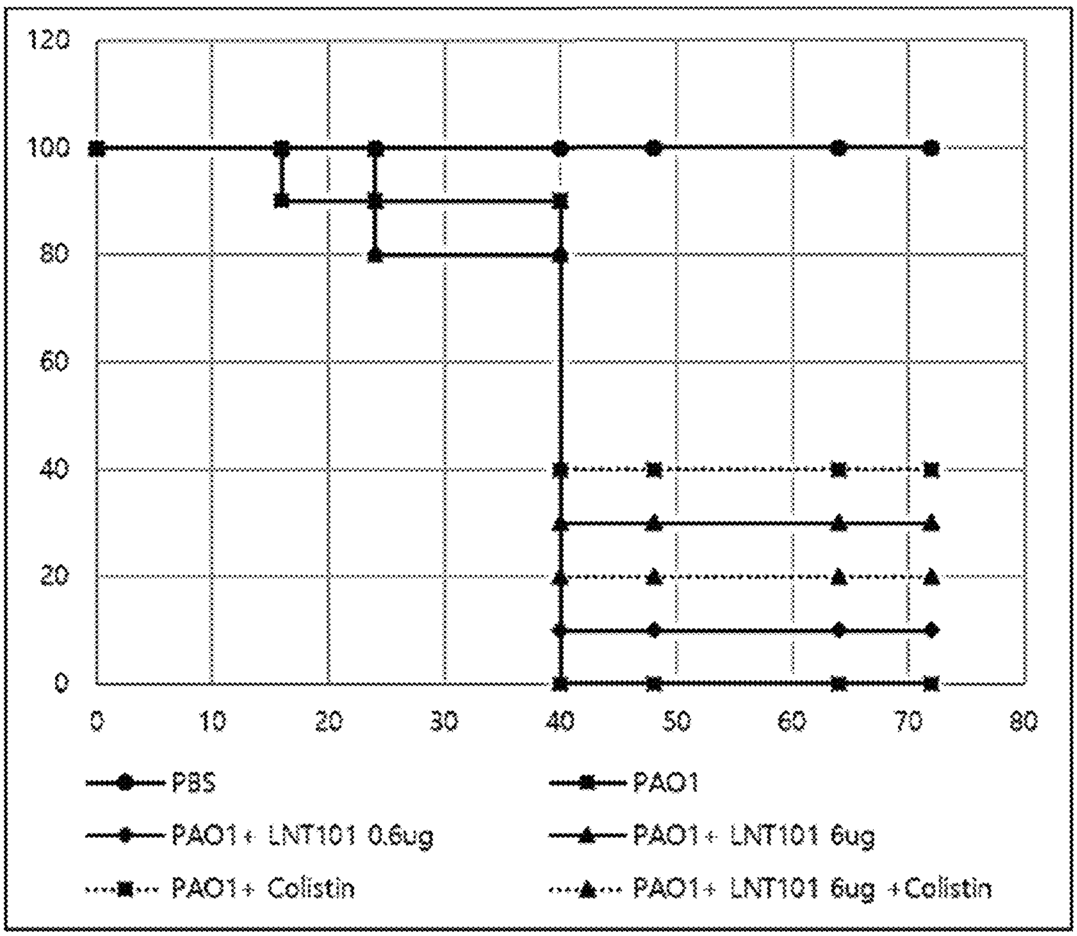

[FIG. 5]

```
LMT101    MGTVLKRGLRGSAVEDLQMKLSVAGYAVSADGIFSGLTSKAVRLFQASKALVVDGKVGEA   60
LMT102    MGTVLKRGLRGSAVEDLQMKLSVAGYNLSADGIFSGLTSKAVRLVQASASLVVDGKVGEK   60
          *********************.****  :*****************.**.  .*********

LMT101    TLAELAKSATVPAKWEAIPFPIANKSRSAAMPTLNAVGAMFGTLSRLLAIFASIESAFLY   120
LMT102    TLYAIAKSATVPAKWEAIPFPIANKSRSAAMPTLNAVGAMFGVLSRLLAIFASIESAFLY   120
          **   :************************************.*****************

LMT101    TVKASTSSATGWFQFLDATWDEMIKAHGSKYGIPKDETSALRKLPRANALMGAEFLKGNA   180
LMT102    TVKAKTSSATGWFQFLDATWDEMIKAYGSKYGIPKDETSALRKLPRANALMGAEFIKGNA   180
          ****.*********************:****************************:****

LMT101    AVLAEVINRKEFSDTDLYIAHFLGAGGAEKFLSADQKILGEVLPPKEAKANPSIFSNKGVP   240
LMT102    AVLAEVINRKEFSDTDLYIAHFLGAGGAEKFLSADQKILGEVLPPKEAKANPSIFSNKGVP   240
          ************************************************************

LMT101    RTLAEIYKLFSDKVSKHRA 259
LMT102    RTLAEIYKLFEDKVSKHRA 259
          *******************
```

【FIG. 6】
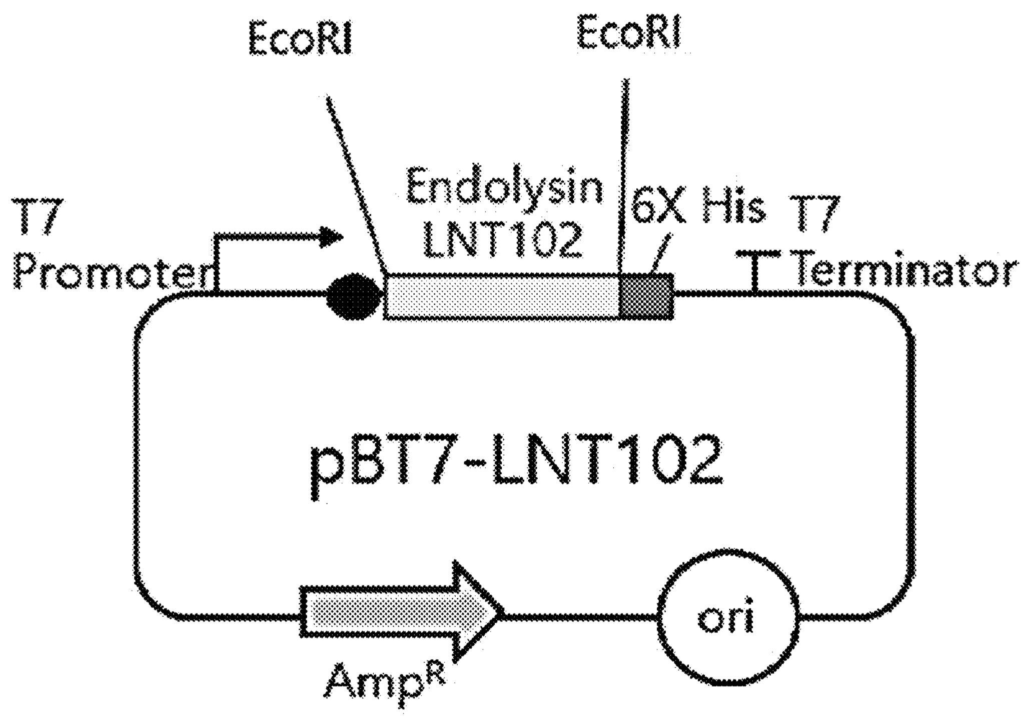
【FIG. 7】
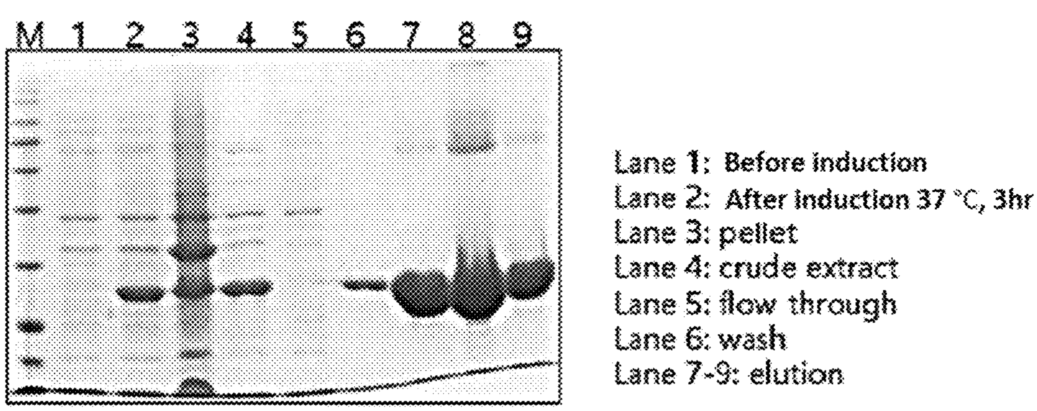

[FIG. 8]
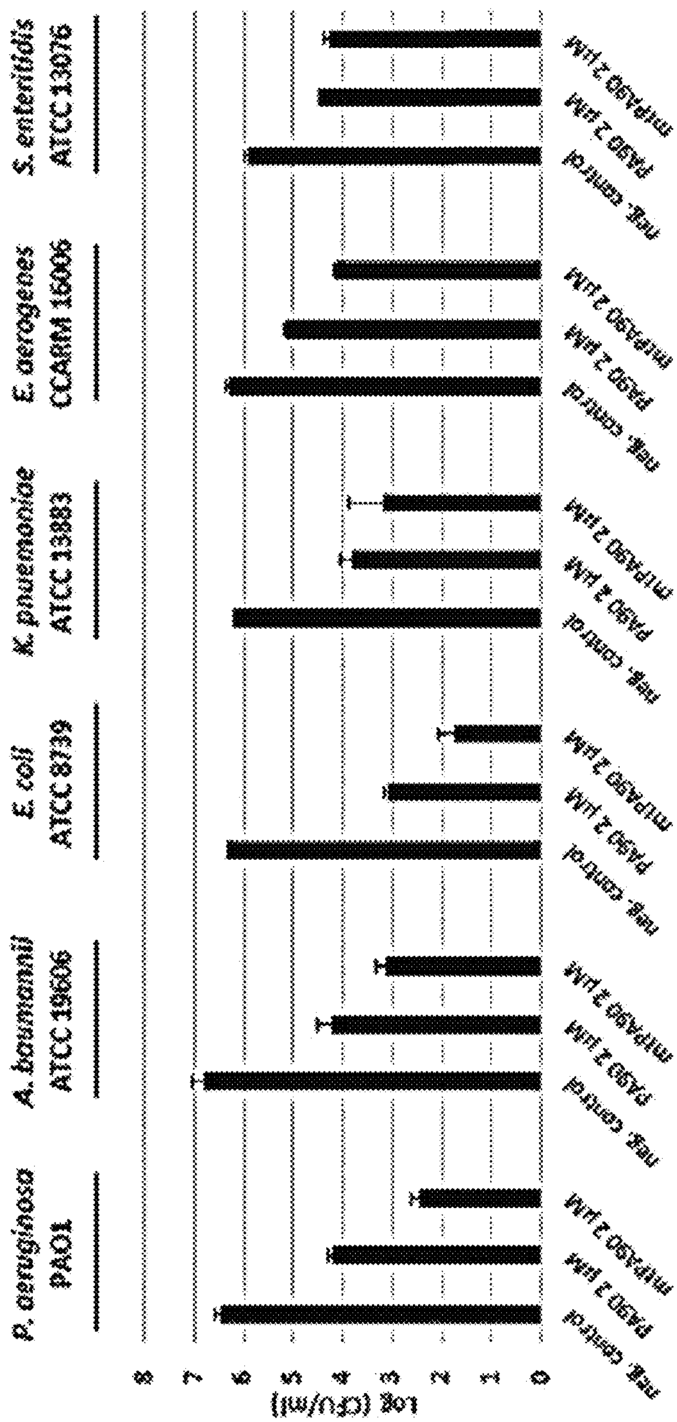

【FIG. 9】
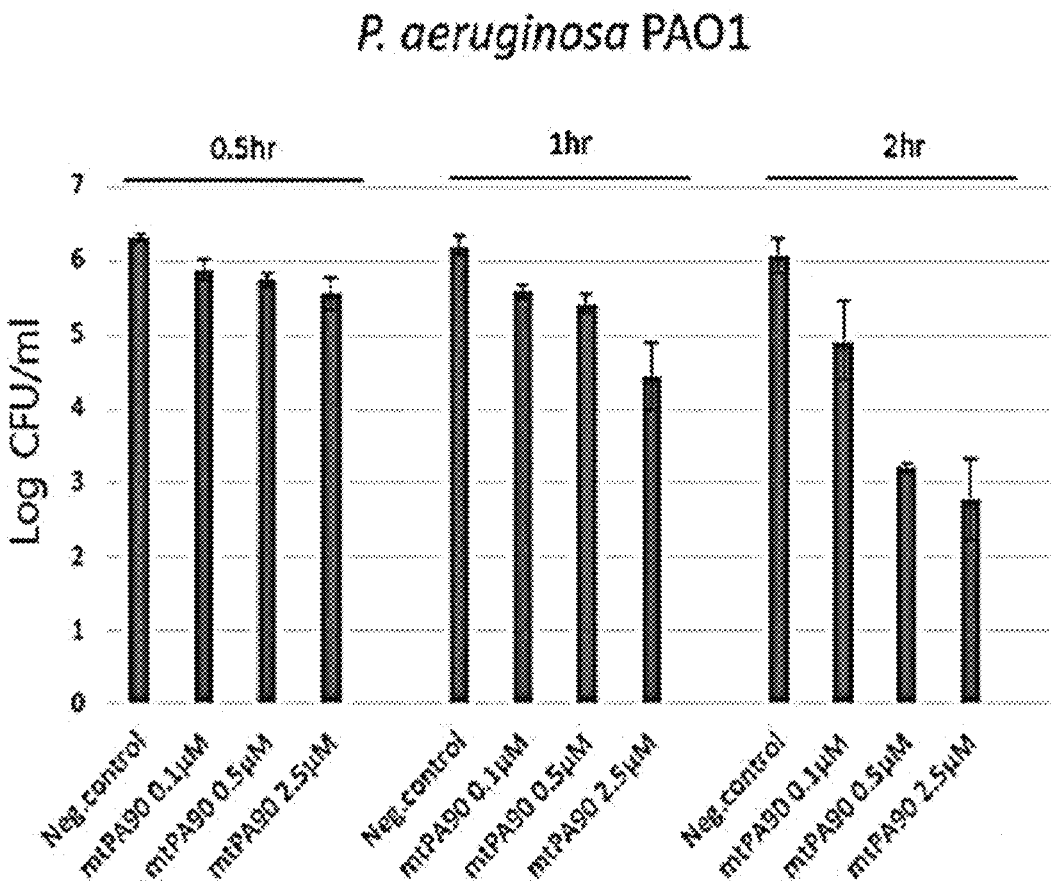

【FIG. 10】
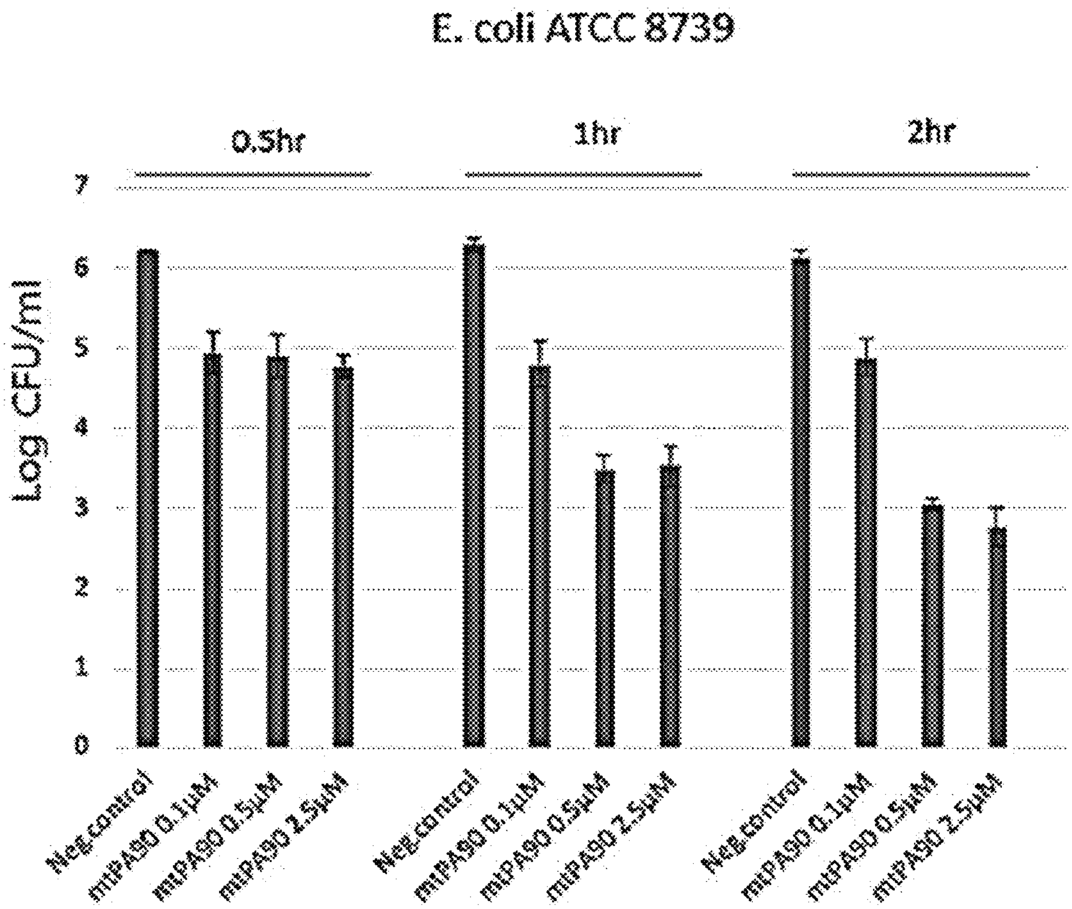
【FIG. 11】
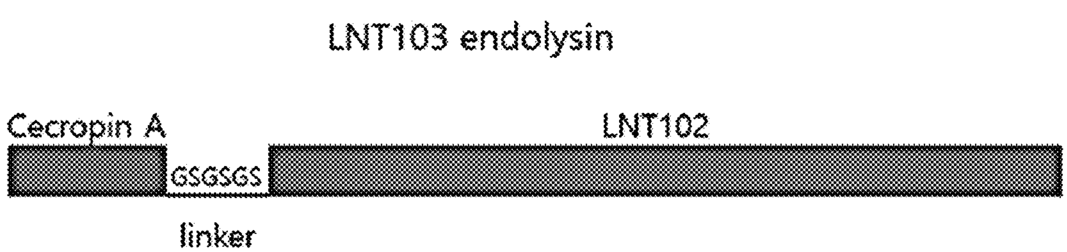

【FIG. 12】
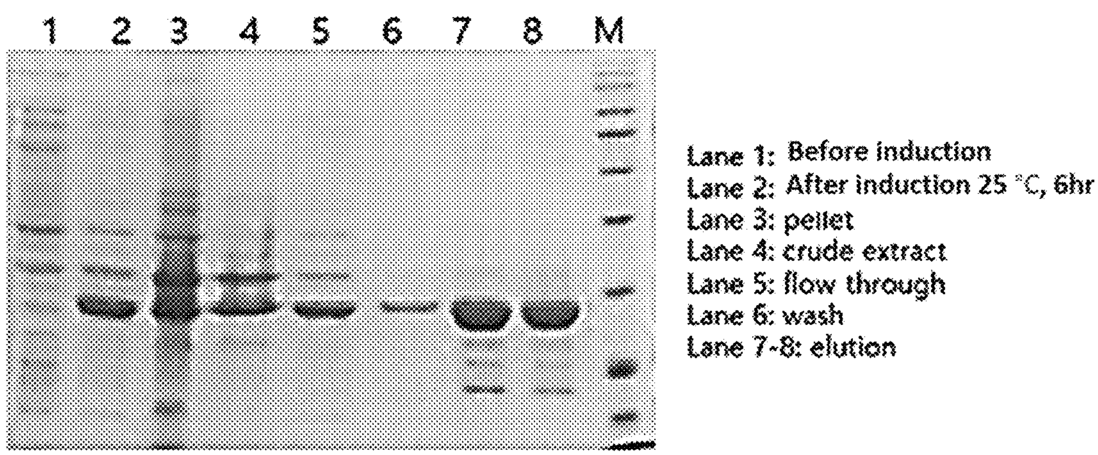

[FIG. 13]
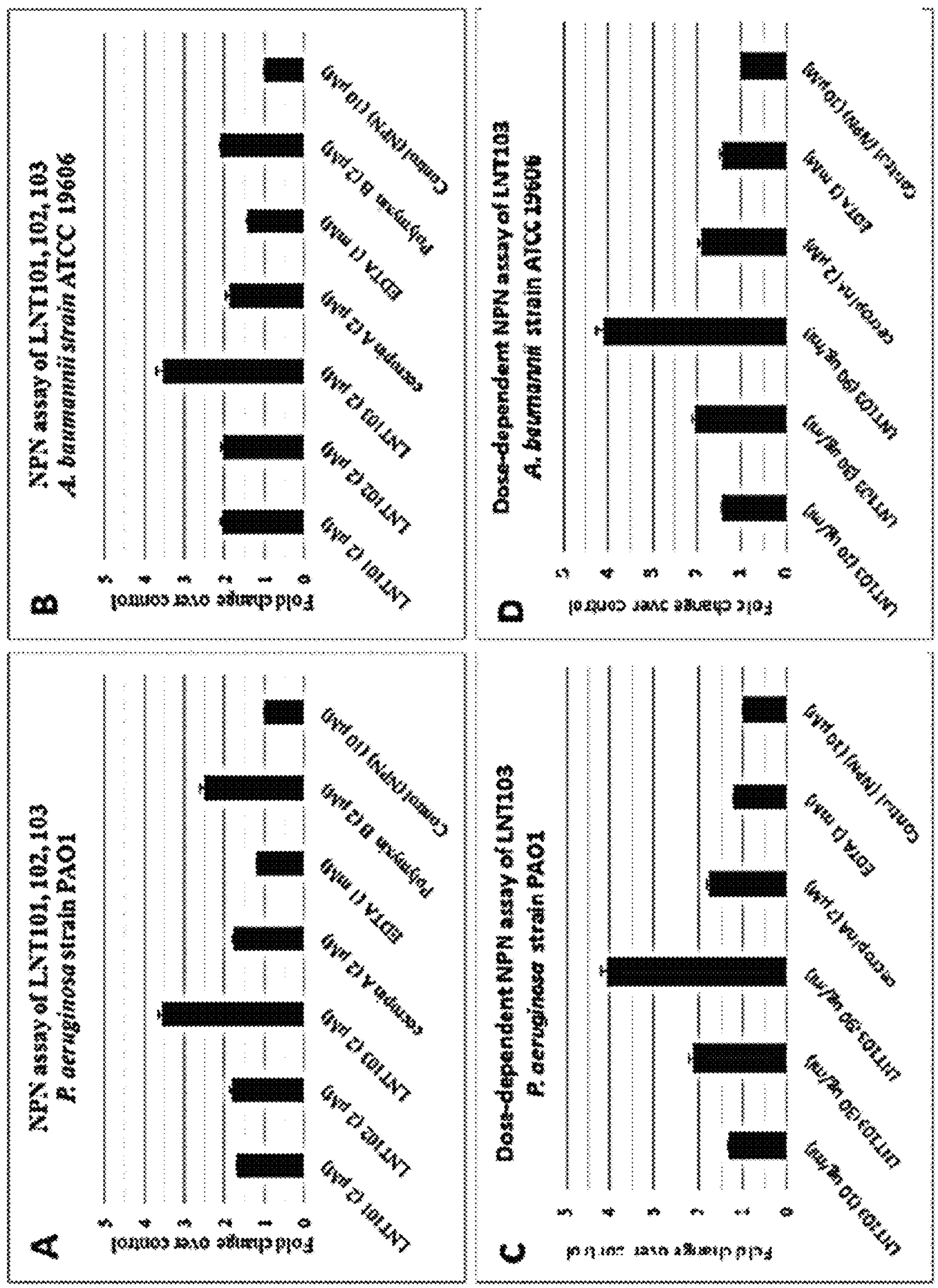

【FIG. 14】
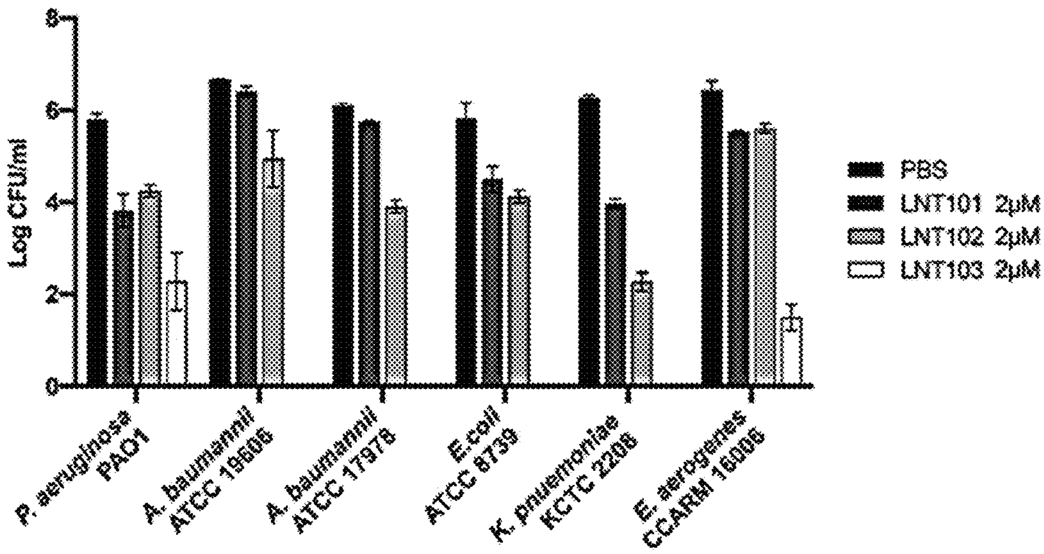
【FIG. 15】
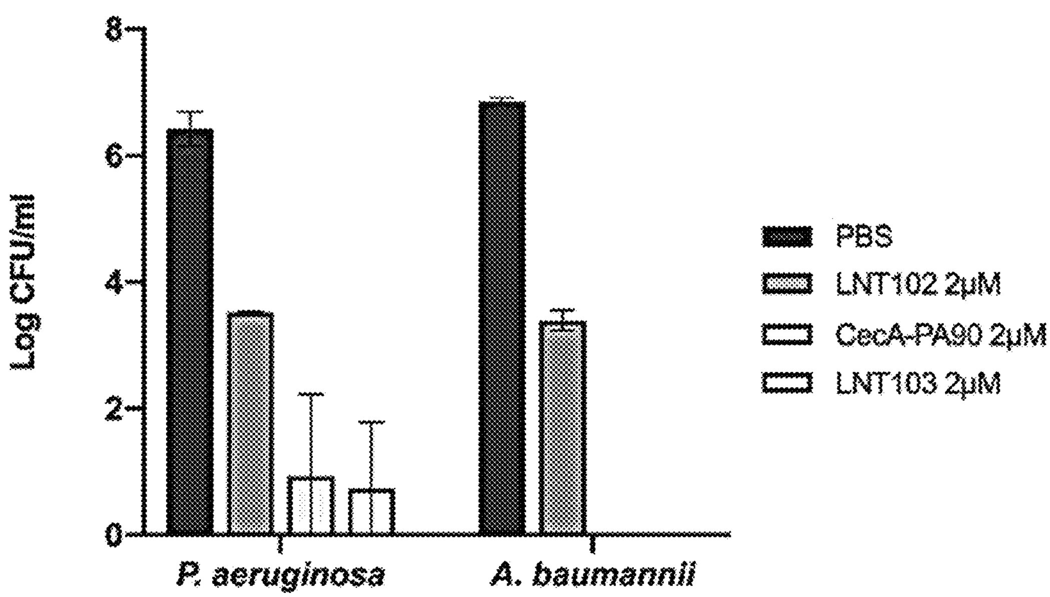

【FIG. 16】
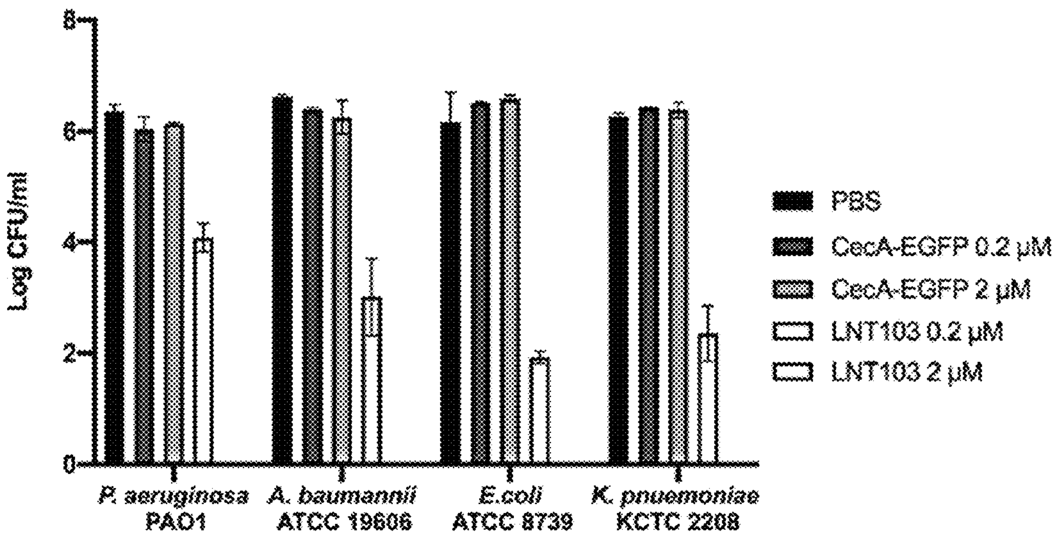

【FIG. 17】
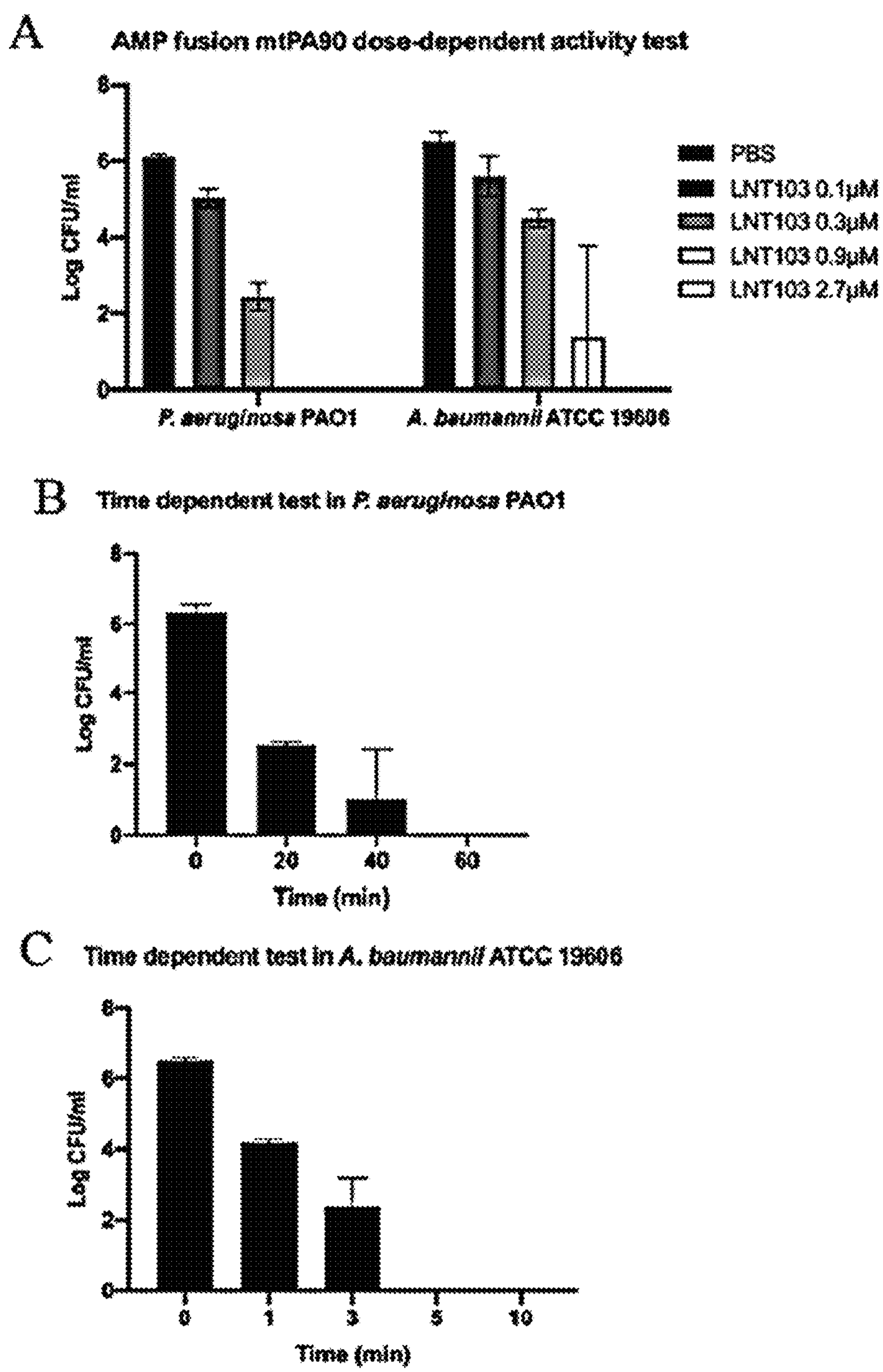

【FIG. 18】
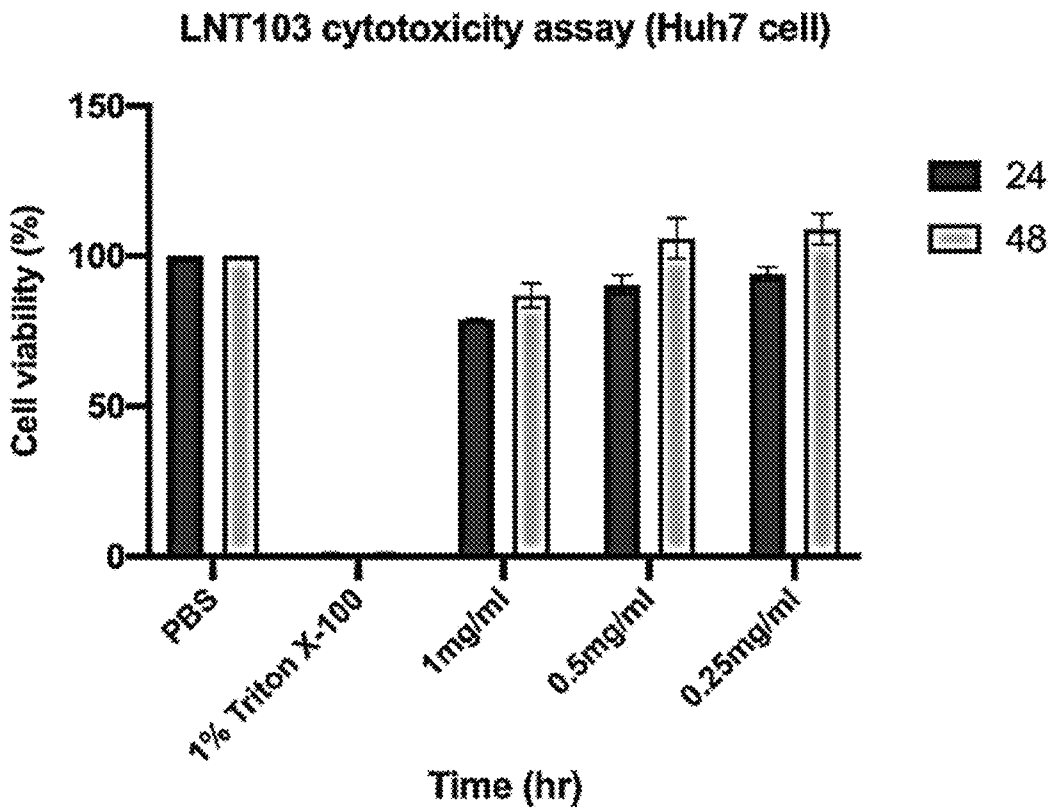

【FIG. 19】
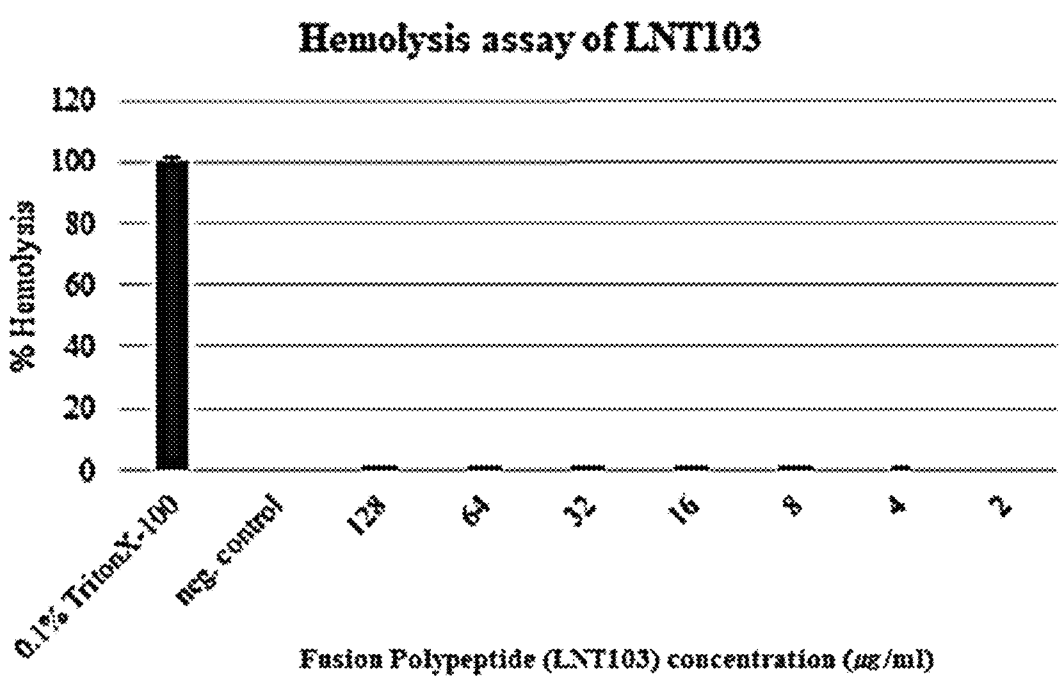

【FIG. 20】
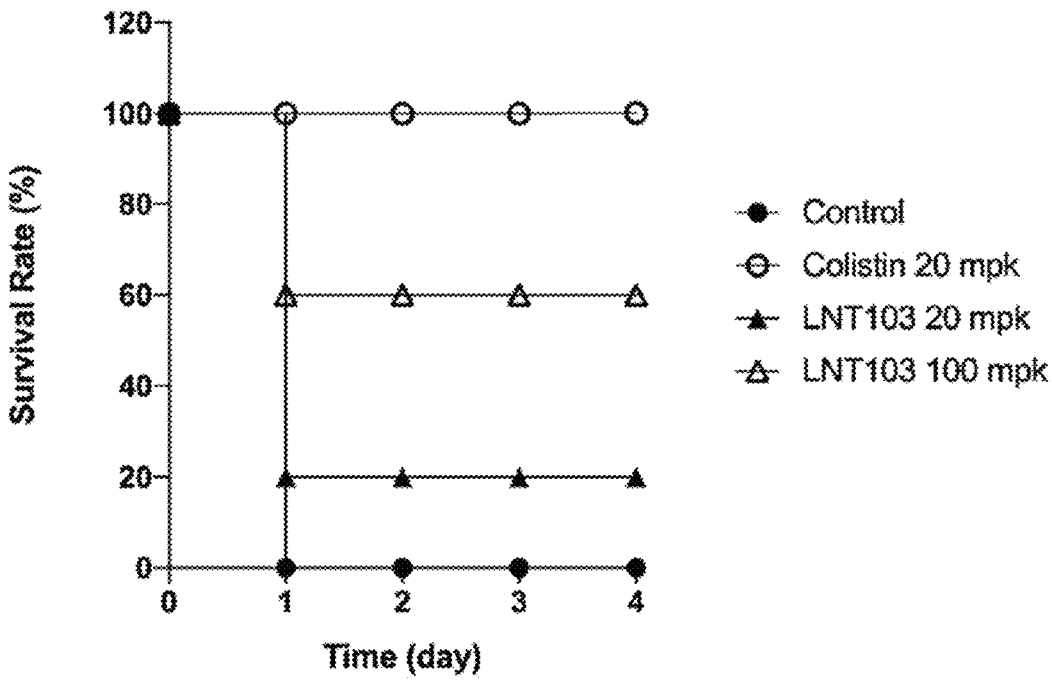

SEQUENCE LISTING

```
<160> NUMBER OF SEQ ID NOS: 16

<210> SEQ ID NO 1
<211> LENGTH: 259
<212> TYPE: PRT
<213> ORGANISM: Artificial Sequence
<220> FEATURE:
<223> OTHER INFORMATION: synthetic_Endolysin LNT101

<400> SEQUENCE: 1

Met Gly Thr Val Leu Lys Arg Gly Asp Arg Gly Ser Ala Val Glu Asp
1               5                   10                  15

Leu Gln Met Lys Leu Arg Val Ala Gly Tyr Ala Val Ser Ala Asp Gly
            20                  25                  30

Ile Phe Gly Gly Asp Thr Glu Lys Ala Val Arg Asp Phe Gln Ala Ser
        35                  40                  45

Lys Ala Leu Val Val Asp Gly Lys Val Gly Pro Ala Thr Leu Ala Glu
    50                  55                  60

Leu Ala Lys Ser Ala Thr Val Pro Ala Lys Trp Glu Ala Ile Pro Phe
65                  70                  75                  80

Pro Thr Ala Asn Lys Ser Arg Ser Ala Ala Met Pro Thr Leu Asn Ala
                85                  90                  95

Val Gly Ala Met Thr Gly Thr Asp Ser Arg Leu Leu Ala Thr Phe Ala
            100                 105                 110

Ser Ile Glu Ser Ala Phe Asp Tyr Thr Val Lys Ala Ser Thr Ser Ser
        115                 120                 125

Ala Thr Gly Trp Phe Gln Phe Leu Asp Ala Thr Trp Asp Asp Met Ile
    130                 135                 140

Lys Ala His Gly Ser Lys Tyr Gly Ile Pro Lys Asp Pro Thr Arg Ala
145                 150                 155                 160

Leu Arg Lys Asp Pro Arg Ala Asn Ala Leu Met Gly Ala Glu Phe Leu
                165                 170                 175

Lys Gly Asn Ala Ala Val Leu Arg Pro Val Ile Asn Arg Glu Pro Ser
```

-continued

```
        180                 185                 190

Asp Thr Asp Leu Tyr Leu Ala His Phe Leu Gly Ala Gly Gly Ala Lys
        195                 200                 205

Lys Phe Leu Ser Ala Asp Gln Lys Thr Leu Gly Glu Val Leu Phe Pro
    210                 215                 220

Lys Pro Ala Lys Ala Asn Pro Ser Ile Phe Ser Asn Lys Gly Val Pro
225                 230                 235                 240

Arg Thr Leu Ala Glu Ile Tyr Lys Leu Phe Glu Asp Lys Val Ser Lys
                245                 250                 255

His Arg Ala


<210> SEQ ID NO 2
<211> LENGTH: 780
<212> TYPE: DNA
<213> ORGANISM: Artificial Sequence
<220> FEATURE:
<223> OTHER INFORMATION: synthetic_Endolysin LNT101 coding gene

<400> SEQUENCE: 2

atgggtactg tactcaaacg tggcgaccgc ggctctgctg tggaagatct acaaatgaaa     60

cttcgagtcg caggatacgc agttagcgct gacggaatct tcggtggaga tacagagaaa    120

gctgttcgtg atttccaagc ttctaaagct ttggtggttg acggaaaagt tggacctgct    180

actctagctg aactagccaa atccgctact gttcctgcta aatgggaagc tatccctttc    240

ccaacagcta ataaatctcg gtcggctgca atgcccactc tgaatgcggt tggagcaatg    300

actggtaccg attctcggtt actcgctaca ttcgcttcca ttgagtctgc ttttgattac    360

actgtcaaag catccacatc ttcggctact ggttggttcc agttccttga tgctacatgg    420

gatgacatga tcaaagcaca tggttccaaa tacgggatac ctaaagatcc cactagggca    480

ctccgtaaag acccacgtgc aaatgcatta atgggtgcag aattccttaa aggaaatgca    540

gctgtattac gtccagtaat caatcgcgaa ccgagtgata cagacttgta tttggcacat    600

ttccttggtg ctggcggcgc taagaaattc ctatccgcag atcagaaaac tctcggtgaa    660

gttctattcc cgaaacctgc taaagcaaac ccgtcgatct ttagcaataa aggtgtacca    720

cgtacccttg cagagatcta caagctgttc gaagataaag tttcgaaaca tcgggcatag    780


<210> SEQ ID NO 3
<211> LENGTH: 32
<212> TYPE: DNA
<213> ORGANISM: Artificial Sequence
<220> FEATURE:
<223> OTHER INFORMATION: synthetic_Forward primer

<400> SEQUENCE: 3

aaggatccat gggtactgta ctcaaacgtg gc                                   32


<210> SEQ ID NO 4
<211> LENGTH: 35
<212> TYPE: DNA
<213> ORGANISM: Artificial Sequence
<220> FEATURE:
<223> OTHER INFORMATION: synthetic_Reverse primer

<400> SEQUENCE: 4

aactcgagtg cccgatgttt cgaaacttta tcttc                                35


<210> SEQ ID NO 5
<211> LENGTH: 304052
```

<212> TYPE: DNA
<213> ORGANISM: Artificial Sequence
<220> FEATURE:
<223> OTHER INFORMATION: synthetic_PBPA90 genome

<400> SEQUENCE: 5
aagggtcccc cccacatata attactattt atataaaatt tcttttaaag aaaaagcatt 60
taataaggaa aatactcttt attaaagata tctattcttt aacaacaagt tacttatgca 120
cggccggccc cgcgaaaaaa aaaaaataaa gtggaataac cctctcccga aggagagggc 180
tttatgcctt aacgattact aagcttgatc atggagacaa acttaggatc ccaagccagc 240
ctatccatat caaagtaacg gataggatgc atcatgaatc caactgcaac tccatgatag 300
atactttcga catcatcaac tgcgataaca acagaacggg tgtattcatt cgcatcgttt 360
ttcattacgt gtacgaacga tttgacaccc ttgctaccag tcaaccattc aagccgtcgt 420
ttagctacct ccgcaaaacg cagaacctct ggacgaaccc attgcggata atgtaagaca 480
ttattgtttt ccagtttacg aatagaatca gtctcttcat cgagatcacc aaatacatag 540
gacgatacca aacccatgat ctggaaatta accggtttat cagaggcgtc tgtaatcacc 600
tggtacacac cagtagtatt agacaagaag ccacggtcag agaactcatc tactacatca 660
cgatacgcac gttgaatacg ttgttcgatc cacccacatt tttcaatgta aacgtcacgc 720
aacaaagact taacatgggc aacgtacgat tcctcattga aagaagaatt caatccacgt 780
acgttcaagt aagaacgatc tcgtccttcg aacgtgacag ttggtttact ccaaccactg 840
tggctttcca cctgtacacg gatgttgtac gcatccaagg cgccattacc tgtaatatcg 900
aaccagatgg tgtctagatg gtttttggtg agccctaatt cttttgcgtt aaaactaaaa 960
tcaatattgc tcatcgtaac tcctatttag tgattgaata tcattttagt aatatagatt 1020
taaaaacaaa tacaacataa agcctccccg aagggaggcg tttatattac tcgcgttcaa 1080
cccatggacg aagatccatt actgtgggag cagccttctt aatgtaagtt aagatagagg 1140
ctttgtcaac tgtaggttct aaagcgatac cgattacgat actatcttta ttacggatca 1200
gtagacgtgg tttattgctc tccagacgtt gttcttcgaa gagaatctta cttggatagg 1260
gtaagtcata gggaagttga aaaagcttat gtaggaccat tggaacgatt tctagagggg 1320
tacctagttc ggcttttatt tcttccaagg taacttcaaa ttgtgttgtc atgttaaatc 1380
cttagattgt gtaatattcg tgataacggc gaagtttgtc atcatccaac gcgatctctt 1440
gataactgat cgtaatcttc atgtggttcc atggagatcg gaatgcgcgt ccagttaacg 1500
atacttcacg gtaatcattt acgtgttcgt ctttcacttc ttcctcgaac acgaccccga 1560
gtttactaaa acgtttaatc agtagttcaa tagatctacc aagctcaccg gggacatccg 1620
gaaattctgt tgctgatgca attctaggca tgatcacagg accatcttca acttcataat 1680
ctaccttgaa tacaacaaca cccaaatctt tttggattgg tcggaaaata cgataaccat 1740
ctttggtcct ccgaagctta tatccatcat ccggatgtgc ttcttgtagg gcctctaaat 1800
gatcctctag tgcgcgaacg ataccacggt tataccgtag ctctctttca cgataatcgc 1860
gttcaaacgc ttcctgcggg ccttcttttg taaattcttt tacaacggtg tattcaatcg 1920
tttcaccagt cagatgatcg gtgataacga ataagtacgt catggcatca accaaagaat 1980
gttgaacgct ataccgggtc atatcacatg gaatggcacc agctcgttct tctttgagat 2040
aatcaaacat gtctttgaga tgggcccaaa catcacaatc gctacctagt ccatccaggt 2100
caatcgatgt atccgggatt tctctctgag cacaacaact catacgcacc tcttcaatta 2160

-continued

```
tatttggcgt tcacatgata aaagaaaaag gcgacatata gcctctcccg aaggagaggc   2220
caatgccagg ttaagatttc acctgttcat ccagggaagc aagaaacttc tcccaagcgg   2280
ggcgaacccc atggaggtag tagctattct gagtagtctt tttcagggac tctacggtac   2340
attcttcagg atcccattga ttatcgccac cactgcccgg actgagccca tagcagctgc   2400
aatgtgaacc gtggacctcg tagtatttac catcgcgctc aaagagcacg aaagcactac   2460
ccgagtaatc ctcgtattca taccacgcaa aaagaatggt agcattatca agttcaccat   2520
tagtcagacc gaactcagaa attacatctt gctcattttc aaaattaccg aagtacatga   2580
tttcacctct atgttgtctt tgcggaatgc aaaaaaacgt ttgcaacgtt catgcaaaat   2640
agacaacagg gaaatctaac ctgtattaaa tactggatct cagtatttat tcgtcatcaa   2700
actcaatgac taaaccaatt ttcttataaa gcgctatagc tgcttcattc tttttgtgta   2760
caaaaacttt cttggcttga atgtatcgta ctagctgttc accatacccc ataccttggg   2820
ctgactctgc tatatacaga cagtccaaat gcatctccgg tgtatagaga atagcataac   2880
cacgcaaatc accatcaaac caaataccat aggctttcct agtgcaagcg aaagctttac   2940
tggttaacaa cgttcgtata ttaccctcgt aatcgagaag agattcaaga tagtcaggga   3000
ggacaacatg tgtcctctcg acctttatga actcaccaat tacttcatgt cgaatttcac   3060
caatctctaa catgaactat ccaaacactt taacgaatgc ttctggccag agcattgttt   3120
tgaaatcaac cccattaagt tcaatgacaa gaagaccttt atccagcttc agacggatga   3180
tatcagtctc gtccatctca cgctcagcta catttgacat gtaagcaaac acagcctcgt   3240
tcggaatcat gtatgtctca tccacatatg cctttacaac gaacagaacg ttctggcatt   3300
ggatgtaatg agtttcagag agttcatcat aactgaatcg agctcgaaca gcagtcttct   3360
ggtgaagact atttgcggtg atctcgatat ccgtgatgac agccatcgct ttagacaatg   3420
caaaggtaga catgctacca gagcctaacc aaaggcgatg aatttccgtg ggagttagat   3480
caacagcgga catgggaatt tcgatagtcg aactatcgta aacttcaatg cagtcactgg   3540
catactcacc attaatcaag aaacggaata cattcccatc ttgctcatac ttccagcggg   3600
aaccaacatt gcgcatcatt ccatccagat acagtgcgac aacgtcagac ttacttgggg   3660
atttgaaagt tacttcttca ttacgcaggg ttggttgaga catgataact ccttagaaat   3720
caatggtgat ggttatttcg tctttgttat cgtcaaaggc acggagacta atgacagtct   3780
cgtaatgacg aatggactta gaaacagata ccagtttagt ggcaccgagg gcatggagag   3840
tatccatgat ttctttggca ttaacactag gagactgatt tccgtaacta actatcagtt   3900
gttcaatacg ctcctgagta agaggttcaa cgaatgccgt ttgctggtcg attgcagggt   3960
aatgaccaaa atgacaaatt gtgtacttac gtttaagaat gccaccaacc tgactaacga   4020
catccacacg ccgatgcgaa taactgtagt tttcaagaac atacagattg tcagggtaca   4080
ggggagccaa cttatcaacg aaaccatttg cggcttcacc aatggtggaa tcgagttgta   4140
ccattacatc gtcaccggta taatctatcc gcacacgggc gtaaggcttc gcatcaatac   4200
agcggtctgc ttgttgctcg gagtgtaggt aattcagagc gtagccttta ccagttagtt   4260
cacccgatac tttagccagc agtgtcagta gttcactacc agctggactc ttttcggcat   4320
actcgccata aagcattgac agctctttac tcacagatac tttcgtgaaa tcgacatcac   4380
gtagaacaat ggtgtcactg taattacggt aagggtcgtg gtaaccaccc tcttcaccaa   4440
agccatagaa accaccatcg tatttacgta cgattccaat agtgccaatc atcttacggg   4500
tattgagatc gaagatgtac tggctcagct tcgggcattg atttacagaa acttgggatt   4560
```

-continued gttcataacc agcgttatac caatcgctga ctagtagatt accatgaaca ccaggttcga 4620
tcagatcaag accaacatat ttagctgacc agttttccca ggtgaatttg ggttcttcgt 4680
gttttacagc ttcttctttt acaacaacat tggacatatt gcaaaacctc tttttaacgg 4740
aatgtttagc ttgcatgtaa tatagatcta agatattttt tagcgcaatg atctgattaa 4800
tcaaagaggt ataaccatgg ctctcactat tcgtcaagtt cttgacaagc atttcgaaga 4860
tgtcaagttt gaccgagacc tttgcaaacg aatcatcgac tacaccgtcc gttacatgaa 4920
ccgtaatgaa gatcactctg catttttttgg tggagttctt ctaggtgttc aagaagttcg 4980
cttctatgat actgaccgtg agatttggtt tgatgacgtg ctacgtgtag atgacgatct 5040
actccgtcac gatttcgtta aagctgaagg tatcgatcct acacacattg tggcatctga 5100
tccattcaac catattccag gttatcttac gatccaactg aataaacgta atgacattcc 5160
gttgaatatc aaacaagaag caattacatg cgctttcatg gtgctacatt ttaaatatct 5220
aacatctcta ttggttagac gatttaaata tccggctagg cgtgaagtgg ccgaagcgac 5280
atttgctgcc cttaactaca agtttgatat taaagctatt ggtagctggg gaaaattaat 5340
tcgtgaacgt tccgagggga tttcttcgaa cgacacttcg aatatttatt actcgtatct 5400
tcatgataag atcgaggata aagacggcta tatgtcgaaa cgtgttgtaa ctgacacgca 5460
gtcacgtatt cgtgaattga tcaataaata ctacgaagtt tatatccgta ctttacaatc 5520
tggctctaga ttggttatga cctctgacat tggtgtcaat actgatggag atcaaatact 5580
gagagataaa gttaacggct attcgggtta tcttcgttac atgcatggtg ttgttaacaa 5640
cgaacagaac tttattagac ctgagctatt gggtgtgatt gagaactcaa tggcagctat 5700
gcctccaaag cttctagtgg aatcgctaca gtacatgtcg cgaaattatg gtcaaccgag 5760
aatgggtcat ctagagaaac tagttgatga atgtctgctc tacgcgtttg actacatgca 5820
gtcgattaaa acctctgtac agcgtaatac cgacctaaac ggtattatcg tgaagatccg 5880
tgctaagctg atggcttcgc gttcagaaga tccacgtgta ctctttatgc gggacaccgg 5940
tgaagcaatg gtgaaagaag caacgaagat taagaaccca gctgttattg cagctacccg 6000
tactgggatc atgctttaca ttattcttcg agctatgacc aggaattatt attccaggta 6060
aagaaaaaaa aacataaatg ccctctcccg aaggagaggg cttatgtcgt gttacttgaa 6120
taagtggtct gccaggatta caataaacaa agcgagtaat gtatttctcc cgcctttgaa 6180
tacgcgtatc caccacttag atcgtttcaa tgtaactgag tcacacccag ctagcttttc 6240
atgttcatat tgctttgtcg aatagagata tccgatattt aaaatcattg caataaagaa 6300
cagactagcc aaaccgaaag cgatcattag ttattgtaat caactacaga tgcgagaaga 6360
tcagcggcag tccgatcatc agcattccat agtttatcac accactcctt atcttccgga 6420
ttggtgattt tgtgaagttc catgtgacta tggaaagctt gaccccaacg tagattcttg 6480
tcgaggttct taaaggaagc cagtcgggtg tagggaattg ttatggccat aactcaccgt 6540
atgcatttaa gggtacgttt agtttgcaca ctcagaggac cagtgcagtc accagtcttc 6600
agtgctacca gggtttgata aaactcagtt aacagtggtc gatatttgtc gatttcatgt 6660
tcactgtatt tgcctttagg aaaagcgatt gtgtaaccat caggtggcgg catgtcaaac 6720
tcggtgaaca agtcaccatt atcgacataa ttacagatac ctttgttaca gtagatcaga 6780
tcagaactat ctaccatttc agcgtagagt tgggcatcgt attccaccgg attgaacgga 6840
tcagcgacag cgacttgtaa tgcaatagtg gataccacag cgatgaacag tttacgcatt 6900

-continued

```
tcgatgttcc ttacttagcg gttttgaaat ggttggttac agcgttgatc aacatctctt   6960
cgatatcgac cttacggtat tctggttctg agttctcgtc ttctaccata tcccagtaga   7020
tagtggcacg cagcagcgct ggtgcaatga aacgaatgat cttgccagta gcatcgaact   7080
ccacgctgaa catggcatat tgttcagagg taccagcttt gtagaagatg aacgatccgg   7140
cgaaggtacg aatctccagt tcaccgaagg tactgatacg gacttgttta tcgaagtact   7200
cacctttggt gcgcatattg tcttcgataa cagtgaacag ttctttgaga agttctttat   7260
tgaggtacat ttgtagatcc ctattgtggt gttgaattca catttgtaat ataggttttt   7320
aatatattta aatacaagcc gacataaagc ccagccgaag ctgggccata tatcaagcgt   7380
actgtgcgtt tgcttctacg ggtaaaccac gagcgatgtt atctgcatcg gtagctacag   7440
aagcagctac tcgattaata cgatgccaaa gaccattatc ttcagcagcg acatcagcag   7500
agatcaaatc gttgtacctt tcaacggaac ccccttgagc gggagtttgc gtcgaagcat   7560
catctagctt aaggggatta gccattagtc agcaccatcg taggttacac ggttagtagc   7620
ggatttctcc agctgatcac gcagaccaat gttggcagca cgtacgtcag cagagatgga   7680
ttcaatccaa ccacgttgtt cgttcgggtt catcccttta atgttcagtg tacggaacag   7740
ttgacgagca tacatggtaa caccttcaga tacgtcagtc atcgccgaga actcaatact   7800
gaggtcaagg ttctggccga tctgagcggc atctttacgg ctctcccatt gaccagtcga   7860
cagcgggaac atgttggtgc agagatatgc gctaacaacg tcttggaaag tcgggtctgg   7920
ttcaacgaat agaatcgtgg caccgtagaa ggtagcatcg tatttctccg gcggaacgtt   7980
accttctgca acgatacgcg ggatcttggt attctcgtca ccgataccgt aggtgatcca   8040
ccacttcagg taacgctgga tagcacgacc ttgcagttcc cagcaaccca acgacggagt   8100
cgaacgagca cgggtaacgt tggtggcagc ctggatggct tcaccagaac caccccaagg   8160
agcttctgcg gtatcaacag ttacagtctg ctgtagacca tcgatagtac gaacatggtt   8220
ctctaccagg gctttaagcg aacgaactag ttgccggcta ttgctagcgt attggaagaa   8280
gcgtggagct tccagaagga acgggacgag gttccggcta acgtaaggag tgttactcgc   8340
aaggttagcc agatcaggac gaaagacatc cgtaccagcc tgagccaggt tgatggtgtt   8400
cttggaacca cctgcaccgt agccggactg aggagccatc gggtcattat aacgtttcat   8460
ttcgattcct caaaaatgag tagttaccga gcttattgct gctcggtaac gttctcgcgg   8520
cgaacggttt ccagttggaa gttcagagtg gtgcgcgggt tattagccgc aacagtcaca   8580
gtgcaagtcc agctggtgcc attgttctca tcaataccgg tgatctcggt acgcgggatc   8640
acgtctacac gaccaccaaa cagatcacga gtacgatcaa ggatctcttg gtcgcaacgt   8700
tcaacaagct gttctttagt caggaaagcg ttacccgaga acttagcgtg gatcttgtgg   8760
atcaaccgca tgattacgca gcagatattc acagtgatcg ggctaagcag taccgatgtg   8820
tcgtccagat ataccgaacg tagacacggg tagtaattcg aacgatggtc gtacgaagta   8880
gagtaagttg caccattggc ccagaggtta gccgatgtac gagcattgaa gaacggtacg   8940
ttaagcttct taaccatggt tacacggtta ttcggatcaa cgtccatttc agcgcctgca   9000
cgtaggatac cggtgccagc accagcataa cgcgaccaca tcatggcaac gtcgagcaac   9060
tgcggaacaa acttattgta accgccgcca acaagcttac cagattgcat tacaatcatc   9120
gcacggcaca caggggtacc atacagggta gcttccggga aagccttcag acgagtcatc   9180
agagcctgta cacgggatac ttcttcagat gccgtcggaa gacgggtctc accttcaaca   9240
aaggtagtga agaagtactg tacgtcacga cgagcagaca atacttgcat tgctttatat   9300
```

```
ttcgaggcca tcggcagacc ggtgtcgtac aggataccga attgatagag cgcaacgttt   9360
tcgtactgat caccaagctt accaaagttg gtattctcga tgtcaacaag cttgacgtat   9420
tcatccaggg tagtggtacc gtctttaccg ccttgggcgt agacagtagc gttcttacct   9480
agaagcacac caccttcaat cggaccttcc agtttgatgg attgatacgg gtcaccatct   9540
tcaccaagca tagtgaggaa gtcaatctga ccaggtgcat cgatatgtgc attgattgcc   9600
gggtttacac gggtctctgc atcgtagata atctcgcgaa cgagttctac gttgtcacga   9660
tatacatagc actgcgagaa cggctataa agcggggaca tacccgactc aataccgtcg   9720
tcgttatact gatcgataag aacttcatcg atggttagat cacgatcata ctgttccgac   9780
caaacacctt cgtcgaacga tacgttgacg tagtcttcat cggtcttggt cttgatgatg   9840
atcggagtgc ttgtcccgtc catgagttca acgaattgaa cacgatacag acgagtcttg   9900
aagcgctggc cggtgaattc atcgtagcca tccggatcga gctgagtcgg tgcccagata   9960
cgcatgccca ggttattacc gggctgaccg aagaacgaag cgggtagttc gaacagcgga  10020
tatacagtgg actgactacc gtccataccg gagaccatgg tacccggcag gcgccgttga  10080
gtacccactt cggattggtt atcagcaatc agaacgatgc gtgcacgata accttcaaca  10140
gtatcggtac cagaagcaat cggaccgtta ccagtgtcag ttacagcatc aggatagtta  10200
aagccactga gacgggtcac agaagcagga atcatgtctt ggaccatttc cagggccaca  10260
gtgattcgag cagggttacc agcgtcttcg ggtttcaggc gtttaacata gaaaccgtta  10320
ccttgaccaa gcaggttcag cgccagcagc gattgctggt taaaatactt gctgcgtgga  10380
tcaagagagc tttgaccaaa gatagacgcg aagccatctt cggaatcacc tacataagtg  10440
gtttcagttg ggccagtctc agtgaagaga cgaagcagag gagtgtgttg ggcgaaagta  10500
atctcgggac gaatgaacgc ccgacggcta cgatctcgaa tcccgttaaa cacaacctta  10560
ggaacagcgt tgtagtacgt ggacatcttt atgtttctcc cagatgtgga gctttaaact  10620
cgatgttatg agtgttaact aacagtcaat cataaatatt gttcatagtt ggctgtgata  10680
gttatttttc cctacccatg aaaggagtaa aacggtaatg ttttcgctac cgtatcaaac  10740
aacagtctgt gggatctatc ctaaatatca acaggtgatc gcagcagccc gtcgggcaga  10800
aattgatttg ccattccccc tggtagaaac acccggtgga aatcagttaa tgaactctgc  10860
gttcgtaaca cctcgtgaag aacacgaagc aattccgaac ttcactcaga ttatcaatgt  10920
gggcgaaccc aataaaccac ggcttcttat tgatagccgc caatacatga agtttgacgc  10980
tcgatctcag aagtattctt tgatcgctca aaacgactgg cagttccaat gcgttcgtct  11040
agctttgaac aatcgcctgc tttctggcga cgaagctttc tttaatcgct tatcggacct  11100
acctgcaaaa gtattccatc gttgggttag cggtgtattg gttacacgct acaatctacc  11160
gatcgaatcg cagatggcac tctttgtcat tacggcttat tactattacg ccatgtccac  11220
ccctgaactt cgtcaaccgg gtgaagagcg tgagaaattt gcaccgatta tttctcgctg  11280
cacttcggtg ccgccagaat ttgtactcga tgttgccgca acgatgggta agctggagaa  11340
tgcctctgac ctcattcatg agatgtcagt taactcccgt caacagcgta ccggtgaatt  11400
gaagtttggg gatctttttg cattgatctc gacttcttgg ttcggtgtaa actcccgtga  11460
aaacgtgggt gtagccctcg aacatttacc gactttcatt gcattgcttt acatggcaat  11520
tgcagaacgc tcataccgta aaacagtaat tactcaacga gtagaatcgt tagctcgtgg  11580
aaacgagctt aaagtcttta ctgacctcgt tttcaaagcg gtttccgagc aattcacacg  11640
```

-continued tcttcatcag taatgggtga ttaatgaacg actatctatt gcgctacgca attgagaacg 11700
tttggtgtaa ccctactcag gatcgacagt tcgtatataa gctccgtcaa ttaactcccc 11760
gctacggtgt acggggtagt tacgttgtgg agcacgaacg ttataaactt ccacaaatct 11820
ctactcgtga cttctggcat atctaccaaa tcggtcaggt tattcctcgc catcttggta 11880
ttccaaagct gttgaataac tggatcagcc ttgagcaact gggtaaagag gtacatactc 11940
tcgcggaagt ttatgtcagt aatggaattc agttcccacg ttctgaaaca tatatcctgg 12000
taacccaaac gcaaaacttg cttgtagcta ttcgacgaaa tgatcgcttc cctgatttgg 12060
acgaagctga gaataatcca tatctccatg tttatcacaa cgcgtatttc aactctgatc 12120
gtagcgatat agcagcagcc cgttatatcg atgtgatgac tttgacacct aactctaacg 12180
aagaacttcg tcaattccaa attcaaatta tggacttgat tgaaactaaa ggtggttacc 12240
cccagtactt cgttaacggt aggttcgtac aagagatatc gttagtaaca gccggtccgg 12300
gtgattactg tgaattcatc cttgatccaa gtattaaacg tgtagtcgat ttagatctac 12360
gtgatcttaa aacattcaat tctacgctcg ataaagaaag gaaatatatc cttcactacg 12420
acgataagaa tgtcaacacg attgagtact tcgacgatct agatgtttat ctttgcaaaa 12480
ggggttcatc gcctggtcgg ttcagtggtg tgatgtatca ccacaatgaa ggtaattggc 12540
ttcgaatgtt gacgcataaa gactattcgg ctcctgttga tcgaattcag tctttcatca 12600
caagtcaccc tgaagaccca cgccatgcaa atgatccatc gcgctggcct tctgacaaat 12660
ggacaggtat tgaagataag ttccttcgcc tttacattcg tcattctgga tacgaacgac 12720
ctctggtagc cgatgttggt cgcattcaag aactctatcg tttatcctcg gataatatcc 12780
ttagggccat gactggagca gacgctactt gcccattatg gagagcagag aatcttgaac 12840
aatcggctta cgttcaattc atgtccgctg atccagatgt aatttaccct atcgctttcc 12900
aagatcctga tgagatatct cagggtaaga tcgatgccca gaattttgcc ggtgatgtat 12960
tcggttacca taaagccgca gatattcagg cacataatcc aaccaaggtc catgttgacc 13020
aaggtacagt atatgcaagt cttccataca actattggga aaatgctact gttttcgaat 13080
atgattcgaa agggattttg ttgggttatt accatcatgt cgcagggcgc cgataccgcg 13140
tggtaaatca aaccgaatgt aagatggtag aatgtattac tggtaaaggt gataccaatc 13200
ttcatggtgt atttggtaat ggaacagtcg atctttcgga aggttataac ttccgtcttt 13260
acgtctgtaa agtctgggct ggtgtaccaa ccaacgaatg gattgatatc actgacctac 13320
ctaatcgaaa tgattggggt ttccatgata caactgatat tgaacatcct aaatggacat 13380
ggactgcttt accaaatgaa tggtacggtt atgttcgtat ggataactac ttctacctga 13440
aggaaatgcg gtttactaaa gatcagggta ttattcgatt tggaatcgat aactgggaag 13500
agcataacgg tgaactaatc aacaagctca tggagatccc attcggacaa ctagatatct 13560
tcttaaataa tcgaccgatc ataaatggtc tcgattactt tgataaaggt attatgactg 13620
tactgaataa ccatgagtat ttggttgatg gtattaatac cgttcttgta cgaggtaccg 13680
gttactgtac tcctgatctt cagcgttata aacctggtga agttggttgg gtagagtata 13740
atgttctttc caataatggt atttatgata tccatacgca caaaatgcaa aggatcattg 13800
tagatggaca ttaccgcgcc cgtgaagatt tggtgtttga ggaggataat aattctcttc 13860
tgattaccga tgaacgaaat ggagcaccct tccaaatcca aacaccgcaa tccactttcc 13920
gtgatgttta cgatactgat cagcacgcac gtatcgcaga tgacgaacgt gataaacaag 13980
tttccgatta catgacagcg tatttcccta agagaacacg cgatcaagtt gactcggtta 14040

```
cacgtcgtta tgtggtatat tcggcattct ctaacaaagt tctccatgac attgttaagg  14100
gtacgctgaa gccaccgctg gttaatggtc gttacaacga gatggatatt gctcgggtta  14160
tggcatccta cgagtggttg gttccgtttg atatcctaaa cacagattac aacaccaacc  14220
atgtggtagt ttatccacat tggcatagtg atcctattgg gttagatact gatcagtatg  14280
acttctacat tcgtgtactg aagttgtatt tacagcgccc tatggacatc gcgccattcg  14340
tatacctaac gaggacttaa catgcttcct gtaccatacg ggaattccga ctacatggac  14400
cctaataggg gttggtgggt ttggaaccgc aaagatatcg tccagcaagc tggacaagta  14460
aataagtggg tccccaatat tggggacctc gtttgggacc gcgagaatgg ctggttcaca  14520
gttgaggatg tcgaagaggg tactcacgta gctactctta aagaatggta tcctccaacc  14580
aaagttgacc ccgatggcga agaaaacgta ctggtgggcg taggtccagg ctatagttcc  14640
gaaagctacc gtctattcct tgataccagc gttattcccc atactctcgc acccgataaa  14700
cgtctgcatt tttatggctc gatggttgct agttacaaag tctttaaggg tagtgatatc  14760
tctgaagaat ttggtaatat catctctgct ttcttcactc cctctggtga ttacacgggt  14820
ccacttattc cagttgagac agtaaccgtc ggtaatggct ctcagaacgt cattaaggcc  14880
cctatggttg gttttacagc cgaggagatg gatgacggtg agcgttgcac cttggtggcc  14940
tacgatgacc ttggtggggt tgtgtctata gcacagttgc tcgtacaaaa cacgaaagca  15000
attcgacagt ctgataattc gaagaagtac attgccggta tcgagatcga gagtccgttc  15060
ctgtctgctg ccgatcctaa ggttattgaa ttcccgctga acgtaaacgt tgaatctctt  15120
ccgatggttg gtatgattaa ctatcgtggt ggttctaaag tacggcgcgg tatcgataac  15180
tcgacaatgt tcttgtttgg catggaaaac tatatcgcta ctgagattgg acaggagttc  15240
ccgcttactc ttgcttacca gttagcagaa gatgaaattt cctatgcgtt gacaccaaca  15300
gcaaatcgcc ggattacaga aaactacatt gcccgtacaa ctgctgccga tggagcttac  15360
gaatgtcgtc tattcgttta tccagtatgg caaaacgtta ctgctggtta ccgtctggaa  15420
ttctggcttt acaacttgga tcgccaacgt ttctacaacg ttacttcttt ggttgaactt  15480
ggtgttaact cagcgccatt caatccgaag ggttatggta atctacaaac gcttacctac  15540
gctgttaacc tgaacaaggt cgatggtcgt ttcgcaccac atcgattcgt tactacattc  15600
caagttgcac tcctgacatc tggtgaaaac cgtgatgcta actgggaaat ctacactcgt  15660
cctgatgtag acgcagctta tggacgtggt ctgaaagccg atctggaata catccaaacc  15720
aacgcttggg atctacgtct ccagaacgga gctaatacca aagaagcatg gctgcggaag  15780
atgtatgaag cagccgagcc tcttgtaaat ccggactctg aaattgtggc acctacacca  15840
actcactttg tattgcattt cttgcataac aaatacgagt tcagtgttga acaatggaaa  15900
gataagttgc gtgttaataa cgatcttgcc gatggagaac ttctctacat ccaatggatt  15960
cgtcgtgaat acgacactga tcttcaattg gcgatgaccg gtattccagt actgaaacgc  16020
gcttaaggca tagtgccgtc tcattagaga cggctttatg tcgttttagt atgtaacaaa  16080
taggagctgg accatgattg aaattttatt gtcggtcaac tctaaaagag ctaaaccaag  16140
tgttttacct accgaactaa tagccggtga ttcaagtcta ggttattacg gtatagtaac  16200
ggctgccgat tttattggcg ctgaacaaat gaacgatgta catggttttt ctggtaatcc  16260
atatggaaca cgaataccgg atcaaacaga tgtagattgg ttaatgttct ctttaaatga  16320
cagacgactc ttggtctcta caaagactat ccgtcattca atgtccttta atcaattagt  16380
```

-continued

```
tttggctgtt aataacttca atactaattc atctaaagta aaagatattg actgtaagat  16440
agcttatctg tcaggcggcg ccagtggatc tccagctaac tcggagtggg gtcagttgat  16500
gtaccgtata tcggaaaatg atccaactgg aacattctgg gaaaatttaa gtaatgagga  16560
tcttggattt gtacatccaa gtaacctcgg tatttggaca tggacaccca ctaatggtaa  16620
cactgggtct cctaggttca aagtcttacg tggtggacct aatggcgtaa cagggtgggg  16680
gcagaacgca ccatctcaac ctaacgtagg ttatggttgg cgcccagtac tagagttaat  16740
ctagatacag aagctttccc ttcgggggaa gctttatgtc gtaaattaac cctaaaggta  16800
tgaacctttt gtttctttaa ggaaacggtc atggaactta ttttattccg cgatgattgg  16860
gagaagttcc caacagcaat agcggataca aaaacgtcaa ataaaacatt cttaaaatta  16920
gcagctcttt atagagatga gcttaaaata gcaaactgga aattcatttt agcattactc  16980
cagcctgatc ttcagggagt agatccctat gatccagatc tagatgatgc tacaaaaatg  17040
aagattgcct tggaatgtaa atacaatcct tggtattact tccgtgaagt tgcccgtgtc  17100
ccagcgacat ctggtaacgt cccaaaccct ttccgcgcta accgtggtaa cattgcactt  17160
ttctggtgtt tctttaacca cttagacttt ggtctgttac aaccacgaca gactggtaaa  17220
tcggtttcaa ctgacatctt gatgacgggt atgatgtata tctggggtga gaacaccacg  17280
atcaacctga tcactaaaga taataaactt cgaacagcga acattgaacg tctaaaggta  17340
atgcgagatc tattacctga ttacattcac tgggctaatc caaatgacgt agacaataac  17400
gagctgatga cgtgtattcg tttaggtaac cgttataaga ccgcagttgg tcgtaacgat  17460
aagattgctg ccgacaaact tggtcgtggt cttacagtac ctatcatgca gttcgacgaa  17520
tttgcgtaca ttaacttgat tgagatctct cttcctgtag ccctggcctc tggttcagcc  17580
gcccgtgccg aagccaagcg tcaaggtcaa ccatacggaa acatctttac aacaactgct  17640
ggcaacatta ccactcgcga tggtgcattt gcttacaagt tcatgacagg tggacatacc  17700
tggtctgaaa caatgttcga tctagtgaac caacgtatgg cagtgttggt aatggagaaa  17760
ggatccaagg ctgatcagaa acctatcatc tacggagctt ttaaccatag gcagttaggt  17820
cgtacagatg aatggttgtt ccaggaactt aaagagtcta gttcttttgg tgagatcgct  17880
gaccgagact tcttcaatat ctggactgtt ggtggtgaag gttctccatt atcacccgaa  17940
cataagaagc aactaaaatc atctgaacgt gaaccaattt ggaccgagat cacgccagat  18000
ggttacacca ttcgctggta tatccctaaa catgaagttg accagagaat ggctgaaggt  18060
cgctttatga tgggcatgga cccaagtgaa cttctaggat caggtaatga cgccactggt  18120
atggttatat tcgatgtgga gacacacgaa gtagtagcag ctggttgtta taatgaaacc  18180
tctgttcctg ttattgctgc attcgtcggt aatctattaa ttcgttatcc gacgattaca  18240
tgggtacctg aacgtaaatc gatgggcact gctctcattg acttcgttgt aatgcaactg  18300
cataaagctg ggatagatcc gttccgccga atctttaata gaatcgtaga tgaacacacg  18360
gtactagaat ctgagttccg tgatattcag actccgttgt ctcaacgacc tgcttcgttc  18420
tatgatcgat tcaaacgtta ctttggtttc aacacctcag gttccggtcg gtattctcgt  18480
aacagcctgt tccttgaagc attaccgagt tcaatggatt acggtagccg gagaatggcg  18540
gataagacgc tgattacaga actacttgct ttgacaatta agaatgggcg aattgaccac  18600
actcgtgata atcacgacga catggtaatt tccatgctgt tggcgcactg ggtatgtatt  18660
cgtggacaga acctttctta ttacggtatt aatccagcaa caattttctc ccgtgctgtt  18720
actcgtgacg tagagttaac tgctctggaa aaatatcgtg aagataaaga gaagcaaaac  18780
```

aaaggtgagt tcgaggactt gattgctcag ctaaaaggtg agacaaatcc attcgtaatt 18840
accaagcttg agatgcgcct tcgtaatctt tcgaagagta ttaacatgga agaaacaacc 18900
ggtgttggta tcgacgccat gttgaaacaa gtacgtgatg atcgtgttag acgtgtccgt 18960
acttctcgtt tccaacaaga acgtagtttc aattcacttg gattctatgg acggtaagtg 19020
acaacataaa agccttcccg ttggggaagg ctttatgccg ttaagctctt tgacctaaag 19080
aacattgttg ttcaagtcga cgtttctctt tcttaacatt cggtttagag ggacgtgtaa 19140
caattcggta gctatccaca cctgcacgaa tcaaaccacg gataattgga ttaaccttag 19200
atacttttag cgcctcatag aagatatggt ctatctcttt tcgagttacc ttaacttctg 19260
tctctttccc atctaccatc tggaagatag tgtatgtctc acaaagctta tcatgcaacg 19320
ctgctgcctg accatgctta cctaatcgag ggatcaacca acgtactggc cgtggaatag 19380
atgcaccatc tgttaggaaa catttattaa caactgcgta tttaccagag ccttcacttc 19440
caatgtcata ttgaaaggtc tccataatcc gccagtagtc atcacccaga ataacagatg 19500
catcatcgtc atactggata gacatcttgg cattaaactt agtatagcta ctcatttaca 19560
atctccgtta accacagagg attgggttaa cgtcttgccc agtattgcaa actatatcca 19620
agacctggat tacggggagc gttagttaca cctttctgac aggaaatgaa tcgccattta 19680
attggatcaa tatattcctc gaacttagca acgtcagtta cgtcatcgga agaacaatca 19740
atgtccatat caacaatcgt gcgatagaac tcactacaac gagtgatacc atctttaaat 19800
agtctttcac caccaatgat aaaaaccttc ttttcatttt gggataattc tagtacttcg 19860
tctaaagact taacatggat atatccctct cccttcaagt tatcactatc tgaagaaagg 19920
acatagttag tccgacctgg aagaggttta tttcctaacg attcccaagt cttccgcccc 19980
attacaacag catgccctaa agtcttttct ttaaaccatt taaagtcttc aggaatatgc 20040
catggaatac tcccattgat tccaataatg ccattcgtgg atacagcaaa gatcattgct 20100
agggtgggca tgattaactc acttactcgg agaatttaac gttaaaggca aagggcgtcc 20160
aatggaaagt atattccaca tcgaaagtgc cacggaaccc agcacactcc tcgtgtagat 20220
tagcgatgca atgactcaaa gcaatctgtt gtagaatact gaattgatta agagagaact 20280
caaactcttt tttactaatc gtggaagacg gatcaaagtc aggatgtcca tcaactgtcg 20340
atttatgtgc cagcgtacca cggaaaatag ctttattacc agtgggaagg acatcgataa 20400
aatattcggt aattacaaat cctttctctc caacttcctt aagatcctct agcagatatt 20460
gcgtgataag gaatagttgt ggcgggagtt cgagtgaagg gtgcttacca gtgatggtat 20520
caatgaggct agtgatttga ctgaaatgaa gtgaatgaac aacaccgtca ttatcaagaa 20580
tagagagttc atgcgaaatc atcgtttcgc tctcaccctc ggcttgatgt tcaaaaataa 20640
gaccttttgt gatcttatca aatttatcca tggtatctac aaacgggtaa ttaacagcgg 20700
tcatttctta actccattgg taacaacttt ttcaaagatc gcttcaaatt cttttttatg 20760
atgaagcctg taactcagaa tacgtttctt gtcatcccga ataaactcaa tatagtcacc 20820
tggacaaaca acagcgggac tatcgtcagt tcgaacttta aggatcccat gaagggccat 20880
cttacagtta cagtcaggac agatcattcc accttgtata ctaccatggc taatatgccg 20940
tccaacgata gccccttcgt taattccatt aacggtgcgg tccatgggat ggtcgccatt 21000
tttaaaccat tggtgagctt ctacgagtgg tagaatagct tgataataag gcatttgtat 21060
tctccagatt gaaataaata gcatatcctt ttccatctga gtagttcttc tttttaggtg 21120

-continued

```
ttgtatggta tgctgttaga agattttaac ttatttaaaa ctaaatgatc gtaaaaatac  21180
ttgcgtggtt ttagttatgt tagaattcat caacttacgt tttacgcaat aaacaactgg  21240
aaaaatagag atgattgaaa ctattatcaa actggatggc actgaacaac ccttcgataa  21300
cgagaaagca aatggctggg gcgagtgggc agcggcacgt ctgggcaaca aagttgactg  21360
gggtagtatc gtactaggtg ctgtaagcgg taagcccaaa aaggttacat ctcaggagtt  21420
ccagggttgg ctgatcgaag aatgtcttaa tcgtaagacc tggtcgtatt acctaatggc  21480
tggtcgtctg tacgcagtat ttctgcgtaa gaaaatctat ggactgggcg gtattccgac  21540
agtaaaacaa cttcatgcca aaatgcatga agatggagta atgatcaaac tggattataa  21600
tgatgatgaa tatcaggcta tccaggagat gattgatcat gatcttgatt tcaattcccc  21660
tcatttcgct ctccaccata tccgtggtaa gtattccctt cgtaatcgcg tgtctgggaa  21720
agagtatgaa actcagcagt ttacatacat gcggatggca atggctcttt ctgagaaaga  21780
acctaaagct gagcggctgg aacatgtgaa gaactattat gaattgttct ctcaaaaaca  21840
attgtcggcg ccgactccta actacgttaa ccttggtact gtactgcggg gctttgcttc  21900
ttgctgcctc ttcgcttctg gcgacaacgg tacttcgttg gctatcggag actacatcgc  21960
gaacatcatg acccagtcct ctgctggtat tggcgttaac atcatgtctc gttctgttgg  22020
agatcctgta cgtaacggtc tcattgttca ccaaggtaag aaaccttaca tcgacgtaat  22080
gggtaaggct gttcgagcta acctgcaaaa tggtcgtggt ggcgccgtaa ctagcttcta  22140
cagtctcttt gatccagaag ctgatatgat ttcccaactc cgtaaccctc gctctaccga  22200
agaccgtaag aatcgtgatc ttcactatgc agcaatgggt aacgttcttt tcgcagctaa  22260
agcagctaag aatgaaaagg tgttcgtatt taacccgtat actgctcctg acctgttcga  22320
agccttctac ggtaaagacc aagctaagtt caaagagctc tatgaaaagt atgaagctga  22380
tccgaacttt gctaagacct acatcgatgc acgggatctt ctaaaaaacgg ttcttaacga  22440
agcctatgaa accggtgttg cgtatactgc tcaaatcgat gaaatgaatc gccatacccc  22500
gttcaaagaa ccgattcata gttcgaacct ctgtatggaa attgctgaac cgacaaaacc  22560
ttactatgac atgcgtgacc tctattctga ggaagaccat ggtcgaggtg agattgctac  22620
ctgttcgctg gcggctattg ttgttgacaa tatcccagat gcagcaactt atcgtaaagc  22680
tgcttattat gcgctgaaga tgattgacta ctgtattctc aatgcagaat acgccttccc  22740
tcacctgggt ttcactgcta agcagcgtat gagcgctggt gtcggtatca tgggtcttgc  22800
tacccatatg gcccgtgcag gtctagcata ttcttccgaa gctggtaagc gtgaaatgca  22860
ctttgttgca gaacggcata tgtatcacct gatcgaggct tccctgcgta tctctaaaga  22920
acgtggtctt gctccatgga tgcataagac tctgtggcct gaaggttggc tgcctcttga  22980
tacctacaag cgaaatgtag atgaaatcgt acctggtggg tttgagaaca tttataactg  23040
ggagaaactc cgtaaggaaa ttattgctaa cggtggtatc ggtcactcgg tgctcgttgc  23100
atatatgcct ggtgaagcat cctctaaagc agtaggcggt gctaactcga tctatccggt  23160
tcgtcgtctt gttattaaca agtcggacaa taacaacctg attaactggg ctgcaccgtt  23220
tggtgatgat aaagcgtaca agtatgaact tgcttacgat attccaacta aggatatgat  23280
cgaagcttac gctatcttcc agaagtggac tgaccaaggt atttctgctg acctgtatcg  23340
tcggattatc ggcgacgaga agattagctc taacgaaatg cttcgcgact acttcttgca  23400
ggttaagctt ggtatgaaga ctcgatacta catgaacacc gagacttccg ctaatctgtc  23460
gcttgctgca ttagaatccg cgtttgaaaa taacgatggt tccaaaggtt gcgctggtgg  23520
```

agcttgtact ctgtaacgac atatcgccct ctcctaaagg ggagggcttt atgataacaa 23580
acattaacat cactttaata attagaagaa ttactaacgt tctatatcaa gtgtaagtaa 23640
tcttgatatt aacaaggaaa cgaaaatgac tgacaagctc cccaagaaaa tttttaacgt 23700
agaaaagact gactatgacg tacccgaaat tatccttggt caagaacctg gactcctaga 23760
ttctattcat acccacttcc ctgtaccatg gtctctctac aaacgtctac gtaagcttga 23820
ctgggacgaa ttggaattcg atttccaaca atgtcttatc gaatttgaaa catgtaataa 23880
atcgacttac gacatgatga tcaagaccct tgcatggcaa tgggaagctg actctgtagc 23940
tagtcgagcg attgtgaata ttcttggtcc ggtgatgacc gactctagga tctggacagg 24000
ttacgttcga atcaacgata acgaagacgt tcatgctctt acttattctg agattgtgag 24060
gggttcgttt aagaatcctc gcgttatcct cgatgagatc ctgcgtgttg aagaagcaca 24120
agaacgtatg gttgctgttg cccgtgtaat gggtgaagca catgacacgt ctcatgccta 24180
tgcattgaag caagtaccga ataaccagga gacttacaat aagatcttca tgttcttcat 24240
tgcactttat atgctggaac gtattcagtt catggcatcg tttgcagtga ctttcgctat 24300
ttgtaaaact ggcctgttcc aacagattgg tgaagcggtt aagaagatag cccaggatga 24360
attcgagatc catgcacaat atggccaaga agtaattaag gcactgttga agaccgaacg 24420
tggtatgact gcgtatgagc agtgcaaacc tcagatcatc gaactgttct gggaaatcat 24480
ccgtactgaa gttacctggg ttaaatacct gttctctgaa ggtcgtagcc ttgctggtgt 24540
taacgcacag aaacttttcc agtgggtact gtttaacggt aatgctgctg gtactttcct 24600
gaacatcatt cctgataccc tagagaaaca ttcggcagaa tatctggagc tgactggtgt 24660
tcctctggaa ttcccggaag ataaccctct gccattcatg gttgaatatc tcgatatctc 24720
tgcaacccaa gcctccccac aagaagccga gaaaggtgac tacatggtta accttcttga 24780
cacacgtggc gagaaagatg agtttgatgt ggacttcctg taatgaaaaa gatcgctctc 24840
gctgtaactc tgatgttccc tcttactacg atcgcagcgg gggagatcaa gtcttctaca 24900
actggtatcg taaagcaatc tgaatgtcaa ctgattgcta aagataatag catcgttggc 24960
gcgactgtcg gcggcacagc tggcgcagtt ggtggtgcaa tgctcggtcg tgctatcttt 25020
ggtaaatctg gtggttggat cggtggtctc gttggaggtg ctgctggcgg cgccgttgga 25080
aacgaaatgg gtgccataga gacattccaa tgcaagatga ttatcgaatc tgatggtaag 25140
caacatctaa tgcaaactat cgttaacaag aaaccagagg ttggtaaaac gatcactgtt 25200
cttgaaatgg tagatggtac ccgtgaagtc atgtaatcat actgccctcc ttcgggaggg 25260
ctttatgtta tgtcaattct aaaggtaaca accatgccta acattaacct tttgttgcga 25320
tatgcgatat ctctcgaagc ggaaatggat gatctaatca atcagttatt tgatgaggtc 25380
aataacccgc gtgccgatcg cccttacgat gtatgggtcg agccagattc tgataacggt 25440
atacagccac ccaccataac cgagcttatt aataatacgg acgatatgtg gacatattac 25500
aatcgttcag gtagatctaa tgtaaagagc tacaaatatg gtcctgattg gatgcttgtt 25560
gaattcggtg gagaagtgtt ttatctttat acactaaaga gcatcactga gatacaacta 25620
caggacatga aatactttgc agatggtggc gctggtctga atagctatat tagcaaggtt 25680
attcgtggcg ggtatgtagc taaaaacatt aataatgaaa ttattctaac cccaggcttt 25740
gaaatgtata agtctgaagg accaataatt ttcattcatg taagaaacaa aaaagaggaa 25800
aagaacatgt cttctctcac taccttaact ggttataaag ctgccatcga acaagctggc 25860

-continued attgatggtc ttagtcaacc tgcacgcaaa ctaatgcaaa tcggtctatc tcagatagat 25920
accgaacatg gttttactag cgtatctact gaaaactttg aagaaagtat cacagtagaa 25980
aatattgaag agcgtattgc cttcattagc aatgaagaat aacttaccca ctatgtaatg 26040
atatgtagag acgtcactcc tcgtttttac atagaccaca gctcgccgga gccagcaacc 26100
cttccagctg gcttctagga agtaagactc cctgttgtgg tcccctcctt tcagttggta 26160
agttgtatct ttctccttgt tgtgttgatg agcataatgc ctcccatcgg gaggctttat 26220
gttgaaaaat actgaagagc ctctatttat agagaagaaa tgcccggttg gtgaaattgg 26280
tagtacacaa gagacttaaa atctctcggc gaaagccgtg tcggttcgag tccgacaccg 26340
ggtaccaaat ttacggagtg tagcgcagtt ggtagcgcgc ctgctttggg agcaggatgt 26400
cgggagttcg agtctctcca ctccgaccat ttaaatatag agcccctctg tcatagaggg 26460
gttttatatt gtatcgagat aatagacatg aatatcgcaa caatgtttgt tttagcgatt 26520
cacgtggggt tgtttggaat tacatccaca gaagaatcga ctatccagtt tgaaaataaa 26580
gcacagtgta tttcgcgtct agatatttta gaaaacaagt accgtggata cgagatacta 26640
cgaacagaga atacgttgaa agttactaat cctgacgagt attctatttt tattttcaaa 26700
tgtctttaag agaaactatg gaacatcaag aacaaaaagc gctactaaaa gaaccattgc 26760
agaaactcta caatcttacg tttagtcccc gcttacgtaa tggagcgaaa gctcccgatt 26820
ggattcgcct tactgatgaa gtaaccctat tcccaaacgg attagatatt acaatcaacg 26880
ctattacacg ttgtatcaaa tgggaactta tcgaggagag tataagtaat attacttatg 26940
ttgaaaccat gttctttaat aaaggtctta aagcagttga aacctatctc aaacatacgg 27000
agtaaatatg aatcatctaa ccccaacaca gaacgctgta tatttcacat ttgttagtcc 27060
tgagtttatg aaactgactc ttgttgaatc ttttgtagct atccacaaga aacatccaga 27120
agtaaaacat tgcgttaaga aaaagattag tgataatgaa actcagttta tctttatctt 27180
caaagatgga actgacaatc taatcatcac acgtaagact gaaccctgtc ctgaactgga 27240
tagtccagta ggcgatagaa ttaagttgtc tggcgaagaa cttaaaaata ttcttaccaa 27300
acatggccgt cctaatgatg gtaactattt caagcactgg actgaccgtc catgatgtca 27360
taagagccct atgtatacta atatgtagat aatgaattag ggtctatagc tcagttggtt 27420
agagcaggcg actcataatc gcttggtcgc aggttcaagt cctgctggac ccaccaaatt 27480
aataaagcat aatgcctccc ctatttaagg gaggtattat gctgtctatt ataataaaat 27540
aaatatctga gccgcaaagg ttatcctatg atctaaaatg atttacttga gagcacactc 27600
atgtttgaat tactattatc atcaggttta ggcgatgaaa caccccttggt tggatttagt 27660
gaaattataa aattaggtga cctaccagta gcattggcag gtacgatgtc gtacgtagat 27720
ggaaatacgt tatatgttgg atccggacat catacggaag gacaatcagc agcaactgtt 27780
ttcagacggt tcactataaa cccatttgca gagataagcg caacagcatc tggtacattt 27840
ttaccgggtg tatcacttgg atttggtaca ttacataaaa ataactttat tgtttatggt 27900
ggtattactg gatggaacgc agcaggtgat gggggtacag gtacttctaa ctttatacaa 27960
cattttgata taagcacagg tagtcgcgtt gagcgttata gtggtcctgg tacattatgg 28020
ggaactgcgt cagcgtctga tggcaatgat cttattatgt gtgttaatcc agttggtaca 28080
aacgccatgc gattaaaacc atcgactaag aactggctcg gcggtcaaga ctatagcggt 28140
ggacctaggt caggtcaaca attattttat tataatggtt atttctacca ttttggtggc 28200
tgggataata ctaagaacat accaaactta gaagtctata gatacaatgt tactacactt 28260

-continued

```
atatgggaac taacaccatg gctaataata cctgctgaca aagcaacaat atggcaaggt  28320
aatggttatg tagatgggga atattttaat taccttaatg cagttgatgt cggcggtgta  28380
actaaaatgt ttgcacagcg ttttaatatt aggcgccgga aatgggctga accatttgaa  28440
ctaggtattg gattccttaa tatttcatct atagccaaag gtccagataa tagcatgatc  28500
attgcaggtg gatctaaaat gccagttggt ggtggagcat atatgttaaa aagccaattg  28560
ttatcgggta tctatcaggt aaaactagca ccattagcca ttgattaaaa taataatatt  28620
tataataagg ttaactacac gttatttaca taatgtcata aaaaataaat aatactcaga  28680
ttgtaataat atgtagtgaa atactgtaat tcagttactt gtgatttttc tacaagaaag  28740
aagttgttag taattcttcc gcgatagctc agtcggtaga gcaagcgact ggatagtttt  28800
cttggtaagt acccgagcgg tagcaggggg cggactgtta atccgttggc gaaagcccat  28860
cgtaggttcg aatcctacct taccagccaa tttcaaagag tagctccggc tactctttat  28920
tccgtcacat agatcgaact agcgatctat ttatatatcc taggttcgat atgaaagaga  28980
aaataattaa cggctatagg gcattatatt tacccgaaca tcgtcaagcc atagctaacc  29040
ctaaaatgtt tggatgggtt tacgaacatc gagtggttgg agaagacaca ttaggtagac  29100
cactttacga tgacgaggaa gttcatcatc tggatgagaa taagcttaac aaccatccag  29160
agaacttatt gattctccct cagtcacaac acatgaagtt acatggttgg atgaaacggc  29220
tcggtattga tcctaggaac tatccaacta agctttgtgc tggctgtggt attgtcatta  29280
gtcaccgact gataacattc tgtagccccg agtgttcagc caaaggtcgt cgtaaggtgg  29340
atcgaccatc caaagaacaa cttgccctcg atgttacatt gctatcactt gtaaaaatag  29400
gagagaagta tggtgtatcc gataacgcta ttcgtaaatg gtgccgagca tacaagatca  29460
atattccggc taggtttatt agggtcggtg ctaatggggg tattagcacc ttggtcccca  29520
cacaataaaa aaaaaatata ctgggtccct ggttcgagtc caggtcgcgg agccaaattc  29580
aattgagtag ccattggcta ctcttttatg ccgttagtgg ttatcttatg aatcattaat  29640
actaactgag agcacgcaca tgttcgagat attactcagt tctggtgcaa tggagagagc  29700
tccatatgta cccttttata tgcgaaccaa gaaggtagct gaccttccag tgggtattgc  29760
aggtccaatc gttgcaatgg ataacgataa cttatatgta gttggcggtc aagattctac  29820
tggggctatc cgctctgcaa ctgaaatatt taaactatct gatatgtcga tgactgttgg  29880
tggaaaccac gctagaacta tttccatcaa tggagcaact atttataata atagaatgct  29940
aataccaggc ggccaatttt ctactaattt agctggtctt ttatcaacga caggtgcatt  30000
gaatttacct gggttaacta gtgcagttga gttaacggga cgtttaccac agacgtcgta  30060
tgggaatgct gtatgtcagc atagagggga catatatgtt ttacccagtt ataaagccgg  30120
attctataaa ttaaatccac ttactggcgc gactcttgaa aattatccag gattaccaag  30180
ttttgatgat gtcggtggtg ggatattagc aggtatgtca atttttggac atggagatta  30240
tatctattgt ttgggtggat gggcaaataa tcagaaccta agaatacatc gatttaatct  30300
gatttccaaa caatgggaat tatggcagac aatggaccct gcgtatcacc atgtatggca  30360
tggtggtttt attgatgagg aaggttacta taactatacc ggctggggta acctcggtca  30420
aggtaacaaa atatacctcc atcgttataa tccagtcaaa aaatcttggg cgcgctcgtc  30480
ggataccgga ttatcatatc gaaacatgtc gggtgttatt ggactaaaag atgatattta  30540
tattgtcggt ggtacatctg aaccattctc tactaattgg actagcacaa caaataaaat  30600
```

```
aaaagaaatc tacaaggtat ctcgtgctcc cgaaaactgg gaacctgtcc cagagaaaac  30660
atgggtaaga aaagcagaca tgcctggcgg tagggtgcaa gcagccgtag caagtactta  30720
ttcagaactg ttcgttatgt ttggtagtga tggtgcagta aagaatacaa acttgattta  30780
cgatgtattt actgatacgt ggaaagaagg accagttaaa ccatccgcac gttatcaatc  30840
ggcagccaca actgtcgccg accagattct tattttctct ggtagtaact attctccaga  30900
cctgtattct tataaccatc tagaagacaa gtggagtgac agtatatctg aaccaaacgc  30960
acccacatgg cggacaaacc actgcatgac atcttttggt agatatgcct atctttttgg  31020
tgatgatgga cgtaccgata gagctattta tcgttatagt ttagatgctg cggctggaag  31080
caaatggtat aaattacctc aacttgctcc agaaggattg gctagagcgg caatggttat  31140
tgtgaataat aaactttaca ttgcctgtgg ttggattagt tccaacacca tgactaaaac  31200
cattcgtgtt cttgatttgg tcgctggtac atggtctacc atatctaacg tacccgccag  31260
ctttgttgct cgtgtaggtt gtctattagc tgcgattgat aataaacttt acataggtgg  31320
tggcgctagt ccaagcactg gattgaatga tttctgggaa tatgatacag tcagtggtgc  31380
gtggacaaga ctccccgaca ttcctataaa cggtgatgct gctatgatgg ctgcatgtgc  31440
tgatacctta tatatcgctg gcggtaatag gccaaacggt gtgaaaggta atgagctcta  31500
cgcatatagg ccataaaaga aataccggta tggtaatact atgtaagact atatcggatt  31560
tcggagagat aggaaaattg gtaaccccag ctgactgtaa atcagccgtc cgtatcgggc  31620
attactggtt cgagtccagt cctctccacc aatgcgtcat agtgctctcc cttcggggag  31680
agctttatgt caactattac aaaaggaaat agcatgtcag cattaagttt gattaaacgt  31740
tggtcgcccg cagtacctaa gattctattg agtccacagg acacggtcaa tgagactaag  31800
atggtcttag ataacgagag tggagaatat ataaagttta atgacttctt gatcctcctt  31860
caaaacggcg tgtacctaga agccaccaaa gagatgcacg agactttgtt agatggtaaa  31920
gcacagcaaa gtctcattgc tcgactcagt cgcatgggtt atgaagactt tgatcaagta  31980
atgaaagtct tagaagaaca gcgtgattct gtacttaaga agaaagaata tgaaatttgg  32040
caagaaggac atcgcgctac tggtgaatct agtatagcca gctttgtagg taaagctgaa  32100
ggttattctt tcttagatgc tgtagacaac tacatgaaga cagctagtgc ggaagttaag  32160
aaatgtttcc gtgctgaact agatgcagct tatatttggg gctgtcgttt gtttgacaat  32220
gaagccgacg cacgtaaatc tttcgggtga cttatggttc ctaatctttc tataaaagca  32280
attcatgctc gtcaaactcc agaacaactt gctggcaacc gagagaaaac tcttgaggcc  32340
ctggctaagt tcaaccaggc tcaacgtaaa cttgaagagc attgcaaacg caatggactt  32400
gaagtaccaa ttatggtttg ttaataatga ctgatgacaa aaaagaaaaa cagcataaag  32460
ggcgacaagc cctcaatgta gttggtgaaa tcattggcgc tgtgttcgaa gctatttggt  32520
gggtcttgac ctgcccgttc cgtttaatcg gtgtactctg tacgcttgat taaaataata  32580
cctagttgat tacaatatgt aacgaacaaa gttacttcat cgaaagctac ctgtagaaac  32640
atctcacatt aggtccagca gactgtagta tttcgatgtg accatttata gcacccggaa  32700
accaaaggct aatagtggca agccgatgat tgagggaagt cgaatgggcc gcccataccg  32760
aaaggtgtct cttcagttcc actaactgtc acctcacgat ggacattacg atcaaaaaga  32820
gactggtttt aatgtccgat atacgactct ccgataagga gagttttatg tcgttttata  32880
ctgggctata taacagtatg tcaaaggatg taaagaggta atcatgacag ctttcatgcc  32940
atgtcatact gaggctgata tagacctagc ttcaagaaat aaaatgttgt cagagctact  33000
```

```
tatagaagaa ttcccaaata cagaagggat gtcaacaaaa gcagcagaag actatctacg  33060
gtctaaggtc atagataaat tcaatattaa ccatcctgaa tatcaagcac atgtaagcta  33120
cgattgtatt acacgtggag atttcattac agcttgggta acccaccggc tagcccttgt  33180
aaaacttgct ataactacag aggaacaaaa atgtacgaaa ccgctccgtt ccaagacgat  33240
ggacttggcg cactcattac ggaaattttt agtcgggacc tgaataagaa attccaggaa  33300
tggtatcgac caattatgga tgacccgaat attgaaaaag taccagtttg tcgaaatggt  33360
caaattgtaa aagagcctgt caatttcgtt gctcttctta aagaatggtt agctaatcaa  33420
gattaaaaac ataaagcctc ccttcgggga ggttatatgt tatgattttg acgaaaggta  33480
atcgttatgt ttgaagcatt gttaggaatt ggggaatata aaagtaagca aggttgggtt  33540
cagctacagg gacccgacgt cggaagaaac cagtcaacct ctgttgtcgt aggagacaaa  33600
ctttatatct tcggtggtag acgtgctacc actaacgcgt tcaatactgt atccgtctat  33660
gatttcttaa cagacgaatg gaaagaacta ccggcaggag caaacgttaa tttacgtgca  33720
gctggtggtt tagttgataa caagttttat gtattcggtg gatacactgg ttctgctgat  33780
acaaacacga tgattgagtt tacgattgat ggtgagacaa ttacacctgt aacacgctct  33840
aatggtggat tggccgtacg taacagtcat tgcatgtcag ctattgataa taaggtgtac  33900
ctatttggtg gtaacggtgc acaaggtatt atgtatgaat ttaagagcta taataccgat  33960
aacttcacag tagctaactt gacaccacct tatcaaattc gttatgcgac cttaacaagt  34020
catggtcgac gcctctacac gttaggtggc tatgaaacag ctaatacgtc agttacgtca  34080
ttcagaagtt ataatgtcga caacaacaca tggactgccc acaagaatgg tcttgtaaat  34140
aggaacagac attcagccgt agctcttaat aataagatct atgtattcgg tgggcaatct  34200
ggtacaagtt ctactcctaa cactattaat aacgatcata ttttcagtgt ttacgatatt  34260
gaaactgaca catggtcaaa tataattctt cctcctggta agatgccgcc tactcggttc  34320
tacgccaata tggaagttta taacggtaag atttatttat ctggcggtta tacaaatggt  34380
gtctatcata atgacctgtg ggtttacgat ccagaaaacc cgtgaaaaga aatactggta  34440
tagtgattat atgtaagaat tagcgttaag cgctatttta catgggagca taggcgaatt  34500
ggtatagcca gctggtttag gtccagccgt cgtaaggcac tgtgggttcg agtccctctg  34560
ctcctaccat tttaataagg cctgccgaaa ggcgggcttt atgttgcaaa ttgtatgatt  34620
tagtcttttg gtaagtacct ataatgggga ggccttagac ggaaagggag taggaacgtg  34680
aagttctata cagccacccc tctgtaaaca gtcacttttc aatggataaa attatgttcg  34740
aatcattatt gtctgcactc attaaggcta caggaaataa actaccgggt ccatctacct  34800
ttgaacaagg tgattcgaca cttggtctgt atggtgagtt gacaagcgac aagtttataa  34860
cttaccctca gttaagaaca cttgttgagc ttgactccat tggtactata aatacagatg  34920
ctggttggat taaagtatct agaaataatg ttattcttta ttattcgaag acagctattc  34980
tccattccat tagtccaaac caacttgacg aggctggttt aatagatggt agtaaagtta  35040
ttgtaatcga tgggaatatg tttaaagttc gtctaatgaa tgctggagta aatccttatt  35100
cggatatcac tactcaaggt aatgaaggtt ctgaattgtg ggatattttt ggcaatgtta  35160
caactaaagg aagttgggca aagtacacag atgaacaact tataggcgcc ggaaacggaa  35220
gttataactg ggcggctaat agaaatacca atagtaatta cctacagttt tcaccatcga  35280
caactcatcc tcaggcaaag aatggccttt atatttacga tggtcatccg ccaacagaag  35340
```

-continued

```
ctactagtta tcgtggatgg cgaccggtac ttgaatatat tccgccaaag gaacttaaag  35400
gtattacctc tgtattgtcg actgtaaatc caccgccgca acatgggatg ccagtactcg  35460
cgtatgattt ggataacaac gatatttaca tggcctgtgg atatacaaca ggacctacta  35520
ctttcatgtc cgacttacat cggttagacc gagatactaa aacatggacc aagttaccat  35580
ctacagttcc gttccaaggc gagacaacta caaccaatat ggtttacaat aatggtaagt  35640
tgattttgca tggtaaccca ttgtctactg gtccgactat ttatatttac acgatagcta  35700
cagacacatg ggaaactaaa aagctagctg ctattccagg tttagtcgat gcatattaca  35760
tcgaacgtac agctagtata gttaaagacg atatactgta cattgttggt ggtttctctg  35820
ggcgcagtga taaaatccat aagaacatta taacagttaa ccttacgaca tatgaaatcg  35880
gcatgattgc tgatgttcta ccaattgaat tatggcatca taatttagga tttaacgata  35940
atggtgaatt agttatcgtt gcatctcaag gtagattaac aataggtggg acaaacatct  36000
cgccaacgga ctacgtaaag attagttctg attttagtac aactgaagtc attcctttga  36060
atgcgcctgc caacaaatat tcgacgtata gaggaatcat attcggtaat aacatctatg  36120
tgacgaataa ctccggaaca cgattagctt tggtgcaact taataaagag ccagaactaa  36180
tcggagatac tttcccagct atttcttcgt atgaagagat gttagttgta tccgatggag  36240
tctatcgatt tggtggtgat gtatccaaaa caacacccgt agtcgaatac gaaataaaat  36300
aatacttcgt gtctaatagt atacgagagt attcagtgat gtagattcca gtactcaatt  36360
caaatttcgc cgttatagct cagcaggtag agcaactgac ttgtaatcag taggtccggg  36420
gttcgattcc tcgtggcggc accagtttaa aaattaggct ccatagttca gttggttaga  36480
acatccgcct gtcacgcgga aggtcgccgg ttcgagtccg gctggagtcg ccattcgaaa  36540
ggacaagtct atgaaacatt aaatagactt aggtctattc caattggagg tatagtctcc  36600
agaggaacta aacctctcat ctatccctcc tcctaaatgt gctctggtaa atgtactgtt  36660
taagtacacc tagctaaaag agtgagcaca gatacagccg taaaggtagc cgaaaggcta  36720
cctttattcc gtcaactaca aatgtaattt actcaagggc ttcactatga atgacaatat  36780
cgttaacgca cacattaact acatcaatat gttaatcgag gattctcgtc agattaatgc  36840
aatcgcaatt aatcgtggac tacttcgtat taaacaagat gcggtaatga tccgtgaaca  36900
tcaaaccgta ggattccaca cgggtccttt gttgaaccct gatcaattca ttattgattg  36960
gtacgtagct aatgcagact caacattggt gattccgtat agttccgaag atggagctaa  37020
aatcactttg gaagtagcgc gacgtatgcc agaagtaaac ccacaaagga acttcgatca  37080
tatccgttcg ctctcggttc gacctgccga tactatcgag ttctctagta aacaagaaca  37140
catcaaatac gtgatcttgc agaatgctag caacgtgttt acttacggta ccatcaagaa  37200
gaaatcattt tacaactggg ttgctaaatg gtttgctaaa gatgtttatg taattctcgt  37260
taactaaagg aaaatacaat gttgaataaa aaaaagaaac acgtaacgta tttctcgcta  37320
ttactaatgt taaggtaatg agattgctcg tgtagggatt gggtgtcata acttcaatcc  37380
cttctcctgt gttgattatg gtgacaaaac agtaaactgg ggaaacaaat atgagtaaaa  37440
ctctagttcg tgcaaaactt atcacagaag ctgatacctg gatgtcttct gattggggga  37500
gtggatttat agctagtcgg ttcgttaaga cgggtggtga taccattacc cctaatgaat  37560
tcgagtctct gatcactgac tttgaagttg gcaatatgct cgttgtatgg cctaacggat  37620
tgagaacttc ttataaaaca gaaagctttg ataagaactt tacacacgtg aaggacgagt  37680
attatcaaac tgatttgcgt ccattgttct atacagggag taaacagtaa tggctttcgc  37740
```

-continued

```
atgttgtaat gccgtctata tgaactacat caatcgtgat ggtagtttta acatcgatgt  37800
attaagaaag atatttggcg ttgtagacga tatcgttcag aaagaacgta cagatgagtt  37860
agctgtatgg catgctaaga aacatgacgt acctgtagct aaggctacgt ttgtaatcat  37920
aggtggaatt gagcaagaac tctgtacctg tgattgtcat aagcatgacg gtttgaacgt  37980
tttacattga ggtgattatg agtacactgg tacataaata cgttgcgttc acgcgaactt  38040
ttaaactcac tgaaatcaag atggataagg gtgatcgtat ggttcgtgtt ggtggtggtt  38100
tcaataaagg taaagggttt tttagagtag acttaggtgc acttggctac cgtataactc  38160
gccgaaatag ataacataaa agccttcccc actgatgaag gctttgtttc gtcattagag  38220
atcgttagaa ctcccactgc actgaacaac cccgattacg ctcgtcttgc tcgtggtgtt  38280
atgacaaaga cagttgctac cgatacaaca aatagagtgt tgtggccact gtttaaatat  38340
agagggcgag tttaatgaag attacgtttt atgggactgg agttgcttgt aaggaatatc  38400
gtgtttatgc atcagccgaa atcactgatc ttaatacact aacgccaatt gcaaccattc  38460
cagctactcc gccttaccgt aactatcatg aagttgattt caatgccata aagaacgttc  38520
agtactatgt tgttattagg caggtattag aagaaggttt attcttagat accggtcata  38580
ctacctgtat agaacgtaat actggtgcct tgtctaataa tgcggatatg ggcgtagata  38640
ggctacaaag gggtgattct acattgggct atttcggtac agtccctatg gaagacttac  38700
ctggactaac agaactcgta gcagcatata gctctctcag gagtgatgac ctcaagggta  38760
ctactaaacc tccttatgga aagtttatgg ttaacaatga ggtatatttc attccatcca  38820
gcgtacataa ctggttgtat ccaaatgaaa tatatgcagc tgggtttgca gctatcgagg  38880
gaacacttga cggcacttat ataactccgc agatcaaaag tgacagtcga tttaaatgtc  38940
tagttgaaca aggacgcgat attatctatc aaggacatac ctaccgtcca ttcattatgg  39000
atcaatggat gtttgataat ctgttcactc cgatgaacaa taataaacag ttgcggacag  39060
catctaactt acaagttaaa tatgatacaa taagtaagaa ggatgcttat acagcagttg  39120
cgctttctaa taacaaggca tctaaatacg ttaggcaaaa tacagtcggg gcaactattc  39180
tttggtacga ccactggcta ttgtctaata ttgatatctg ctggaagctg atggaataaa  39240
aaaaaaataa ggcataagcc ctctccttcg ggagagggct atatgtcgtc ttataccaac  39300
tcgactacat cgtaatcgtg atgtttacct ttaccggtcc accaggcaaa tttaccgtcc  39360
ttgttgatcc gataaccatc tctttcggtc agaggattca cagccagata ggtagcgaat  39420
tggggatggt cgttatagac tggaaaacga tcgataagga gtttggaaaa tgggagaatg  39480
tcgcgcatcg acttatacag cggtgcggtg atagcgcggt tatattctgt caggatgcga  39540
ttgacctcaa tgaatacagg atctttttca tcgatcaacc atggcgtttc accttcattc  39600
agaaggagct gctcaccata gatcggtata gcaacttcat aatcctttac gaatgcgaga  39660
ccacctttat taccggttac ttcggtgtga atgatattac cgttatcatc acgcatttgt  39720
acacgccagg tcataccgag cagttttgca gcgtgaacca tcctttcaac aaaggttttg  39780
aaagtgaaga gttcttttgc aatagcgatt tcatgttgag acattttaat ttccttttaa  39840
aaaagttgga taacagaaat gatgacaacg acactgatga acgaccacat caatccacgt  39900
tgtagcttat ctttacgcat atcacgttga cgacgtttaa gccgttcttc agggaggttg  39960
cgcattatat ttacctattt acgatattaa ctgggcgtgg tttagagtta accgaaatct  40020
ttttcactgc tcgactagca acccaatgac gtgcacgatc actaaggtcg ttgtcacgtg  40080
```

tgagtatatt agattcagca ttccagtggt caaaccgcct acccaaaacg ggataatgtg 40140
cttgcgctag aaccatacat tccaacggac tcagtttgtt ctcagccgag gtgaatacat 40200
tattcagcag ttcaaccgct acagcgcatc caaagatgat tggtttccgt gcaggcgtgg 40260
aataataatt gctcctaaac atgtcatggg ttgattcgaa cacatgaaga acattatcct 40320
catcgatgag gatgtattcg gcattaggcg taagcaggtg ttggaaattc tttgcggtct 40380
ctgctagact atgtacatca tctcctgtct ccaagaaatt cagccagcaa tgacgatgtt 40440
ccgtatctcc aaccattgta aatgctttta tagctcgacc ccagacttta gcttcccatt 40500
tgttctcaga agcaagatag atcttggact tgtcaagttc cacgtagtat ggttgtggtg 40560
taccatcctc tccagtgata tcgctctggg tgatcgtagt aactcgatcg accaaaagat 40620
ccttaccatc ccatatgaca atagtcattc tttatattct cctgtttaca agctgagacg 40680
gaataaaacc cgctccgttg aggagcgggc tattcgttag attaccttac cagaaagctg 40740
gccagctaag gcaccgatta cgggtcggca cccatctggt taggtaacgc cactcgggga 40800 taccccctctc aactggaggt agtaaccgtc gtaacttcag atataaagac ggccaagtca 40860
atatacctgc ttcggcttga tcctttggca tggatcgctg ttagtctctc cgatcttatg 40920
cggagagagc ccacttacac cgaaagctag tgggaataag gtgaggtcac tgcggcaccc 40980
taatatggcg acggggagcc ttaggggaga tgatccgggt gacctctgtt ctgttgggac 41040
attagtcctc gtatatcatt acaactcaag tattctttta cgagagttta acttctacgt 41100
caactgactc aagaccagcc ccgtttcttt tattagatcc atgtgctagc aggtaacgag 41160
accaggtctc cgcttgtact cggtcaaact taaagtagat atgctgcatg atcatcttac 41220
tcaggtcagc gatttctttc gacaccatat caaagaacag gtctttgtcc attacatcag 41280
catcataacg agccagctca acgttgcaat actgtgcttt cacttcatca tagaactcaa 41340
caacaggttc ttgatgaaag taatggactt tgttatcttt gatttcgata ccatggagag 41400
taatctcgat gtggttgcta tgatagaaat gttcacgcat agctttatta aactcttcca 41460
ccatcttatc cagatggata cctctaataa cctctttggc agtgaataga taattaccat 41520
ttggatcaac gtattgttcg cgcgcccaaa gacagcacag accaatagga atgatctcag 41580
tggggatacg tagatcactg agctgcatcg agttgctcct tctttgcatg gatggatttg 41640
gttatgatag tacgtcgttc gcttgctgca ttggacatta ttgtaatttg ttcttgcatt 41700
tgagtaaaca gcaaaagttc caacatggtg agcagcatat gctcaatcca gagacgtaca 41760
cacaccttgt tcatagggc agtgtaattg agaggctgga cgaccttagt aagtgcgcca 41820
gtcagcgggc aggtaaagca gatatgtaga ttctcgctat cgctatcttc tgcccagtga 41880
acatcttctc cctcgccatg taccatattc gttacatgga caaccggctg atgctcaaat 41940
gcttcgggat gaggagtcgt gcctttctcc gcgcattgat caagatagat atcgcgaatg 42000
acagccgtaa gctcagctgg ctcaagagac ggcataaaag ggaatttaag agttactgcc 42060
atttgaaggt tcctattgac gagagacaaa ataaaccccct cccccgatca aggggaggga 42120
gctcaaggtt ggttgtgaca ctagtcacag ggatcagccg atggaagacc cctaaaggtg 42180
atgggactct aacccattgt gtcgatcgct ggatttcagc ccagcttaac caaattgtaa 42240
aagagctatc gtaaaggatc aggaaacgca tatgatagtg cgtaaccttt aactaaacga 42300
ttacctccct aggtggaggt tcgacctttg tccaatctaa agttagagga gtagctatct 42360
cttccttcat tttgaactca acgatagtac gttgtccaaa gtgcttaaca cctaacatgt 42420
acccatcgat ggcaacttcg tattgtctac ataatttacg gatgtataac tcagtgtcag 42480

```
tttcaacacg aggatcttcc gctgtagaac gatgttgatg atcccagaaa atacagaact  42540
ctagtttctg ccagttactg aattctgggt tataggagaa ttgatgtaga tgggtcgcct  42600
catgttcctc tccaacatag aacattagac tatcagtggg ctctctagtc aactcactga  42660
agtcgacttt ttgcccacct ttagtgagat cgacaacaat gagttgagaa gccattatgc  42720
gctccgtcgg ctatcggtca gagaacggat ggttctactg tccgcctcat tacgattttt  42780
attccgcgtg cgttcaacta cacggaatac atttacatgt tgttcatcaa cttcataatt  42840
ctcaaacagt tcaccaaagt tgttggtcaa cgaatctacg atcagtcgtt tggcatctac  42900
ctcattgatg tagtgataga gaataacgcc acgatgatac aggaacagag gatagtcctg  42960
accattgatt cgaacttcag ctgcaaagcc tccgtaagac atggtgtctg aattgatgtc  43020
ttcgcgatat acatccaact gcacgttatt gatcgtgtgc atttggatca tgtcgtttcc  43080
atgaccacca aagaaggtgg gacgcttacg accagttaca acatcttgga tagattccat  43140
cagtcgtgat acgtctgtaa cgatctcgat tacatcgcac agtttgttga ttgcttcgag  43200
gaaacgagct ttcatttcat cgacctcgaa actggaccat gcccgagttt cgtggttgag  43260
aatgttaacg ccaaaccagg cataaccgtt gttatgtttt acctttacgc acagatgcgg  43320
tacatcatcc aaaccagact gatgattcaa cgtataatca ctgatgcgtt tcaggaccag  43380
ttgtacgaag ggaagattga tgatctttgt cgacatggag ctattcctat taattcttaa  43440
aagagattag aggctacata agcactcact agattatgta gcctcagtac attttaatga  43500
cgagtgaagc tttgattcaa gcatcgaccc ataggggaat cgatggtgaa gttttccatg  43560
atctcgattg cttcatcaat cgacttgaac tcagctacct cggtgatagt gaaaccccga  43620
catttcagga tatcttcagc ttgttcagta acgaagctct gaagaagctt gttcgaacgg  43680
aaatggtgag agtgttcgat cttaccaatg tagtacatga acttggtcag tacttcatat  43740
tccgtggtat tattattacg ggttttagtc aggaaataat ccgccgactt atcatggcgg  43800
atgacgaaca cccgaccatt ggaagattta cgtggcgcag ttcgttgcag aagttgatcc  43860
ctttgatcca actcttctcg cagttgttcc acattgatct ccggtttagt acagaaccaa  43920
agatccagtt tttggccagc ctttactgct tcatcaatag caaccggcat gtttgccata  43980
cttccagaac ggaagcgttg cattacagca gaaaatgacg gagactccgc aagccatacg  44040
tccccagtat cgcgggtgac caaagcatac caaccctttt taactttagg tggggttgag  44100
gtattggtga agtcagccat gtatttcatg atcaggcggc gagtattctc gtacgctgcg  44160
gtcttggaat cattagtgta catcaggtac tcctcttaga atttgtattt tctatttaat  44220
tgagaaaagc ggtgggtttt ccccaccgca atatatcgtc aaacgatatc tttcgggata  44280
gactcgatga aggctttaac gtcattgcgg ttttctgcaa acagagcttg cagatcacaa  44340
ccggcaattg aacggaacac aataccttta tctacttgag tagacgggaa catcagctcg  44400
atataatcac gaacttctgc atcctccagc agaccgatct cccattgatg atcaacacgg  44460
cccttacgaa ccaatgctgg atcaaggtgc tctggatggt tggtagttag aagaatcagc  44520
gatccatcca acggaacaac accatcaagg gcattcaaca ggccagagag tgttaggcca  44580
cccatgcgag tatcttcttc acctccatta gcacgacggt tatgaagttc ccatatgcga  44640
agcataattg ggtcatcggc aatgtattta gaaaggggtt cttccggcac cggtgcatca  44700
aagctgtttc caatgacatc tcggtattgg cgagattcag ttgggttatg ttgctgatac  44760
ccaacactga aatcttcacc gggtatatcc catatacaca tgggtccgcc gccattatct  44820
```

```
atcactcgat agttagtcaa ccccatctga gtgataaggc tatccaactc atcttcctcg  44880
ccagctgtca gtttcttaag cgaacgattc tggactgcct tattggtatc gaagtcctcg  44940
atcatcagaa cactaccaga aggcatagac gtaaccgctt tacgaagcag ttcatcggag  45000
atactggcta aagacaacca ataaatattc ttattaaaag ccgaagcgat tgccttaccg  45060
atagatgtct taccagtgcc aggggggacct gaaagcatag cgcacatttt gtacggcatg  45120
ccacgggact cataccactc ccgtccagag aagaactctt caatcttacc aatgatctcc  45180
gctttttgtt tgcggttcat gataactgtg ttcagcgcgc gtttagtaat cgggatagaa  45240
tcaccccaac gcaagccttc ccatggaatg acgcagactt ctttatcatc tcccttaaca  45300
cggaattcct ctacaagatc taacagtagt tgagtgttcc tagtcaagcc gtggatctca  45360
atctggaatt tttccatatg agtaccagag ctatccagct tagagcgatt gaaccagaag  45420
aagcgccctt tgtagaagaa gaaatgggta ccaaaaccag cgccgatatc ggtgctagga  45480
gagggactac cattccacat agagttcaac gatagcttcc gactgaacct ggcgataggt  45540
tgttgtttga accacttcat gaaggcgata cattgttctt cattagggcc atgtccacca  45600
ttgttcatta tcagagatgt gacaacctga ttccgaattg cgttgaacat tttcttaggt  45660
aaacttcgcg ccatcataag cacccatcca cccaaaccaa caccgactaa agatgcgaat  45720
gtcggattga tcgacatgat ctctttgtac caggacataa actcctgaat catttctttt  45780
ccctcacata gctgaagttt ccacgcgtgt aggtattttg gatcggatgc ttctcgataa  45840
tctcatggtt ggccatcgaa agcatgtttt cagtgagtgc gggaatatat tccccaccga  45900
tcatgtaacc gaggttcttc ctttcttcat cgccaatgtg acgttgatac aaaggttgct  45960
cataggtcac aatgaataga ccagtataac acttgaagat gataaagcat tgtccgcgga  46020
ggaacttata acgccattgc tgctttttaa ttttctcaat agggaaccgg tattctttac  46080
caccttcacg ggaaatacga cgaagctcac ctgcacattt ctgtgcccag gatccttcac  46140
cgacgacata gatttcttcg atcaaatcgt cgtaaccggg acggaactca gcctttctcc  46200
ctcgggcatt cttgtaaatt ttgtacgact gaacttcagg accgaaccag aatccttcag  46260
tgaagtttac gacgtgtggt ggacgataca cattacgtgc gatttttaca tccaccttaa  46320
cgtcgccatt aagggtgaaa tcttcgatat atgccagacg acgcatcagt tgatgatacg  46380
ggtaaagctt ttgcgtttgt tctcccggca aatgaaaacg aagaagatgt ggttccacgt  46440
tatcggaaat acgcatccga tggttcttgg tgagttcact cagattgaat gacttaattt  46500
cctcacgcgc agctcgcgct acatatttcg catatttatt ttcacggtca tcaacgtaaa  46560
tgttcatgac agctgtgaca ctttcattga agttcattgc attttccttt tggttaagct  46620
taacggcata aaagtaatat agacctctaa acggttagaa tagaggtcta ctttttctag  46680
aacttcagtt catgttccct ggctttgaat accagaggac gtgcacgatc ctgaacactg  46740
accacaaatt gatcagtccc aggaatctga ccgagcagag ttaggggttc atccttttct  46800
gcacagagat aagaagtccg ccctttcaag gctgaagctt caattcgttc actagcacga  46860
acagtaacac gataagtcat ttcattcact caaagtcaat tacacgccaa cgatcatacc  46920
cgcacgcagc gagcaaaccg acacgctcca ttgcaggcac atagcccgac agtttgacgg  46980
tcttcaattc tccggtttcc atcccatgat acaacgattt cgcaatagca gtgtccagat  47040
accactgcgt caacggaatc gaagtattat aggtataacc gcagaacaca tcataaacgt  47100
gatgatgttc attaatgaac aggcagttac cttgagcgcc gttatcgtga tgggtttctt  47160
ggatcaacgc gcggatctca ctcagatggc cggaagtaaa gctatcgtaa aaccggccaa  47220
```

```
catcatcatc ccaaagcaga tcacgaatac gacgaaccag agtatcttca ccaccaatga  47280
tgatacactt gattttctgt ttgcgttctt cctgcggggg atggtaagtg ttgtcgttat  47340
tttcatggaa gcgaacgaca tgggtattga aaccgcaatc cttacgaccg aagaaaacaa  47400
cctgatcggc aaaaactgcc tgggcgaaat gcatttgtcc tttcatattc actcctccaa  47460
aatatggatg gcttcaccgc gttccaagaa cggcagataa gtctcgtagt tgttgatgac  47520
ccactgacag gattcgtgct tcggggtatc ctgaatgaat acacgcataa aggtcagaag  47580
gtagatcaga gaagcacggt tgaaactcag accagcctgt tcccattctt ccttgtattg  47640
gcgggcctta tcgatgtgat aatccaaacc ttccaatgca gcgatgttaa caccatcgac  47700
agcgttagcc aaatcctcga tcatgtacgg gaaaaccaga tcgacgtact catcatgttc  47760
aacagcgttt acttgttcga tagcgttcat acttcatttc cttgtttgta ataaaccgat  47820
ttacgagaat gtggaagaca cgacatatca cggacgggga agatcccgtc cgcgtatgct  47880
gttatcacct gtggtcttgc ccgagtgggc atctcagctt cagctttcat ggttacaggc  47940
agtacgcctt tactgagaat atcatcaacg agttgattcc aggcgataga gtacattatt  48000
cggtaccttg ttccgggagg aattggttaa tagcatcacg atagtctcga tcagccagag  48060
ccaacagaga ccatttagtt gctaccggaa gttcacggca tttactggta acctgataga  48120
gcgtgtagcc agccacacgc tcagcaatcg gatccagatg ccattgagta tcgcggattt  48180
gtttgatcgc tttcggagaa accagatcgt agacaacacc atggctggta ataccgatga  48240
tggtaacctt accagcagct cgacgagaaa tctcctccat atccgattct ttcaggagcc  48300
ggctccggcg aacgatgtgc tgcaaatagc ggcgagcatt tcgcagtgcg ttatgttcac  48360
ccatgaagta gaactcacga atgaacaggt gttcgttgtt gtcggtacgg atttgaacag  48420
gacgagcgaa cccatcacca atacccagtg aacaggtttc ttcacgggac attccgaaga  48480
agtctacatg gctcttacaa agcagataca gatcaccacg tggtccaagg tataccttag  48540
tggcgctgga atcttctacg tcgacttcat tgtgttcgca atagataccg aggccattca  48600
gaatcagttt agcctgatga agctgctctt ccatataacg actgatgtta ccaccagtgt  48660
aagcgactac accagtcagc aagttctctc cattacaggg aatgatttcc agatcgtcaa  48720
gttcagttag cttgaaaacc tgtttgacct tctccatatc gaaacggtcg tagataccaa  48780
tgaatttagc catgtcgcat tttcctcttt tggttaaagt aattacatac aacgggggtg  48840
gggagtgtat tcttactcgg tacagctact cttgaggtag ctgctatccg aggaactatt  48900
atgctggatt gtattgggag tttaatactc atttcggatg tacctaaagg tagtgtatat  48960
taaaagaaga ataaagaggg gtaatctccc cctcattaga tcaaggtgat ccagtataaa  49020
attccttatc ttttttagat aaggttattg ctccaggtga aaccatcagg agcattctta  49080
ctaaagaatt cattacccca accaaaagaa atcttaaagt ctttaactac acctgaatcg  49140
gagttaataa ctttatattc actgacctca tcgctattct gcaatacaat caacagagcg  49200
ataagatctt caggattgcc aatacagagc tcatgacgct tgtcatgtct cttaaagata  49260
actgtcagca tatcaaacct catgacggaa taaagagagc tccgaagagc tctcagaatt  49320
tatacatcaa tacgtctttc ggatatcgac gcagaagaac cttgaaatcg gtatccatgg  49380
gtgcagtggt cgaagtaaca actttaccct tcataacttc acgaaggtct acctcttcaa  49440
ctgtgacatt gtggatagtc ttccgagtgg tccattccgt atcaatgttg ttatacggat  49500
tattattctt ctgccatcca tctgaatcgc ggaagggaat agtgtaaaca taaatcgtca  49560
```

-continued acttgaggaa ttcttcaagt gtgattaatc gatcggagaa gatccatata tcaccattga 49620
tctcaacgaa gcgatcagag ttaaactctt tttctacagc actacctatt ccaagtagtt 49680
cagcttctcg tttgacagag gtagcataaa gatttaggtt agactcaacc ccatccccaca 49740 ctgttaactt accggacctt ttaaagccag gcatgagttc cttctgtttg tagagagagc 49800
catgatacaa cagctctggt ttgtccatga tgcgtttctc ttgataaact catacgatgg 49860
atgcctttta caacatccat cgtctatgag ccttacacgg ccttgtagct atcatcccata 49920 tcgataggac ttccataata aatctggaac ctattgaaca gactgtccat gtctacacgt 49980
agagcacgga tattcatgcg gttatcactc ggccgccctt cggactccca aatggcatgt 50040
gcgatcgaag gagctacgtt attcaggtag tcttcaacct catgctcttc gagtaacaga 50100
gtatcctgga aaccgatacg ggagataata gcatagtcac gctgatcgtg ttttttagaa 50160
ccttcacgta ccaggtaact cgtgccagat ccattcctac aaccattacc atgaatctct 50220
acaacgaact taccgtgcca tttgtagtcc atgcgaagta ctcctttatt tgatccgctt 50280
cattacaaga gggacagaca aagtaatccc attcgacagt tttccagga tgcggtttac 50340 agcagcagcc tcttgggcgt tctcacaagg gagcataata gcatccccgt agtaatgact 50400
gtgatccaga cgatcacccc agacactgtt tacgaaacca tattccatgc cgtcgtttgt 50460
agttacaatc gcaacgacat ggtcaggacc aatcatacca gtttcgaggt caccaacaag 50520
atccagcttc tgtacaacgc cccgctggca gatccatact tcatgataac gataaggagt 50580
aaggtcacca ccagtgctcg gatcgacctc gctaacgaaa tacagagtac cccagttcat 50640
gctttgaaac tgaacggtct gcttgtaagc ttcccatttg tcttcaagac agtttacatg 50700
tttgtcgatc cacaaaccct cgttattgag gctatcgacg ataccgtccc ggacacgtac 50760
gacatgaaga gtcttagtca ttttcaatct ccttttaata gtttctgaat cgatcgtaag 50820
tgactttttc tttaagccga tcgataatgt aattacgacc ttgagtgaac tgaagttttt 50880
gatgactgtc caactcgctc cattcggtca agcgaggaag atctgaaacc tgatcatatt 50940
tcgccttatt gagcttcctg atcatgtccc agatatagtc accttcaatg aaccagcgga 51000
gaccagtgaa cgtatccacg tcagttagct tgaccccata gaggctaaga tcaactcctg 51060
cttcttctgc catcttacag gtctttttat aggcatcgaa taccgcacga aggcgatggt 51120
cgaaaccatc accctcgcac atttcgatag ctacgatcaa catcggaaac gtatcactgt 51180
agaacttgat cagcttccgg gtcgctgctt ccagcgcttt ctgcttttgc gtttttgcca 51240
tttttaatat ccctaaattc acgaaggaat tctttgtgtt catcgtaatg tttaaaagcc 51300
agtgcaagca cattaagtgc cttcccgaaa gcgcgtcgtt cactgacggg atattctgac 51360
cagattttaa acttgttctt tggtagttga aagttcagat gtacgatcgt gtcccaatag 51420
gaatacgaaa acaaccagct cgcatgttca tagacagtgt ggttagcagg gtctacaccc 51480
atcacatcca tgtagatgcc gttttctttc gccacgcaca gaagattcct gtgacaatgg 51540
agaaggtcag tcatcacatc tacgtctggt atgcctttac cagaataaga atggaactta 51600
cgaaccatta ccatccaggc ctcgaatgct cttttaaatg cagcagtctg ccgacgcgtc 51660
ttcgttgatt tcttagtctc catcatgatg ctccactcga ccagaaaggt tatattcaac 51720
cttgaactgc attcttaccg gagcgtaagt ttgcggatat tctggaatac ttttgtattc 51780
accttcaaaa caggtgaaca acatttcacc cgtattgact ttgtagatac ttggcatgta 51840
gtgtacgtac cacagcttgt catcttttag aacataatga ccaaaactgt tttcacgacg 51900
agcatctttt atgacctgga tattcttacc aagtacgtct ccgatgaaac cgaggtgatc 51960
atccagatcc ataccctcgg aatcaccatt catgactaaa gcttcaggag acaaatacat 52020
ctttcgaatg gtggcattaa ccggttcgag ataacctttc tctacacccg acatccattt 52080
gttgaaagaa ccaatccgct tgggatcgtc tgtacctacc aggatagtgg tatcgtcata 52140
aacgatatta atcaaatcgt agccagctgc acgattacgt tgaatgatcc aaccatgata 52200
gttgacccgc agaaaagcca ttgcatgtag tttgcctcgg agggcttcca gagtaagctt 52260
tttcatttta gttccttagt aaacgccatt gatgatggcc tcgcggaaac gagcccactc 52320
agtttgacca actaccagct ctctttcttt tggacgccag aggtggtcgc cgcaatcaag 52380
acctaggtaa agcatattag ctttccattg gttccgatgg ttacgcagtg tagccgacag 52440
actgaactca cgcataactt cattaacatc caaatgaacc agagtttcac tggtcattcc 52500
gctcatgctg ataccaagaa cctcacgaac acgaatcaga tcatccgtca tcgaacgcca 52560
ggcttggata tgtgcgtaat actcatctgg agtcatgctg tttttatagt tcgatgctcc 52620
gggcgtcatg gacatccaac tcggaaattg gatagacatg tagtaaagcc agtcgctatc 52680
gtatcgcagt tcgttcagtt tttcctggat aatggggttg gtggttgctt tagccattag 52740
actactacct cgcgtagata agcaatgagt tcctcctgga actcagccca gacagatttc 52800
atatcaaccc cttcaggttg acgtgcacgc catacatcgg agtctgccgg tagttccagc 52860
gctttacaga tatcacgcca ttggtgaaca tacttacgga caccagccgg agtggaaaga 52920
accaccagag aatcgatggt agccaattta acgaaaggtt cgtcttcaat cggcatacca 52980
ccccaactga catcaatctc acgaacgatg tcattcagtt cagccaggcg atgatggaac 53040
tcgacaacac cttcacgacc aggtttgtag ttcagaccag acggcatggt acgcatcatg 53100
gccgggaaca gctcggtcag cacagcgtag taacgctcgt ccttggccag atcacggagt 53160
ttgttttcga gcatggaatt aactttaggc atttctattt cctcagggct tgatggaatt 53220
aagcagttgt aactttaggt tggacgggtt tgataatttc gttataggac attcagttgt 53280
aggtggtgaa gaacttcgga tgacttactt tcaaccattt aacgaactta ttcagttctt 53340
cttcccgaac gaaaccatta ccgtaaagat cacggcggca cggatcaccc tcgggcattt 53400
cagcgcagtg ggcatcatgc atttgtcgga tcaactccaa caaattttct ttacgtccaa 53460
tcaggaacgt aaatacatgc agcggatccc aacttgtcat ggtggtccac atggatttgt 53520
tggcagtcag atttttgagc ttgagctctt tcaccttatc catcaccaat ttgcattgga 53580
ccaacatccc ttcaagttgt tcctccggat ctccgtcaat aatccagtga gaaccgccag 53640
gcatataacc gcagaaggtg taaaggttat cacgcagata cgcatgacga ccacgttcca 53700
atgcttctgc tttcttttgt tccttagatt tagccatctt agtaaccctc gtcagatttg 53760
aatgtgcgtt caggactgaa cacgtatttg atatcgtcaa tcacagctgt gatatagacc 53820
tgatattctt ttgaaataga ttccatcaac tctaccgata cgtactccgc agtttgaata 53880
cggttgtaag catcgtcaag catgtcatca tcatgaccga acaacaaacc gagatcagta 53940
gaattgatta ccgggtaatg tacccagtta cggatatacg gtttaccaag atgaattact 54000
tgaataactt catcatgttc ctgtttcttt ttcttgttta cgtatttgac gtgacgttcg 54060
atgaaagcat agataccgga accattggtg ttaccgtatg cagccagttc gaagccgtat 54120
ttatggtcga tgttattggt gtcacgacgc cattgaggaa tgaaagcact catttgaatt 54180
cgtaccatcc gttaatgatc agatcaagat ccttccagaa caactgagag aattcatcga 54240
aggtatctgc gttctccagt ccatcgagat caacgtcagg agacttaacg aaactcatac 54300

-continued

```
cagtttcggg atagatatct gtgatgaccc tagtactgtt gtcagagtaa tcacgggtga  54360
atgtggttac cgaatggtca gtaaaaagag cgacacagat atcaccttta tgattcccca  54420
gttcatcggt aagagcatcg atgatatcga catcgatgat atttccacca aagtcaagaa  54480
tttttagacg attacggaca agttcatttg ctgcccaatc gccagactgg ataaccaaaa  54540
gcttcgcggt ttcaccgcga taggttacaa gatcttcttc gccttctcgc cgcatacccc  54600
agtcgaaacg gatgtccgta tcttcattgg ctttatcacg tgcgatgatt acaccctgct  54660
taccataaac tacgatatgt ttcatttgta tattcctttt ggttaattga aacggctata  54720
ttcaacccac cactcttcgt cacgaatgtg aagagtagta cacaggtcga tgattgcatc  54780
gaaaagcaga acagtcgttg gattgcgtcc aatgaactga cgttggaaag aagtgaagat  54840
agcgatgatg ttatcgccat cttctgtgtc aaacaagatc tgatcatgaa caagagacat  54900
gtcatagaaa tcaatcttag acaatgcctc tagaagaact tccatgcgag tgagggcggt  54960
attcagttcg aatacaatca gcggactgca accacgctcc ttatggtgat gcatgcgatg  55020
tttggagata cgttcgacga taagccgggg aagaccttgt acatctacga gtttacgttt  55080
catttttgat tttcctcttt acgaaataga agccctcccg aaggagggca attatgttgt  55140
tacaggttga taacggttac gaactcgaat acacgacaga gttcttcgtc acgataagct  55200
tgacggaaag gtttaccttc tttaccacaa tacgggaaga acagtttacg atgctccgta  55260
tcgccaaacc agaaggtagt ggtattggaa tcgatgatcc cgtgtgtagc cacatcccgg  55320
atgttctgga atacatggac cactttgtcg gcgataacgc gaagttccac accatgctcg  55380
gtcatcatgg ccagaatgtc ttcacgactg tagtcggtcc gttcgttgtt ggtcatgatc  55440
tcgtgaacca gagaacgctt ctctttgtca ccgaagcaga tgcataccag atgaacagaa  55500
gcaccttcga tcttcatgcc attgataggt ttaaacagaa caatgttctc gtatttgaaa  55560
tcgttggtga cgatcaatac cgaactatca cgtacagcga tacccaggct ataggccatg  55620
acttattcct ctttagcgat tgaaatagtt gtacttgccg caatctcatg atcgcggaga  55680
tacacaagtt taactttgta attacccgga gtttcaccca ttgccaggat caacttaggt  55740
aggtcaggtt gagtggttac atgtgccagc ataagctgag ctgttttgaa gtctttccac  55800
cggaccaact cctcattaac ataagaagtg acccattcag cgatcttctc accgcgcttt  55860
cgaacgaacc acaaaagatc ccgaccatct tcggtcgaga ccttcatgta gtacggcgat  55920
tgaacgggga gcatcaggtt acgaatatta ttcgctcccg atgtatccca gttaaatacc  55980
atgcttacct cacagacttg gtagagggaa cgccggattt acacggatat cagtttcagt  56040
gacatacacg taattgatgg tggtttcatc tcgacgaata ccatacatca atggagcttt  56100
tgccggatcg actaccatga ttcgacccgg ttgatctgct tccatataga tctcaccttt  56160
ggcattcttt acctgattat tggtgagaat gaacgtacca catttgaatt tcttttccat  56220
gtttacctca attcaaccaa cggttatcgg tatcagcgaa acgtgcagat gcacgatgcg  56280
ggtaaccgta agggatttgc gggaggatag gttgatcgat gagattagaa ggataacctt  56340
cttcatcagg gaaataccca tccagggagt aaatcaattg cactacacgt acacggtcgg  56400
agttcggtcc ataaaaacgg ccgcagttca aaccaactcc atgcatgaac tgttcggagt  56460
caataggaat gaaccgatag tagtagcgaa gatttttggt cgacaacagc ttttcgttca  56520
gatagtctgc ccagtctcca gcgttgtaca gatcccgttc ctcaatatca acagtatctg  56580
cggctacagc agctgcacgg aaaatgtcac gcacgtagtc tttttcagta agacccatgg  56640
taacaaattc aggtaacccg gttcgaccaa gaccaatggt gaaacgtgct tgcggcagtt  56700
```

cgtcagcacg acgcgtataa ataacgtagt cattaccttc gaattgatta acaatcgcct 56760
tctggatatc tgctactttt tgttcgagta catgcgacat ctcgaataca gggttgttcg 56820
gttgaatggc cataccagat acagttcctg caacatcaac tacattagac atgttcgctc 56880
ctaagggaat aaagaggacc cgaaggtcct caattgagta acagatagct atactgcgtt 56940
tcttttaggg cgatccgaat gcgaccttcg atttgtttgg cttctgcttg acttgcagga 57000
aactccaaca attccagatc gctgttttct ggatcacctt ccatcaatcg attcatctta 57060
ggccaagggc tagcttgtcc tttaatgcgt acgatcaatt ggtctacatc tttagagact 57120
gttttacttc gccccatgac gaacttaccg gtcccaagat ggacaatgca gtacaaccca 57180
ttcgttacaa catctttacg tttcccccta ccccagatag tcgaagacca tttgttgtat 57240
tgggtttcac catggaatgc ctgttgcatt tcaaaatcct tgctaaatga ctattacatt 57300
tagcagccca gtattacttg tggtattctg ggaagagcag acgggattct tctcgatatg 57360
taacaacaag cgattccagc ttactgagaa tctcagccat gttgagatac gcatctcggc 57420
tagctttatg ttgctcatac ataggatcga atacaccaat agattccatt tcggagtcga 57480
gttgaatggc tttgtccaat gcctcgtcag aaatcataaa gatctgacga ccttccatcg 57540
ccaccttcaa ttgcatttcg aggatacggt tgtaaccttt gcggaagaac tcggggctac 57600
catcatatcc tcgtgcaaca gcacggcgga aaagttcagg atcgactggg atatcagtgg 57660
ctaccccatt atgaggtccg accacgaatc gacgtccgca gctatctaca ccgataaaca 57720
gtgtagtgcc ttccatttct ttttcgaggg taagtaccca gccaggatga taggttacat 57780
tcggattatc ctgcgtgcgc agtgtggtgg ttgtatagaa ctgatcacct actttcattt 57840
tcgaatcctc tattaatgaa tgacaatctg actacgggag gcatagaacg atacagcttc 57900
aggatcactc gatagaacaa cctcgtaagt gtccccgctt accttacgaa tgatcttgag 57960
ttcatcacct ttatttgcca ttattaaacc aggcccacta tcactaacgt tggcagtgat 58020
gttttccaga gcagtagctt taacactcat ggtttattcc tcttgatcga gataactatg 58080
tttatttacc atagtcgttg aatgtatctt ccatctcact aaatgggatg gtttcaatct 58140
gattgaaatt atcatggttg attacccgga aaccaccagc tggattatct acatcctcac 58200
aaatgatttc aaggtcatca ccttcattgg catactttgt ttcggtataa cctttttctc 58260
tatcagtacg ggtaataaag atatccctgg ccgcctgcaa taccatgcct ttaacgacat 58320
cgttctttgc caggttagca ctaagtttca ttgtatcact aatgagagta ctgaagttca 58380
tttcttttta cctttcgctt tatctgtcac tacatcttta cgctctctcc atttttggtc 58440
gagtatcgtg ttgatgatat atttttgttt acttgttgta acttgttgca ttttacaccg 58500
ttgaagcaat tacagcgaca gagattagtt cacgttggaa acgatttgca tcgggccaat 58560
tcagagtgtg atttgcatgt gcattgatct cacccgtgga acgatcaacc caaacagtga 58620
ggtaacggcg atcccgtccc tcgaagatac agtttacaac aaacagacgt tcatcgtttg 58680
cgttatccct cagttcagct ttgaagtcga aacgattgtt gaaagcatca acgatagcat 58740
tcgttgcagc ttcggtcgtt acaccagcct tatgttgttg atcgtaataa atacgcatga 58800
cgctagttac agccgcatta cgtgattcac ggatcagtat atccttcatt acatgttccc 58860
cggttgacca agcttgtaat ataggctttt aaaacaattg aatgtaacga cataatgctc 58920
tccccgaagg gagagctcta tgttaagcca ccagagagaa cttaactccg ataatcggag 58980
attcccgatc gatcttgatc acagcacgac cagtaacacc atcgacttcg aaggtagttc 59040

-continued

```
cccaccgcag tccatccatc ttggatacca taccaaaacg gaaaagacca tcgcgacgaa  59100
tttcgatagg atcgtgttcg gtgactttgt ggaatagaat attatcaccc gaatcaacgt  59160
aggcgacttc ttcaatcttc agtttacgaa tgtcttcatc accaccgcag agtgcaaaga  59220
tattgaacgt ggaatccacc ttcacataac tagacagtac cgaaccaaca ccttctatat  59280
caacccgata aacaggcata cgtaaatgtt gtgcgaagtg tttatcgctc ttacccattt  59340
ggtaaagcgg tacacggata gaactagaga ctttctcagt catcagtatt ctccaaattt  59400
gaaattgaag ctaatgggtt tatcagatcg cgttctaatg actcgaacaa attcattcaa  59460
tgaagtttca atgacataat agaacgagga ctgatatatc aaatcttccc tatagcgttg  59520
atctagtata accatgtcat tagaaagata gacataaaat gtcgaatcta agctatcgac  59580
cacaacagga ttcgaacaga ccggagtcgt ttttataccg tcatgtgagt atcctactac  59640
ttctatattc acgcgcttat tattcactac aagaggacga tgaataataa tcattaccca  59700
agctagtagt aatgcagtca tgaataatag aaaagataac tcaatgagag ttttatccat  59760
acggaatctc cgtgttagat tgtcctccaa tcaataacgt tattgttacc cttcaaatcg  59820
aattcctcga atttataagc accaccgcct cttaaccaga cttggtgata tttgaagtac  59880
agggtatcag catcgttgga gattaaatct atctccagat tggtaaggtt tttgtggtag  59940
gtcacttcac catttctaac tacaacatag aactggttcc taccatcacg cagcccatag  60000
caattacctt tatttttaat tggtattttg cgactcactg cacctcggac atgtagtaca  60060
tttacgacaa aatgtttcct gatcctaaat acaaaacgaa cgattgtata agcaagtgca  60120
attacagcaa ctatgatgca taagttaacc agtgtttcaa taaacattga taacctcatt  60180
gaatattaag ttggcgtgca agaccatggt tagatgggat ttcaaccaca tcaagatcaa  60240
tgttgtcttt cacccgataa acccgttcta gaacaccact catattgcat tcgaaacgaa  60300
gacccgagtc aggatgaatt cctagtgaca cccaactggt atcatcatcc agcgaaaacg  60360
taaacttgtt ctgagtttcc attttctgta ccagccattc gccttcgttt tttaccagtt  60420
tgatgttaga attcatgtct attctccggg taattttacg accttataaa cagactgacc  60480
attgtcatgt gtctcattag tcgtatgttc atctaaatag agataagcta tctgcacagc  60540
tttgctaatg gtatcggccc agatgcacaa ggttttagtt cgatatgttt gtttttccca  60600
cgagtacttt ttaggttctt tgtaggtaag ctcgatgcta agcgatacga attgcttcgt  60660
agccttagcg gattcaaaca tagtcttctg gtcttcatca gacaccaaga gtttattggc  60720
atcgatgaag gatccataat agcaactacg gccacatagc atttgtgtca gagtggcctt  60780
tccattataa tggcgaggct ctatctctac acgccaactc cagtccaata gcttctttat  60840
cttttcgtcg agttcagtca ttatggcatc tcaaattgaa tggtgaccat agatttttca  60900
gggttgtatt cgatgtaagg gttgacataa cccaaacgga aaagccattg ccggagttct  60960
tgatagtctg ccatgttcca cggcatactg cccatactga cgcgatagac cagaccttta  61020
gtgtggtcat cgagtttcca gttctccggt tccaatacac cagaccgaat aataatgcgc  61080
gtttgatcaa cgacattgaa catttctgga ttagcttcgc gtaccttacg gaatgcttca  61140
gaagccttac tcgtgttgtc gaagagagac aacgactcgg ggagtgaacc ccaaccttgt  61200
ttaacttgca ttttcaagac cctaaagaaa aatgtataga aaggggaccc gaaggtcccc  61260
tgtcattagt tcagagaagt gcgatgagcg tactcgaagg tatcgacacc atcaaccatg  61320
ttgaacacag cgatgatcgc gctcatgggt ttcttgccca tgttgaagtg cacgatgaag  61380
ctgtctttgt aacactcgat ggaacgaatg ccataaacga cattgatgcg atcgatttgg  61440
```

ttacgaataa ccagcgcttc ctcatcggtc atattttcga tgtagttctc gatcagctgg 61500
aacacccgct catcgcccag gatcagattt ttacgttcga cttccaccgg agcgaaggtc 61560
agtaggtgag gcatgaattc cggaagagcc tccacgttga acaacagctt gtcgtccatc 61620
agaggagttg cacgatacag atccgacagg acgatattac cacccacgat ctcgattttg 61680
ttttcttgag ccagagtgga agcgaggcgg cgatcagcag tattattaga accgaacatt 61740
acattttcct ttttagttaa tcagtagatt gggattccgg gttagacttc ccaggtgtct 61800
ttccagcgag ttacaggaag ttggaacatc tcacagagtt tagttactgc acgatgttcc 61860
aggttatttt ctggatggaa tgtgatgggg cttatcgaat aaccccagtc aacacgacag 61920
ccagtttctt tatggatttc actgagagcg gtataagaac cactgccatc atcgtaaccc 61980
attttgtacg ggttaacgca gatctgggta ttacgcttca tcagaacctt atcaacttca 62040
atcgacaaga gtcggacgaa ttcgttggtt ttctcgatgt catcaaccca gaattccaga 62100
aggatccatt ttccacgtgg gtcattatga ccgccttgga agaatacact gaaaccttgt 62160
tttgcttgat agaacggaga ggacatcagg ttacatgtaa caacccgatg aacagcttcc 62220
catacacgct cggtgacata gtcaccatag agttcaatgc atggaccacg accagggaaa 62280
ctttcctttt cagcgaattt gagttcgaac atgttattct cccgagcgat agcggttgta 62340
acgaacccag tttccatcac ccggccgctg gaattcaatg gtatccatca tgtggtaacc 62400
gaagtgttcg atgatccaca gagctacttg cttggaacgc ttcatgccca tttcacaatg 62460
gacaacgata ttttcgccat tacaggcttt cacccattcg acgagctctg cattacggct 62520
attgatggga ttatcgaatc catcaatctc gaagacattg acaccgtcag cgataccgta 62580
attatcagca cggttgtatt cgatactgat cagattggta ccgggattaa cggcacaccc 62640
aacaccacga ggaacatgga taacgccttt acgcttacga gtaaccttta cagatacgat 62700
gctcatttgg aatcaacctc tcgcagtgct tgaatcagtt tttctttggc ttctacgctg 62760
gaaccccagc attcgatcac gtcgtagccg cgcccatctt tcttcatgaa agcacgtgca 62820
tcatgtccga gtttaccagc cacatgcatg ttgtaagcct ggaagcgctc gggagtcatg 62880
gtaaccggat ccagatggat gatggtaacc atatcgttca ggatgttgta agtcagcatt 62940
ttgaattttc cttttaaata ttagtggtgt agtggcgaac gacactatgt gtacgctctg 63000
cggtttttcg gagaacactg aagttaacga catcatgatc gttgaaaact ccagttttga 63060
tgatttcggt tacggacgcc atctcgcatg cgagtccaag gcgagcgata atcatgtcag 63120
catgtccaag attattgaag ttacatgcct tgctgatatc cgatgtgaag tgaagagaat 63180
tgggatcatc tccaacagtg agaaacacaa atttgttccc agccgagatc tcgatgataa 63240
gttcatcatc accgttttg tcttccagta gctcataaag ctcatggtat ttgatgcacc 63300
cttgtacccg cccgagttcg atctcggtgt taccatacca ggtagcttta gcgagttgca 63360
tgaaattcat cgcggaatag aaatccacga acacagcacc gtaacgacga acatcgtcta 63420
catcgaaatc tttagctagt tgattatgga cgatgaacac aggtacgtta aaaatgaaat 63480
caacgtacag gtgaagctca catgcagacg gaataccgtc gatggtattg ctcagaattt 63540
cttttcgcaa ttgtttcatt gtactatcct ttttacatgg tggaatatca catttgtaat 63600
atagggattt aaaaggttta aatataacct tctattatca cagttgtaat ataggctttt 63660
aatgcgttta aatataaaag aaaaaaaagg acataacgcc tctcccgaag gagaggcaat 63720
tatgtttact caccaacgtc gggttcggtt tcgccgccag tctccggagg agtaccgcca 63780

-continued

```
gtgccaccat tctcaccttc gttatcgccg ccttcacccg gttcaggttc taccggagct  63840
tccggttgtt cttcaacata gaagctaacg aacatctcat ttccattctt gatttcaacg  63900
gaaacggatt tccaaccggc atcttcaatc gctttcttta gagcagcaac ggaagtttca  63960
gcaatggtga cattacggaa atgacggtga acgaaatgga cagcttgttc cggatcgtta  64020
aggaaatcaa cagtcccagg aagagacaga tattcgttga tagcatcttc gtactgagca  64080
atctcagcat cggacatagc cttgccggct tcgtccaggg aataaatcgc cattgggtga  64140
ttctccatag tcatgaacag cggtattgct gtacataaca tcggtcactt catagcgata  64200
ataccaaagc caagttcagt ccgtacaccg gtttgcccct cggtaacctg ctctacttta  64260
acactccatt caggatcgcc aaccaaagta acttctagaa tagaatgcgt atcttcccct  64320
gccattcggt atgccgattc aagagattgg tatacttcaa ttgttctatc ctgacagcaa  64380
agaaacacag tgccctgggt atctggaaag tctagataca ttcgacggaa gtctgaataa  64440
gcaataaggt tactaccgac gtagtgtgtc atactaccga taataacacg acgcttttct  64500
ttctttttg gcttttcttt ctttttgat tctgttggta gtgttaacca aattaaaccg  64560
gccagaatta aaagaataat agccgatgtc ggaatagtaa atggcatact ttccacctaa  64620
aaattaaacg gtaaaaaagc tgtccccgtg ggacagcct tatgtcagat cagttgttga  64680
cagtggccca gtaggatgcc gccagatcaa tctccagagt attcggagcg acttcaaccg  64740
tctgagattc accactctca ttaacaatga acttcggtac cagatggaaa tcattctgga  64800
taccggccat ggtaccagcg atagcacgat cgataaatgc cgaatgtact ttgactgctt  64860
cggcttcaac atcaagacct ttaagaagat cgcttttgag atcttcgcag tatttcagta  64920
cagaagcacc agcgttggtc agagccgaat gttgttcaat tacgttttct acatgttcca  64980
ttttcgtatc cttaattaga gagaaggtat aactgcgtct cctaagagac gcagattaaa  65040
ttacttgctg aatacacgat tgctcatgcc agtgctgttc agtgcttcat atggaacaaa  65100
gatggacgag ccggagttac ccagactgtt agccattttt tcttgaactt ccagagcacg  65160
atattgcaga agcttctcgc taatacccgc tgcaacaatt tggttctgat cacgcagggt  65220
acgtgcttta gtcagctcaa cctcacgatc agcttcggcc agtttcaagg cgttagtgcg  65280
tttggtcatt tcaatcgctt gctggttatt ctcggtctga atagcaagtt cacgctcagc  65340
ttgtttctca atagcttcag taataacact cggatacttc agactgccga gagtaacgtt  65400
agatacttca agcggagaat ttttcattgc ttcttggagt ttggccagaa gatcagcggt  65460
gatcttatcg aagtttgcag gaacttcttc gactttatat ttgccaagta cagaacgaga  65520
aaccgagcta actacatctc gaccatagat actgtaaact tgatccaggg taacgatatt  65580
gtccacaacg gtgatcgagt tgaacatggc gttgataact tgttcgttac cagcaacgcg  65640
agtccggaag ctaacggtaa aagtcagatc gagtttatct gccattttta cagtcagttg  65700
ttcgtttttg gtctgtaccg aaccatccaa caggataagt tggtctcgtc cataaacggt  65760
gagtttacca ggttcaagaa cttccggaga gtagccattc acagtgagta gcttaccttt  65820
atgtgccgga ggaataacct cgaacgaaca gccggtaaca gcgagagcga tcagaattgc  65880
aaaaacaaat tggacgtact ttttcattgc gcgttttcct gtttagattt cttgagttgt  65940
tcgtcaaaag agagttgggc tttcgacaca ttatcttgag gtttggtaac tttttccggg  66000
atcgatgttt gatcaacaat aggtgcatcg aatcgagtta ccgctgattg tttcaccgga  66060
gtggtaattt gaagcagcga caattggaag aagattacga tgaccaaagc gatgaggaag  66120
cgttttgcaa aaccaagttg ttttacccag ttctttttag agaacagaat ccatcccgcc  66180
```

```
agaccaatcg aaatcagtgt gaggattcca tagaggaatg gactaccaat aataacgatg  66240
tttagattat gcatacttac ctcattgatt aacgtgtttg aaatattgat ctgctaaggt  66300
attgttatta tcagaaataa gtctaacacc aacagcgcga tcagttacag atttactccg  66360
cttgagctta gagtcataat ccctggagca acgatagtta cctgaactca ggaaccgaag  66420
ggccagaagg ataccttctt taattccttc atcgaacgcg tcttgttgtg cagcgtccgt  66480
gtaacggagc acattttctc ggctgaacgt ttcatgagtt tctgaaaact cttggaggaa  66540
taagtcattt gctcttaacc actcttttgt aggtttaaag ggacaatcat ctttcgtatc  66600
agtcacgtgt taactccctc aaaaagagat tgcgtgagat caggatacca cggcgtacta  66660
gtgaggcgga ttttaccctc ttcatcgtac acatcactac cgacgatcat gatttgacca  66720
tgagtctgaa tagcatcgat agtagccaaa gcagcttttc ttgcagtatc agtgaagagt  66780
ttagacatca ttcgtccttc gccgttatat gaaatatcag cgaaaccttc attgatgatg  66840
ccatctaccc gttcgcgaat ttcatcttgt aggaattttg ttttcccgct ctgaaattcg  66900
ttatcatggt aggggtattc tactttcgct tcttccatac attcacctcg gttatggaac  66960
tacgcttcat tcgccgcctt agcgatgatg ctgctttctc tgttgtctcg gtccaaccac  67020
caccgaagat gatgtgatcg tcgttgatct gtgtatgtag ttcatgtgta gccattacgc  67080
cactaagacc acgagatgcg taatactcga taagagcgtt agccggatca ctcatgtgtt  67140
aaccctgtcg tagtgatagg agtagatgga acccacaacg tgactagcag ctgaagtatc  67200
cagagaatgg ttctccacca ttttcacagc ggagaggtta atatcaccga gcttgtaagc  67260
aaagtcagtg agccattcac ggacaggtcc ttcagctata cccgtcttgt caaccacgtc  67320
aaccgttgct ttatccagaa gatcatttaa cattgcaaca ccgacattga taatggattt  67380
ctcaaggtcg ataacaacgg cagaaaactc cccactcact cggagcaagg agtcaaggtc  67440
tggatcgttc caatctaacg aaggaacctt catcaggtat tcacggactc gaagtaggtt  67500
tccgagagcc cggagacaca agtgagattc acaccagggt cttcatcgtg gtcggtagac  67560
ccagtgatga tatcctcgta atggttttca acagcgtcga gaacaccacc caccgcatag  67620
tcaatagcgg cagcagctgc cccgcaaaga acatcattgc cgtcgttggt gtcatcttta  67680
ctgagttcac gaactttgtt cttgaacagt tcaattgcct cagtacgtac ttctacagca  67740
gcgccaatca gttgagtagc cattaagctt ctcctacaag ttgtttggtt ttaagacgta  67800
gtttgtgttg ccggtatttc agaatggatg atgctttaac ttcacccctc agaatgcgtt  67860
tagtttcttc agtcgtgaag tcagcatcga cttggtagat gtaatgcttc tcgtagaaat  67920
gttggtatcc atggaaacca taataaccac gtagaagttt tgaaccagtc aatcgtcgta  67980
gttctttcac catacctgaa ccgacgcctt ttcgccggaa ttcgggttta acgtagaaca  68040
tacagagatt acgacggcca gtattgtgca agatataacc aaccagtgca ccatcagtat  68100
catcgatcgc cattaccaca cggtaacgtc tcacggtacc atttttcaga atggttttga  68160
tataacgaca gagtgaaccg gattgttcgt aaagtttgtt ctctatgatc gaacgtaggg  68220
acatcttcac aagaatggga gcttcgatga tactgtagtt cattagctgt ttaccaattt  68280
gaaataatca actaccccat cggaaatatc gattgcttcc acatcttcag atgcgactgg  68340
aatccagttt ccacctgctt caatagcttc ggctttttct tcttcaccca ccttaggaat  68400
gagtgaaaaa ccgggacagt cgggatggtt accttcaatc acaccgagta caccagagac  68460
aatatcatcc gccatggcag cattcggatt gacatatgcc tcatacttac cttgttcagc  68520
```

-continued

```
ttcagcgaga atttcatctc gtttactatt taccgcgtct ataaacagat cacgtacttc  68580
actgaacgtg gctgcgcgcg gttcaccagt gccttcgaaa tatacggtca tggtttttcg  68640
atcgctttgt tgagttcttg ttctagttgc acgagttctt catcggtgag atcccttgaa  68700
gcacacatgc aacgccctgg tcgtttgtac cacgtgatac agacatcacg ccaaatcaaa  68760
gcaccctcat cttcacctgg aatcctgaat gtttcaagtt catcggtgtt aagagtggga  68820
ccacccggat aagggttaac tcgatcgtgg tctattttac taaacttcat caggaggtcg  68880
taaagaggac cggtagatac gagtttccaa tgcgaagcaa gtttgatgtc ttcactcggt  68940
atagtcgccc agtattcttt ttcattttca tcaaggtctt ctggctcagg cagaccaccg  69000
attaaacaat aggcatgttt agccacttct actaaacggg tgtttttcat agcttgatcc  69060
tgatctttgt aataccgcaa ctatgttcgc agaactctac cttcgtccat cctgcttctt  69120
tcaaccgcgc tttaacaact ttctttacag acaaagcaat gtcgtcttta tgttcgacaa  69180
caatctcata gtttctgaca taatggaagt tattgaaacc aggtagatct tcaaggatct  69240
ttttacggat gcttgcacag acttcattag cctggcgttc taccagcatc gcaataactt  69300
cactttttgt cggaatagaa caattgtcgg tttccatccg gagagttttg attgcatctt  69360
ccagaagcga ttttgaaata ccaagggtca tcggacaagc tctccatgag tgagatagat  69420
tttaatacgg gtcacaattg actcacctgt ttcattagta gggctagcct catcaatgat  69480
ttcaattgac caaccatgct tacccattgc ttctcttaga gagagtttta actcttttgt  69540
gagtatgtgg gatacatgta tttcgaacca ggctgctcca gacgaatcat attttacgtt  69600
cgcgtaattt ccaccataat catccaattc catttcagaa cggatatccc gaagaatttg  69660
agttgtcatg tagcgaacat atttgtcata gaactcttct ttagaatcta tgacaatggt  69720
tctatctcga agcataaaag ataactcttt tttatttagt gacgtgacat ttgagtcatt  69780
caccgaagcg gacttgcttg agaagttcca aggtagccaa ttccaacagc tcatcttctt  69840
caacctcgat gtctctcagt aagtacattc catcccattc aaaacaccgg tctttaagag  69900
cggcattaat attacttggg atcatcaggt aaacatcata ctcttcacct tcatcgtcca  69960
actggccgag attatgcatg gtgatactac ctgttttagg aacaggtgtc attcgatgaa  70020
tacctggttt atttgttacc ttgataaaag tttcaatgtc atgcgtaaat gacattgagt  70080
tattaatagc cttatcgaga acagtatcat cagtcagatt aatcagactg aattgaccac  70140
cagggatata acgagtacaa tttgaattgc aatacgtctg aacaagcgga acgacagcga  70200
gttcccagcc ggtctcatta tctggatcag gcatccatgt accgtggatt attgcgatct  70260
tgttagccaa ttacaccacc cctcaaaggt tctggatctc ggaatgtaat ttttacagtg  70320
ggaagtaatt caccagaacg ttcttcccaa cctatctcaa gactggtgat acgttttgcg  70380
atatctgggt ttgtagcgat aaccgattta ccaccattta caagtacttg aagacgatca  70440
gcggaacggc tggacatgtg taactacctc ttgacaagaa aggggatatt ttttacattg  70500
ctcaacttga cgttcagcgt gtttcttcgt gtagatacag gcaataatga caaagacgac  70560
tagtccaatt atcattaacc agatagactg tttcctctta tacgtcattt gtaaagtcct  70620
tatggattca gcaaatacgt aatatagatc tgaaaaaaaa tttagtacat acagccctct  70680
cccgaaggag agggcatatg catttatttc ttatcggctg ggttaggtac cgtaaaaggt  70740
ttaggatcga aactcttact catccgacat gcagaaaaca atctttcagc cgcacgatcg  70800
gtcgcagtca tcccattaaa accatttgga ccaaactgtt tcctgtatcg cgtaatgtca  70860
acatggaagt taacgatctt gtctttgata taccacagag ccgtaaggtt tgcagtgatt  70920
```

tcgtactcca tggatttcgg catgtctttc actttattcc atagagtcca atacgcattc 70980
tgaacagcaa tcgaagcttg atcagaatta gcgttcttct cctcaatctg attaccgaca 71040
acgatgctgg tttgataaac caacgcacat acatcatcgt tcaacacgag atgattattc 71100
gcattgactg caaaggacaa gacgagaaga aatagagcta ctacatgttt catgaaatat 71160
cctcagttta aagggcgcga cctacaatag gacgaaggta ttcgaactta gtgccgattg 71220
ctttttgca atcgaggtaa gctgcaccgc caataaaatc agggtattgg ctgagattac 71280
ctttcagatt aagccagcta agccggtagg ttttactgta gaggttaccg tgcaacgttg 71340
gcgaatagac cgaaatgaaa tggaatgttg cccaactggt tgggtcttta ctctcgttat 71400
taagaagagc agtaactact tgctgagaaa gatcccgtgc acccacagaa ctctgcatgt 71460
tatcgatggc aagagcagtc gcgataatct cgactttttc acagagctca gtgtcaacca 71520
tccggatatc ccgcatgaaa cctttaggta ccggcgctgc attggccacg ctcattaccg 71580
ctatcattac aaaacctaca ataagacgaa cgaacatatt catttactcc ctgcgaattt 71640
gtaacccatg ttagcttcac aactttcgat tacggcctga ataatatctt tatcaggaaa 71700
acgtttagtt atgttgcgtt taatatctat tacaagaact tgtgcataga tggcaccagt 71760
acgaatgtca tcgttatcag tgtcgcccat gcgcttattc aaataggaca ttgcttggaa 71820
ctggtcaccg ccattccgaa agatcttgat aacatcgcgg gacatagata cagcgatctt 71880
acaggatttt tcggttatct gttgatcacg ttcagcgaac gatggttggc aaccagtaaa 71940
catcatgatc agaaaagcga ttatatagcg tttcatctcc ttaacctctt ttgagtatat 72000
gtcaagtttg ttatgtagtg attcaaatgt tttaaatgta atatccatcc aacataaagt 72060
cctccccgaa gggaggacta tgtttagata gcatacgact ctacaattgg accgaccaga 72120
tagccaatcc atatagcgaa tacgcatggc atcaaaaagt tatgtccaat tacccaacgt 72180
ttataccaca cgggtgacca tttgaaaata tctttccaaa taccacgtgc ttccagttgt 72240
atataaaggt agaaccagat ggatgtacct atgaacataa ctatcgctac actctcatga 72300
taagcagaaa tataggcggt tactatacca actataaaag caaggtagta tgacattaag 72360
cctccagttt agcaaatgcc tcgtctaaga aaatcttgaa tacatctctt actaccggat 72420
gagctttagt cattcgatta tagaggtcca atttctcttt gaggaagacg ggcgcaaact 72480
taggagcatc atcaacgatg acatacacgt tggtgagaga ttcaataagt ttgcacgtct 72540
gtgtaacgtc acaacattct tctaattgcc gatgatacgc atcgattcga actttccgag 72600
gagcatcaaa attcggctgc gttaaacctt gtacaagttt ggtgatatac ggcgtgaaat 72660
gagttagaac gtcatcgaga gtccagctac tatcttcgac gatgtcatgt aaccacaagg 72720
cagcctgttc gccaggacca agtccaaaca ttttaccgat ggatgctgca ttgtgcaaat 72780
gtgtccatac cggtagccca gaacctttac gtcgttcacc agaaccgatc gtataaccta 72840
caccaatagc tgctgctaac tctactgtgt gatgcccttt ccatagcgga agcacgttcg 72900
ccgggatgcg agtatccaag atagctttaa cttgctgata tgcttctgct acaatatcca 72960
tcatttactc cacgttaagc gttagtacta ttgaggaaaa aggatcttct cgttaggatc 73020
aacaaagaat ccacaattaa cgagaattac gtccatccaa gttttagttt ggagaatacc 73080
cgtttcatat gcatcttcaa gatcgattag atcaagcgga tcgaatgaac cataatagat 73140
cggaccatct tcaatctgca attgatagaa tcgaagtttg gacatatcct cttcgtctag 73200
ggtatcatcg aggtcttcgt cgtcatcatc ctcatcgtcc acaccgctca ttaaatcaag 73260
cacgtgttca cgataaagga attgttgacc actttcaact gtgaaccaat gtttcttatc 73320
tttaattgga atccggcgct taaattgagg ctcggcaaag aatgccctat attcctcttc 73380
aagctcgtcc gctctaccgc atgccatggt agaagaacgg atggctgtaa gtacaaccgc 73440
ctccaaaata ggatgtagtt ctatcatgga cacctcctag taatgagttc atgatcatct 73500
acatgatgta gatctgagat aatctttaac ggtaaagaaa aagatagagt accctctcct 73560
tcgggagagg gctttatgca ccttaagctt ttaatgcacc gcagttctgg gctacgtagc 73620
gaagcacttc atgaagaaga cttctcatcc aaccctcgga gcgacttcct tgacgatatt 73680
tcttaaagat cgtcaaatgg ttcatacagt ctatgtcgaa ttcatattcg atccaagatg 73740
tctctttgtc acgagttgcc gtgatatgga cgatgaaacg ttctggtgct tcagatttcc 73800
aatcaatcct cacatcaacc gagtggttat ctggaccagt gatgttgttg aggatatatg 73860
gaagcttctc tggtgtaact ttatcgagaa tgaacctgaa caatgccatt gagattgcat 73920
cgtgttcaag gatataaagt tcattacgac gaaggcgatg gaattcttga tccattactt 73980
tttccttatc gagttacata ctcggcccat ttcacaagaa cctgcgcaca gtcacggtat 74040
agctcagcag attcgataca accgcgacta gcgtagtcat taattattac gccaccgtca 74100
tgaacggtca catcgaagtg aaggatacca ggaccggtac ctacggcgat tgtccaggtt 74160
tttacttccg gatcaaaact ggtatcaccg attatcacct gtgtcccatc gcagaaatgt 74220
acatgctctt tatccaagca acttggatgc gacatgaccg tatcggtgac aaccatgact 74280
attgttttct tccacagctc ttgataacgc ttatcggtat ccataaatta aatccttgca 74340
atgagggtta gaagaaacag ttagacttta gttttaaccg tgataggttt accgtattga 74400
tcgaagttag aggaacagta tgcaactgcc tctgtaaaca aactgttcac ttcttccata 74460
tccgaaatga tgtcatcaga aactgtacct ccaactagtt ggaagtcaat gccaccaggg 74520
acgccatagc tatattcctg tacgacgttc cacagacgat cagatacctt tacctcagca 74580
acgacatagc tcaggcgacg atcaacggag cgatgatgga aggtaacagt agcgtcacca 74640
acctcaacag tggggagggc attagcagct tcacgacgga aagcgttatt atagtaaacg 74700
aatacagctt ctgcaatgcg ttgcagaatg gtgatatgta cgctggtttg gatttcggtg 74760
ttcatggaac attcctctat ggactatcga tgatcttctt tacgtatttg aatgatatct 74820
ttacgaatat caaattggta atgtaggttt ttaatgtatt taaatgcaaa aaaaagaaaa 74880
gaacaaaggg gagccgaagc tccccgtgat tcagatggag cgacgcagaa tcggatcgag 74940
actctgggta gattccagga acaccgaacg cagatcgata ccccaacgac taatggcttc 75000
agccgcagca ggccaatgct ctgtaccaag aggacactcg atggcgaaac gaggaccatc 75060
gatatcacgt agagtgaact tgttagcatc aaccagtttc aggtgttcta ccagaatgtg 75120
gtaaatggcg ctacacagaa ttgatttacc acgatgagta ccaccaagaa cagcaatgcg 75180
gagttcttta ctccaaagtg ggttaattgc attattcacc ggtggagaca ctttggttcc 75240
acatggatga atagcatgtt cactgacagt gagatgatac ttgtcttctt tgaacttacc 75300
caagattaca gcgggatcga gattatcata gtcttcacga ccggtgtgca ttacttcgtg 75360
gttaagacca agagatgtca acccattaga aagcacattg cgaatagcca ggctggtagc 75420
agggtcatcg gtcataacga ggatttgatt acggatactg ttagattgca ttttattttc 75480
cttcaagttc tttttcgatg gcgatgtaga tttctttgat ttctgagaag ggaggataaa 75540
caatttctgc ccttctattc caaacccatc tgtaataaga ttcgatatgg aatagatctg 75600
ttcggtaaac atactcatct acaccgactc cattccaatt aggagagtcg atccaaatac 75660
gacaaatatc gaacagccaa tcgagttcgg tttgaatttc tttttgaata gcttctttat 75720
cttcttcaac cattactctg taaagttgaa cgagataatg actattgttc cagatgagag 75780
gagctctggt tacgttttta taaaaatagc gtacctttct gacaaactct tttttgaatt 75840
gctcgaattc agtacgtgga agttttatcg cctgattcaa ataaatgaag cggagataca 75900
cttcgtatag atctatgttg attttatttt ttgctgacat cggaataccc taatcgatat 75960
aaagcccagc taacgccggg cttatatgac gttaagagaa gatgtagtct tcccaagaat 76020
cagaaacctt cataatcgtc tctcatagag ctttcctaat gcgaatagaa agagtactac 76080
catcgtcacc tttgaactta aacagagctg taccaggttg aagaatcgaa ggtacaacgg 76140
tgactgtcca tgtacgcgct ttcttacgac tgcgtacata atcattgata gcttcactca 76200
actgttcagt ccagtgatac ttttcgaaat gtgcaattac ctggagaata tactccttat 76260
ctccaacaaa agtagctcga tcttttagat agttggggaa accaacagtg gcgatagcat 76320
gcagtcgttg acaagcagaa aggagcagac tcataatgac ctcgttaagt aagcgctaat 76380
gatttcgata ccaatccaac atccagagag aaaggcgatg cagaaccatg tccacggcga 76440
tataccgtca aacagattga atcgttctct gggtacaaac ttgacaccag atttcttctc 76500
attccaatct atgtctatcg tcgaatagac tggatcgaca ctcactggaa ttggttcttt 76560
caatggaggt gggacaggaa ctaacgattc gatgtcgcga taaatatcac ggacgtccgt 76620
agcattcatt cgcggcttcg atggtttcct tgtagtagtc ggggtttccc atgatcgcct 76680
tatatggttc cttgacgtac gcggcgtagt attcttcctc ataagctatc ctcgtattaa 76740
tatcgccatt aagaagacga taaggttgcg caccgatctt ctctgcaaag gctctaaccc 76800
gagcgacagt tattgggtaa gcatctagac gctttttatc aagagtatac aggacactga 76860
tatcgtaatt gaagaagctg ttatttagac taaccccttg ttcaattgct ttatcataag 76920
ctgtctcaag atagtccagc ttattgttta caacacgcat ccattgatca atacggaaat 76980
cagattctgc aatgagccga ggggttcttt cgatgctccc cttcgactca aatgtgatag 77040
aatgactttc caaccatttc tttgcatcgg gaagacgatc tgaaataact tgtggaccga 77100
gagcagaggt cgtacaaaat tcagaaatga attcgtcaag cagacctttt tgtgtcagtt 77160
gttcaagaat tttcatttaa accgttccag gaaagtccaa cgttcatacg cgctatacac 77220
acgaagacca ggattagtaa ccagttccag ttgtccacct tctacatagg ggcgcatcgc 77280
aatttcgaaa ttctcttcgc caccacagtt aagatctacg tcagattcga acttaaagtc 77340
ttctttaaca atggcaatga ccatgttatt tttaagatcg ctaccactat aaacagggcg 77400
agggaaaaga acaatcattt caccggcttt atagtcaatc ttaccagcag tcatggtttc 77460
aaacagaact tcagttcgat ccttcagatc ttccagcgta gtcggcagat ttttaccacg 77520
aaggaatttc aatccgagat catgacggta gacagtaact acgtcaggat taaaatcgag 77580
ttcttctgga gtggcatctt catagcagag acgtttaaag tcttcagtaa gaccacactt 77640
acggacgatg tcaaaaacgt cagtcggttg taggggagtc tctttacgag gttccagcgg 77700
agatacagtc aaatcgattt cttgagacat tttcgtttcc tgtttatagt taataacaca 77760
ttatcagtta actcggtatt ttctaattcc gagaaaaaag ttcacgccag cttcgtttcc 77820
atttgtagtt aggtgagtat atactacaga aaccttcatc tgccatgaag attggattaa 77880
ctcgttcaac gatttttaca attgcgtgag ggctatcaga attagctaga atacattctc 77940
tagcctcttt cgtgtaagta ccccaatcat caatgtaacc ttccttcagc tgatcaactc 78000

-continued

```
gaccaatcca acaccgaggt ataaacagac aacggaacca acccacgaat agaatatgga  78060
tcaaccacat tgacagaagg agagaacaga aatataacgc tgtaaagaac gtgtgtccat  78120
cagatgcatt agctgtggtg agttcttgcc aaccacgttt aatccaacta atgggattcc  78180
accaaacaat ttctgtttta ggttgactag cgtaacggta aaatattgac atgtttatcc  78240
ctctacgtca agaatagttt cccaggtttt atccgtctga agctggatct ttatttgatt  78300
gacatacatc tgatccgagt attggcggaa tatcgtcatc cggattttct gccatagtgg  78360
catataacga cgatagctga tggtgaagcg ctgatttggg tcatacgctt caatagcttt  78420
cctgattgtc tcagcaaaga aagcaaacga atatacattg ttgttataca gcaatgcagt  78480
tatggttttc ttagagccga cgaggtttac cttcatggaa gatgtccatt acgtcaatgg  78540
tagtactata ctcgacacga gcatatccag gttcttcaaa gataacaata ttgaatccat  78600
cgtcacgcca gataaactta aagtagttgc gaacaacact gatgagatct tcttggaact  78660
ctggaagatt atgttcggcc cggataagtc gacaaagttt ccaaatggcg ttatcgaact  78720
tatagtagac gcgtcgccct tcttcaccca tttcttcaga taggatacca actgtctgaa  78780
gaataggaga gagaacctta tcggtcttcc agttcaatat caggtatagt tcttcactat  78840
ccaaattacg agtcaggaat tttagagctt gtgacatata ttcaccttct tgacaaaaat  78900
aaaaaaggga gctagagctc cctttatgtc gttatacagc gtcttcttta gcagctgctt  78960
tctcttcttc ttttgctttc ttgagaagat atgcgttact gatagccttc caagatagta  79020
cacgttggtt ggacttaaat accagacctt cccggtatcc acgcttgttc ttaaatgcag  79080
atggaccttc agccatagcg agaacatctt taacagacat ttccttagaa ggtttccagc  79140
acgggtcaag cacgggaaca taattcagac caaggtcttt tacaacagct cgtgcttcgg  79200
ccggcaggag ttcacgatta ccatcctcat acacgttgaa gatgtaataa tcgtaatcag  79260
ccacttcttc aaagttatct tgaatagatg gtccaatcag ttccccttgt acagaaatga  79320
agcgaccggt gttcttgtgg aacttgagaa gacgttcgat gatctgttgt tggttagtta  79380
cacgtacgaa gttattgtct tcgatagcgg tacctttcgt ccaaaggggc agaataatac  79440
cattacgaag tttaccttct ggagtaaccc aggtcttctt acggaacaga ttacggttac  79500
ggataaggaa gttaccaacc caataccgaa gctgctggat gaatccccac ttctcaccgc  79560
ccattccgag ttcgtagttc cgcgaacaaa cgccagtacg aatacctttg tcatcgacac  79620
agaatacggt catggagcta ccatccagct tataggtaac ttccatgtca tcaccgtctt  79680
ctttcaggtt ataaaacgca acggtcttat tctgaatgcg gtcttgatcg gacttagtta  79740
gcatctcagg ccacggtttc agagcgccac ccagattacc aatcagcttg gcaccaagtt  79800
taacgatcca cggagcgtta cgtgccgcat gagccttcga taccatcgga ggagcagact  79860
cgtacttaag gatacccagc ttcagggtca ggttagtatc aacgggttca tctttgaact  79920
catcgggaat cggaaccagt agtccttgag agagctcttt acgaagcttg atagttttca  79980
aacgatgata gtttttaccg tctacacgtc gattgtcgga ccgacggctc tcaagaaaac  80040
cgaagagctt aacgttatcc agaggaagaa gagaatcaat ctcgcagtaa atagcgcgat  80100
cacctttctt atattcgccc atctttacac aaagttgcca accaccaaca atagccaatt  80160
ccagagcatc ggcattaggg tgtttcacaa catcatcgat ctcaacaatg cgtgcaagct  80220
tacgagtttc ttctactaca ccaaaacctt cgcggatcgg tttcaattca tccatttcaa  80280
tcgtcatttt atttaccttt atcagtgatg gttgtgcgaa cgtcattacg gaaccgccgc  80340
actatttcga gtatttcttt ttgatctaca taacgaatgt ctgtcagttc aatttcacga  80400
```

caagccaatg aaatttcagc ttcaatctga tctgacaacg ttcgacgtaa accatctatc 80460
gttactttac ccggtggcgg cggcgctgcg atcatgtatt cacaccccag ttataatcat 80520
agaaggtttc aacgaaagac ttaccaggta gttcttgtac gacctgctct gtgctattta 80580
ccaaggttac agcttgctca aatgggacag gatgcccact taccggcgag atgatcttgt 80640
aaccattctc gcgtaggtga tcaacgaagt tcaccatacc agtttcaaga ccgacattat 80700
aaatatcgtt ctcctggttg gtagtgattt cataggtctt tccagcaggg atatcgacaa 80760
tgggagtacg gtcgtcactg gtacgtgcta cgtcgcccat tgtacgactt acagcccagc 80820
agaactcatt gagaactggg ttcgattctt gccattcttt cttttcatct aaacggtctt 80880
tattcgacat tgcagttacc tcgttgtgga tacaagagag taatatagat ttgaaatctt 80940
ttttatgaca taaaggggag ccgaagctcc ccatgtctat tacagagagg tcgcaatccg 81000
ttcccggatc ttagccatcg tgtcgtgctt gtagaactca ccattcttga agaacagttt 81060
aagttcaccc gattcggttt ccaaagcagc ccagctaagg tcagcttctt gttccagaac 81120
gaacttacca tcttcggttt tcaccacacg caggaaacct ttagccgact tcttggaaga 81180
agcagcttta ggatctttgt acagttcaac gaactcgtct tcgatctgaa cagcagtagc 81240
tttgacagcc atgccgaaag tatcgcgagt gttgtactga taggtgaagc taccgatacc 81300
aagaactacg ttgctagaag cgaagccttt acgttccagg cgagacatga tctgctcggt 81360
acggtctaca gtgatcgagt caccatagat caggccaacg tattcgttca ggcacttgaa 81420
gcctttactg ttctcagtgc cgccgaagga gtcccacagg acttcaattg caccacgtac 81480
ttccacctca gggatttcag tctcagagag gaagtcagac agactgacag cgaggtcgtt 81540
gatctcgtag tacttaccac ctacgctaac aacttcgtaa ccagcgtact caatggaacc 81600
gtattcggca atgtgtttct cgaaatcaac acgatcagcg aatttaatcg gataagccat 81660
gtagccagtg atgactttaa ccggatcacc agagtcagga cgtacaacaa ctttcgccag 81720
acccagctcg ttcttcagac gactttcgat ttctgcacgg atgctcggga gaacatcaga 81780
gataacaccc cagaaatcga aggaatcaca gaccagcgaa ataatgcctt ccgggacttt 81840
ctgaagaatg atctccagga tatagtcacg ttcagcttcc agtcgcagtt ggtcatgcag 81900
ctccggagtg atcacagtac cttcctcttg gaggaagttg atcttcattt gcagacggta 81960
caggatgttg gttgtggcga cagcgtgttc agttgcagta actgatgcac ccaacaattc 82020
agtatcactg ttagcaccgt aatacatctc agcgtaatcg agagccggga tggtatcggt 82080
accagcgaag ctagtcaggt gagctgtacc agaacgcatt gcatcttcag gaccactcat 82140
accacggaag ctgaagtcgt gtgcctggaa cttgacgtgc tcacggttat cgcaggtgcg 82200
atcagcgtag tggttcagta cacgctgata ctcagctgca atagttgcgt tgcagatcat 82260
cttccagttg taggcactga cgatggtttc caggtagttc accagccagt agtgatcatc 82320
gtcacccagg ctgttgtaaa ccacaaaggt aggtacgcca acatctacac gttcgccttc 82380
gtcaatagcc agcacagtca gaggcaggta acccagagca tgcagcttgt acagacactc 82440
gtgtttgata acgcctttac cgcacatgtt gtcgaaacga cgtgcagcgc gtttaacagc 82500
gatttcacga ggcagattga agaaggtacg atcccacagt tctaccagtt cgtgccaggt 82560
accttgcaga ccgaagttaa cgactttgtt gtcgtagaac gcagagcaag acttcgaccg 82620
caggaactgc ttagcagaac gtggggtgaa gtttgcatac ttacgttcgg taccttgcgg 82680
gtacagagcg ccatggccgg gcttgtagca gtcagttgcg gttactgcat agagagcatt 82740

-continued agacatattt ttgatcctcg gattagaaaa cagaatgaga gaagaatttc gggtcacgta 82800
caccatcatg ccgataatca tttacagcgt taggatgata ggtgttagtg gtctggatat 82860
aatcgtagta ttcgttcagt tcatcgaaac ccttggagaa aataccatgg gttacaaaca 82920
gacccaattg atctacgatg cactgctcgt ggataacctt agcaagttca atgaacgtgc 82980
ggccaccatc acagatgtca tcgataacca acagctttgt caatcgagga acgtcatggg 83040
cattcaacaa agacgtatga gtgatcttac cagttgacag ttcacggttc ttacaagcgt 83100
acagtacgcc agcagcaccg atctctttcg caatggcttc ggtcttttta cgtgcacctt 83160
catcaggggc aaccaaccac cagtcactcg gattttccag aagttgtcct tcgacacaca 83220
cccagctttt gatgatatct gcttgggtaa tctcgcggca attgttgatg agtggcagcg 83280
acacattact gtgcggatcg tacaggtata cagacgtagc gtccaatgca ttgatcaaac 83340
cagtcatcac actaatcgac agaggttcac cttcatcgca aacacgatct tgtcgtgcgt 83400
acggcagata accaataacc aagtgtattt caggacgaat acgctggcga cgaatagcgt 83460
cgaataccag gaacagttcc atgatatcgt cactattacg aagccaagca ttgattatga 83520
atcgttcgcc tttctttctg agatctttca gagggatctt gataccgatc tcaccgccag 83580
ggaatttaaa gggttgacaa tcgtagtgat ctgccaagcc gttaccgtga agctgagtaa 83640
ttcgaatcat ttatttttcc tttagggaag aagttgggga ccgaagtccc cgttcgggtt 83700
agcccttgac gcaaacaatc tgacgcaggg tgtggacgat ctcaatgagg tcatcctgag 83760
cagccattac gtcttcaatg ttcttataag cctttggagt ctcgtcgatc acgtcaatgt 83820
ctttccggca ttctacaccg gcagtatcac gagcgtggtc agcaagagtg aaagtcttag 83880
cggcttgggt tcgggacatg acacgtcctg ctccgtgcga acacgaacag aaggactcgc 83940
ggttcccttt acctttcacg atgaagctct tcgcgcccat cgatccagga ataacgccca 84000
gcataccctc atctgcacgc actgcgcctt tacgagttac ggatactttc gcaccgaagt 84060
ggttctcgaa ggagacgtag ttatggtgac attgcacagc tgataagctg gtattgattg 84120
gtcgacccat gtaatctgca actgcctcga tagtggcgcg catcatgatc gtacggttga 84180
gcgtggcata acgctgagcc caatgtacag cttcgatgta gtcgctgtag tacttggtac 84240
cttccggtag ataagcgagg tcctgatcag gcaggttgat gtggtagagc cgcatctcct 84300
cttttgcttt ctcaatgaag taccgaccga ttgcgttacc gatcccacgc gaacccgaat 84360
ggagcatgat ccaaactcga tcttgttcat ccagacagat ctctacgaag tggttaccag 84420
tgccgagggt accagcatgg ttgaatgcac ggttagcagc cttacccagt ttcgggtgtt 84480
tagccacgat gagcttcagt tcctcttcaa gcttcttaac ctgagcttgg agctccggtt 84540
cgagtttctt gtaaacgagg ttgaagtcac tccatgcacc acggtcattc gggccaccat 84600
tgtcagtacg accatggggg atacgggatt cgattttata acgaagatgt tgcagaccat 84660
gagtcatgtc gttagctgtc agatcagtaa gctggcatgc aatcccgcac ccaatatcga 84720
cccctaccgc agacggaatg attgcacccc gcgtagcgat tacggaaccg atggttgcac 84780
cggtaccaag gtggacatca ggcattacag ccaaatgctt gtaaatgaac gggagtcccg 84840
cgatgttctt cagctgacgt tttgcatcag cttcaacagg gacgccttta acccaagctt 84900
taattgggaa ttcattttgt tcgttcagca taacgtattt ttgagtagtc attgtagacg 84960
ctccgagagt tttaaggttt aggaattcaa cgatttaacg ttgtgccaag gtcgggatcg 85020
cagaattcca aggataggta gagtaatgtc atgcctatcc gtattagata agacttttga 85080
gtaaattgtc atcagtccga ttcaacggcc atggataact ctttatgttt ccttcgtctt 85140
tcaatattag caaaccatgg tcttacactt aaccatattg caggccaact gagaatagcc 85200
gctacagcca tccacactgc actgagtagc acccatgcgt cgttaccatc gtcaacatct 85260
cgtggagcta tgtcgagttg atagtcagtt ccaacgggga catggtgata agtgtaatca 85320
cctagcttag tttcgtatac gaaggggaca cctttcatct tcccttccca acgacccatt 85380
agctctgtgt agatcccatg tttgtatttg tgggtctctt cccatttcca ggtcaataca 85440
acctgggtct tacgtttggt tacgtagtca gagaagaatg agttgtagac tgcaccaccc 85500
ataaatgcta agcagattag gtagagcacc acacaacgca gtttaaccca cttggagatt 85560
ggtacatacg gctcttgttt catagtcatc gtacagccga ttgcgtttgc ataacccaag 85620
ggattccttg atgccattgc atttattgcg gctgcctcca gagttatact catttaggat 85680
tctcatggat aagctggaat gtgtcgaact tgtattgatc aacgaagtgc cacgcgagtt 85740
cactcagctt aaagatatcc ggacgttcgt atttaccgaa gtcgggtttc tctttagcca 85800
aatggaaatc gatgaaacgg tccaatacag ggcaacgatc gatcaagtct tgttcagtgg 85860
aacctacctt acagttgacc agttcctgaa tacgtttgta caaggtggga tcagacagaa 85920
tcggtaggag ttcatggaat accatcggtg gatgttcacg actagtctca acccacaatg 85980
ctgctaacag tggacggaga gcatagaagt atttcttcat gcggactttc tcatccgaca 86040
gccaacgcat cttggtttgc ttggccatgg agatatagtg catgaagctc gattcgggaa 86100
tgaagtgctt gatagcgtaa tcacgaatca gtttgtaatc ccattcgttc ttacggtaaa 86160
cgatcgggga gttcaaccac tccaacagag tcgggttaga cttgtaagcc agttgaagtg 86220
tcttggtgat actccaacca gccagatcga gttccttgga aaccatctct tcgatggtgt 86280
cacgaccttc gttatcaacc cggacataat gactcggatg gttaacgtag atgaagcgaa 86340
catcgtagtc actattagta gaagcgaaac cccaaccacg actaccggac tcacaggcgt 86400
aaatgatctt tacaccatac ttctgttcga tacgagttaa ctcggtgtct ataactgcac 86460
gcatctcatc actaacaggg tgacgtggat ccatcattca cctacctttt caagtttgag 86520
tttctcttct ttacccgtgt ccaaatacat gaacatcgaa tttcccagta ggttgtaata 86580
catccaacct tccttaacca cttgatcgcc atacgtcaga ggaatgttca attcgtaaat 86640
ggcgtcataa gggatgacta caggatcttt gtcaggcttg ttgaggacga gtgcatcgtc 86700
agtaagctca agccattgct tacgactgat gaccccaaga ccgatactga attcgctacc 86760
tgggtctttc ccattgaaga taccacagcg aacagcagga tcaactcgat caccagcaat 86820
accgatctta agagggtcag ggtctacgcc catcaattca acaaccagtt ccagttgacg 86880
cttgagttca atcttgttca cagtgtaaat tccttcgtgt tgtattgacg tgcagagtcg 86940
gtccaccatg taggtgtctg tgcgtagtag tattcaccaa agatacaagt ggctaaggtt 87000
ttatccaaag cttcctgata agacatctcg ccatctttag tagcgaagtg aaccatgttg 87060
ttgaagcagg taatgatgtc agcgttttct tttgtggaga aaacaacggt acctttggct 87120
cccacttcgg aatggatcat cgagctccac ggacgaacac cacgatcagt gaccagatag 87180
atatcttgta cagccgatat ggagaagaac gtacgaagaa ggttaccgta atcgggtagg 87240
tcttgctcga acagaatatc gaggatctta cagaccttat cgatcttctt catttttctcg 87300
gtgtaacgcg caccaccatc attctcagtg caaccgatat tgaagatgat actgtaaatg 87360
gattccacaa gcttacagca tttgtagacg tacggagttc cctttacttt aggagtccat 87420
acgaaaagat tgctctttcc tggattaggt tgcttgaact gatggatgcg gtacggaata 87480

-continued cctttttcaa acagcatgaa gtccattatt ttctccaaag gaaataaagc ctccacgaag 87540
ggaggcgttt atgttaaaca gcaactttac cagcaatgtg cggatggaac tgataatcca 87600
gaatctcgta atcttcccga gtgatatcaa ggaaaggttt acctttggcc tcaggcttga 87660
agcggatggt aggagtagga taagtattcc gcgaacgttg cagagtaacc tgttcctcat 87720
ggttactgta gatgtgacag tcaccaccag tccagatgaa ctcttctgct accatgttaa 87780
actggttcgc caactgatga gtcatcagcg aatagaacat gatgttaaag ggcacgccca 87840
aaaattcgtc cgccgatctt tgatagagtt gacaactgat agctcgtttc ggagcaccat 87900
gttgatccaa ccattctacc actgcttcat cggtagcctt ttcataacca cgacagatac 87960
gcagaagtgc tttaacctgc tcagcaccac cgaatggagg ttgaccacga gtagtctcac 88020
cactaatctg atcatggtaa gcatcagctt cgaaatgcgt ttggtctaga gcttgcactc 88080
gttcatctac ggtaagttca cgggtccaga actgaataaa tgcatggcat ggcgggagtg 88140
cctgatcttc gaccaaacgt ggatcccagg cacagataat cagtcgacga ctatctggat 88200
tgttttccag ttggtaaagc agttcttgaa cctgatccac acgccggcga ataacacact 88260
catctttcgt gtaatcaaca ccaggtacgt caactacgaa cttaaagccg cgtttctcgt 88320
aattagccca gtctacttta ggaacgatac gaacatcgtc gatatcacgc caggttttac 88380
catagaccgg accaagatca ccaccaacca aacggaaggc agccaacaga ccatcgttgt 88440
ctttaatcac gatcttcgca tcgccaatga caatacgata tacgcgtaga gccatgccat 88500
agtagtcgaa tgcatcggga ccaggaccga aacgacttac atcagcccag gctttcaggt 88560
tgatcaacag tagtgccgat ttgtcctgtt caggatcaat ccacctccaa tcgacatcac 88620
cgatctcatt gctgaaatgc atctcaaacg gaatgttctt gaacttcttc tgaacagctg 88680
tagtcagcca atcatcagaa accttttcga atacttcagt acccggctta acccactcgt 88740
tccagatggt gacgttcttg ctcaggagat actcaaggcg agtgtcacca gacttcatcc 88800
agttgagttc ttcttcaacc gacggaagat gaatcttctt ggtggtcact acagggaggt 88860
taccgttacg aagatcatag cggaactgtc taccgaacaa agaggtagta cccgtaccag 88920
tacggtcacc tttaaataca ccgtacttct gggtatcttc aagtagttgt agatactgat 88980
gcattaaaca cctccatcgt tagaagctac ggtcaacttg ctaggaagac ctagagtttt 89040
atgggtagtt tcttcaatag ctttcagaag agcttccata ttaccagtag gatgacccag 89100
atgaggatca ttttgataac tgatttcgaa ggtcatgggg acatccacga catgactgaa 89160
atcgacatca ccaacattca ccggataacc cagactgata cctttaataa ccttacggtc 89220
atgaccgata gcaatgaagt ccatggtagc acggttatgg acgactgccc aagcaccagt 89280
ggattgcagt aggttacgac ttacgatttc agagattgtc atcttcaact acctttagga 89340
actttgcagt tacttggaga atgataccag attcggcacg ggcgtcatca ccatcagatt 89400
cataatggat actaccgcca tcaacccaca cgcgagcacc gttcggaaca agttcatcag 89460
ttgccatgta ttgaacttcg gtgtaatcgc ctgaactatt gctagtgcga gagataccca 89520
tcaggtgatc gcaactgggt acgatgatac ccatgttacc tgggttaatg taagcagtga 89580
cttcagtcaa cccgatgaag tagtgaccac gagacggcgg tacagtcagt ttataattgt 89640
tgaacggagt caacaaaaat ttgacttcat tagtagttgg aagaggtaaa gcgtttacgg 89700
ttggattgtt catttttcac ctttgaattt caccgagtga ggaccgaata tgaattcata 89760
attctcagtg tgtttacgtt cggtaagaag acgaatactg ttattgaatt catcatattt 89820
gacaacagct acgactaggt tattacgttt atcgtaatac tgataagtgt tatcatcagt 89880

```
gttgatttca cccagttcga aaacttcatc attttgctta atggcaatca gtttacgggg  89940
agttggaata gtaccgaagt cgactttgta tttaaccagc gaatcttcag tggtgctttc  90000
agcaacgtaa ctaatcattt cttttcctca gggtcgtagg atttcgggat accagctact  90060
tcgtagaaat gatcccaata tggactttcg tcacggcggt gcatattgaa attctgataa  90120
tccgtacaga tgactttaaa cccatctgca actgattcca cgaccggcat attaccagtg  90180
tgactgttgt cgataacgaa gtggatgtta ttattgtgtt tgtacttcag atcgaattct  90240
cgtttgcgtt caacaggggt atagctaatt aaggatgcca tgtttattcc tcaagacgaa  90300
gtttccagaa cctgccctct tctttccagg tttcacgaat agcgttgtca gtacgttgac  90360
cgtccttaaa cagcttctct acattggacg ggtaagtata gttgtacaac gcaattgcaa  90420
attgggttac agctactcgg gctggaataa caccagtgcc ggttcccatc aggcaaccga  90480
ggacacggaa agaatctttc ttttgtttac cgtaccattc acatccagca atgccatcga  90540
gggctgcctt agaggctaga tacggaacat ccgaaccttt gggtagcctg cgaggaacac  90600
gcatcgtagg ggtgtacagg agtgttgcag tgataccatt aagtttggtg aattgaacgc  90660
aagcacagga acctacgttt aactcaccgt tgtggaaacg attgatatcg tgaaccacat  90720
ttttctgcat gttaacaaaa cgggcagcta gggcaccatc atatccaccg gtcatatgcc  90780
cgtatgagtt acccgcggtc atgtagtagt caaactcgtc cgcgtggtct ccgagtgcat  90840
caagcgtacc atgaaacact ttaaggtcat gtccaagttg cttgacaaaa tcagagatag  90900
ctacgagttc ttgaaactct tcataactgg gggtgcaaaa tacgaactcc agtggtttgc  90960
gtccgatatc tacagtacca agagaaagac catcagcgat ctctttatgg atacgggaca  91020
ttacgaatgg agatgtcatt tctatacctc acgacaaaaa gaaaatagat ggagctcccg  91080
aaggagcccc ggtgcgctga cctttacgat caactacata atattacatt gaaacgcatg  91140
acatttcgcg acgaatgttt ttattatcga attcgtattc cagaaccaca ccggcctgag  91200
tacgaacgac tttaacttta gttccattcg ctgctgttgt atcttgaata gcacctacag  91260
ctttccaaca ggagtcaatg ctttccatct tagtggtggt ttcagaagaa ccaccagcat  91320
aaataccaga gacaatagta gtgctaatga gaatagctcc tgcaagagac attacttttt  91380
acctccttta attacggtaa gcttcggctt gcctttataa cgggatggag caacattaac  91440
tggtgcaccg ggaagatcgc caaaatcgag aagaggttta tcaacaacct tcagttcggg  91500
ggatttcttg atcggactaa cctccacacc aggttgatta gcaatgaaat cttcagcttc  91560
ttccagttct tttagtttcc gagtatttgc acgttcggaa acataggaca agaactgaga  91620
gaacaaatcg tcatcgttgc taaccatgtg ctgtacatgt tcaagcgctt tctctacggg  91680
aacatcggtg attcccttct ctgccagcca tgccattaca tctacgatat caatgctgac  91740
ggtaccaggc gcaccattgg caatatcgcg gaagggatga acatacgtcg gattctcggc  91800
atcaaacaaa atccgatcga cattagggaa cggagagaac acacttgcat tctcagagat  91860
ctgcacattc acaccaatga aagaatgcca tggcagatgc aaacgagtag gcatacccga  91920
gaaagcaatt tcaccataga agcaatcacc cgaataatca atgtggcggc acgcatttac  91980
cgacagattg agaacgatgg taccattagt ggcattgaaa tctttcgaac gcatcatgat  92040
tttacgaagc ggttctgcca gataacctac atcgataaca cagtcgaagc gatacatgtt  92100
gttatcggca ttccagttgt agtatgcttc aaccagtttt tgattcagtg cggaagtgag  92160
tttgatcatt ttgagtctcc agattaaagg aatcgttcag tgatagaagt gatcagtttc  92220
```

-continued ttttctttat tgagagaaga catgtgatca cggtatttct tgaagtaacc tacatcttca 92280
ggaccatttg ccattttggg attggccgtg agtatgtgat ggatctgggt acccgtatag 92340
acactaatgt tccatgtctt ggattccgag attattttct ttacagctgc attagactca 92400
tcgctatctt caatgagata agcatcgatg gattgactaa ccgatcggct gaattcatcg 92460
agagcactaa gatcaccttt gggaaggtta gcatgtactt ctttgagttc ttttaaagta 92520
cgcggtgcta cacccggaac ccaacgattg gtaataacat caccatcaag ttcatgacgt 92580
ggttgcagct cattgggttt ctggaatgga tacatgatta cctcaacgga acatgttctt 92640
tatgaaattc catggcttaa gataccatgg agttgtcgat gcatagacta caccaggttc 92700
gttcgaaagt aagtttagat tgccattgcc atcacagata taaattttcc cttcaccaat 92760
aacaacatcg tcttttactg gagtttctcc attaggacga atagtaacac ctcgtgaaga 92820
acttttgtag taatcgttga tagcttccgc ttcaagctgt acgaagacat tgttcatgat 92880
cacacatatt tctttgtcca gttcttccag tcgatgatcg aatgaatcct cgtcaccacc 92940
actgacaacg aagacatctg gaatgacaaa tagatctttg aataaaatac catcaatatg 93000
caacctgggt ctacctatta catcgccaaa gaacaaaatt gctcggtggc gacacagttg 93060
taaatgtttg cgatgctgtt ttctcaattc cttatagaac ttccaattag tgaaagattc 93120
cgcagatata aaagacattg attttcctcg ttgggtgtgt agggggatca aacacatgat 93180
gtagatctga gatatttttt agcgtaagta aataaaaaaa cgacatatag ccctccccga 93240
agggagggcc aaatgtacca ttacctaatc acgaccattt tgccgtaatc ttcagacatg 93300
catgaatcaa acgatgccat gtatgcgtct cgcggactat ccttagcgtc gtatatacca 93360
cggacgtctt gaatagcttt gggcaggatt ttgtaaagaa cgttatcttt gtccttcaca 93420
ccgtatccct ttagggcaag gaggttctgt ttccattttg caatgggttc agaacggccg 93480
cgggcttctg ctgtagcatg agcagctagt gctagtgctt cacaataaac ctcatcgaca 93540
cgcacctctg tagcttcagc ttgcagtgga accattaaga ttccagctac aaccattagc 93600
cgcattacgt gtgtaaaaca ttgcatcacg ttggtacctt tggttgttag gtcagaatat 93660
aatacactac agcgtatctt attctttctt tggggtagcc tcattaacgt cgatgaagac 93720
aatggaatac atcttagttc cattgggtgt cccatctgta ataagttcaa taaatgtatt 93780
ctcgtctcca aatatgacat tagagttgtt actctcgaaa tattctttaa cgttctcaac 93840
cattgaattt atagcatgtt cagtcagaag acccctacca tttattccat agagctgact 93900
tgttgtttcg taaacaatgg atctagggtc atcataacca gaaacatcgg cggataccat 93960
aaaacgaatt agttctggat ccgactttgc agttgatgga atccactcgc agttattatt 94020
gaaccactca ataaactgcg tatatagact tgaccctttc tcgatggaga gtgaattaga 94080
ttctgtatgc tgttgtatga atgtcacgag tttgtgatac tgaataacag cagtgcagaa 94140
cgacaggccg tgcgagaatt gatgaatgtt tacggacata tgctctccta ggacttgcga 94200
ttaactttac gttgcaaact agccaatgct gtctgctggc gttcgatgat ccgtcttgat 94260
tcacttagca tttttactat agattcaaac tggatcgcca tatcgtctaa acgctgctct 94320
agtagagcta tacgttcact cttatcaccc attaaagttt acctttatag tgaatgtcgc 94380
catgatgggt attgttccga tacagcagag ctggatcagg ttctcgattt gcgataatta 94440
aattaaattc catcgtgaaa cggtttttca tatatcgctc agaaacttca acaacataag 94500
tatctgcaat ggtgtcgatt tttacagtag ctacaagttt aggcgtacta ttacgaagct 94560
tatcccaaac ctcgaacgta agattgtttt cgtatcgagc agttgtaggt attgtcttga 94620

```
attcgaaaac gtttaatcca tctggagtga agacagctac tggtactagc caaaacactt  94680
cagttaattt taaattacca tcacgtgaat agaagaactg cttcaagtcc ccttttaccc  94740
cgtggtacat tggtataata acacgttgtg ccgacattat aattgctccg atcccgacca  94800
attacgttta gatgtatcct gtactatctt aagacgtagc ttaaaattag gcatgttcca  94860
acgcgtaata ggtttcttcc aatatatacg tttcttatcg agttcaacat gcagctcgac  94920
taagacacgg tttctttgtt tttcgaagat ggtgaaacag acatgtcttg gtttttctaa  94980
ccaagtttct ttataaaact ttagtgtgtc tgcatctttt tgtgtatcac cgttgataat  95040
actttcaata tctacgtctg tgaattccaa tgcttcaata ccattcttac gaagtgattt  95100
aaagcgctca gaataggttc cacggaaata gtattcaaga tcaacaaaca cggagtttaa  95160
tcgagtactc atatatcctc agattgtaat aatctacagg attggttagg aaaataaaaa  95220
aaggcataaa gcctcccctt agggaagcga tatgccagat ggtgttttga tatgaataaa  95280
acgttttctt aacccggcaa tgaagaatgg atcgccagca aaacgacctg ttgctgagtt  95340
gtatctaaac caataccgtt tgaactttag gaagcgacgg cagttcggtt tagcctgaat  95400
tgtaactaac cattcatcat cgaacaagtc atccaactcg actgtaatgg aataggtatt  95460
gtcaacccta cctttacggt ctagtatcga tatacagtct gttagatcac catatttaaa  95520
aataacatgc tcgaagttat tgtctaaact aagcggtata gttagttcca ttatcaacct  95580
ccaaatcgaa tgttacggaa ataaaccgtg ttcgataact tggacttaca aaggtttcaa  95640
aatggtttga accatactga agttcgatat aagcaacgac aataccttgt tgatcacgcg  95700
gaacaataaa gatagtgtca accaaaccat ctatattttt tgaccgactg atagaccaat  95760
taaactcgtc tgtaacttta ttatcggaga ggatctctac tcgtgttatt gcctgttgta  95820
gagtgagatc caattcttct gtaaacaggg agttcaactt ccctctgtaa accgtaaata  95880
aatcgatgtg tgtttgcata gctgagtcct cgatagttca ttatagtacc cagctcaagc  95940
tgggattatt tttgtatggg ggtgtcttta aaaaccatgg aaccaattag agtaagtgct  96000
gaggcgcgcc ctggattacc tgattcgaca ataagaatgt ctctcacagt gtgtcaccca  96060
tcgctacacc gacgtaatga ttcattaacg gcgccttaaa gtacatgttg ttggcactct  96120
tcattttgtt tttgaattgg tcaatgatta cacgttcatc ttcgccattt gcttcgacca  96180
gatacatcct gagatcatag atccatttaa ggatgtcatt ttggtcttgt tcctttttat  96240
gacgtttctt cccaattcgt ttctttagga agatactgct tcgacgtggc tttagtttac  96300
gagagaaagg aatagttttg attaccccgt tctcatcaat gaccttcatc ccttctgcaa  96360
tgacatccat gtaatagtca ttgtgcagag ctatctgttg atgcatattg tccatagctt  96420
ctttatgatc gtacattcct atttccttta aatagcatag acaacatatt accccatcct  96480
atccggaagg agtaatatgc catttcggtt tgagggtgtt gcttacaaat ttgcttccca  96540
gggtgacggt tctggtctac ccttatcgag ttcatgcaat tgtttcctaa ctgcaaaacg  96600
tactcgacta taccataggt acacattttc cggcataaaa gacgagagtt ctttagctaa  96660
gagtattgca tatctttgag ctgcggcatt ttcttgcgta taggctaacg agaaaatctt  96720
cgccaataca tcggtattac gatgccattc gcggagctct cttgcaataa tgtcgcagtt  96780
acgattatct ccaattgact cgattaggaa acatgtgaat tcatcaccta gtccaatact  96840
aacattagtc aagaagtcaa tcagagcaat agactctttc attttattag ggttgaacaa  96900
cttccgctta ggatcaagtc tttgtagtct aaaccacatc gcttgtgtac cttcacgatg  96960
```

```
tagtgaatgc acttgacgga aaccccgcca catcttaaat aatccaatca tcaggacctc  97020
acggaatata gcctgtcccg atggacaggc tatttttatt taactgcacg tgcaaggttg  97080
tagtcagcat ggaaattagc gtctgcaagt ttccattcca acgaactatc tacagggtta  97140
ctatagaatc ctgctcgtcg agcttttgct ttaacgatgg ggtcaactat ctggactcgg  97200
gtaatgaaag ccaataccca gagtacccgt ttagctatta ctttaaccaa tcgcagcttt  97260
ttcattattg agacctcgac cgaccctaat ggaaggggaa cttacagcgc tttcaacgct  97320
tgctgatgtt cccatacgat ggtcttatat tcaacctcaa gttctacacg ggcgtcatta  97380
gaaatgctga tatctttagc attcccaact acacgacctt tacgtacagt cagaccccat  97440
ttatcgatct tgtcaaggaa agccttaaca tctttacggt gtttttcttc cagcttggca  97500
atccgaatag aacgaacatg gttacggaac cattctttga tagacgcgaa cattgtaatc  97560
tcctaggata attaaggaag ttggaacatt tcaagtttgg atgggtcgcc ggaaagtata  97620
ccatcagcat cataggtaac atacgggaca tctaattcaa tagctgtctt tctcttgtgc  97680
tctgtgaatt tagtcccaag gacacaaaag tacgtattac ctgttacaga cgatgttact  97740
ttcgctccta gatctttata gtactgagtt atttctttcc tcgacatctt accaaattgt  97800
gaccccgtaa tcattactga tttacccaca agtggacctt ctggtttctt gggagaaatg  97860
atatttaccc cttccagatg tttcttatag gaggactgcg gtcgtgagtt atcctcgtcg  97920
aagaactcga atatactcat tgcagttata ggaccgatat catcaatctg ttcaagctcc  97980
tctgtagtgg ctttactcag tgcttcaaga gaaccgaagt gctgtgctaa cctaagagcc  98040
gtgcctttgg caacattact aataccaaac gccatgatga ttcgttctaa ctgaatacct  98100
gctctaactt tgttaacttc atcaatgatc ttatcggcta ttttctccga tacattcagt  98160
tgaagaagaa tatcttttgt cagacacagt agaccgaaca taccttgagg atccaccatc  98220
ccccacctat ataagtcttt gatcatctca ataccaatac cttgaatatt gagaacttct  98280
ctgcttacac aataggcata atggttaata acgcgatcag tacatatggg gtttgtgcaa  98340
tataattcag tacatccaga tgaaccatta ataacggtat caacttgatt cttacagcat  98400
gggcacactt tcggaatttc aacttctttc agttcaccca tccgcatctc agttaacgcg  98460
ccagttattt tcgggataac gtctccggca cgctttacaa caatcttatc acctatcatt  98520
aagccaaggc gacgaatttc atcgatgttg tgaagagtga cattcgagat ggttgtacca  98580
tggatataca ctggttcaat gcgagcaaca ggggttaact taccagtacg acctacttga  98640
aattcgacat catgtaaagt actcactcct tctgaagctg gaaacttata agcaattgcc  98700
catcgcggaa aacgacttgt tgtacccaac tctatccgct tacccatgtc gttgactttg  98760
aatacaatac catcaatatc gtagccatag gtatttcttt tttctagctc ctcttccaga  98820
atttcttccc agtaaccgta ttcgagcgct ccgggtatag caccatcgtc gacagatacc  98880
gacgaaaaac ccatttgtcg taataggcta gcaccttctg tccaagtcgc gtagtggaga  98940
tccgacgagt caagcgaata cgcaatgaac tcgacacccc tagctcttgt ttcaattgga  99000
tctttgtttc ggagtgcacc ggaggcgtag ttcctcgggt tcgcaaattt gtcttttcca  99060
gctgcttcga gttcagcatt gactttttca tagtgctcat gacttacaat aacttcacca  99120
cgaacaacaa cacgttctaa cggtttacta atatcgagtt tagacggtac ccctttaatc  99180
tcaagtgcat tcaaagttac atcttcacca accaatccat caccacgggt gattgcttga  99240
tgtagagaac ctttaacgta aataagatcg agggaagcac catccagttt aagatcgcgt  99300
gttacttgac aacgaggagg tagggtcttt aaccaaccaa ccaattcctc tacactaaat  99360
```

acgttatcaa gactcaacat gggaaaatca tgtttagcct tggtgaaatg tttagcggcc 99420
atgtaaccaa ctgtttgtgt tggagaacta gctgtaatca gttcggggta tttctcttcg 99480
agatcgatta gctgtttacg gagttcatca taaaccgcat cagttatagg agatccgttt 99540
tcctgataat acttcttatc gtaatcacgg attactttac agagtttggc atgttcctgt 99600
ttatagttac tcaactttat tcctcgctcg cggatacagg tcgtcgatgt atacaccggt 99660
ttcaccaaaa aggttaagtt tatccataga cttgatccag tcaatcaaat ctttatcgaa 99720
cggacacgaa cttacagatc gtaccatgac agcagcttct gttgcattac ttgtaataca 99780
tgcattctca cggaaggacc aacccataac agcttgtcca ttagcatagt ggtctttacc 99840
attctgtgcg tacgtaagaa taccacgatc ggtcaggatg taaatcttgc cgtggtcgtt 99900
ttgtagatcc attatgttct taagaacggc ttcactttgt ttatcaccct ggggtacatg 99960
ttcggtaagc tgttctagat atttcccaag aacatcaatc tttttgtcta gatccttacg 100020
ttgcacgatc gctcgtacat taaaataatt tccattgtag aatgctttcc aaggtttctc 100080
aaatggatga actttaagtt cattattact cgcttggata atgaccgctt cattacgacg 100140
aacgaacaaa taaccaacca tgaacaaatc tccgatagtt atacattttg ataatgtaga 100200
tctgagaaaa aataaaaaga aagcaaatgc tcctacccga aggtaggagc actatgtttt 100260
aaacctttac acggaactta gaatcataga gatcttggaa ctctttgatc attgcccgtt 100320
gagtcggtgt ctcagttgca tcattaaaga actcatcagc gaattctttc ttcttgcgaa 100380
cttcacaacc aaacagttca agaccgagac aatcaagttt atttttaaag tgacccagtt 100440
cagacaaacc agattggtcc ggcttggaga cctctttctg cccctcgggt ttaacgcgga 100500
aatccgttac ttgggcgtag cgaatttcct tttcaggtgc aggacgatgt accggatctt 100560
tcttcttgtt cttcactcgc ttaggtactg taggcatcgg aagaacagtt ttaggtacag 100620
ctacaggctc tgccttcttc ttttctttct tgggtgccgg tacagttgca ataggacctt 100680
gagcagcaat aaggtcttta agcgagttga atttaacgcg tgccatgctt gtattctcct 100740
attggtggtt tgtagttcac atttgtaata tagcctttaa aaaggcttaa atgtaaacca 100800
aaccacctta ataaattata cccgaggcag aataacctta tctgcctgtt tcatgtattt 100860
accaccacga tctgcatagg aagtttcaca atcttgatcg agatcatgga acaccagttg 100920
caaaacacct tcatgtgcat agaacacgtt agggcgatta gtagtgttct ggaactcgaa 100980
cgtgatatgt ccttcccaac ctggttcgat cggagtacac agacagttcc aaccagctcg 101040
cgcgatggta gatttaccaa tacacattgc gattacattc cgaggcattc gaacatactc 101100
tttcgaatga gtcagaagga aaccacctgg gggaactaca actttatcac cgtagactgt 101160
atcaaacaga tcagcgctga tgttcttgta atccagtaca gggtgttcaa gttctttacc 101220
tgttacccag gctttgaaac gttgccaaag agtgaactta ggtagagact tgaatacttt 101280
aaactcagta ccagctcgaa gatcataacc cccagaggac agaccatagg aagcgatacg 101340
ctttccatga ctatcttctt tcactgacga accgtgaaat ggttctatca ttggaccatg 101400
tgcaccgacc attgtgcctt cgcagtattc acgaattgtt ttatcagaga gaactgtcat 101460
tttttaattt acctgttgga gacgtacact attaacatgg tcagtaaatc aacactctac 101520
cagagtctct tcgtcagatt tatcagtcag agttgcgaca tattgcttca gagcagctgc 101580
acgatcttgc tcttgtttac gcaggtcata cggaccattc tcttttacca tgtattcacg 101640
gaactgcatg acgccttgaa cataaccttc cgggagaaca gtagtcagac tatcggcagt 101700

-continued tactttacgg gtgcgaatag ccttaccagt ttcaagaaca tggtggatac ggatgagctg 101760
acggttggtg tcaatacgct ccgatacaca cgggaagtaa acgggatcat cgccctgctt 101820
actattgccc atgtccactt cagcgtataa tgtcttacca tgattagctt caaagaaagc 101880
tcgtgcttcc ctaatacgtt tcgtgcgaat aatctccgct tctctaaccg ctttctgatg 101940
tgctggttgc aggaaaggat tcatctttcg aacatgtcgt cgaatcagtt tggtgctata 102000
acgcggcgag gtatcggcca tagcaacaag attgttgtat gcttcgatgg acatgataat 102060
ttgttgcgga tcattattgc gctgcatggg aatctccgtt agtggtaaag taatgcttct 102120
tgaggtgatc cggattaaac tctgctttac ggaattcata tttctcagcg agttcaatga 102180
ttggattttc atctcctttc attgacagtt tgagtttccg acgaacccaa tcctcagatg 102240
ctttaattgt cacggctttt ctccaattga taggtgggag ctctttttcc gaagataacg 102300
tttctacaag agaagcatcc acaaacagtg ctcttcggtt ccgacccatc gagcgaaata 102360
gcttgttgca gcaaacattc atacataccc tctacatcgt tacctagtaa gatttcttca 102420
attatagtca attcaatatt agccaaaatc atctgttcat ccaatggacg ttgatgaaca 102480
tgatgccatt gaactgacgc attagctgaa tccagtgtac ctttgatttt ttccagtttg 102540
tatgtttccc ctgtgttccg tttgagttgt ttgccgaact caatcggatc aataggggaa 102600
ttcttgaata tgacgccttt tatttgttta ttcaaaatca agtatcctcg ggtcttgtgg 102660
atgatggata gctgtccagt caatcggctc gtatggataa tcaagctcgt atttatctag 102720
gaacttgatg acccatttta agtcatcatc gtagtacagg ttcttacgga taggaacacc 102780
agcattaaca cttaagcgaa ctgctgtgtt agtaccgccg tctaccactt cattctcacg 102840
cttcccctta gggacggcat aatagaagat accagtgacc aactcatcga gagtatgacc 102900
atggatctgg aagacgttcc gagtatggag agctttaccg taatcgttca acccaccaaa 102960
actaccacga gcacaagcag ccatactttc agctgtagcc catgtatcgg taaactggga 103020
tgcatccata aagaaagcat tatcacgaat acgatagaag cttctacctg taccactagc 103080
gagatatatc ctagcaccta cctcaccata cttacgcgac tgctttgcac cataccaacc 103140
agcccgatca gaatcatagg cgtcgccaga gctaatagcc caaccgtagt ccgtgagcgt 103200
acgaccaaga cggatcatta cttcaaggat ccattcaggt acgttacgag aacctacgat 103260
tgccatgtat cccctagcca cgataacgac tcttcgatga atcccattga agccgagcaa 103320
gttccatcgg cgtccatgta cctgccggtt tggtgatagt caattggttc agatcaacca 103380
attgctcacg accattgaaa ccatgttctt tgacacgaat cttaactcgg ttaggaagat 103440
aaacagaaag taccttaacc gggataacga cgaactcgtc ataacgcatg taaacagtag 103500
tgccgccatg agcaccaacg aactgcttga cctgttgttt caggttagca tagttgcgac 103560
gagcctcttg agtatcttgc atgtgtttat cacgtaacca agtgttgcgt ttacgtgcgt 103620
gcttgtgcag agagtttgct ttctcagggc aaccagcttc ttcacagcca atcctcgcat 103680
acgccatcag ttcttcgaat gcattcgtac taagtacaat aatggattcg tctttgttct 103740
tgtctgtcat ttcaatgcct cgggattttg tagtaatctg ggccagccat gttaaagaca 103800
taatggttgt gatctttatc catcggacct gggtatctat ccactggaaa cttatgtgga 103860
atcagtgctc tacgtgctgt agcgaataca gtttccttat gtcgaatttt gtaatcgcta 103920
agaacacgag tcatggttac acacggctta catttgccac aatgtttttc atcattaggc 103980
gtctcacata tccaaatgtc gttcagtact ctcttatcta gatcatgaag aatatcgacc 104040
ttcgtcatgc cgagtaaagg gaactcaatt ggaataggat cattaacaca agataccttt 104100
tgtagattat accaagcgtc ttcgatgtac cgtatatgtg atccgaagta ggcaccatca 104160
tcactgacat accctatcat caacttgcta tgtcgagccg agtcagctat agccagcgcc 104220
ccaaataacc acggtgcaac ttgtgaccat ttggtattat caccttgtaa ctgggtactt 104280
ttcagacgtt catattgcgc ttgtactttg taagggtaga actcagaaaa cttttcgagg 104340
attacttgac gttgcctgag ttctaacttc atcttttctt cgtcttgacc agcattgatg 104400
tacatgacat ccgctgaacc ttcctgaaga tactgctgga gcatgtaagt ggaatctaaa 104460
ccacccgaga ataatatcaa tgggttcatt gctatttcca aaaagaaata aaaaggggag 104520
ccgaagctcc ccgttttagt tacagcttgt ctacttcttt cctaaccaga tcacgggctt 104580
gtgctcgttc gatccgatgg catttcactt tagcccattt acaggaagtg aaataacgca 104640
ttggacggcg actccagaac tctttggacc actggtgttt ggaatgattg ctacgcgaca 104700
tgagagtgcc tcctttggct ctacgttaat aaagccagga aacacttggt tgtagatagg 104760
catgttaaga cctcattgct ttttaattac gatcgattga atacagcgag attcatcaaa 104820
gaaattcccg ctccagttca tacggtattc gaatccgtct ggcagctgat caatatgcaa 104880
gaacttaggt gccccagcag aaacgatttt agccgctttt gaaatagcga aaccataacc 104940
ctgtccagct ggattaatag cttccaggaa aaggaagtca ccaccacgtt tgaattcaat 105000
tgtgagttca tcacccattt cattcaatac ggggctatca gtgtgaatga ttgaccagcg 105060
atcgttacgt tcttccagat ggacaaacat gtcactttta ccacgaccta tgtttttgag 105120
ctctacatct ttaagctcaa tacccaagcc attgagggtg acagtaacga gttgacgttg 105180
tttctttttc gacattagta gccccttcta gtgtggaacg gaagtgttcc ttcaatgtag 105240
cgacgttggt acgaactgcc tctaactgta attccgtttt ccctctgtac agacaaatgg 105300
aaaggtcgat gtctgtatgt agtacgctta gcaatgtatt tacgaaccca aggagcctct 105360
ctctttgact gacatctaag tcgagttcta aggctagagg tttcatagag tagatcacgc 105420
agtactccta cgattgcatc gcgcaattca acggttttct tattagaaga ctttacgatt 105480
tctataagat cgatagtttc aacgaacatt agtacaaacc ttccgaaaaa agctcatctc 105540
gtgtgcaatg ttcagggtaa cgcaactggc cagttttctt cacgtgttcc agtgcatcac 105600
ttctagacca gaagacaccg tattgatcaa tgaagccttg ttcatagtca tctgctgcat 105660
aagccctgag tgcgtccata ccaataagat cgatttgcgc attcatggaa acacagtaat 105720
gacgagaacc cgttacaatg taatctttgt aacggttagc tgcacagacg atgtagcggg 105780
tattattata cttatcccaa cgccatccag tgaaaccatc ttcatcatct tcgatccagc 105840
agcgctcacg gagagtttct ttatgtttgc gtacagctgc ttcaatgatc tttattcgat 105900
gttcgatagg gacagcacct accgctgctt tcacttgatc ccaagcgtct tcaaacgctt 105960
ctgaatgtgc cattcttttt ccttagaaac caatacggtt tgctttacgg ggagaactag 106020
ctgcatcagt gttcaatgct tcagccagag tgaagttatt accaacgaaa tccacaggtt 106080
caagaccgtt agcaatacga gcatcgttcg cttgttcagc cgtaagggtc ttaaaggtga 106140
ggatatcgaa agcacgtcca ggacgaacca gagcctcgtc aacatcacga agagttggga 106200
ggttagtaga gatgatgatc ttggttttgg tagacacaag accagcagta gcattcaaca 106260
gaccggccat attactgtta ccatcctcgc gcttggcaac catcttatca gagtcttcag 106320
taatgatcag cgagttatcc tcaacaccac gaataaagct ggtgagatca ccatgactca 106380
gtacggagtc ttggtcagcc agatagacgt tgcgatcttc ataaccacga gcacggacca 106440

-continued

```
tctcgttgat gaagttcgac ttaccagtac caggcggacc aatcaacaga agtacgttgg 106500
cctcagatgc tgcaaactca gcccaggttt cagccggaga acgatccagg aacggataca 106560
tatccatcag cttctcgttg taatcacgag tagcgattac ttcactccat gcatagagtt 106620
cgtctttctg gcgattcaac cggatacgct tgatgcttgg cggtttggtc tgatcgaata 106680
ccgattcgaa catctcttta aacttggtag agaagtcttc agtagagtag atagagaaac 106740
catggcaggt cgcttcctcc ataccctcga taaggaaacc gagaatacct tcgtcgtcca 106800
acaacgccca accaccactg ataccaaatg catggagatt gaacttggcg atgactttgt 106860
ccttaatctc ccgtatgcgt tctttgatgt acacttcacg atctacaccg aacgtgtaat 106920
agatgcgaag tttctcactg gctgattcca gaccttgttc gttaagagtg aaatggtaag 106980
cgctgtaacg gttacctgcc tggattgcct tcatgcacag atgagtataa cgctcaatcc 107040
aatattgctg gttaggatta agtttagggc cacgataaga catttgattt tccttttaat 107100
gagagatggc ataaagctcc ccgaagggag cagtatgtta gtcaggtttc ttagcgacta 107160
ctagacgaga ccactttgta gaggaattac cttcaccttc aacattgaag attcggtcct 107220
ggctattagg tggcatgcga ccagtaatac tactgaggtc tttaataatg aaaccagctt 107280
cacccagatc tttaataagt ttggtgatta cgtcggaatc agtaatgtga ccaaggacgt 107340
ggaactgaaa agtactagtt ccattgacca ggcgatgacc agctttaact ttatcagcat 107400
ctgccatgtc ggcttctaat gcagctacga ctgctgcgga gtcaacatca tcagctttga 107460
taatatcgac aagttcatca aatgttggga atgccatgtt acaccttctt ttgaatagac 107520
atatcgttaa gcttcatttt tggaacggct ataatgtaca gtacgaagca taccgtagac 107580
tcgaccatta gccatgtcta atttaccatt acaaaaacga tctttcttga tttcccagcc 107640
aatgccctga agaaacttag ccacagctgc actacgtgat acgccagcct cgcagtgaac 107700
gattaacgtt tcgccatccg gaatcttatc gatgaatgta agaatcttat cagcatgcac 107760
gtaatcgaac atctgatagc ggttatcgac gtaatcttcg acatcatcga aaacaagaac 107820
caatacagct ttgtgttcgc gtacaaattt tacgtcttgt tcgggacagc gaatagaaat 107880
aatgtagctt tcgtcagtca atgcctgtgc agctaaccgt gaatagaatt ttactctcct 107940
catacagcta cctttcgatg taacatgaga cgagtccaag aaccagaggc cataccagat 108000
acagcagtag acgcaccagt ccaaccttgt tctttcagaa cgctgtatag ttcattcaag 108060
atatcaatat ggataactcc gttgataccg aattcgtaaa tcaacatatc tttcttttgt 108120
cgaactgcat gttggccagc acatttaacc ttatcagcat tctgccattt gaaagtacgc 108180
agcaaggtta agatatcttg gacagacaga atatcgaatc catcaaagaa atctggagtc 108240
acacgagcat taagctgttc tacaacgacg gaatccatgg attccttatc atgaacgatt 108300
ataggtttct cttccgtcac atgaacgggt gggaaaacat aaccggcttg aacatctccc 108360
tctttactaa cggtgaaacc taaacggagc gaattatcat attcgaccat acagggagct 108420
agctctatgt cccaatcacc aacccaggct gggtaatcca tattggctga cttaataaga 108480
ctctgatgtg tacgagtcgt tactaaacag tatccaaggt taatgaagag actaatatca 108540
tcttttaccg ggttaaatag agttgctttc cgatggtctc ggtcgagcct cgctcctgcc 108600
agatcatcac aaagatagaa atgttggcac tctccatcaa ctcgttggtt gaactgaatg 108660
agataaaatt tgttattgtc tagttcctta ataagctcat ttactttttc agcaatattc 108720
atcggtattc tcctttcttt gaaaagatgt tctcttaggt aatatagatg taagataatt 108780
tttattaggc aatcctatag ttcttcctta acagcaaagg tgctaatatg tttgaagtgc 108840
```

-continued

```
tgttatcatt gagtcaaaag aagcaagcta tagagtatcc attttctgga ccaggaagta 108900
aattcctaat aaagggtaat gagacacttg ggtatttcgg tctagtcgat tcgaaagata 108960
tttattttcg tgaacggttt atcgaacagg cagatatagc cgactatacc aactctattg 109020
taggttcatt cgctaatcaa caatgggtta aatatttctg gatgggtaag gtttgttttg 109080
cacctttatc tatctacatg accaacgtct catggaaggt tctttacgac aaaggccttg 109140
tatttggaga caacacgatt ggtcaaaata ttccaagtgg atataatacc gttcaagata 109200
agttctatca ttttactgac gatgaaggga gctggcagtt tagaatccgt atgggtcatc 109260
taactgagaa cccattcact ccaactaata atgaagaccc aacaagtgaa cttggtcagg 109320
tatttacacg agtgactaat gggtcttggg acaatagacc cacaagtgtt atcggtcttg 109380
gtaacggtac atggacaaag gcattgaata cagcccagcg cccaatgtat cagttttaca 109440
acacaagtat cacgtctgta aataataatg ccccaacgaa taatggtatt tggcgtccgg 109500
tattagagct gattcctaaa gatgaatatc acctagtacc aatagaaacg actattaatg 109560
cttacagtaa tttagccgaa gctagtatta taactaatac agaaatcagc tctggtggaa 109620
ttcaacctat tattcagctt acttcactac caactcctgt aagtattgct tatattagca 109680
atgccccaca agatgaaacg cttatcgact tgaacagtat atcgcgaaag atagataaaa 109740
cagctgaagt tagaattaat agctttagtt tcacatgagg atgatttaac atggcattta 109800
caatcaatct acgttgggta aacccaaacg acgcgtccgt aagtattaaa atttatcgat 109860
cagcaacaat gattgataga aacaaccctg gtacaccaat agcagaagtc aatggtgacg 109920
ttgatggtta tgctgacgaa gggcttacat atggacttat ttactactac atgtttgaat 109980
catcgaaaga tggggatgta gctaaatctc gtgtattcca gttccatgcg gtacctttca 110040
ctggacctgg tccacagcgc ttggttgcag gtaacatcaa ttatggttac tacggttctc 110100
ttcccactgt tgaatttatt tcggacagtg aactaatcgc tcgttgtggt ttgtcctgga 110160
acgcagctaa taatgctggt caacgttggc ataaattcgc atggaaagga cggactttct 110220
atgtacctga atattccatc gcaactggta ctctgtactg gatggacctc tataatgcgg 110280
gtctagtata cagtaagaac gcagtaccat ccgctgtccc cggtgttact actcctgttc 110340
ctcagggcaa gcgaatcaat tttgctctat ctgaatttga agtatctttg ccttccgttc 110400
tagttgatca cgatgatcct aattctgtta gtgatctatc gtcatccgca gcgactgcat 110460
taggtaattc tgacccatct ctcagtaatg gtaccgtcga gttattttta gccggtatga 110520
ctagtcagtt ctatgctaat aaaacattgg aacgagttaa cgtaaccggt gataatgagg 110580
ctacacgtgt taatagtaaa gctattctaa cacgagatac tccaaccact ccagcttctg 110640
catatatttc gcgaaatacg agtgcaacga aagcttcggc ttttgtacct caacatacag 110700
gtagaacctc aagttcaaac atttggttcc ctgtactgga acttatccct ggtaacttcg 110760
ttgactttga ggtgtaatca tgggtattaa agtacaatgg ggtttgacca atgatcgaga 110820
agcagtcaca tttgatattt ttcgatctga aacaaaattc gatgaatcga cattacctag 110880
tgtattagtt aatgtgcaag gaaacatcaa agaatacgat gatacaacag ctattagaaa 110940
taaagtctac tattactgca tcggttctaa ttttgaaaat ggtgatgtaa cctattccaa 111000
agtggttgca cttgctaaca tgccttacac tggtttcgga ccaaataccc ttcgttctgg 111060
agactatgaa ttaggttatt ttggtgaggt tccagatttt gtattacctg gtgaaataac 111120
agatctttgt ggactcagtc ttttgactga tattagaatt ccacctgtaa cggatttcat 111180
```

ttggcataag ttcgttgtag atgggcgcat tttcatgctg ccaattcgct acgtggctta 111240
taacctacgt tgggccgatg tctataatgc gggttgtgct tggtcaacgt ccggagacca 111300
ttgggatgat cttcctgctc ctgttaagac tgtagttggt acgccaaccg aacaaggtaa 111360
gactgtcatt attaagaatc atagttacag agttggcctg cctacatttg ctggtgaacg 111420
atcactcgca agtatagctg ctggacaggc tgtctatgat cagtttaatg atctacttgg 111480
cctcacatgg gatcgtctaa ttgcatatgc atcgaacatc aataagccta accttaaaac 111540
acgcgttaac tcgacttcaa cgaacgttgt aatgacgggc ggcgcacctg gttcgggtat 111600
cttcatgacg cgtacattcg taggtgaaac ccagtctata ttggtcagag gtgcagcgct 111660
tataaacgtt tccagtactc tggtaaatag cgcggctgca ttcatgccaa ttctagaact 111720
agagctatag gtgattcgat gattaaagta ggcttttcgg ttacaggtga tattgttgac 111780
ttaaaagctt atcgttctac agaaccattt gatgtgaata atcttccagc tgtttttaag 111840
cagctggatg ttactgatcg agaatttgta gacgatactg ctttgaaaga tacaccttat 111900
ttctatcttg ttattggtat ggacaataca ggttctttcg tattgagtga tgtaaaagct 111960
atttgcatta ttgattacac taataaagga cctggtcccg aaactcccgt attcggtgac 112020
tggtggattg gctacttcgg aacatgtcca atcgaagatg tctttgaggt ggctgatttt 112080
aaaacaaatt tggctttacc atctaacttc acgaatactg ttgatcaacc aacagaggca 112140
tggaaaatac agttcaaagg tgtaacgtat tacatcccga acagagttcc atattctgga 112200
atgtcattca tggatgttta taggacaggt gttctccttg atacggtaga agacggtgtt 112260
ggtactttgc catcatctct cactaatcca gctgtaatgc agggtaggat ctattctagg 112320
aatggtaata gttttgctgt tggatgtatc ccacatggtg ataaggtagt atacaccaat 112380
gctactgatg cgatggtaag tctccatgtg atgaatgatc tagctttaga taccttcgaa 112440
cgtctattca atacagcagt aaacccaact ggacagttgt attctggtta tcaacgcagt 112500
cgttatggta atcagttacc atcgtctata gctccaggta atggcttgaa tattttctat 112560
aaagctgtta ctgaagataa ccgttgtatc caacgtggat ttagcacatc tatcgctcac 112620
cagcttgaca atgcttttac agcttatggt agtagctgtg gattcaatcc agctttacgt 112680
ttgattcgat gagacaacat aaagcccggc attgagccgg gcgatatgtc tgtttagatt 112740
agagagtcca aacatagtcg tcaaggcacc gtagttagat actcgtcttt gctcccgcaa 112800
atactttaac gtatcaagtt aaagaatcgg ctggatcacc cccttaaagt gcagcgctat 112860
gcgcgactgc cttgactata tcattactgt tttagtaatc tttttctaaa tcttacacgt 112920
aggccaattc tatgaattta ccccttaagg ataaacccac atgttagact cattccgttc 112980
gatatttggc ggcttgacag tcaaagaaac tgaaacggag attatcatct ctggtattcg 113040
tggcttcgac atagtccgag atatcagtaa gcattggaag acttccaaga ttacaaccaa 113100
cttgttcaac aacattggtc ggaactcatt aagcttctat aagttctttg cacctgaagt 113160
aatgtacatg ttggaaaaca ttgtctatta ccgttctcga tacacctctg taaaaatgat 113220
cgctgctatt aaagatgcgc ttttacagaa tacttggctt gcctctacta aagccattga 113280
tgagaaatca gtacaagggc gacttaatct agctaatctg tctcgattaa aatttgatcc 113340
aaaaccgtat caattagaat atttcaagaa ctatacctat cggctagatc aatacaatct 113400
aaatggtgac ttaattgccg cggccgccgg tacgggtaag gcacaaccac taaacgccat 113460
ggttaaaatt cctggtggct ggaaacgtat gggtgatatt caagttggtg acatggtcac 113520
tgcttgggac ggtaccccga ctaaggtcac cggcgtttac ccacaaggga agaaacaaac 113580

-continued ttttacggtt acattcaaag acggtcgcac gaccgaagca tgtgatgagc acctatggcg 113640
agtctattgc tataattgga cgagggacgg tagtgatggt tggcgagtaa tcaacaccac 113700
caccctgttc ggttacatgt ctatgaaatc ataccggaat cgactttacg tgcaactctg 113760
taagtccgaa gaaggtatgg atgtcgatct accgatcgat ccgtataacc tcggggttat 113820
tcttggcgat ggcgggatca gttcgagttg tgtgaccatt accagtggtg accctcaact 113880
attcgatacg ttcagtaaag ctctcccgga taacctcaat cttatcgccc gtgacgccat 113940
taccatgggg gtcatcaaca agaaaggtga gcgtaacccg tatatcagtg ctcttcgaga 114000
tatgaatttg ctaggaacga attccctttc taaattcatt ccgcaagaat acctattcgg 114060
ttctactgcc cagcgattgg ctcttgtaca aggtcttatg gacacggatg gtacagttga 114120
cgagaatagc aacctaagtt tcaccagttg cagctacatg ttagccaagc agttccagta 114180
cctagttcgt tccctgggtg gaattgccaa actggcgttc aaagagccta cattcacgta 114240
caacggcgtc aagaagtacg gtaacatgtc ttatcgggta gctgtccggt ttgatacccc 114300
cagtgcactt ttccgccttg atcgcaaaat agctcgatgc aacgacaata accaatacgc 114360
ggataatctt cgtttacagg tgaaacatgt taacctgtcg gatcgagtgg agtgtcaatg 114420
tattcaggtt gaacatcccg atcaccttta cgtgaccgat gatttcgtcg tgacacataa 114480
cacatatctt acttcagcta ttgccgagat gcttgatgct gaactcattg ttgtaatgtg 114540
ccctaagaat gctttggatc tagtctggtt agattccctg aaagagatgt tccataaacc 114600
gcaaacagtt tggcatacgt tcgaacctaa tatgccctac aaaggacagc gttggatcgt 114660
ctgtcattac gatgcaatgg ataaggtagt agaacttctt agaaaccgta atatagttgg 114720
tagcaaacgt actgtgacga ttctagatga atcgcacaac atgaatgacc ctaactctac 114780
acggactaaa ctttatcaac tcattgtaaa gatggtcggt tctcgtaata atcttttagc 114840
ttcgggtacg cctgtaaaag cattgggtgt tgaactgatt aacttactgc gaatagtaga 114900
tcctctattc actccgcagg tagaagaacg cttcaagaag atgtatggta aagaagcctc 114960
taaaggactc gatattatca gacatcgatt aggtcttgta tcctacaagg tagagaaaca 115020
agaactcgat ctagagcccc cgatcatgcg tccttatcca attaaaattc cgaatggtga 115080
tgacttcacc cttccggcta ttagaaaggt aatggaagca tttattcaag aacgctgggc 115140
ttactacaag aagcggagac ctgaagatga tagacgctgg gcagagttct gtggactcca 115200
tcgaaaaacc ctcaaaacag ctgcacaaga aagagccttc aaagagtact tggatctggt 115260
caagtatgtt caacagatcc ctgatccacg ctttgcagga gaggaaatca aagcaacgaa 115320
ccaatatgaa aaattagtat ttggtccttc ccttccaaag cagttcatcc atgagttcag 115380
ggatattaaa tcggttatca aatatactaa cctcaagatt caaggtgaat gtcttggtcg 115440
tgtgttaggt ggtaaacgta ttgaatgtca tgtggcaatg gtcccgtatg ttgactgggt 115500
cggtattaca gaatccactc acaagaagac gattatgttt actagctttg ttgaagcagt 115560
agaagctgcg gatacacatt gcgttaagct aggtatgaaa ccactggccg tttatgggaa 115620
gactactaat gaactggctg aaatcgttaa acgtttcgat tcgagtaagg aactaaatcc 115680
actcaatgct acatatgctt ctctatcgac agctgttcgc ctgacaatgg cagatactct 115740
gattctattg aatagtccat tcagagctta tattctagaa caggctatat ctcgtgctta 115800
tcgtttaggt caagattctc aagttgtcgt ttaccagtgt tctctcgata ctggagatat 115860
cccaaatatc tctacccgat cggctgatat tcttaaatgg agtcaagatc aggtagaagc 115920

-continued gattatgggt atcaaatctc catttgaaat tggagaagca atggaagatc atggtgatga 115980
aacagagttc gatgagaaca aagtaataca caacgttctt cagaaagcat tcgaaaaatt 116040
cgacatcgag attccggcag ttgatttcga gatacccctt aaacccaaat ctaatgttcc 116100
cgcatatttg cggtgattgg agtctacaat gagtgataca aataaaggta tgattgcggc 116160
catcaaccgt tatctactta agatcgaaga actaatcgct ggcggcggtt ctggtggagg 116220
tggtgcagca gccatcatct acgagagtac aacggtaccg gcaggcggaa ctaagacgta 116280
tgatcttgtt cctttgattc cagctggttc agaggtaccc cgtgcagctt ctgtagaagt 116340
aaagattaga gatactgtaa gtggttctct caccgaaggt tgttacattg acgcttctgc 116400
tgtattaacc tggggtatta aagacgatgg tacgttagtt attgctaacc cgtcgtctgc 116460
cactgttgca tacattgtca ttgtcagagc accccataaa aaaatcgtac cttaatagga 116520
gcctgaaatg gcatatgcta accctgacaa acaacctggg gcctatccta gtacccaggt 116580
tgtaaaatgg acatttgatt ctaatgtcgc tactaatggt gtcgcgtatt ctgttaatgg 116640
tttaccgcca gtcgtttctg agtatatcgc ttacgattct ttaagcccgc ctactccatt 116700
cattgccgtt acccaagatg gtaacggtaa cgttgtttac gatggtggtt ttccgaagtt 116760
catgaatcca caggcagcaa acatttccat gactcagggt gttctagatt tctcagctag 116820
actacaacct gatgcaaacg gtctagacct ttgctactat gaagtaatta acaataagac 116880
ttacattgtt aaaagtggag atgttcttgt ttatgaccac tatgtgttcg atgatgcata 116940
ttttggttta gactgtaccg tttatgatga aactggtaat aaccctgtta gatttaggga 117000
ctacagtcct gtaatcaaag acaatggtaa ccccgctact gcaacacatc cagttatgtg 117060
cagagacagg ccagaatgga aaaacaaatg ggtaacacgt acagtcccat tagaagccat 117120
tgttggtaag agattatcga cttggactgt agcattcgag aacgatgcag atcctatcct 117180
tgcaagagag tatcgtggtc agctgagaaa tgcacgggtc cttaacggaa caactgttgc 117240
ttttgatgtc atgacagata atcttgtagt taatccaaca acaccgcaag attggatagg 117300
tagttggact gttacccgta aacgttatct tggtccaggt aaaaacctaa actctagtca 117360
gatctatttt aagaactgtc ttgactttat tgctaaccct gcaaaagttg ctagtggtaa 117420
taaaaacatt cttgtcctag gtgatgcaac tactggtagc tatgcactga agaccgcgtt 117480
caatgaatac attactaagg ttgcaggggc cggcggtttt acatgtacat tgaaggatca 117540
gaccgattat gatggaaccc atttaaatcc aaccttaacg gaattaaaca attacgcagg 117600
gttggtattt gttggttctt taagtgatcc ggatcaatcg gttaacggta agttcacgaa 117660
aactgcggtt caggatattc ttacatatcg gaaagccggt aatggtattt tcatattcac 117720
tgatcatggt ccagctatta acagtattga agaagcatat ccggttccaa ctgcaactaa 117780
ctgcttcttt gttactgcta accaacttgc tgtaaacttc aacgcatact tcaatggctc 117840
cgttgacaga tcaaatgtga atgttggatt tatacgatcg acttatgggg atcatgtcct 117900
ttataatgat ctaaccgatg gcgattttat cgtagccggc ggcagtgaat cgagtgtagt 117960
cgttaaagaa gttgttttcc aaaagaagga tccagtaaca ctgaccctca accctggaaa 118020
acatactgtt aacttcttgc tgaagcttac taacggcgac gtcgttccaa tgacgtttgt 118080
ctacttgatc ggagcaggta agtacgttat attccgagat aacaagggag ttgaaattac 118140
acaactactc aatgacattt ctgatatcgc tgatatcgta gttgaattgg atggcacaag 118200
tgttggctcc atgatagcgg atatattccg tgtagacata actaaagtag atccatttag 118260
agatattaaa gtgggtactg ctgtttacga tccggcaacc ggaagtcatc aaactatcta 118320

-continued

```
tcctgttgat ggtatctacg ttaacaacgc ggatctcatt aaggtacgta tcactcaacc 118380
attcacttat gaagcaactc ttcctgtgac tcggtatcaa cctccgatcg ctggtaaata 118440
tggtcgtgcc gagaatacac ttccgttaat gccgcgatat aagacgggtg gtactaccac 118500
tgagccaatc tactcgatct ctcatatcca agttccacgg agaattattg aagagatcca 118560
agttgttcga cctgtgtaca accttactgc gataacgcag agtgtagctg atcacttcaa 118620
aaatatcatt agttactttg ctggtgagct tcctcgtaac gaagggcaag catttgccta 118680
taaaaccgct gctgacacaa gtgcagctct agctcgacta tctccaccga cacctaagca 118740
aatcttcgat acatgggatc gtttctatgc tgatgaatat tttgctaaag gtcaaggtat 118800
cccaccgttc ctttccgatg ggactacccc tcatccagcg ggccgttggt attgggacga 118860
tacgatcaaa gctgctgtaa tgcctgacaa tacaagttcc attactggtt tcctttcaga 118920
tgaagaacca gaacaataca cacttgaagt tacatgtcaa tctaacaatg gtgacgacga 118980
cttcttgggt gtggttctgg cgtttgttaa agagggcgat caaagccatc atttgacact 119040
cgcattgtct cgtagtaact cgaatggaaa tggacgaggt aatgaagcac agaacatcat 119100
ctacgatttg agtatgggta ccagacagaa tatcatttct gttaatactg gcgattactc 119160
taatcaaggt tggaacggtg ctttcaaacg agttaaggtt attaggactg gtgatatatt 119220
taacatcagt atctccaaat ggggaacgac cgaatatgat ccaactctgt ccatgacggt 119280
tgacctgaac agtgatccac tattggctaa gtttaaaggt cctaagaaat acggttacat 119340
ggccttctcg caaccgcaat cgtatttcaa agacatcgtt tatactggac ttccacgcaa 119400
cattgtttgc gatatgggtt ccaataaagt ttattcttgg aatggtaccg gttgggtact 119460
aatgcagaat acaacaccta aaacgattta cggtgcacca cgggtaatca gaagttttga 119520
ggacccaacg caagcttgga gaattccagt taatggaact ccggtacctg tgcaataacg 119580
gcataatagc ctcccttcgg ggaggcttta tgttgtcagc ccttgctaac gccccagacg 119640
cgcttacgtt gatccagaag cagaaaggca ttctgtgtaa ggactaggtg gaaacggcgc 119700
ttacagagcg aagcagtgat tgtttctact acaccttcaa agtcaaggtt agtatcgata 119760
gcagtttgct cagctttcga tttacgacgg tcagattcac gataacgaca tttccatgta 119820
gtcgttgcaa tctcagtacc gcgtttaacc ttaacttgag aacggtagaa aacttctagg 119880
agtttaactg ctagttgttc aacatcttcg atgcgatcat ctgcattaga tagagtcaca 119940
caagagcttg ccatgtgttc atgcgtatca acactgtcat tcagtgcccg cattgttgga 120000
tcgaaatcaa gacgtttaac aatgatgtta atgacatcgc catctcgtct aatttcaata 120060
cagcggatga agtcgaacat atcaaattct ttttcgatat ttcgcattag tactgcaagt 120120
ttttcaagcg actcttcgtc atctgttcca gagtgcttag taaaagcaaa tgttagatcc 120180
gacagaattg tctgtggata actcgtggag atcagaagac gtaaaagaga ttcgcctcgg 120240
catttacgac cgggtttacc tgtcatctgt tcaagtacgg ttgtcatttc tatttatcca 120300
aaatggtttc atgtatagcc attcttttta aaccagtcct cgcgtgtcgc cctggcatcg 120360
aatagcgcat tatgcaaaag tttagatcct ttaccactga gacgatcatc gatatcaaaa 120420
gtcaatggtt gaatcataat ccacttcccc ttctccccta atagggcttt gttaaaataa 120480
ataacatcgt tggggtggtt aacgattata ttcatgccag caaattgtga tacaaatttc 120540
tcaaggcgga tctggaattc ttcaaacgaa ataggatctt tctgaagaat aggaatgacg 120600
ttagccttta cccagtcgtc ttgaatatgc ttatgttcga gtacttcata gaactctctg 120660
```

ttaccatctt cggaaacaat agcaagagaa attaaactat cagttggtac atcaaattca 120720
gcgtcacaaa agaatctcat agggagtgaa cctttacgat aaggaagtca taagaataag 120780
ggactacacg aaataaaagg agcccgaagg ctccagttat tttgatagac cacggatatt 120840
acgaagaatc tgacaactag caattatctt accacgagat accctggaat aatatccttg 120900
tgcctctaga tatttctttg gattatcatc ggataaagct tgctctagaa taaatgtatc 120960
aattccgtag ttagttagta caaactgtgc cacctcatga tcccaacgtt ttgcaacggt 121020
agaactagct ttaagataaa catgagctgt ttgctcagag taacctaaag ctactaacca 121080
cgctattcga ccagcagcat aaataagtcg agtgcgtgta ttcgatggaa ccgccacaat 121140
ataccctgtt ccgggtgacc tctgttcctc tactgttctg atattccagt caccgatcat 121200
acgagggatc tgagatagat catctccttt accgaaatac ccaatagata aacctttggc 121260
aacttgagag tcaatctcag tagcagtatt ctgactaata accatcttcc cctcctatag 121320
gggccacggt ctcttccaca acacgaaaat atatatcctt atactttcat cagataaggc 121380
ataaagcccg ccctaaggcg agctatgcgt ttatacaggg agttgttgca ggaagtcaaa 121440
ctgatatgct agtagaatta cccaaagtac cttacaccca atatgaatcc attggtcagt 121500
atggaatcca attttaccat cacatttcag ataatctgtg atgcaatgga taattgtttc 121560
agccgcccct agaacaaaac tacccgttac tacgtatacc caacctccat ggataagacc 121620
atgtgctgga agaacgtagg gccaataggt cttacctagt tcagtagtat ggttctttgc 121680
agcggccata aaatcattct gtagcgcgta atcgcaaaca gcatgaccga cgagtaatac 121740
gaagagaagt tcgataaggg agaatatttc catggtgatg ttccgggcgg tgggtatgag 121800
gctttgtagt ctttgctaca tatggttaca acttaagtat ttaactgcga cgaacattaa 121860
aaccagagat attctgacgt ctcccttgtc gacgtacttc cagattacgc aatgtttgta 121920
taccagaaat agttggagta ggtgccatta agtcatgtac caaacgaccg agcacttcct 121980
tctgttctgg aataaattca aaatgttcat ctggtggaag accttgacga gaaccctctt 122040
gccaagcttt atcaatcgga tggataattc catttaagct accgaattct aagaatggta 122100
catcggatgc agtagcatta tgttcagctg ctaatctaca agcgcgaccg tgtgctacgt 122160
atagtttaac atcagcttcc catgcgtaca tttcactaac atcgcggaca ataacttcac 122220
aaccgagatc cttcaggaaa gaagtaacct cagcgtaata cttttcagat agttcaattt 122280
tcccaaattt gggactacct ttgatgacta ctactttaac catgatcgta tctcgaatgc 122340
tggattatag gattgagagc aaaaaaaaag aaagaaggta ttggagtccc caaggggact 122400
ccatttatat tgttatttga tgccatcgta aatatcacgt cgcgcggggt tgataccagc 122460
tacttgagat ttacggttat cgatgtaaca aagatactcg tcacatgttg cagtcttaac 122520
aaagggaacc aattgagcca gctctagtag agtccactct ttcccaagat agttacaacg 122580
ctccatctct acattacaat acacattgta aagtgcttca gtaaaacgta aatctagagt 122640
ttcaccatct gctttcttat cgttgtattt agaaggcaga agatcacgaa ttgggaactc 122700
atgtttcaat gacccattac caaatttaat agcggtgaat gagttattaa ccatggttaa 122760
gtaataacca cgaggaagtt cccaataggt agtacccgaa tgtccacgta ctacaccaac 122820
gagttgtccg tatgcatccc gacaatattc atcaatgcat actacttcta cattaccatt 122880
agttacatag ctgtagacct cagtaggttt agagcgacgc gtaacggcta ctgtgatctc 122940
atctggccat gtcttccatc cacacacccc atggcgtgag tcattgttaa agaaacaagg 123000
tgcaactttt ggagtgaagg tagaaaagaa taaaggtgtt tgtgcgtata tcagcgggtc 123060
tttcacttct tggccaaaca cagtgcatgc aaatgacatt agaaagaggg cgataatctt 123120
ggtaaagcgc atttgaagtt tcctcttgat aacataaaga ggctcccgaa ggagcctcct 123180
gtgtttacaa cttaaggagc aagttggtag tacttaccaa actctgcacg aggtagggag 123240
aaaccatcct gacggtcacc catgcgtttc agatagatct tgttggtttt aactttatcc 123300
aacgtgacag cggtggtaat accgttgcgc ttaacgatga atgtacgacc gatatagtcg 123360
gacagagtat cgtcgatttc cgatgcttgg atgtaacgtt tcacagagag agtctcagac 123420
atcatgtttc cttttattct gctacagcgg tttcaggttc aaccggctcg tctttgttga 123480
tcagatcttt ccagtcttgc agacgttcat ggaagtggaa cagagaatgg atttcgcggt 123540
tcaactcacc aacacgcgct ggatggaaga tagtctcgtc attggtcttt tcgaagatct 123600
tacgtacaat cttcttggcc aggtctttgt aatacggcag gagttcttct cgacccaaaa 123660
tcacctcttt gataatttgg gtttcagcgt attgctccag tgccacttcc agatcaaaga 123720
cagccggttc aacaggttct tcgtcaacag aagattgttg tacaacatca ccgctttcat 123780
cgtgttcttc accagggatg gtttccggag gaagatggcc gctgttctcg gttttctctt 123840
caagctcatc tttagctcgc agagcttcgt gggcttgaac agtttcaatg atgaattgaa 123900
cttgttcatc aatgggagcc gtgccgtcaa ttaccttagt cgaaggacta aacttaatct 123960
gagcgtatgc gttgttaaca cgagtttggt aaacttcgtc atcttcataa cgatccagag 124020
aacgaccact gttaaccata cgttctttcc gtacttcctc aggagtttcc agatagaagc 124080
acagcggttc aggaacacca tcaccgataa catgcggcat tacacccatg aacagatctg 124140
ccagattcgg attggtgtcc agataaggag ctacgttcaa gcaccaagta gagaaaacaa 124200
agcgatcaga tacaacccat ttaccttcat tcagagatgg cttgacgata ttctggatat 124260
tctgtcggcg atatgccata tgcaggaaaa tatctgaaac tgggtcaatc ttttcttcac 124320
gatgtttcaa tagaacagtg cgaatctctt cagccatttc cgttccaccc ggttcacgaa 124380
gagccacgtg gtcgatacca tcagctttga gtcgttcaat aagagcacga tgcagcgtcg 124440
atttaccgga gaactcgggg ccttccagta cgatgaaatt acggctagca gatttggtca 124500
tcttgtttcc tgtatttaca taaaaattaa ttagatggaa aggggctccg tagagcccca 124560
ttcgatcagg tatttacttc ttcgaacagc tggttgatgt gagcgcaaac acgcttcatc 124620
tcagccgagt tagtcttggt cgatacggta acaacactat ggtctttacc atcacgacta 124680
aagataccag ctacctgaga gttggtggta cccatattgt agttaaagcc gatctcagaa 124740
agatccggat tttctttcat gcgagctgcg gcttgttcac cagcaacaag agtaacaccg 124800
gccagaagtt caccttccag tcgttctttc ttcttcagtt gctcaaggct gataccggcg 124860
ccacccagaa ccaccgattc atagagatcg ttcgggatgt cgaaggtatt ggcttcaccg 124920
agaatcacct tctcgcggag tttgtgttct tcgatgaatg caaagctctt cagatcttta 124980
gacatgtgag tatttccttg tgaaagtttg atgtgttaat tatgattttg aggtgcggtt 125040
cggaacaacc tactctgctg taagttcctt acgatcatga gaggctgtaa gagaagccat 125100
cgtattacgc tcatcgaaga tacgcctgga cattgcaacc agttctccaa gtcgaggtag 125160
aggcatcata cgcatgtccg attcatcgaa cttagctcca ccagcacgac aaggagtttc 125220
ccaacagcag gagcaatcag agagagccat aacgattcct taggtcatac gcgccggaat 125280
accgaaacga gtaatcaact tgaccggttg attttctttt tccattatct ccacatctac 125340
accaacgtaa ccgtcgtatt gcagacgttc gtaaacactc tgggtaatca acggccagaa 125400

-continued tttcttatcg gctccaaata gagtctcgat atggaaaacc agtcgaccat tgttaccagt 125460
ttcccagtta tcgggctcag caagggcctt accgattttg gacatgatgc cttcaagcat 125520
cttgtagaaa cctggaatag ttgcacgaag gagacgagta gactcggacg aatgaggcat 125580
attgcggatg ccttcctcga tatgttctac cttggcttta ccacccgtac cgacagcata 125640
gtcgatctgt tctttcaggg tgctacccat ggtagtatgt acacgcgtat tgccttcagt 125700
atcactgacc acgtaagtat aaggtttatt gtggtcgatg ttctgttctt tcattttta 125760
ttaccttctg ttaaaggaat taacttgttg ttcatggtat cgttttcaca aatgaataat 125820
ctgttagctg ttacatggta ataccctcaa gatgttaatc tctaatgcat acctgtgata 125880
tagatttgaa attattttta atggaacata aagcctcccc gaagggaggc gtttatatca 125940
gttaccttcg taggtacctt cagtgccttg tgcttgacgg cgctccaatc gagcacgaat 126000
cagttcacga gcagcgttca tatggaacag tgctttggca ttttcttcac aggcaaactt 126060
acccgattgg aaaccttcga atacaatgat cgaagcagtc agcagatctt caacagttac 126120
cccgttaata ccaacttcag ggattactcc gttttgaagc aggataacca gttcgagttt 126180
attatcactc ggttcagcag ctttgtttgt agatgcatcg aaaccagaga tcacaatacg 126240
ttttggtgcg ccagacattt catcgacacc ataggcatca atagtcttac caccggaact 126300
accggatacc tgaccatctt ctagttgttc aacggagata tctaccgtag tactagcctt 126360
aacatcgtcc ggttgggatt cagcattagc attatccaca tccagattac cttggtcgag 126420
atctttaacc tcagtttcag attcgacatt actagcatct accggttggg cgacaccatc 126480
ttggctctct acactaagag cccagtccag acctttcatc agttcacctt aagagtagcg 126540
gactttaaca atttgcagaa gcagttctac agcgtagtta ccatcagcct tagcgatacc 126600
cggcatctgt gcacgaatag cgaccatggc agcagcctta cgcttcagaa tattacgttc 126660
tttgctgttc tctacttcgg ctacaccacc gatcagtgca ttgactgcga tgttctcaat 126720
ggaagaattg atacgagcac cagcagtata tttgcgaaca agtttacgaa gctcagcttc 126780
caggttctga ccacggtact gttcagcttc cagataacca gaagccagtt cggcgaagtt 126840
acgaacaccg gacttaccaa ccagcagatt ggtcagagta tctaccggaa gagtcgacgc 126900
gagttgagcc aggtcattac ctttgatctc agagcgagcc agttccagta cggattcaac 126960
accaaggagt ttcagagcga ttttgcgaac gatagacatt attgcgtttc ctatattaaa 127020
agcgatcaga agtttgagcg aaggcagaga ccgtacgggc gacctcacca tcgagaaccc 127080
aagacattag gttcgaagga ctacgccaag acttgaagct ttgaactgca cgagtcaggt 127140
taagattcaa acgtttacca gcgtaataga aatctgccca ggattgtgac gttagagtcg 127200
acacgtaatc ttggaacaga ctttgttcat cccacaccgc tccatcagta agagctagcg 127260
cagtagcaat accaccatca cctgcaacgg cttcaccggc tgtagccgaa atagcacgac 127320
cagcagtacc caaccaactc ggactagcaa agccagcctt cagtgggata tgcattagct 127380
tagatagatc tttaacactg aaggttactt cacaaccaag catttcgtgt tcagcgttcc 127440
aaccaacgtt accgacaccg cgacggatct gaatgctatc cacgatcccc agttgtctct 127500
gtactcgacc tttatggaaa atttgacaga tgaacggaga ggtgtaagca cttcgaccag 127560
ctgaccttgg taatcccatt gggagaatca tggctagtgg tacgtatatg ttcatgaacc 127620
tggatatttt atttccataa ggggagatca attgaacagt atacgaagca gatggtaaag 127680
aagccatcgc tgattcccag tactctggtg catctacgaa agccgcgcct gctaatgtct 127740
caagtccaga taagttaaca gagtctagtg ctccggaaat aaatccttta agcatgtctg 127800

```
taaccgcacc aacgccttcc gtgatgttac cacccatgaa gtcaaacgat gcagctcgac 127860
cttcccctac cttcgtatta agtgtttgta caacacctac atctcgtgta gtgttagtaa 127920
aggattcaga tacttcacca ttatagtcaa cacggaatgt aacgaactga gaaccgtcgc 127980
gctgtgcgcc tacaacgaag tcatatacgt tcttcaattc accccaactg ctaaaactct 128040
cggtatcaat aacaccattc ttttcggatg gtttcttatc agcttccaga tacttcaaga 128100
aatagtcacg tgcgtcagcg cctggtttag ggtctgttac agctttggcc atttcagatt 128160
caataccagc ccgaagttcg gcaagggtac gcgccttctc tgccattgca cgcattgatt 128220
tttgagcttg gtcagacata cgttgcgtac gtccagccaa agacattaca tcgacgccgc 128280
catctgggcg gaagaaacct gggaagattt cgtgcatacg tttaacatca tctaatccta 128340
ctcgatggcc tgggtcttct agaggacgtt gagaatcatc gagaatacgc gggaccatgc 128400
ccatagcgat agcgaactcg ttagctagcg tattcacaga cgaccagtat gcatgcatag 128460
tcggtttaaa atagaaccac ttcgatggtt gtgatttagt caagaaacta ataacacgag 128520
atacgccagt taccccaaga ataaatggtt gtagcggtag agtgatgaaa taaccagtca 128580
cgttacctaa gttataccaa aggtcagatg taacaccagt attagctagg cccgccgccg 128640
aacgatcata gaagttcgta aagaacgagg tccagcttga ataacgtgga acaccaaacg 128700
acatatggac ttcttgttta gtatcgtcgt gtgcttctga atagtaacga cccataccta 128760
agaaacgatc ttcgtaggtg cggcctcggc caggctggcg aatatcagca tagcgtgtgt 128820
attgtgggag agggttgata gcaaaactac cacccagcga cgtatttgta aatttgaaag 128880
cagccgagtt agcataacgc cgtttggtct gagaaccata cgagttctta ttgtcattaa 128940
taggcaataa gaaagcttgg cgcaaccaaa taggcttaac atctgttgcc attttgattt 129000
cccttcttaa cggaaaataa agcctccccg aagggaggct ccattgatta agttagcgag 129060
agcggcgacg gtcgattttg agccgaggtc gatctcatta acgtggaggt catactatta 129120
tttcctccgg cttgggtttt cgaagcttct ttggtaccac tgtccttttg ttcgttcaat 129180
tgtaccaaac gcttgagatg atcacgcatc tcaattaacg tcttaagctg ctcagcttgg 129240
atatcatcga tctgttgagc cttctcgtta ttacgacgta cttcagcttg acgagtcgag 129300
ttctgttgct gtgctgcttg aagagctgct tcttgttggg cttggataac attaccgcca 129360
ctatcagcag atggattagt tccgctagta gttgttccac ccacggggtt cattggagta 129420
ataccaggaa gtaccggtgt ttgggcagcc gtaccagtgg cactgtatgc ttcttcacga 129480
gcaaccgctg cattaccagc attgttacta tcatcagtat tccaaagttc ggcagcagac 129540
gccttagcat tagccttggc ttgttcttct gtcgcctctt ccggagtcat ggttttaccc 129600
gcttcctgtg tagctacaga actaccttca gctccaccac gatgctttgc aatcttctct 129660
tcgaacattt gatagatttc cccgagagta cgaggttgtc cacctttctt gtagaagatc 129720
ggtcggttag cagatgctgc ttcagggaag accgatgcgc cgatggtatc ctgattacga 129780
gtcaagaact tacgtgcacc acctggtccc atgaagtgag cgatgtaaag atctacgtct 129840
gttggatcgc gtcctaatgc atctttaagg taggtgtagt tatctttaag gaagcatgca 129900
cccattaagg cgttgatcct cggatcaaca cgtaaactac gttgggcgtc gtctggagga 129960
ataccgaact tggagccatg tttcgccaac attgcgtccc atgtactatt aataaactgg 130020
aaccatccgg ttgcagacga tgtcttagct ttgacggtgt aatcaaaacc agactcaagc 130080
gatgcgaaga tgaacagaag ttctactgga ataccgacca tcgctgcaac tgcttggaat 130140
```

gtttcagcag ctgcttgacg agacttattg gctttcggat atggaatctg ttcccaagct 130200
ccaccgttac cctttgtcag ggttccgtat gtacgacctg ttgcagatac ctcgccagcc 130260
ataccaagtt tgtactgtgt gttcgccgca gcgtcggata cataatccat tgctttagcg 130320
ccagctgcct tggtattact ccatgcgtta cttactgttt ctttagcaga ctcccaagta 130380
ttcgagatag aagccattgc cctctcggca aagctaccac cagcggctgc gttttgtgtt 130440
ccagctgctt ggtcacccgc agattgagtc ggcgtagaca tgatgtcttt gcttgcatct 130500
ttcttcaatt gttccaaatc agcttcagcc attttcttga gatcgtcttt gctaccctta 130560
atcgggaaga tagaatcaac ctgccataca ctagagccgt cccaattagt gacgcccaat 130620
acggcattac ccacaataac agcatcactg ggtttgagtt tagattccat gttcgcaatg 130680
gttgttcctt gagtcgaatt acgcattgca ccgtagtaag cacgagcaac aggcatgaaa 130740
cgaccaacga accaatcgta ataggtagaa cgatcctcat cgttaccaac gatatcttta 130800
ccaaataacg gtgctgtttc ctgcatgatc gattctaggt caccacggaa ttcaggaaca 130860
ccgccctgaa tagatagacc atcgaatacc attgcttcag cattgagaag aggatagacg 130920
ttgtagaaac tcagtacttc caaaccgtag gcacgcatcc ggatggattg gagtgcagtt 130980
agcttagtag tagctgccga agtcgcaacg attggagcac ctgttgaacc acccagacca 131040
gggaaagcct tcttagcagc agccaagggc attgctgact tagtaggatc cattggactc 131100
ggtgcggttt taccagttgc tgtatctgcc gctttcttgg cgatatcctg agctttggta 131160
gctacttcgg tattagccgc tgtagcaggt accgtatcat ctttcttctc gcccgcttta 131220
taacgaacgt atagagcttt ccaaagttga tcagctgctg ggatagtgtc ttccaattcg 131280
ccttcttcgg agaatgggtc aacacgatac tgcattggtg tatcacccga tacagaaatc 131340
ttaacagctt taactaatgg tcctttcaat tcttgaggga acttactatc aatgtcaacg 131400
agtttgactt cattcttttt gagtttagct agtgctttaa cccaagtcaa gaagaccgga 131460
cggaaacgca tttccaacca gcgggacata cgcattactt gaacttcatt cttaacatcg 131520
atgccaagaa tatcaagaat agccttacca ccaactccac tgatattaaa gtcgggttct 131580
tctgtccgtt cggttacgcg atcaaaagca tcttcaagtg cagaaacttt ctgttgttga 131640
tcgtgatcgg taataccgta ctgtagcatt ctgagtcggc ggaactctgc tctttgatcg 131700
ttcatctgac caaagatagg tttcaggata tagcgagcag ttaattgtcc aagtggatta 131760
agactcattg cagtcagaat acctgtctgc tttgcatcca ttccatcttt gctataacca 131820
taagccatag cacctgtacc cactgcggca gctgtaccac caagtatcca aggaactgcg 131880
cgtttagcaa ggcccattaa acgaccttta gcgccacctt tcataccacc gcccatcagc 131940
acgtcgaacg caccagagcc ttcttcacct tctgtaccgg taagtttact gaagatacct 132000
ttaagtccat ctgacaatcc cttcaggact ttattttcag ctttaccggt atcgccatct 132060
cccttaccct tcaatttatc catcaagcca gcagcgcctt ctttggcctt ttctgcttta 132120
tcctgccaac taccagcccg gagcttttct ggaacttgtg cttgaagagt ttcaagaatg 132180
cgacccaata gtacttgatc agttgtttcg aagtcttcgt atggtacgcg ttcaaagata 132240
cgtccaagaa cgttaccacc cgctttagcg aaaccaccta acactttctt agctgcacct 132300
ccatagaact tacccgtctt cttcaatgcc caacccatgt acttcatgga agcatcgata 132360
tacttcgaac gagcagcgcg aataccacgc catacagtct tacggatgat acctttattc 132420
ttagctaaga tatgtttggt accgtcgtag ttcttaaggt ctttatacag agatggttct 132480
attacaggtt cgcctctctc gttaaagatc gtgccataca catcaccaaa gttttcaatt 132540
acgcgacctt tatcgtcgaa gtacttacca gcgttaacca gtcttcgttc gagtacaggt 132600
acatcgtcac caggtaaata agcattctga gtttcaatcg tgaaattgaa tagggccgaa 132660
cccataccga tcgcagtctt agcaccaaac ttcagtgcgg accacgctaa ggtagatgta 132720
ttcgttgcca tgaacttggc gccccagccc gctacatttg ctagacgccg acctgtctta 132780
gtaagacgcc aacgtttacg agtagcacgc gaccatagac cagaagctag ttccttagca 132840
gttgcaatga tagatccatt cttatcaagt acatcacctt tgatgtcttg catcgaatta 132900
atctggtcac catctgcgtt gaagtattcg ccgttcttta gaccacgagc agagatagta 132960
ggttcttgct caccatccaa ataccagtca tgcttatcat cttcagctgc ttgtttttgc 133020
tgtgcgtttt caccttcagc aaactgttga gccggaggag tttgtccacc cattagagca 133080
ccgcggattt tgtccgctgc attgctcatg aaggcaggta attcaagacg cattcctttc 133140
ttatcaaaca gaccttgggc aacttcagat gctgttagaa ccgtcatgcc agttgtagaa 133200
acaaccttac cggtaatgtc gtgtacagat tcgatgatct ttttggtatt aaagtcaaca 133260
aagttacctt gaacaaaatc aataccttta ataatgggtt catttggatt aaacttcgtg 133320
aacacatcga tgatcttatc tttctgaccg attgcatatt gggttggatc attctggaac 133380
tgatccatgt gttctccaaa cttagcacgt gtcttagaat agagatcttg acccattaca 133440
ttcgcatcat tccaagctcc ttgcagacca gcaacgtaag gaccaaattg gccattacgc 133500
atgttgttag caaagtcatg gataccggcg ccgtgcttat tgttcaggta ctggaatttc 133560
ccctgtgcaa tacggctgta gcgagatagt tctttcttga ttcgatcttc ttgtggtgca 133620
tgtttatttc ggaaacgacg cattgcatta agcgcattgg ctttagctgc acctgggtaa 133680
gcaggaccaa agaagttctt atcattcata tcaccagaag cttcaggttg atagtcacca 133740
ttaacccatg ggttggtatc agtaacgcca gagcgcatga tctcccaaat acggttatag 133800
tttatcctat cttgtccttg ttcagtaatg atgataccga gcatccgtaa aggttcagtt 133860
tgaccagcat taataagacg atgtacttct ttaactgggt cacgacttac agaacgaatg 133920
tcaaggaagg cacgagagta ttcatcccgt agacgatggt tttcagcatt atctgccatt 133980
ttacctttat cgtcatactg gaacttactc ttaaagaacc tttgaatttc atccgtggtt 134040
gtggcatcca agccatccat ataaccgccg gatttaaggt aagcttctgg atcaaatcta 134100
cggtttgtag atgcatcgcg aagcatacgt tcaccaagtg ccttacgtgc agctggagaa 134160
agtttaccct cttcatccat caagttcaat gtgtcattaa tggcaccact cgcacttcga 134220
attgctgctg ctggaataat cttcttctga agacgatcat ccgacagcga ttgaacttcg 134280
aatcgaccag ttgtaatatc gaatacttca cgctcgatat catcgcgacc agtgcgaatc 134340
attcgcaatt cttgaagctg gcgagacagg taacctggga tgacttcaac gatactacgc 134400
tgcgtcaatt ggttaaaggc cgcgccttga tcaattgttt gatagtttcc gttttccaaa 134460
cgatcgttca tgtggtactg aggaacgaat ggcataatag catcacgaat aacgccacgg 134520
aaaccataag tgttttggta gttattaacg aactcttgta gatatgctgg aacgttgtct 134580
agggcatacc ctacctgatg atggcgtcca ccaaaacggt tggatagttt ttccatagtc 134640
ggacgaactt tacgacctgc ccatggaaca atagacgatt taaggatatc ggcaccgtat 134700
tcaccggcga tttgaccagc gaacttatag cgattatccc aaacggatga acctgccata 134760
tcgcccatgc gtagaccggc tacgatctcc gatagacgtc cgcccaggcc gctggcaaca 134820
cgttcgttta ctttgttacc ataactaccc aagaagccat gaaggccctg tgcagctccg 134880

-continued ccagctaggc gtccgagcat gttgccccgg ccgcgacctg aaccaaaact ggttagatcg 134940
ccaacattgc ctttcttgta gtctggtaag ccggtattac gaactaatgc ttcataagcc 135000
ttattctgca attcaagatt agcttcttgt actttaacaa gatccctaat acccatgtag 135060
gtacggaact gaagttcaag gcctttacgt tgaattccat aattaacttg ttcgttatat 135120
cctacaagac gagttagact atctacagcc atccccatcg aacgggacat aaagtcaaag 135180
cgtccagcac ttactttatc acgaattcca cgttctgctc tttcaacggc agcgcgtgca 135240
actgcaccct gttcactacg ttggaagttt tctctgctta ccagcgtatt ctgatcgaga 135300
gcagctttaa ttacatttgc atcatcattt tcttgccggc ggcgacgaat agcgatttgg 135360
tccctttggg aatccacttc gtactgatat tgttcaacct ttctggtgag cgtatcagag 135420
atattttcgt ataaggcatt tggaatgcga tcttttaact ggggtagata atcctgtgct 135480
ttacgaccaa ggtaatctag gtcggatgca ttgactcttt cgaccgtatc tttgatatcg 135540
gttaccgaag ccattacatc atcataggca ccaaaaagac gcgcgaaacc atcaggcgct 135600
gcgcttcgta agaaattcct tacgatgtct ttggttttca atccaccgag gaagccctct 135660
ttcagaccag atttgaaatc ggttactgga tcaccaggtt tggtggtttc accgacatca 135720
tcaaacaggt cgtccagctc attaaggtca agtacaccaa ttctgttctg ggcattcatc 135780
ccagcaggtt ttggcagctt ggtctttttt gtagccatgg tcaactccat cgatataaac 135840
aatcatatcg tttagctttt tgtaacccct aagaggaaat ttgaaatgaa gaaggcacta 135900
gtcccattca acattgatct tttgattccg acccaagcac agctttcgat gttgggacaa 135960
gtaactagcc acgagatctt cgaaggtacc ggtggtaact ttcatgagaa aggtttattc 136020
tccgtagaga ttttcggacg agtaggctct actgaacgtg aaggtcgatt cggttatatc 136080
aacatgggtc ttgagattat ccaccctgtg atctatcgta accttattaa actaaaggct 136140
ttctacgaag agatcattct tggtaaatca ttcgctgtat ttgatccagt tgctaaagac 136200
ttcgtacgtt ccaatgagct tgaaggtaaa accggttacg cctttttctt tgataactgg 136260
aagaagatcg atttcggtga aactaaatca tctattcgtc gagtacgggt agagttgatg 136320
aagaagtaca tgaaaaactg tacattcaaa aacatgctcg ttattccagc tgcatatcgt 136380
gaggccgaga ttgatgttga tggccgtgta tcgatggacg aagttaacga acactatcga 136440
tatctgctta accagtctta tggtgtccct gaatatttcg gacctaatga cgatctgagt 136500
atttatgatc gtaagcgtac ttcgatgcag ttgactgctc ttgcgattta taaccattac 136560
gaaaacctat tatctggcaa gggtggttat attcaacaga aatgggcatc tcgtcgagta 136620
tttaatggta ctcgtaacgt tattagttcg cttgatacca atgctgctga tcttgatcag 136680
ccaaaccgtc ctaagttcaa agatgccgta attggtattt atcaagcagc tgtatccgtt 136740
aaaccaaaga ctatttacca tttacgcaat ggtgttgtcg gtcaagtctt cgatagtctc 136800
tctactcgtg ttgagcttat caataagaag acattgaaac tggaatgggt taatattagt 136860
aacgaagaga tggacctatg gggaactccc gaaggtcttg aacgcgttat tggtgaacta 136920
aaggtcatcg aaaagcgttc tcgtgcaatt gagatcgctg ggcattattt ggcattggtc 136980
tatcttgatg acaagcaaaa cttcaagatc tttagggata ttgaagaaat gccgaagaag 137040
ctcgacaaga agttcgtgcg tcctatttcc tatgctgaat tgatttacct aagcggatta 137100
cctatgtgga aaagaaactc cgcattcgtt actcgttacc ctgttgagaa ctataacagt 137160
tctattcctg taaagatgta cgtgaagaca actgttaaag gtgagatgcg ctacccactt 137220
ggttgggact gggaacgaga tactaatgct gagatcgcat tagaatatcc aatcatcact 137280

```
attaacgaac cggcgcaatg gcatgactcc acgtctattt ccccgtctat tcttgctcct 137340
cttggtgcgg acttcgacgg tgacactgtg tcattcaacg ccgtgtattc taaagaggct 137400
attgaagaat ccgatcgatt ctttaaatct cgtttagctt atatcaaggc tggtggtggt 137460
cttgcattca gtgtcaacat ccacacgctt aatctaactc tccggtatat gaccggggaa 137520
ccgaaaagta ggatttaacc atgcgtttga aaattcatca gtttctgaag aattacagtc 137580
ttcgaaactc aggcgaacta ctgcgtcctc gtctgttccc gttgacgaag ctagagctac 137640
cccaagaggt agtgtatcag ttccttgatg acaacgctgc tgtaaagggt ccgagtcaat 137700
cggacccccct ctttgctaag ttgcagggaa aggtgttcat tgaacacatt acacagctag 137760
aaacactcga tggtaacgct cggcgtactt ctcttattcc gactaccctt gaagctgatt 137820
tccgtcgcca acaccgtttc ttcaaaccac tgcgtaaaga tgcggctgta aaactcaata 137880
ttcaaaacgt tgctgtgttt aactacagca tgctaaaccc actctggaag taccaagcta 137940
atttcaaatc taactggtat cgctggagta acaacaccgc taccttctgg aaaggtgttg 138000
tcgatgtaca taaacgcttt ggttggaatc agttcatcga actccatatt ccagaatcca 138060
tgccaacgtt taatgaattt aagatgttag agcgcggtac cactcaggca ctacttgaga 138120
aattccgtac taacgctgta ttaaacgttt tcgatcttta tcgtttcctt ggtgataatc 138180
gatcttcgtc ttatatgtcg atcgtaccta aagaagctta cgaaaagatt aacttcctga 138240
ttcgtgtcca gaataacttc tttgttatta accttggaca acttgaagca tggcgtgatg 138300
ctccagaagt aatagcggaa caagagacag tagctactga aagttttgtg gatgaactcg 138360
gtcttgaagt tttctataaa ccggatgtaa tgcaacgtcg agttatcagc ctgttgacta 138420
ctttggttga gttcaataat ggtaacgaca ctctaatgga agtcgaacct gaaactccaa 138480
agatcactga cctgatcgaa cccgaagata aggttgacac agacgacgaa gaagtcgaag 138540
aagttacaga acgtgctgaa gaaactgaag aagctaacga cattgatgcg atcgatgatt 138600
ccaatgcaac tggatctaat gttagcacat tactcgatct cgggatgctc gaagttgttt 138660
atgatccacc gcctgaatct gagcttgaga aaactactct cgtcatcgag aaagatccgc 138720
tcgaaacggc gccgatcaat aaaacaccaa ctctcaaagt agagacagcc ccggtaacta 138780
aatcggtcgt acctgctttt agcagcggtg acgctttagt agaccctgtt ggacaaaaag 138840
catttgaact gtatcaagtt ggcatgatct ctggtcgttc gtttgaacaa gccgttgatg 138900
atgcttctat gtacaagtct attcctgatc catttggatc tggtaaaact atcgctgagg 138960
cgatggttta tgaagaagaa gactttaaag taccagtcga acagttcgct gataaatcca 139020
cgattactga taaatcgatg ttgggttcta ttcacaaatc gatgatgcgt aagtacacga 139080
agactcttct acctaaagac atcatgcaat ctatcttgtc tgttcaagcg caaggtgttg 139140
cagtaactga tgttcgtatg gaagaagtac gtgacgcgat gaaccattat cagtcgttca 139200
ctgtaacagt caagcctatt cgtggccgac cctctcaact gcgcttccgt attccagtta 139260
tcgatcgcga tggacgtttc cgttctaatg gtgtaactta tcgtcagcgt ctgcaacgtg 139320
cggatattcc aattcgtaaa gtaaacccac ttaaagttgc tctgacaagt tattacaata 139380
agacattcgt tacacgttct gaacgagcag aaaacaacta cgatacttgg ttgattcgac 139440
agattggtgt tagggcaaga gataataacg atgtctctgt aactgaggtg cgttatgcag 139500
aactagacca gtctatgttc gttctaccgc gagtgtactc tgcattgggt agagcttatc 139560
gttctttcaa gaacggagca aatgagttct attttaagtt cgatgaccat gccgaatatt 139620
```

tccaaaagac ttacggtatt tcggtagaag cattagagaa agatgggatg gttgtagtag 139680
gcgcccataa taggttacct attctagttg acagctcgtc tcagttctat gttaaagaag 139740
gtaatgaact tgaacccatg ggcaccatgg tagatatcct aggtcttaat caggttaaag 139800
ctcctcttga agctattcta gtttcagttg ctaacaaaga gcttccactt ggtttcattc 139860
ttggttatcg ccaaggcctg tccactctac ttgatacact tggagttcaa taccagagcc 139920
atccgcgtgg cactcgcatt agtgttagtc ctgatgatta tacactggca ttctctgacg 139980
agatccttgt attcagtcgt caagattatc gtgcgacatt ggtgttgtcc gggctgaaac 140040
gttaccatca atctttgaag aagttctctc gatgggactt tgaccggcgt gatgtttact 140100
tccgtctatt agaagaagct ggtatgtctg cccgatacac tcgtgaaatc gatggcttgt 140160
ttacttcttt cgttgacccg atcacaaaag gtcttctgga agaaatgaaa gaacctactg 140220
atttccaagg gctactgtat cgttccgtag agctgctaac taatgactgg tcaccagcag 140280
aagtagatgg tgcatatatg cgctatcgtg gttatgaacg catggcagga actatctacg 140340
gtagtctgaa ccgcgctgtt cgtatctaca acaaccgtga aggttctgcg gatcaacaga 140400
tcgtgatgga ccaacacgaa gtttggcgta agattgcatc tgacccaact gtagctacta 140460
ttgaagattc taacccaatc gctaacttgc gtgagcaaga agccatgact tatcgtggtg 140520
atggtggtcg tgggtcgact tcaatggttg cccgtacacg tatctaccat gaatctgacg 140580
tgggtgtagt ttctgaatcc actgtagact ctggtgatgt gggtgtaatc gcttatctat 140640
ctcctgatgc taacttcaac agcatgcgtg gtacaactcg gttgtttgag aaaggtaagg 140700
atggcgccgc taagatgcta tctaccggtg ctctcaccgg ggttgctaca acaaacgatg 140760
acccgaaacg gattaacttc gttagtattc agcaacagca aggtatctat gcagatggct 140820
atgaggtaac tcctcttcgc actggttatg agcagattat cgctcaacgt accagttcga 140880
tctttgcgtc tgccgccgaa caagatggag aggtgattgc agtagacggt catggcatta 140940
cagttaaata tgctgacggt gagatcttta gttctcagct tggaaccgtc catggtactg 141000
ctgcgggtgt aaactatccg catactctcg ttaccacact taagaagggt gataagttca 141060
aacgcggtga tacgcttact ttcaatagta agtattttac cgaagatcgt tatacccctg 141120
gacaagttct ttggaaagct ggtgtcatgg ttcgtgttgc attctgcgat aaccttgata 141180
cacttgaaga cggatctgtt attagtaaag acgtggctat taagcttaat actcagacaa 141240
ctgacatcaa gaacattact gttcgatttg atcagtcgat tgagaatttg gtcaaagttg 141300
gagaacacgt agacttggat tcaattctat gtactattca agaccccgaa atggccgaga 141360
actctctgtt tggtgccgct gctattgaaa cactgaagaa actttcggct aatgcacccc 141420
gtgctaaagt cgtagggacc atctctaaaa tcgaatgtta ctatcatggt gacattgaag 141480
acatgtccag taatcttcag aagatagcca gagcatctga taaagagaga gccgataggg 141540
ccaagtcgtt gaacgaacca gaattcacag gtgaagtcga cgcatccttc cgtgttaaag 141600
gtcaaatgct tgaacctgac aacatggtta tccgaatcta catcgaccat gatatccctt 141660
gtggtactgg tgacaaaggt gtagtagcga accagatgaa aactgtattc tctcgggtaa 141720
tggatggccg taacgaatgt gaagacggta ctccgattgg tctgatcttc ggcaacactt 141780
cggttgaaga acggatggtc atgtccccta aactgattgc gaccactaca atcttgcagc 141840
aagctctttc caagcacgta gctgctctct atcgaggaac cacaaatgca aaatcaaagt 141900
aacaacgtag tactcagtca gaacatcgct gttctgactg ctgctgccga acttggagcc 141960
gaagctttgc ttcgctccat cggcggtgac acctcggcag ctactctaga aggtgagtat 142020
ctgaccaaag aagatattca ggcagctatc gttgcccgta tgtgcaaatt cctcggttaa 142080
ttaggagtca acatgtttaa tcccgaaact ctggacgctg ttcgcgatgc agctcaagca 142140
ttcactgaac aggaacgtgt tctgacaatt ccgaaccccg agttccctct agctgtatat 142200
gctgacggtt tcaactgtga aaccgaaggt aataaagttg caatgtccga tgaactggct 142260
gcttccgttg aagctcattt cgtcgaaagt aacgttgaag cacccgagaa cgttaatgaa 142320
gaacgtgaag cgatcatcag caatatgcat actgctattg ccaagattca attcaatact 142380
caaaacgtta tcattccggc tattaaagca atggccactg actatgcctc ccgtcagaac 142440
gtaagttctc aagcggattg cgatgtcagc actttcaact acgacccgat tcataacgat 142500
cctcgtctag ttaaccacat ccaaactcgc tatgctaaag tgcgtcctct accggaatat 142560
cgtaccttta tgcttcgccc ggttgatgct gctaccatca tcgagatggt atccatcaat 142620
aacccacacc tggatcaaga gcaagttact gaatgggctc ttaagattcc ggcacaacgg 142680
gtagaaaacg tttggagtga actatttggt actgcacgtg gtttgactgt ttctaacctg 142740
agctttatca atcctaatgc tttcccgttt aatcttgatg aactgactct agcttatttc 142800
atctgtggtc attacatcga gaacccacaa gaagtacctg gtgaatccgt aacatcggaa 142860
gaatgggaac aaacggttcg tctactccac gagatgcttg gtttctacat catccgtgcg 142920
tatgaaaatc gtcttgaaat gcgagagtct aatactcttg tacttcgtta tgaagctcat 142980
cgcccagttg aaaaccgtcg tgtacttgtt actcttaacg gtgacgttgc tgagagctgg 143040
ctcgttaaag gtggttctgt tgaagctctg cttggtgcag ctatcgacgg tggtaatgtc 143100
gtacatgcac aaggcattga cgcacgtgct gatcattaca tcaaacgctg gaccgctaca 143160
tatccgctaa tcaaacaagc agcactcgac tacgctgaga gccgtcgtcg gcaggacgtt 143220
attgatacct tcctcgcaca ctgtggtgaa ggtcctttac gtgaaatgaa tatcggtaac 143280
gtacgtgaac tactggctac cgccatgcgt ttcgttcggc gcgaagatct ggataatcca 143340
tactgcgtat tcagtaatct tatctgccgt acttactaca ccgaaccgat gtataagctg 143400
tatctcgata ctatcgatga atatggccaa aatttccccg gtgcagaact acgtgaattg 143460
aatactcaag ctctgatttc gctgattgct attttccaag cacagcagat caaagtagaa 143520
acattcaatc ctgatgttga tccgaatgca actcttcctg aaccagaaga agtgccagag 143580
gaaatcactg aaccaactag tgaagaagtt gccgatgctg tcggtgatgc agtagaaggt 143640
gaaggtcccc tggctgaaac tccggaagta gaagacgaag aagatcctta cgctgatgaa 143700
actcctactg aatctgagac tgaagaagtc gaagaagagc aggaagaagc cagtgaagaa 143760
gaaactgagt ccgaaactga agaagaagaa caagcataat tgataacctc cggtatcctt 143820
cggggtaccg gagtgtgtca actttccttt ttctaagaag agacttatat gaacgttagg 143880
caattaacac gtgatgctgc acgcgtaaat gcaaatctga ttgaattgga agatggtggt 143940
attgctacaa accttccctg taagattcaa attccagaac gttttgctgc taagaacttg 144000
gctgtattag gtagtgaagt attcatattt ggattctttc ctatcatcat gaatgaagag 144060
ttttacgcgg ttaataatac aatcgcgatg atgcgcattc ttccaaactc tactgagcgt 144120
gttgttgtag agagtgaacc ttattacgaa tttagtttcg agaaaggtga taaagttttc 144180
tattcgacac atcttgtggt caacgacaca ctaacatatt acatgtacga cgagttcgta 144240
tccaaaggga acatcccttg gtatatgaac tattatgaca tggcgaaaat gttcgaaact 144300
gcaaaagaac atgcagatac atttattggt ggtcgttcga ttatcgagct tatcatttca 144360
accatcgctc gtgatccgga tgatatgaca agactatacc gccacattct gtcgcggcat 144420
gatgatgtta aaaataaacc tccagtaacc gtacctttcc gatcggttat ttggaacacc 144480
tcagatacca cctcaaaact taatggtgct tacttcagcg acgctatcaa ctctgcacta 144540
gtgaacccta gtgagaaagt agaagtgatt gaagagctat tgaggacata acacggagtt 144600
gcagaaatgc atcctttggc acaatcttct tttggtgtcc aaaattctcc gcagaatcag 144660
gtacgtattg gctgcactat gttagctggt acggacaaaa aaggaattct tgcgccgaat 144720
gcggacggtt attatactgt agttctgggt gcctatggta cacataactc tgctggtatg 144780
ttctatgacg aagccagtgg cgttgcgatg tttgatccga actcttccct gatgcgtcgc 144840
cttaagaaag gtgttctctt catggagttc aaacaccctg aaccgtttac agacctgatg 144900
attgatggtc gtgttgttcg tcaaccgatg gatgatcgtc aatacctgca acgtattcgt 144960
atgatcgacg ataaccgggt ttgtgcacat atccgtgcat tgactattgt tcccggtaag 145020
aatgaaaatg gtaagactgt taaaatggtc gtcggtgagg ttaaacctta cggtccgttt 145080
ggtcacattt ttaaagagtc tttggataac ccaagtatca atacctattg ttccgttcgt 145140
tctatcacac aggacgacgt aatgcgtggt attaagtata cacgggaaat ctccacctgg 145200
gacttcgtcg gtgagggtgg tatctatatt gctaacaaat atacctcccc tgctttggaa 145260
agtttctccg ataccgaagt tatcatcaca cctgctaccc tttggaagat gcaggatgaa 145320
gcacagaagc gtgctaatat cggtatggaa tctgatccta atctagacgt tactgatcta 145380
attcaacaac taggttggtc gcgtaagaag ccgattcgtg tacctgctta catgcgataa 145440
aaaaaatgga acataaagcc ctctcccgaa ggagagggcg atataccttt atgctacgaa 145500
gccataagct tcttcattaa caggtggcca acggactaac tgtggtttat cattgatctg 145560
ttcttctgtt acatcttgac cgtccaggta gactgatctc ccgaacacac cttgggttat 145620
aagttcacga gctttattta aagcaagttt atacttatct accgaattat atgcgatagt 145680
attactcaca tcatccagtg ctaaaccttc aggtgtaagg taatattccc gcccttcatc 145740
taccgagaag attcttacta atcttcggaa gttctcgtta atgaaaggcc attttttcat 145800
aggtttctat cccatgtgaa gaaagtctga gtttaaccga atcagacgta tcgcaaactg 145860
ggtgagatgt tcgagcatct cacccaattc acgtttgtaa tatagttctc aattaagtta 145920
gattaagacg gcatattacc ctcccttttg gggagggctt tatgtcgcta ttgaatagca 145980
gcatcaggat agaacgactt gatcagctct attgggtttt ccatcttgta gaacggagct 146040
gtcaacattg cttcacgatg agtttcacta ctaagaatca atgtggtcgc atcttcagaa 146100
gcgtgactta ggaagtaaag attccacacg ggttgaccct ggcgccgagt agtgaaccaa 146160
tctggtttga gttgattaag gatgcgtact aaagtagcca tttggtcggc gtagttagga 146220
cgttcctgtg caccagttgg atctgggatc tcaggtccgg ttggattatt cgggtcagga 146280
atcattttag ggaaaggacc accaggtaca cattcttcag ggaacacgta attctgtagt 146340
aactgcgcag gaaaatttgg gttctcagcg atcagtgctg aaacaccgcc atgcagcatt 146400
aacctttcga ttgtggcaag atcagtacta gggctaatac tagcagaagc tcgcttaaca 146460
acagagaatc tgaaatcatc atcatagtcg tattcatact tgttatccgt ccacttggct 146520
ccaaaggttt catcaactag atcgggtata ccccaagctg taacctcttc gataatccct 146580
ttcatcagtg ctgcttcagc accaagatcg aatacacgga gcaatgagtt attagtcagg 146640
tcacccatga acccaataat actattaact ccgctaaagt tcccatcttt aaaataataa 146700
tccttttggt tgagaaccat tttaacgcca tcgatcatat ccgttgcttt acgaacataa 146760

```
cctgtaccgg tatcttctcc ggttaactct tccataatcg atcgttcaac gtccgtagct 146820
agacttacaa tggaactacg tgaccctttt agggcatccg caattcgtgt tctagccatg 146880
ttgagatcaa taccgttgtt aaggatcttg ttaccgatac ctttaacaac accaagtgat 146940
ttttgaatga gttcgtctgc acctacacca aatgctgtta ccttagaggc tagctgattt 147000
tttaattcag cgctttgttc tgtataggca tcaacctctt tgacagccgc atctggtaaa 147060
ccagtaaatg aagggatcgc taattgtacc attgaatttc accaaaaaaa aaataagagt 147120
catacaatga ttgccattag gctctccccg aagggagaac ccaaggcagt cactttacat 147180
acttgaagca acacgtttaa cgatattaac ccattcttct tcagctgggg taataccgtg 147240
agcacgccac acaatctgtg tgtttttatt aagtttaagt tttaggaggg ggtacttggc 147300
aatgcacaca cgaagagttt cctccatctt ttcgtacaga tctggaacga acttgtatct 147360
actttccacc ccagcttctt caaggttgat accatctaga tatttgggat gaacctttcc 147420
tgtaataaga tacaaacgga aaccgttcca gctgtaaaaa gctgttccgg taaccgtatg 147480
tttcaacacg gatgaatgga actgaaggac atcagggcaa aggggagagc tcaggtcaat 147540
acagttatcc attctcttac tccacaacta cagggtcagt tatagtgatc ttgtgaacag 147600
agtccggaag tgattcacgg acaactggat catcggacca acggagggtc agaatatatt 147660
cttccttaac tgcgcgtagc aaatggatgc cacgacggaa gttattcaaa gataccctcg 147720
gatcaagcag agcacgtcgt aacgtgttta cattttggtt cacttctttc tgagtcaatc 147780
caactacatt aacgggattc ttcgtgtaat catcaaaaag cttctcccac cagagtttaa 147840
tatctggttt atctttccct tccattgcaa caacgtgcct gaaaagatgc gccatcaatg 147900
tacctgcggg tttagcattc tcgaatatct tacaatcctg ccaagggaaa ctgttggtcg 147960
tcagaacatc ttcccgttct tcgggatcca tcgtgatgac atacgaacta acacgatcgt 148020
cacgccatgt cagtttaatc tccagtgttg cgtggactgg gttcaggaag tcaattgctt 148080
ttctgaaagc ggaccactgc atcgtgtctg acttaagagc tttattcagg ttacccttgt 148140
cttgattatt tttattccaa ggtttctcaa agaaagcttc ttgccgccgg ttccatgtac 148200
gttggttaat cttacgccac aatagaactt cacgaaacag ataacacggg atatcggatg 148260
ctcgcaacgt tcccttaagg ggatcggaaa gaaggtcttg tacagaatcc atttttcatt 148320
tacacctacg gtgattaaag agaaggtttc gtttcgcaac tctatttatt tcatagtttc 148380
ttccttcatg gtatcaacaa gcgtttgggt aagtacaagg atatcatgat acactcttcc 148440
taaaactctt ctatagaagc tcgcggtttg tgtttcaaga atcattgcat gtttatcaag 148500
atacgtctta agcttttcta aagagtcgac tatatctaca gaataacctc ttgcatcagc 148560
aaagtattca tctaagttaa ctctactgaa ttgagtgaat tcattcttac taatttgttc 148620
taaagctgct tgatcgccgg tggataccat tgtgttaatg acattcatct gttcaatcag 148680
ataagttacg ttagtatgtc gcagctccat gtttactgcc atcatgtctc taggtgaaat 148740
ttcaccgaag tctttgacat cgattctatt ccataattct gcaagcatga tgggataatt 148800
atcacgacgc acgccctcgt cttcaaactg atcaagcagt gctgaataca gttgtttttt 148860
ggatactggc tggaacaccc gtaaccagcg gtgtagcgta ttaatcatat agaaaactcc 148920
ctaatccgca ttttatggca tattgttatt ccgttgagta tttctcaaca gtgaggtagt 148980
aaaatggaaa ctccgatccc ggaatttatt ccgacagaac cagaggtttt gtactctgag 149040
ctttcttatg aagaccagct aaaacttaca caaaacgtta agcatcggat tcttcatggt 149100
```

gtaatgacct cccgtgtgga tggtactatt ccaaccgaca aagaatctat tgattcgatg 149160
ttgaaagtta tggactcgat ggatcgcacg actatccaga atcgtcgtac acagattgaa 149220
gcagaaggta ataagtctgc acgtgatctg gttgaatcga tggcagagtt cattaggcaa 149280
gctaagaaca agaacccgtt cgttgccgta cctggtgaag ataaccgcgg ttcagaacca 149340
gatatcgata atgaagatct tggtgagttt gaacacgccg ccggtgaagg tgaaattggt 149400
gtcattaacg agacatctga agagttcaac gaacgcatgc gcgcggttgc tgaaaagaaa 149460
gcacgtgagg aagaagccgc acttggtctc tcttaacgac atagagccca gcctatggaa 149520
ggctgggctc tatgttgtct taatcaacaa taacgtcttc aaatgtacca tactcatcga 149580
tatggatttc gacggtcggt ggttcaaatt cttgcattgt cttacggacg gtttcttctg 149640
tggttttgac cagatcgtct tgtaactttt ttgcaaagag tacactacct gcaacgagtg 149700
caattccagc aatagagcct ttattctgat atgctagttc aaccaacgga tttatacttt 149760
ctttaaactg ttcaaagaaa cctttcttac ggggtttctc tttattgtaa tctttcagct 149820
taaaggtatc gaataccatt ggcatgtcag ggacttgttc atatttctgg agaattgctc 149880
caatatcaac aataccttgt gcaaaccaac caaatacaaa tcgattagtt tttactttca 149940
gaacgatgtt atcgcctgct ttatagttat cacggatcca atcaatgata gcatcatcaa 150000
ctagatcatc ttgtccttta acttctaaca atacatcgag gtctactaga gtaccatcga 150060
tgatagtatc gtttacactg tcaacttctt catgaagacg aagtacggtg ttgattaatt 150120
cggattcggt taaaccggtt gtttttacag tccagtagaa agggatgttg ctcatgagta 150180
tttacctagg tctatttaaa agaactgtag gataaaagaa tataaagagt cccctcctta 150240
ttcttagtcc tacatatcct tacctatcag gtaaatattc ccatgaacaa acatcactca 150300
aactacttat tccacatccg atagatgtgg caacttgtta cagtaaacat tgttcccatg 150360
aacaatgctg ccatcaattc actagcactc tcctcttcta ctttcttttc attttgtttc 150420
aagtaatcat aatactcctt ttgttcttct tttacttcag tagtatcatc taactcaatg 150480
ccagcaagta tacgccattc gtgatcgagt accttaaatt cagaaaggat tgtttcagtg 150540
agttgctctt taacccactc cccattacgt cctctatgaa gacaccaata ctcgcctttc 150600
tctttacaga tatgtctttc agtaccacgg taatagaaac ggaaatgttc aatctgttct 150660
cttaccgaat ctatgtacaa cagatccgtt aaatgatcga cagcaaagtg gctcctaagg 150720
acctctatgc tgcggtaagt cattctacgt tgattggagt tgcatctgcc tcatcgacag 150780
tagtttcatc attctgatta gtcgcgaata gatctcctcc gaatacgatg gtagcaccaa 150840
tgaatacgcc gatgctaata gcggtcaaag ttttccagtt catgttagtc acctctttaa 150900
acgaacggta tccttagata cggctcaatt aggtaatata gatctgaaaa aaattttatt 150960
gacataaagc cctctcccga aggagagggc atatgcctat ttacaactta cttgaagata 151020
ccagctttgt aaccttcgac gaccgccttc gcttccgata cggacagttc ggggatattg 151080
cgacgaagcg ccaccaccgc tttgatggtg tgttcggtat cggcaacctc acgccagtcg 151140
cccttaccgt tggccagctc tacgtcttgg acgtacagag cagccttgag aagagccatg 151200
ttacgttcaa tcgtcttcat gtccatctcc acgagctgtt gcaggtgaga cagagacata 151260
tcggacgctt cacgaacatc atccatgaac gaacggttgt cggcgttgtt caggatatcg 151320
cgagtgaggg tagccagatt accagccgtc gcggtcaggt taacgaggtg gccagcgtat 151380
ttctgagcaa gagtagtcat tgtatattcc tttcgttggg gttgaattta tgttgattag 151440
aaaagtgccg tacctttcca ctcgttatcc cgcgggggag tacagaagtg ttgagtgtac 151500

-continued agatcgatga aaacaatacg gtagacgtca ccgtattcac cagtgcgaag caagcgttca 151560
atgaaagagg agcgccacat ggcgtctatg acgttttggg tctcagagac ctgacgatgc 151620
agctctttca ctatcgtgcg atatacagcc tttttggcgg cttcctcggc ctctttacga 151680
cgacgttcct ctgagacagc aaaggcttca ccgtaagtag ctttaccgaa aagaatatcg 151740
catgcttcgg aagccgacat ggaattgaat aggcccgata cagctgccca tacgccagtc 151800
ggtggagtgg acttcaggat cttattataa gcatccagag gaattacgaa ctcacggaat 151860
ttttcatccg taaggtccat cattttccag gtctcttcat tggtatcacg ttcatgatat 151920
ttccaaccag tggagttgga agccgatcga accaggttca tcggaaccct acggtggaac 151980
ataggtacgt gcgcgatatc gataagagac tggtttgaac cttcagaaga aatcatatcc 152040
agcgaattct tgacgccata aacctggcaa aggaaatcga tggagtacgt tacaccaatt 152100
gctacgtcac gcgagagatc tttgttaaac atgaaatgta tccttaaaaa gatgtttgtt 152160
agcaagtaca atgtaattgc attctgtatg cagtgcgata gtacgatcta ttgtgtggag 152220
aaggtctcca acttcgtcgt cagtcagcgt acatgtccat tgagtcaatt ggatgtaccc 152280
accaacatcc tctttataat gaccgtaaac agtagcatct ggtcggccat tacgcattac 152340
aaagatgaaa gcgtcaccac tgatatcaag atcatagtaa tgcccatgct ctgatctcag 152400
tgtaacaaac atccgagcgg gacacccttt aataaggcgt atacgcttag ctaaccgatt 152460
gatactgtct acgttaaaca tgactagtcc ttgacgttaa acgtcagcga gaagctcttc 152520
gtagcactta cctacattca tgtcatgata atcttgttca gtgagatcct gaccagaatc 152580
atatttcatg aacgcgtgca agtatgcagt tgaaacagag cgagtgttaa agaacttggc 152640
atataccaag aacttatcga ggtcttcttt aggatcgata ctacttactg caaaataaga 152700
aaggtctcgt cctggaagag tctgctcgaa gcgatagatt gctatcgatt tgtttttgtc 152760
accatcacgg taaccacact caaggagtac attggtttga atattcatgg taatttcctt 152820
ttacataggt agttttatca catttgtaat atagggttta aaatgcttta aatgtaagac 152880
aacataaagc ctcccagaag ggaggcgttt atattaacac gatgctctta ggacatacga 152940
tgaactacca actatagcct tcaacaggga gcgccagagt tgtccattta aaccttctag 153000
gagctccacc ttaacacctt cttcccattc tactacaagg acacgtgttt cattgatcgc 153060
caccgtaaag agcgttttag acctaatatg aggtacttct atacgtagat cccccaacaa 153120
caatctcgct tgctctttaa acacatattc aaaccgacta gtgatggctg aaagatcatg 153180
tcggtaatgt ggtataagta ggtaatagaa gttatcgaag ataatctcca gcaactctac 153240
tctctctttt tcggtcattt gatagactcc aaacagatta ccttgtactc acttgataac 153300
tacgttcttg ttataagctt caggtacggt gatattagtt gggttaataa caactacttc 153360
tgcattattg aaagcaccat gagtagactg gaagtggctg ataaagaaca cttgtttaaa 153420
ttgaccgttc tcgataagac gagagataaa cggaattaag tttgcgcggt gttgttcatc 153480
aaacgtacga ccaaattcat caagatacaa tggcatgtct tcaagaccga ggaacttcag 153540
aatagccatc ttgaatgcaa agttaacgat ttccaattga ctatcggaac catacgaaat 153600
gtcaggtgcc attacttgac cacctgctac tttgagaggg aagttgtagt ctaactcctc 153660
cttttcaact ttagaaggta gtacttccat tgggtatgtc cacacctcgt caatgaatgc 153720
attgacaatg taagtaacac cctgcaagaa gccaagcata tatcgaccca acaatccacc 153780
gtttggagat aacgacttaa ttagaatacc aagatcgcta tgtacttcag tagcatttgt 153840

-continued tacttcgttt tcaagcgtac gtatggtcgt ttcacgttgt tccatctgtg tgagctgtcg 153900
cgttgtttca gcgagtttta cctggatggt tcctatctct tcagtatagg ctctatcaag 153960
caaatactcc gaatgacgct ctactttatc tttccacatt tcataacggt ccaggacatc 154020
atggatacgt ttattgttac gtagaataga ttgttcacca gaccgtagat cttgcatgta 154080
ctgattgata tctgaagctt taacatacat gatgttaatt tcagtttcca attcttcggc 154140
gcggcgtttc atataaccga ttgcatcttg gtctatctca gcgataactt taagacgttt 154200
ctcgatatta gtagcaagct ctagttcagt acgggatttg acataactcc gcatggctgt 154260
atgccattgc aaagcatcag tcttatgcaa tgcaggagtc cgatacattg tcatgttagt 154320
tgcacagtaa tcccacagtt cattaaactc tgggtagtct tttgtcaaag acatgtactg 154380
gaaaacataa cttgaatagt cctggaattt ctcaagatat tcttcgttct ctttttgttc 154440
tgcttcgata cgatcaatag cttcgtggag tttaacttta gaagcttcaa gcatatccgt 154500
ttcagatgga tctacgccag gtttaaattc atgggtacaa gatggacata ccacagattc 154560
acaacctttc aaacgcgaca acctggaatt agcctgctcg attttatctg agacttgtgc 154620
gtaaatattc ctaagctctt tctgacggtt ctgtcgtttg gttgcttctt cccgattcat 154680
ccaaccgtca ccgttatcag ggaaactagt taacagatca aaccatcggt cgaacattcc 154740
atccaactta caaataggat cagcaccggc tgtattaaac ttaataattg gaaattgacc 154800
agtataagtt ttcatcgagt taatacacga ttcaacattc gccagattcg cagcatgctg 154860
ttgtttcaat gcattaacat catcttccga tatttcaatc gccgatggag agttagtacg 154920
aagcttttct agttcttctg caagacgatt aatcactgca ttgatcgaag agtattgctc 154980
cgatacccga ttgaattctg cctggaattc tccatggtta gctacacgaa tagcggccgg 155040
taacattgga taatcacgta ggcaagcgcg tgcatcattc agaatagatt cgagttcgtt 155100
ttcagcttgt tgcacattct ggaaagcagg tcgaacatca ttttgctttt cttggaagag 155160
tttattcaaa cgcttagtaa gacgagaggt ctcttcgcgc atcagtgtca tttcactatc 155220
actaaagata tcgtgatttt cagtgactag gcgttttgtg attagatcga tgacaccttt 155280
ctgactgcga tgttcctgtt taatgtctct gtatacatct aacgcataag tcaaatcaac 155340
agttgacatc cgcgtaagaa tctcgcggcg ctttgctgta gacatagcgg taaatttaac 155400
tcgaccagtt gcaatctcat ggatttcacg cgtaagtcca aactcttgta gacagagttc 155460
ttcttggatt ttatatgtac cgccgctatt caactcttca ttatcccgtt tgaaagagtg 155520
acgaccagta ccatgaccat ataccgaatg aagtacataa aggcttccat tatggtagca 155580
atggaattct ttaaaaccat ctttatcaaa gtttgtatgt cgagatggca atggagttag 155640
ttcatccata actgacgatt tacccgaacc attagaaccg agtataatca tcatgttctt 155700
agtgggggtc cattcgaaga attggatatt tgccgtcata agtcgtttga attttttcaa 155760
acgcagtaga gtgatttgca ttggtaagcc cttaaaatcg tacgttaccc tatagaacta 155820
aggttaccag taattattca gaggaacata tggaagcttc aattttcaaa ttagtaagta 155880
ttggtagagt agctgcaaac aaagaacgtt cttcaaggca tgtggacgtt ttacctgtag 155940
agcttgccac tggtactgat ggtgaagtaa cgtttgaccc attgcaggaa acactacaag 156000
gtttcgatgc cgagggtaat cagtataatg ttaaagctac tacaactaga acgactaact 156060
gtgaatggct accgaacgaa gacaaccgtg ttactccacc agatgtacgt cgtaacgaga 156120
tcgtagagat ttggcgaatg ggagacaccg atcagtacta ttggcggtgt atgggtcttc 156180
gtaacaatct tcgtacatta gaatccgttg tatttgcatg gaatgcttcg cccaaacctg 156240
gtggtggtgg tatcgatttt agcacgtgtt atttcatggc tatatcagca catgacaaac 156300
actggacaat cggtacatct aaagcaaatg gagaaccttt cgcatacaca ttccaaatca 156360
atactgatta tggcgcagtc tatattaaag acgatgttgg tcagcttata gaacttgatt 156420
caactgaacg acgtgtacaa ttaataaact cggacaactc ttttgttaag gtagaacggc 156480
aatggatcga aatgtctgcg gatgatcata tcaaaatgac cgtgggcgga acaactcttg 156540
agctgcgacc agattcgatt aacagtaata cgtctaatac tacactaacg agtagtggga 156600
cacatacaac tgtggcgggt cacattatcg aacaaactgg aagatgggat attgtctaat 156660
gcctggtata gctgtttgta atatagattc tgctggtgga acaataagac caagtggtaa 156720
ttcaactggc ttctataaag gtaatccaat tgctgtatta ggtgatcccg tagatggtca 156780
tgggcgatcc ccacataaca gcgcaaacat ggtacaagct tcaacgaaag cttttattaa 156840
aggcgtgcca attgttctgc aaggaatgtc cgctagctgt ggtcatactg caaccggtag 156900
acccgatgcg actagtagcg gttgacaaca taaagcccct accattcggt aggggcttta 156960
tgccgttata cgccttcagc ttcgtaatgc ttgatgcaat gactaatgaa agtcaaatac 157020
acattaagcg atacagccag ccagtgagta tagaaaccca ttggttcagc taacttcttc 157080
gaaatctcgc cgataataga gagaacagaa ttataggatt tacctgcctc ttcacccgct 157140
tcagcgatct gtcgaatagc gtcgtctaca actactttga ccgtggagaa gtcccgctga 157200
cccgtttcag ctttctctgc tagagaaagg atgctggaga tcaactgagt gatctcacta 157260
agagtacgga cagaaggtac atcaatctca cgttcagaac ggtcagctac atttagctgt 157320
agctcagcga actgcattgt aaacgaacgt cttacaacat cctcattagc gactttacta 157380
ttattcaaca tctgactgat aacgtcaggt ggtgtataga tgaacgctac gttgccaggt 157440
aggacaaccg aacgatggac acctttttcc gcagtagtca gttctctctg ttggagaggg 157500
gcatgaccag gcggaggggt aaaatcacgt tggaggatat ttgcaaatgc ttctacaacc 157560
tcaccagcta cttcattaga gctagcatcc ttagatttat ccaagatatt caggaactgt 157620
cgagaactgt tccgtgcaat ctttgcaacc gatttaggat aatggttgag aatgtagttg 157680
gttagatctt tgatgtcgtt caagtggtta aggtctaacc ccacgaagtt accatcaata 157740
gatagacgtt gtacaccagc tacagacatt ttctggtaag tagttgccga gcctagttta 157800
cctaagcgtc gactaatgct ttcttgtgtg cgacgaacac gacgaatgct accggtgaat 157860
ttgacgtaga aagagttaag caattcccag atgtagcgga caatatcgcg ggtggctttc 157920
gccgccgcga taatgccttc tttgattgct ctcagagtaa ttttagaacc ttctttgata 157980
tcaaagtcag ggtcaatact ctcaagggct accgagataa catcagcagt agcccctgtt 158040
acaacgtcac gtccagctag cagatcgcgg tagcgctcta gagaagaacc aagacgctga 158100
atcttactca ggtcttcaga tacttcattc cattgtgcca gataggacat gctttcaccc 158160
ttaggctttc tcgccttcga taacatcacc atgttcagct ttcagcatgg cttcaataac 158220
agcgatttca gctttaacca ggttcaggca ataacctgta aacagatggt tagcattagc 158280
agtttgacga gccagagtaa tggcaagcag actggaaata gccgagttct catcaccggt 158340
catcagtgca ccaaacagga agctagatcc tttctggtta acccgttggg cgagttcatt 158400
cagcttgcta cgaccttcaa cagctgcttc aactttattg atcagttgct cggtagcgcg 158460
aataacagaa actgcttcac cagcagacat cgttttgatg gtatcggcac caccatagct 158520
atcgccaccc ggaataaccg agaagttgat attaatagcg ttgttgaagt tgaaagtctt 158580
atcggctgcg taatcggtgt tcacaccaac gaacattgca cggttacccg gaagaacttc 158640
ggacatatga accgaggtgc tattcaacat accactcgga actttatctt tctcgttgga 158700
attaacgttc ttgaatccac ggaaggagtt agacagaatg tcatcgatcg catcgagcat 158760
ttcaggagcg agaccgcttt gaacgccgaa gtagtaagta gatttatcat caaacttctt 158820
cagaatttca gcaagtttgc tcggccagtt gatgagaacg atatcagcgg tattctcaac 158880
acgcttaata gcttcaggac tatcgccaac gaattcttta ccaatggaca gacgttgcag 158940
accaccaatc ttaatctgct taccaccatc aagagtacct actttactac ggagagtacg 159000
cagacgttct ttcagtttgg tagcatcttg agtaaaggag cgccagaagt ccatcaatgc 159060
gttgaagata cgcatcagaa cattacgggc tgcttccagc aaagacttca tcttagcagt 159120
gagtttgctt tcagtagcat cgcgagcaga agtatgctta tcgctgtcgt caagttcttc 159180
aacggatacc acggtatcag agaagaaatc aggatcaatc atttccagac cgacacgcat 159240
cgactcagcc agctcgttag taacttcata gccgttttca cgcatgccac gcaggatacc 159300
aagataacgc tcaacggaag ctttggcgtt ttcaatgtcg cccatatccg aagcaatctc 159360
gtttacaacg gcacctttgg catcagtagc ggatgtaagg ccatcggcag taagagcttc 159420
aacagcttca tcgatgtcct gcaccatgtc gtcagcttcg ccaacggatt cagtttcacc 159480
agattcgatg gtatcgagac catcagtgtg ttcttctaca gaagtagtgg tagcgacgtt 159540
atcatcgtca gccgatactt cgtcatgtgc agaaccaaca tccccaagac cagtttggtc 159600
aacggcggtt acgtgattct caacggtgtc cgaagtatga acattggtca catctacagt 159660
ttcggcagta ccatcgccac caccttcagt gggacctggt tcactagtct gtgtgttagt 159720
gaccgaagca tcaacatcat cagcatcagg cttttcgccc tcatcactct tcagttgagg 159780
ttcgagatct ttcttgcctt ccagatccac gttctgatcg gaggcttcag tgacagtacc 159840
agcagctttg ttctctactt cttcagtaat ggattcgtta gagatgctac ggcacagatc 159900
gaaaaggtta gcgcgggcca tttatatact ccacaattgc gggggatttc gtgagtttaa 159960
actacataag gttgttaagg cagcaggttg ttatccttga tgattttctc aagaataagg 160020
ttctgttgct ttaaaataga gttggcattt tccagttcaa gtagacgagc ataatccgtc 160080
gtacgattct tgatcttacc ttgtcgtgct gcctcacgtg tttcgtggac ggctggtgtt 160140
acagcatctg acaacggcat aatgccaaag tggacttctg gattaacacc gatcgtatca 160200
ctaactgcat tcgcagcagc attagcggct gtatctagaa ttacgtcatc tggcaatgca 160260
ccaagcgaca gagtcatgat gacttggttg tatggcttag agctaagatc aggataagat 160320
ttgatgtagc tcgatggtac ataaacaggt gggaatttag gtgacagcaa cgttacgatt 160380
acatgacctt gctgtcgatc tgtcgcgacg cgtgactcgt cgattttcca aggcttgtaa 160440
taaaggtcat aaactgaacg accattattt tctacatcct cgaagtagcg gatagcaccg 160500
cattcgtaaa gttcagctgc ttccaatact ttatcaaacg gaggtagaag aacatatagt 160560
ccctttgtac caattggagg gaccattaaa ttgttagtgg ccatgtatca tactcactat 160620
tgaattgtca tgtaattggt aatgaaagta aagagtggct cggttaaccg agccacattc 160680
ttagtattga cgctctatca gttctgataa ttgccagtaa tatttgttag tccacttatc 160740
aataaacaat gtcactctga tggcttcacc tgattcaaaa taataggtgc catctggagt 160800
gagacttgga taattagaac gtagacgatg ataatcacca ttactgtctt cgtagagtac 160860
acaacctcca cttatgatac ctgtcggaaa gacgatatca catgcagtac cagaaacata 160920
atcgctatcg tattttaaaa caataccgat gtcatattcc ctaccttcat ctgagggatt 160980
accaagtata agaatagtat cgacgtattt agaaacatcg atcttgttaa cggccattgt 161040
gtaaccgtca taactaaact gctcagggta atcagtgatc agaagctggt ttggtgattc 161100
aacaaagttc cagcaattaa ttggattaat gtccatataa cacctacatg ttgttgaatt 161160
cgtaatgtgg tccacgcatg atccatcgaa taatcggtgt atcttcatca atccagacta 161220
cacgtagaat ctcaactccg ttaccaggtt ggataactag ttgaatacca ttccgtttac 161280
caagccatct ctctgggacg ttgaatatga tcgaacgttc gctatggttg aaaactttaa 161340
atcggacacg ctggtcagca ggcatatctg gagtatccag gtagaagata aacgcgtcat 161400
tataatttcc attagcttta tctttaccat cgaaagtacc accggttaaa atcagtgtac 161460
tactcaaaat atcctttcta ttgcttacag tctctccacc tgcgccggca ccagaaagat 161520
ccatggtgat gatctctggc caactaacac acatcgtagc catcattcct ccttaaacaa 161580
gagtttcata agtacgacct tgaccattgt tgtatagcca cgcgatctct tctttctcta 161640
gcggtcgcca gcataatcca acttcatcta cagcaccatc aaacttggaa tcactaaaga 161700
tttctccgaa ctgtagacca tcataagaac cactacttgg taatggaatt tctttacgta 161760
tcggattacc attgtcaaca tagatctcaa ggaatcgatc ttttacttga agaacgatga 161820
attgccattc tcctttaccc atgtgttgac cgccagtaga tacagtagtc tctgtgttag 161880
cagcattgcg agagaatcct ctccagccgt tggaacctct gtacgataag ccgtacttac 161940
agccatagta ctcgccaaac ttaccaagag tcaatacata ttcctgactt acggttgggt 162000
tatttacttt aaaccaacca aacattgccg taccgctatt atagctaccg aagttacctt 162060
cagcaccgga agcttttata ccacttagtg cttgaccaac tttaccaggt atcgtacttt 162120
cagagttaaa tccgaagtta tgaccgccgt gtgagtctgt agcaatccct tccatggcat 162180
accaactaat caagtcatcc atgatagaac tacctacagt tttaccttga acaatatccc 162240
cagaaattgc ccaaatccat tgattggtat tattatccca accgatggca gtaccacgaa 162300
tagtcccacc ctgtttaact gcgattacat tccacgcagg caagaggaat ttattatgac 162360
taagtccctc tggatcaaat gtgatctcat gtccggagtt attgataata atccattcat 162420
gtccaggtac aagtgtagct ggatcatttt catggtaggt aggccagttc agtgtaggta 162480
ccttctcacc ctcaggaatt ggttcgagta cataaacacg gttaccattc tgttgtacac 162540
taagagatac atagtaacct gggttaccaa atgtaccagt aatgtaatta gagatcgaac 162600
cttcgaagat atgttcatag aacccatctg taggttcagg ctctggacca ggaccatctc 162660
cacctgaatg taaccaaaga actagttcgc cggtaaaata cagtgagttg taaatagact 162720
ttaataacca gttaggtccg acttgtccac cggtataatc gatagaagta tcgttaaccc 162780
aaatatctga ttttgttaaa ttcaaagtcg atttacgagc cacttcacca aggacttcag 162840
tagagttctc catctgttgg agttcttcaa cttcagaagc cgtccagtat ggattctcaa 162900
taaaatcgtt taggttaaat cgatcgtaat aaaaatcgta aatagtgtca taagaagttc 162960
ccttctgaat aaacactact gtctggttgg gtctttcttt agttgctgct ggttgtactc 163020
taataacccg agagtttgct tgggtcagac ctaggctgga atatttagcg ttaatcgctt 163080
tataaagtcc aactaatgga ctagcaccga tagggttatc ggcaagtgaa atagaaattt 163140
gacgcatgtg tatcccctaa taaaaggaga gggtttcccc tctcccttat gtttttagga 163200
taattcttct acgctagctt tagctacaac catgtagtta acgttcttaa agtatgcgct 163260
tgcataaatc acattatcac gaatcatgcg agacacccct tgtggaacag agctatagcg 163320
agtcatccct tcggctgctt tcagtagctt cgagaacaac atcatccatt caattgtttc 163380
aggcgacgat ttattgatat ccccagtatc gttagttact aactgataat ctttaaattt 163440
ctgcgagaac tgtgtaatac cattcctgtt ttgagggtta cccaatacgg agaaggcaat 163500
ggatttgtat gtgttcgaag acagctcgaa tttattgtct acgtaggttt gagtataacc 163560
tggcccacgt gctgttcgac gaatcaaagg aagtcgttta cgatggtcta cagtaggact 163620
gtaggtacca gctcgataat cggcttgttc gatagaatac tggttccaga atggagtaaa 163680
gatgaactca gttgtcatga acaggtctgg aagaataact tcccaatctg tccgtggatg 163740
tgcagagtca gccagtagtt cttctacaat cttgtctttg atgaggtcag ggttgttgcc 163800
agcctcgcca tagacgattg caatccaata ggcggggaaa cgcatagaat catcacgggg 163860
attatggtat tcaaacatga atgcccgttg atgtgtatat ggatattgtg cccgcttagc 163920
ctgaacttct tcgatcttct caacgagatc ataatcgtcc agtagctgct taacaataag 163980
cggatcttta aagaaatcgt catacggaat tatcggatgt acgatctcga tgatgtattc 164040
atcgtactga gctgcaaagg attcatctgc aagccagata ttcatctggt tagcttcaga 164100
accaactaat acgaattcaa cccattctgg catccaaatg ctaccgttag aaatcatttg 164160
accactacgg aaactttgga taaccccatt aaactctgcc atcaccagtt gacgaagtac 164220
gttaggatcg gaaccgatcg taccagaaat cgactgttga taaatatatt cacctagctt 164280
aagaacttga tctttgttgt taccagcaac atcaacaacg tttccatcct ttacgctatg 164340
aaaagaaata aaaacaacgt ttggtgcgga cgtaccggtg tggaaagtct tgtcctttgc 164400
ataggttgcg ctgttcgacg aaagttcgcc gagcttcgct acagtttcag gtgcattcga 164460
aatgagtgca gggaagctgt aaaagccttt caaattgtac atgtgctatc ctcatgagcg 164520
agagatcgat ggtcttccat ctataaaatc agtcactccg cttgtgctta tttaaaacgt 164580
cgggtatact aatgctttta aacggttagt atattgtctt taatgtctat tgatctcagc 164640
catccacggc ttttatgggt aggcgcaatg tctaactgaa cagaggaaat catgctcagt 164700
ttaactgcaa aagccttgct cctgttgtgg cccttcctga aacgggcgat cttcggtgat 164760
cgtactgtcc gtgaagtgat gctggaaaac aagcacgtta cgtttatgtt tgcgatggta 164820
ctggtcttgg ccatgtcgct catgttaact atcggcgagt tgaatgatgt taagtcagag 164880
aactggaagt tgaaacaacg tccggaatgt gtatgcgatg tagactctgt cgaatcgctt 164940
caagccaggc gaaagcttct gggtgaaatt ctgaaataac ctttaatggg ctgtaggtga 165000
accacatgtc taaaaaatat ttactagtac tttgtttgac tctttctggt tgcgttattt 165060
atgcaccgag gtacaccaca cagactgtgg ttcagcaaga gacaacttcc agctgggaat 165120
ttagccagcc gcaaattaaa acaataacgg aagtgaaaga acgagttata caaacacctg 165180
tcacagaaca aaagcgtccg ttagcaagct gtgaaccgtt tgtactccca cgtgctgctt 165240
tactccccga gaaaccgaac gaagaagaat tagcgagtgc gcagtcttca gaagaaatcg 165300
atcggaaact ctcggagtat gtagccgaac ttcgtgcgta caatgttgcc gaacgatcca 165360
agatagagca agcccaccaa aagtggttgg atcactgtca aagaaaactc gactgattta 165420
tactttagtt aagagtctgt tgacagaggt aaaaaacaat gtgcgacggt atagtgctat 165480
acacagatgg atcattccgt caaggtctag ctggttgggg agtccatggt tacacttaca 165540
ccaatacacc gatgaagtct aaagctgcta caaaacagca gccaactgca tcgggttatc 165600
aggatgtcgg tgccgaggat acttgtacgg ttattgaata tatcgactcc ttcggtaagg 165660
tagtcgataa tccgacgaac aacaccgctg agcttagtgc ggcgattaac ggctttaaga 165720

-continued ttgcagatgc ctctaaggct actaaactaa ccatgcttat ggatagtgag tatgtcagaa 165780
aaggtctcga atcttatctc ccaaaatgga taaaaaacaa ttgggttaag gtagatggta 165840
atcctgtagc caacaaagat ctatggattg ctctgaacca gcaaaagatg gattggctta 165900
agaacgaccg caaactggaa ctcaaatggg ttaaaggcca ttcgggagat ataggcaacg 165960
agaaggctga cgtcaatgcg ctacgcggag gcggtgcttc ggttacacct aaaacagtta 166020
aggttgaagg cgatgccatc aacaagctga aaaaagttca gatgaatcca ctgatcctgg 166080
agtcccgtct gctctttgga attaatagtg ggaaaccctc ggatgggacc tactacatgt 166140
acaacctcgg aagtatgcat aatgcgggcc atcgtcctag ggatactgcc aaagataaat 166200
tggccaaagc agatttgcta cttgggagaa ggatttccga agcaaccttt ggagtctata 166260
aatctcggga acctgacgag tatttagaga atctaattga gctacatacg aaagcatttg 166320
ggactgacct cccagaactc ggtattctca atctgggtaa tgcttgtgga gcaaagcaac 166380
gccagcaaat cgaatcactt gggcttgatg ctcttgtacg ttttgatgac atctttgttc 166440
ttgcaactcc agatatgggt ctcattagta ggactctcaa cccaccacgt atggctaacg 166500
atgcggtaag catgtttaac gtgctggaac gtcgtttggc ggaatacacg gcgggaacga 166560
taggagagtc ggtttataaa atcgacatta ccgatcacct gtatgaaact gtacagagcg 166620
gtaagaagac ggtaacccaa cttaagaagt ctatcactca aaatacacca tatctcgata 166680
ttcctatcga ttataaagga cagaaggtat cactccgatt ggcattgaca atcgatattc 166740
cttctcgtaa ccaactcgct cgaatcagct gcgagggtgt taaagtggaa gtactgattg 166800
tagctacggg tccgttagcc tattcatact cgactgtgtt tgtaactgat gatggttctg 166860
ccatctatga agcaccgtac acacagttca ttttgaaaaa atagtgggta actcatgagc 166920
cttattagca gattcttgag gctggatgaa aatccattca ggacattctg ggttttcatc 166980
tggaatcacc tggataacgg cttcaaacgg atgtgcgtaa tggcgtcatt gcatgccgca 167040
ctggtgcagt gtcgcgatca cgaatgcgag cggatatctt cgcttaattc agtgatgcgt 167100
ctcgtgaggg atgaaagcgc cttacgctta ccaacgttat ttggacctta cgtttggaaa 167160
ggtatcctcc ctatcgagaa ggttgatctt gaatctgaca agtacttcga aaggatcgct 167220
cgaaagactc cctgctggct tctatataca gacaaggaaa ctttcgttaa agaacttaag 167280
caattagtac accattgcat gaaggaacgt caggcgacag cttaacggca taaagcccca 167340
ccattaggtg gggcaatatg ttgtcttaca gagaacgaag atgtttctct gtttcagcta 167400
agacattatt ggtttcaata attcgtgtca tttgaatgga gaaccactct acccacttag 167460
ctacttgggt tagttcctca gacatcatct tagcgaactc gctggatgtt ttgatatcgc 167520
cttctttacc gatccgttcc atcaaagcag ttacggtttg acttaatgct tctactgcac 167580
tcttaacggt agaggtttca ccacctttaa gaatggtatt aatctcgaac atatgttgtt 167640
cagattcata gaagtcattc atcgaactgt aaatcttacc aaatgcaaca gttgactggc 167700
ggttattagc aaagaactga gcgtcttctt taataagctg gtcaatcgat ttatcaatat 167760
cgataccgta ttggaagtct cgacgttctg cacgatcttc tggagtagtc agataatgac 167820
caaaacgaga tgtcgcgggt cgaataacct tctctactac ttgcgccatt acctgtgcac 167880
gcgataccag accagcggta tatggaagca tttcgccttt aaagccagct ggttgcggaa 167940
caatttcttt ctcaacttcg aaataatcca gagtagccac aaagcctttc atggatagag 168000
gattaagagg tagaagcgga tcatagttcc acgtagtcag ataacggaaa ccgtctttaa 168060

-continued tatgaactcc catattggat actttacggg caaaccaatt agaaacatta ccaatgaaac 168120
cagcttcagt ggaaattgta cccagagcat cgaatagttt gtctgtagga gtttgatcta 168180
caggaagaac ttctgtttca ggggtttgct ctgctgcttg aggatcaccc tcagtgaaga 168240
acttattctg agaactatca aagataacgt catcagtctg gacgttttca ttggagacct 168300
tctcagtgta tttattaaga acatttttaa tcatggttgt tttcctatgg cacaagagtt 168360
gcgaattctc taaacataaa attactctca atatcaataa agtgattggc taatcactaa 168420
aaggtaatat caatgttcgc taaacacttc caacgtccgg ccttccgccc ggcggttaat 168480
atcggctgcc tgatggatgt atccactggt aaatatgaac aaggtaaaca cggcgagatg 168540
atctgtaacg gtggtctcgg tccgatgacc ggtatcgcat ctcgacctaa caactttaaa 168600
actgcactcg ctgtgtatat gctagcgatg gttcgtcgag ctatgccggg ttcccatggc 168660
atgatctatg ataccgaggg taccttgaac ccggttgcac gtttcagtag tcttgcagct 168720
caattcagtg atctgcaaaa gatcgattgg gaacatgatg aacaattcat gttcactgac 168780
ctttctcgat ataccggcga tgagttcttt aaactcttcc gtacagcact tggtgagaaa 168840
gagaaagcag aaaaagaata tcagcgcact actccgttcc ttgatgttga aggtaacaac 168900
aagaaatgca tgtacccgac aactggcctg atcgatagtt tctcgaagtt tatcgttact 168960
gccgtatcgg atatgtacga gaagaatgct atcggtgcat ctggtaacaa caccgatgcc 169020
atgactaatg gtaaggctaa gaaccagctg ttcaaccaat tgcctcaggt atgtgctaag 169080
accggtactt atatcgtact gactgcgcac actggtgaca tcatccaaat ggagatgtac 169140
ccgactgata aacgtaatct ttcccacatg aagaaggata cggttcttaa aggcgttagt 169200
tctggcttct attcgctgcc taacaacgta ttctctatcg agtctaacaa acctcttgtt 169260
aacaaagaga agatgcctct gtatccgatc gataactcga ccgcaatgga aggggatacc 169320
gatcttaaga ttctggaggt aatgaacctt cgtggtaaag gtggtattac tggccttcct 169380
ttccatatcg tagtttctca gactgaaggt gtacttcctt cgctcactga gttccattac 169440
tgcaaagaaa atggttgggg tattggtggt aaccttctga actactacat tgaactttgc 169500
ccagatatca agcttagtcg taccactgta cgtaagaagc ttatggaaaa cgaatccctt 169560
cgtcgggctg ttgaaattca atctgagatg cttcagttga tccagttcca gcgttggacg 169620
gctgaagatg tatgtgatcc aaagacactg tacgaagatc tgaaagcgat gggttatgat 169680
tgggatatga tcctgaatac gactcgtggc tattggatgt gtgaagaaga cgaagctctc 169740
accgataaga aattcctttc gacctacgat cttcttcgta tgcgtaccgg tgactataaa 169800
ccttactgga tgactgatga tgaacgtgct aagattattc cgttggatct ggccaaagcg 169860
aaagctgcct aaagaaggag ttgtgatcgt tgaacctatc cctgccgagc gcggggattt 169920
gggtaaatgc gaacagatct ctttggcacg cgaagccgtt gaaatgggca gtgaaaaata 169980
tagatccact ttatctgacc cagcaaaaga atggtacgag cactatagag caaacgaatc 170040
aaaacaggtt caacctttaa ggatcccaga aggccgtggt tacgcttctg gtagaggagc 170100
cgaggatatg gacctgtcca acacaatctt cgctgtagga gctgctgtgg ccctttctag 170160
cgatactacc gatagtggtt caagtagcga tagcagttgt tgtgattaat atcatagacg 170220
ggagcattag ctccctctat gtcaagtagg tattccaatg aacgtctata cttatcaaat 170280
cgctaaatgg cgaaaggtta gacagaaaca tatctttcct ttggatacaa ctataaaaag 170340
tggtgaggaa ttacttgccc ctacctggaa tatggtaatg ggacataaag ccggtgccat 170400
tacagatgag caatatgagg atgcgtatat ggacatcctc tctgaacgat acgctgcatt 170460
cccagattac ttcgaatggc tgactgagtt ggacaaggtt gcactaggat gttactgtcc 170520
agctggtaag ttttgccatc gacacattct cgttaaattt ttaaaagaaa taactgaggt 170580
aaactaccta ggcgaaatag agtagttacc cgatcaggaa acaaattatg tctaatacca 170640
tcgattatcg cgctgttatt tttcagcgta cccgtgctct tgatgtagag gttgctgaag 170700
atctgtatag acgcatgccc gaaatcaagg atcttgcaac tcttaatcaa ttcttccatc 170760
tgttgttggc tcaatacaaa atcaacaccc tggaattacg ttgtacccta aatgaagtga 170820
atgattttga agcatggtgg cgtaacttcg ctgctaattt cattccgttg ttccgtaaaa 170880
agcggttacc tccatgtaca gacgctgctg cacagccaat gtatcactgc gagtctaaat 170940
caatctgagt aatcgtatgc tcatttgatt tgtagaggta actatgaaac ccgatcgtaa 171000
agtccttgaa aaagaaattc tatacttcat cgacatgttc cgaccaggaa gcgagaacgt 171060
taaaatctat caagaacttt ttgaccgtta ttctgacgaa gagtttttg aatggatgga 171120 acgtctagag gcaggtgaag tgctggctct ctacgctcct aacttagaag aaccaactct 171180
aagtatcgct cagaattata aagtagctga tgctcttggt tttgaactat tccaacacct 171240
tatcttaact gatccgggca ctggtcaagt ttataagact cagaataaac acctagttgg 171300
tatggttccg cttcgtcggc aggttcagat gctagctaag aaagcttcta tcccaggttc 171360
taatactgtt gttgacgagc gttctggaca ggcaactggt gatagtaaag gtgcacgtct 171420
atctgcccct gagattcagg ttaacgcctc taaaggtctt aacaacatgg ttctcgaact 171480
gattaagttt cgtggtggtg atgaaaaggc atataacgct atgaatcgat ccatcattga 171540
aacaggtgaa gcttctctcg attccattat ggtcgagacg ccttctcaag ttaaatctaa 171600
caaaaccatg tccgtctatt tgaaggccat gcatttacag aataacctag tggggtaatc 171660
atggctatta agaatgcgga agaaggtatt agcgaagtat tgcagaatgc attaggtgtt 171720
gcaattagtg aattggtatc tgttgatgat gatctcgtta ttgctcaaat tctagagcat 171780
attaacgaac ttagaaacaa tatgatgatt tctagtttta atgatagagt tatcattaat 171840
cagatttggt caggtatccg ttctaagcag gatgtattgg gtgctcttct gtctaccacc 171900
actacattca ctttagaaat tgaaaacatt gatgtagcaa ttgagtatct cactagacgc 171960
ttggttccat tcacacctga ttcagcaatg gtcgataggg agttactggg taaagcagct 172020
aatgtagatg aactctatgg tacgctacag caaaatcact ggttgttctt ccttgtatat 172080
gcatctacgc aacttcgcca tgtaaataac attattgcac aggcgaaaat gaaatgatca 172140
aacgtattct gatacctctt gatgtattac ttgacacccg tcttggagtc atgtctacaa 172200
ttaacaagga ggcagcagaa cggttggttt ccactaagga atattggctt cgtgaaaatg 172260
atgactggac cactctaaca ggtggtcttg ttacaacgga gcaattcaaa gaagcgtatg 172320
ctaatagagg cggagataat tccgctgata ctatcaacgc ttctatccta acaggtatca 172380
gtccgttctt gatgcgaatt ctcgcggaag atcatgtaaa cagaatggat aacatgggta 172440
atcctgaaga cgagattggt cttacgatca acatctggcc ttacacgtta cctggtgaag 172500
ttatcgatga tcttgaaaat atcatccaag aaatatacgg cgaagaaatg cccgtggaag 172560
tagttagtca tccattagaa gagctcacac ctaaattctt ggatgctctc tatgcgatgt 172620
atatcactta cgatttccat gaatggatgc acactcatta tcttgctttg tctaaagttc 172680
aaatgccatg cttcaatttt attggaccta aactcttcga acgtgacgtt agtaaactca 172740
ctatcgagga gaagaagttt gaactattta agttcagggt cgagcggctg attcacatgg 172800

-continued actttgaatt tatagatgct aaatatttct ccatgattcg tcctggagat aacggtatcg 172860
aagttgataa agacgacata aaagcccagg gttaaccctg ggctttatgc cgctattatt 172920
agtagccagc acctttagcg ccgagccatt cactaccatc ccacagaagg gtgatgacag 172980
tcttggttgc agcagcttca ggagccgtgt tatcattcca tttgaagtta ccgctgaagg 173040
tcggaatgac cgtaccagtt agaaccagta cagctgtaat cattcggcca gacggaccat 173100
cacctagagt gatagtacga gcagcagtag atggaacagt atagcactgt tggttagccg 173160
gagtgatggt gaagttacca gcaggagcag caccagatag cagggagtag gtatcaaatt 173220
ctttcttgat ctctacccac gccgatgtac cagcagcagt tgtctgacga ccccaaactt 173280
tagtagcatc gatacctggt tccggaatgg ttaccagttc tttccactca ccgttagaac 173340
gagtgtagtt cttggcatcc ggagcatccg atgcgataat tgcagccggt acctctaccc 173400
agctggacac gccagcaaca gtagttttac gagcgtacag tttatcatca ttggtagttt 173460
caggtactac cgcagcccaa gcaccatcct tacgagcgta agacttacca tcgctagccg 173520
cgtctttaaa gacatcggtt tcgacccagc tagccttacc cttcagaacg taatgcttat 173580
caacatcgtt ggcaatgaca ataggtgcac cttgtttcca ctcaccgtcc ttacgaacca 173640
ttgcaagagc aatgttggga gtaggaacgt ctggtacagc atctacttca agcggagccc 173700
attcggtggt gccatcagct ttacccttac ggatatactg ttcaccttct tcaggggttt 173760
ccacttcatc gaccagtaga ggtgcccagc caagttgata gcgaaccatc ttcttgttct 173820
gatcggcagt ttctacttcg gctacaggaa catccagaag ttggatgaat tctttccagc 173880
cagttgcgtc acgataccaa actttaccag acttatcaag gcaccagtca tcttgagtac 173940
caatagtgtt attcgggata tcgacaccgt tcggtagaat tacccaacga gaacctttat 174000
caccttttgc accttgaata ccgcgaggac caacaatacc ttggtcaccc ttatcacctt 174060
tttcgccttt ggcgccaacg gtgaagctac ccaggttcag atacttctca gtatcatcag 174120
caccatcgac agcccaaaca aacagttctt tactgttttc aggaccaacc gaatatgcat 174180
caccaatagc actagtcgga tgagcagctg taagagcagc ttcagacgga tagtcgccaa 174240
caattttgat accttggccg atttcaccgc gaggacctac ttcaccctgc ggaccatcgt 174300
taccttgcgg accctggata ttgaacggac catcgtaggt attcgtagag cggttagcta 174360
cgtagattac cttaatggtg tcatcaccct ggataacggt aacaatgtac gcctcgccat 174420
cagcgggatc agtttcaccg gctaccagtt caggtagagc ttcaacagaa cctacttcac 174480
caacgatgcg catcgaggcg ccacgatcac cctgatcacc tttctggcca atgggaccaa 174540
cagatacgaa ctgagtacca ctaatgttta cataaacatc gccgccttta acaacaacgg 174600
ctttaccttt gttgtcggca gtggccggag gaacttcacc tacagtgtca acaacagcga 174660
tgatttcaaa gttttcaccc tgatcacctt tgtcgccttt atcaccagtg tcacccttgg 174720
cgccagtatc acccttatcg cccttgtccc ctttatcgcc tttggcgcca gtatgagtac 174780
caaggtcaac ccatgttcca tcaatgaaca tgtagaggtg gcggttatcg gcagctaccc 174840
aagcttcctg ttcttgcgga tcaggtacgg cttgaatggc agcaaggtca ggaagaacac 174900
cggagacaac caggttctta ccaccgtcac cggtgtcacc cttatcacct tttgcaccgg 174960
tatccccttt gtcaccttta tcccctttgt cgcccttctc acctttgaat tgacctaggt 175020
taatcaggtc gccttcagag gtaacaggag tagtagctac gtagaagagg gtgttaacat 175080
cgcgaacagc gtaagctttc ttgatgacaa gagtagcacc tgcggccaga agatctgcca 175140
tggtcggata cgtaccgagg atttccaggt tttcaccagg agcaccgtct tgaccatcga 175200
taccatcttg accaggatcg cctttatcac ccttatcgcc tttgtcccct ttcgggccgt 175260
cgccaccgat gataccgtct tgaccaggtt cacctttcgg gccctgccaa gtaccgagat 175320
ccatccagcg gttttcatcg acggagaaga cgaatagatg gcgtacatcg tcaaccataa 175380
ccgaatatgc ttcttcaggc ttggcatcgc cagccagagg cagatcatct tcggaagcta 175440
agtcagcttt aatagtgaac ggagtagcgt ccttaccagg tgcaccagtg tcacctttca 175500
gaccacggtc gcctttatca cctttggcac cagtatcacc tttaggaccc tcaggaccca 175560
tcggcacgat ctggatgtat gcatagttgt cagggaagat atcttcttca ccagctacaa 175620
gcatgaaagt gtaaagagca tttttccaac cgtaggtatc gcctttggca gccaagggcg 175680
gaagttcttg gttatcaggc cattgaccac gaataacgag accagtacct tccggaccac 175740
gcatgtcacc ggagtcgatc cactggccag catccggcga accggtttct ggggcagacc 175800
atactttcag tacagtagca gtggaagaac gaacgaacca agcatcacca aattcccaac 175860
tatcgatggg agcaatgttg gtttcgaaat cgtcaagagt tacggtacct ttgatattgg 175920
taacgggacc cggttcacca ggattacctt gcagaccagt atcaccttta gcgccgtctt 175980
cgcctttcag cgattcgagc cactcggctt cagtaccaat aaagccagct tcgagtgcca 176040
gctgataagc ggatttacca tccgcgccat cctcaccttt cattccctcg atttcggtcg 176100
ggtctttgaa agttgtagcc aggccagccc cggtcgaaac cgggatcttg cctgcaacta 176160
tctcaagagg attgtcttcg gtggagatac gttttggtaa ctcaccgtta acgaaaactt 176220
caaatgcgga ttcaccagcc attatacaac ttcctcaagt tcgacgcgca tcagaccgga 176280
tgtgttagat acagcgttag ctgcgtcgca gttataccaa ctattgctat tcttgatggt 176340
gtaagtattt acagcatcag catcgtcagc tttataggtg aagttaagag aaccgctagc 176400
acccttagac aggttagtgc agcgaagttt accagtcata actacatctg taccaatagc 176460
accttcacga ttcgggaaag cagcgataga catggtacga agaacgaagc caccaagggt 176520
atactcgcca ccagctttaa gggtattgac tgtaacgcca gccagacctt tggctacaac 176580
atcggtaaag ttgaagatac ctttagcatc atcatcatga acgagcagtg tgcgtgtcca 176640
tactttctta gctgcatcac ccacccaacc agcagaatcc cagttaccgc caggagcagt 176700
catcacaggg gcttcagcca gcgattgagt cgaagtgata gtgatggtgt gacgctgtac 176760
aacagtacct gcattaccac cagagcgcag acgagtggca ggagtggtaa cagtcagttc 176820
aggggcaccg ttagcaatct taacgattgt cgatgcagta gacgaactac cgttagcagc 176880
acgttgcgca gtgattgtca ggttattagt caggtcgttg taattaccag tcaggtaaga 176940
aacagttttg tttgcttcaa tctgagtcgg gttagttaca gtcagctgac cattagccga 177000
ggtgtaagta gcgctagtag cgttagttac agtgttagca acggttgcat cttcaccagc 177060
tttaatggca gtttgaccag ccggataagt tacagcaccg aatgtaatcg tcggtttcag 177120
gttgttcagc ttgacaacgt tgactttctc agtagtacca gctacgtcgg acttatacca 177180
cgcggagaaa ctaccggagg ctttcttaac gcggatactg aacggttggt tagtagcagt 177240
gttaccacgg tcagcaataa ccagaccagt cagactgtga gtcttaccag cagtcagtgt 177300
accattgcgt gctacgaatg caccttcatc acgaatctca taacctacca catcttggtc 177360
agtggtgaaa gtgatcgaca ttgtgtcgcc tgctttcagc tcggtttgag aaccaggata 177420
ttcacctgta aatgtagccg cagttacaac cggcgcggta tccatgatta catcagtaga 177480
tgccttagca ccatcttcgt gaacagcttc gaccttaatg ggatcactac caaccggctc 177540

-continued

```
aggcagatta atagttactt caccggtcca catcggggca tttgcaccag cgacgagaga 177600
tacatctacg ccgttaactt taacgacagg acgatagtta gtatgaccgg taatagcagc 177660
cactttaact ttaacgtcac gagtagacga agaacattgc accagagaga aactatccgc 177720
ggacttaacc ttctcaccga cgttatcagc ggcattaacc ggagtgatat cagtgatgaa 177780
tacgccacca tttacacctt tcggttcggc aagcgacagg ttaaattctt cttcagtacc 177840
aacgtatcca ccatcaacag cggattcgta tgcggactta ccattagcgc cttctaggct 177900
ttccagccat tgttcttcag taccaacgaa accattatca cgagcgatct gataagcaga 177960
cttaccatca gctccgtgta ggctttcgag atattcttct tcagtaccaa cgaaaccggc 178020
tgctacggct agctcgtaag cagatttgcc gtcagcgcca tcgataccgt catcaccttt 178080
agtaccgtcg ataccgtgga gagattccag gtactcagct tcggttccag tgaaaccagc 178140
ttcgacagct agatcgtaag cggacttacc ttgatcaccc tggtcgcctt tgtcaccctt 178200
atcacctttc tcgccggcat cgcctttgtc accttttagg gactggatga actcggcctc 178260
ggtaccggta aaaccagtat caagagcgga ttgataggca gacttaccga cgagagttgc 178320
aaggaattct tgttcagtgc cagtgaagcc gttatctacg gcaacttcat agatggattt 178380
acctacagcg ccatctgcgc cgtcttcacc tttaagagag gcgaggaatt cgtcttcagt 178440
acctacgaag ccctgttgaa gagccagctg ataaatacct tgacctttta gactttcgag 178500
ccactcagtt tcagtgccta cgaaaccatt ctttaccgca acttcataag ccgataggcc 178560
ttcattgtta cggattttag aaaccatgag acggaagttc ttataagaac catctgcctc 178620
aagacggata acttctacaa actcttcacc tgtgatggtg ttaagaggct gcattccgga 178680
gatcataccc ggactggatt taatggccat tacgtattcc tttgttggag agagtcttcg 178740
caactactcg tgcacgtctt aaaaggaaaa taagactcat agagtagtgt attattttag 178800
caacatatag gagtcccaaa ggggactcca gtatgccttt tcaggagagc atctatctgg 178860
agttgcgact attttattta cgccacaacg gctggatcga gtttccaaga accattttcg 178920
tctttggtaa aaccaatggc gtccagaagt gcatgaatac ctttagcagt agcaaagcct 178980
gtatcatcct caccagcaat gacagcagct tcatcaacct tagtcggaat atccagttca 179040
ggaagctgtt ctattttcag tttaccgtcc tcatcgagat ctgctttctt agcaagagca 179100
tcaaccagtc cagtaacttt atcgatagca atacctgcat cgatgatgac ttgtacttca 179160
gcggcagtta gaccaccgat ctgagcacca ccgacagtaa cgccatcgtg aacataaagc 179220
ttcttattct caagatctac aaagaacgtt ccttctttgc ctgtccaagc tgccgcttct 179280
agagcagagc cgcgatgatg ttgtagaagc agttcactga cttctgtggc acgcccttca 179340
tcgaacgata cttctttacc atcttcagaa acaactacac cgatttgttg tagagtggac 179400
ataaccgcac tcggtgcatc tttgatgtaa agctttcgat caagttcttt cttctgctga 179460
cgagaaatag gtttatcagc atctgctgta ttatcgacct tatctaagtt tgcaaacgaa 179520
aggtcaatta ctttccactc tggaagacct agttcattta cagtgagtac cataccagcg 179580
ttttctggaa ggatctcaaa tagaggattg gttgcagaaa cccattgttc ttcagtgcct 179640
tcataaccct gatcaactgc gatttgatac gcagattttc caacgagtgt ttctaaccat 179700
tcttcttcag taccgacaaa accagctttg acagcgccat caaaagcaga agcgcctaca 179760
cgtaatttat ctgcgagtac acgatagttc ttataagaac cttctgtatc gcgagcaaca 179820
acctctacga attcctgtcc ggttagacca gacagaaaat cgagttcaga aacctttttc 179880
ttttcttcag ccatcataga tgtccttcag gattggctgc gttgcacata ttcttttaac 179940
```

ctgataatac caccttcaaa cctggggaag tatcaggtta acaaaatcct tttctaagtg 180000
ttaccaccgt taaaagaaca ggtggacgct atgcccgatg tttcgaaact ttatcttcga 180060
acagcttgta gatctctgca agggtacgtg gtacaccttt attgctaaag atcgacgggt 180120
ttgctttagc aggtttcggg aatagaactt caccgagagt tttctgatct gcggatagga 180180
atttcttagc gccgccagca ccaaggaaat gtgccaaata caagtctgta tcactcggtt 180240
cgcgattgat tactggacgt aatacagctg catttccttt aaggaattct gcacccatta 180300
atgcatttgc acgtgggtct ttacggagtg ccctagtggg atctttaggt atcccgtatt 180360
tggaaccatg tgctttgatc atgtcatccc atgtagcatc aaggaactgg aaccaaccag 180420
tagccgaaga tgtggatgct ttgacagtgt aatcaaaagc agactcaatg gaagcgaatg 180480
tagcgagtaa ccgagaatcg gtaccagtca ttgctccaac cgcattcaga gtgggcattg 180540
cagccgaccg agatttatta gctgttggga aagggatagc ttcccattta gcaggaacag 180600
tagcggattt ggctagttca gctagagtag caggtccaac ttttccgtca accaccaaag 180660
ctttagaagc ttggaaatca cgaacagctt tctctgtatc tccaccgaag attccgtcag 180720
cgctaactgc gtatcctgcg actcgaagtt tcatttgtag atcttccaca gcagagccgc 180780
ggtcgccacg tttgagtaca gtacccattt gtctgtctcc agtaattaat gttccagctc 180840
acgaatcaag ccgtcttcca ttagacgata accaccatcc tcaagtagac gtgcatattg 180900
gttaccttca accatttcga tcgtaacgat agtcgaaccg aagtaggcgt aactaccagt 180960
cattgcaacg agttcatatt cgaatacgtc gtctttggta ttaatgacag tggtagagaa 181020
ggatagatcg tccggaccga atgtcatctt acgggaacgg ttgatctctt ctgcgatggc 181080
cgcaggtgta gctacaccag atagtttaat agacggatta ggtccaagac aatcagggtg 181140
agacaattcc agacgacgat aaacgaacca gtcttttaga ctagctttgt tatcgatcat 181200
ctcgatataa gtacgccccg gaacaccaga agtaggactg aagaacatat cttcgaagtt 181260
tacaaactcg tcctgaatat tcttgtgttt agacgtttcc cgaatcaaac ggcaaagtgc 181320
cgcacgagac gggaggttat aaggaaaacg atcgctcatt gttaaaccct caattgtggt 181380
ttacaaaatt tacttaaccc acatagcatt ataaaagccc ctccacttaa ggaggggcta 181440
atattattgt tactgagtag aaattaccat cttaatgatt tcaataaggc ccatacctaa 181500
agttttaaag atatcggcta cttctgaagt cattggacca tcagtgttaa taacactcat 181560
cactacacca gtggacagta tagctaacaa ggcacttgca gttaaaatag aactgcggta 181620
ggtatcacta gctcgaacac cagtgtattc tttttcgaga agcttcgact gcttttcaag 181680
atcagaaaga gaatagatct cagttaatac ttcatcggca gttgtattcc cattaacacg 181740
tgcactacca tctgcatgta acataccgtt caagtatgct acgatttgac gatagttagg 181800
agctttcgac aaaggcttat cgccaaggtc acttaatatt ttttccagag tcatagcttc 181860
tctccatctc tgactgtttt ttatcccagt cacggagctt ctcgatttgc aaattacacg 181920
aaccgagata gtcagtctgt aataaccagt gatctgtcat caataggaaa cgagcttccc 181980
atggatcagt gatcccagct actttatacc gactaggtgc attgatgaga tcgtcagctg 182040
acggtggagg agctacatag caaagttgag taaagctact tggtaccgca ctgcgggtcc 182100
agccgcttgg ctttgcagta gtgctcgtac atcctattag caagggtgat aagagcaaca 182160
tcgtcagtaa cactaccatt atctttaatg gcggcggtgg gattcttccg aatagattca 182220
tcccgaattt tttccacagg gatattttct gtagtagacc acttgacccc agaattcccg 182280

-continued gataagttaa tgtactcatc aatcactcct gctcgtgatt gttccagctc tctcagctca 182340
tcgacttttt gagtggtata ctgagtaacg gtttcatcag tgatggcagc tgacttaccc 182400
tgcatttcga ctttgacttc tagttgacca tttttctcaa ctaaactgcc attgtgtaca 182460
agctgatcag tatactggtt atagaagaac aacagtccaa gcccaccggt aataactata 182520
ccgataaaca cccaattaaa ccacttgatg ttttttaacc agttgaacat actacctcgc 182580
atctagaaca actgcgtaag gaaatagtaa ccgattgcta cagcatcgat ggagtgttca 182640
tctagttgat tatggtcaac atcaccccaa acaacatcgg gtctacttac caatgcacgt 182700
cgcacatctt ctttgtctgt acccttaatt ttcttcatac ccacgttggt tttaactgtt 182760
gtagggtcaa ccatgtaaag cggtataaaa gggtcatact caaaaagagc acttcgtata 182820
acggcaacac attcaaccaa tgcggcaaag cttgtggcaa atctacctag atagttagat 182880
tcaacaataa cagcatgtgg tctatgtgtc cttaagaagt ctagtatcaa atctcgcatg 182940
atcattaatc ggactacccg actaccatgc aattccccga acattgaata gtccggatga 183000
gtatctctaa gaacagaggt ataggcggtc ttcaccgcca caccttcatt cttaaagcca 183060
tgttccagca gcgcttgacc caagttagac gaacctgggt cgaacgaagc aacacggaat 183120
ggttcatcgc tttcaggcat ctgcaacata accaagtcct tatacgaact tagctacgtt 183180
tactgccttg tcgccaagag taggctcaac gccaccaata tcgaaggtca gattaagacc 183240
attcgagtta taaccgattg gatggttagt agcgatatgc acgttaactt gacaagcgat 183300
tacttcgaga tattggaacg atccaccggt accagctggt gcgtcaacct tacggtcaac 183360
accagagcaa agaccaatct cggaaataat cggagagcgg gtcgaggcag tacggattcg 183420
atgcgcattg gtgatctcga taatatcttc agcagacaaa cttaccttaa caattgcact 183480
agccgagata tttacgttag aaccgataac tgtaccgttg ttcgaaatag ctggcggtac 183540
tgggttaaga tcatcaacag ttggtgtgta cggtttcggt gttggaatac cattaattac 183600
ttcgatttcc agaagctgtg gttgtacacc tgtaacgtta atgcgcattc cataataggc 183660
aacgtagttt ttaccattat gtttttccgg aacacgtaag cagaaccgat cccgttgtgc 183720
ggctggaaga tcatcagtta cttcacgcag tgcaaacgga atatggttat aaagtgcagc 183780
atggttagaa cggtgaatac ggttttctac ttcatcggag ccatcagcgg ctttgattgt 183840
gtagtgaccc atgttaccaa ttaccatata acgcacgttc ggaatttcac ccgctgctgg 183900
agttacgcca ttttgtacac cgaacttctc attcagagtt gtatgtgcaa tcacacggaa 183960
cggagataga ccgagatatt ttgtagtttg cagataagat gcatagcacg tacgtactac 184020
gttgataatc tgctgatcga tagggttact agccattctt ttaatccttg acttagaaag 184080
ttcattgtac cattgtgtaa gaatttttgg cttgcctccc gttagggagg tttatgccgt 184140
taggtgtact gttggaagtc accacgtatc attacacatg cccacaactg accatggtcg 184200
gatttaggaa tcgcgtgaac tgtactaagg ttaaaggcga tctgttcacc tttacgaagt 184260
tcgatcaaac gtccattaag ttgaatggct tgtctatctt ttaatgcagt tgcgacgatg 184320
gtacctgcac cagttttatt gacccacgtt gtcatctgat cgaggaaacc acgaccagct 184380
ggaatatcta ggaaccaacc ttgaacagct ttattttgga tatcttcact aaaaccaacc 184440
ttgaagatat ctcgttgttt agatgtccaa tcaaaccact tagaatagtt gtaaatactc 184500
agtgctttgg ttttgttctt accgatacgg caacgagagc catacgagtc tttatattta 184560
accttacgag agaggtctac taaagtagtt acttcctctt cggtaagggg gtcgtaatgt 184620
ttatacatat ctgtcctact cgtagagata gatgagaacg aagcgtaggt gttttacggg 184680
tggtacagaa tgcggtggtg ttttagctgg aaagattact gctcttccag gaacatctgg 184740
gatgaactca ccatttaggt cgagtccatc tccattatca cacaatgcaa tcaccatatt 184800
aaatcgatac attgcaatgt cgatatgttc cggcatacca aaaccaacct cgtacatatt 184860
gacacatgct tctttgggtt ttatcccatt gatagttggt gcaatttcaa acagataatc 184920
gctaagttct tttggcatct gaccattacc aaggaaccag tagtttgctt ccactgtacc 184980
cttggtaggg atactattta tcttcttgcg attgtaccat cttgcacgag gtagcgcttt 185040
taagtactcc accagtcttt cactaactgg ttgcgaaaac acgaccgcct tcgatgtttc 185100
ttgggccaat gagttcatgg agaccgcctt cgaaggtagc agctcgatct tcggcttctt 185160
gctcattggt aatgtattcg tagttgggat cattctgata gaactctttg tgatttcgac 185220
tagtatcttt acagagtttg atatagtcta gcatctcact aagttcagta agttcaagac 185280
cggtcttctc tgcaagagcc acgattgcac gcccaagcac gtttacttgt tctacgacag 185340
gataacgttg agtgatcttg taagccatct ggttgtccag ctgtgcttca tagatcagac 185400
gaggaccttc gttctctcca agaatagagt agttcttttc ccaggttcca tcgtcattga 185460
tggtgaggtc accgacaact cggtcaccat taaacagatc catgttgtct tcaacataga 185520
tcacgtttgg gttatctgga tcgcattgat cgatagtcat cgaagtagca acgatgaact 185580
taccattcag acggttaaaa caaaggacaa caggtttacg acccttttca ggttctggta 185640
cattatgaaa atcgaacatg tgtaatttcc tttagacgat tcgagtgaga ctactaccgt 185700
tacggcgcat tacaaccatt gttggcattt tgcgaccatt gttgaagtcc agcaagtatt 185760
gagcaaatcc ataaccacca tcagcaatct gcgagatatt tgcctggaga gcactgatag 185820
cagcttgagc gctagcataa cgcccaccag cataatagtg cccgcgtgca ttagcattat 185880
aagtcgcaaa tagatcacgg aagtgaacga tttgtccatt acccataatg cagtagtcag 185940
acgggatatt tggacgacct tgaggatcag ttccagtagg aggccatgga gttgggaaag 186000
tcgtaacgaa ttgctttaat tcaaagcgag tgatattcca aacgttacta gcatctaggt 186060
caactcgtgc agggaaatac aattgttccc aaccaacccc agccaaccgt ttagatgtaa 186120
atgcgcgttg tgtacggtga agccgttgtg cataaatagc atcgatttca gctttactgt 186180
acaagttcat gatcgccagt gttaacccat gagggttatt ttgattacga atgtgatctg 186240
taatctttgg aatcaaaatg gattggatca gattgaaaat accaccaatc ggcatataca 186300
cattggttag gctagtatct gttgtctgag cttttgtagc cattggccag ttgttaattt 186360
gcccaagctt aatctttacc ttatccgaag agtgcggatt attttcatcg gttatgtgag 186420
cgttcacacg gttgatataa ttctgcacgt cgtctttcgc aagctgaacg taatatttgt 186480
aataatccgt accagccgct agaattgcag ttcgacccac tgcccatgca tcacctaaac 186540
ggttaatatt gacaaccgtg gattcaagac catacaactg ccaatatttg tgcatgtgtt 186600
ctgatggagt atatgcagtt ggtttaccga tgatttcttc ccaagtaaac ttaagattag 186660
tctcatctat cttctccatt agtgctttaa gttcttttac agaaacacta aagaatccac 186720
ctactgcatg atattccgca cgaacgactg gtgtgacgga ggcgttgatg ataacaacga 186780
gacccatcac attttgacca gtcatttcag aaagcttttc gtagtgatac gttagaacat 186840
agtctttacc acgcacaaga gctttaccag tagagtccct cagtacaaag ccattcgtat 186900
agaaaccgcc atgggtacaa acgaatacgc gatgcttctt accaggaact tgaattagag 186960
tgtgttcctc acctttaatc cagttatctg gatcttcacc ggtaaggtca agctcaagaa 187020
aagtaatatc gttcatttat accttccagg aatttaacga tgtattaaat acagcgaaac 187080
caacggagtt aatatacgtt gtgattgcac cgttaccagt accgataccc cagccaccaa 187140
gataacggaa aatggccgtt gtaccagcag ggtggttcct acctagcacg ttgttcaact 187200
gagcttcagc gtttgcaccg ttaggatcaa atgaccctgc cgcataaata acgctctttg 187260
gtttatcgat ccatgctgtt tggatatcga tccaatgaag ccagcttgct gcatcagcag 187320
aagcaggaac aaggaatgcg tagttgttag caggtggaat agccccactt gcaaaagttt 187380
gcggtggcaa caaaccagtc ttcagctgtc caaggatttc atcctgacga gtgaactcgt 187440
aaagctcttg gaaagtcatg ccattgttag tcgtattgtt gttggcatct ttaacgccac 187500
caatacgttc ggtactgtta acggtttcac cacggttgta atagttccca gcaacttgct 187560
gatgttcttg aacggtatac gtaccaagtt tagcagctgt ctctttgtgt gggttattac 187620
ggtcatcaac gtgcgcctgt agaatcggta ggaagttctt gtcgatactt tgcttagctc 187680
gtaatggcgt agcgtaacga tccagaatat ccccgttagc tgcttcagct tgatctttcg 187740
tagcaatagc agcattcttc actttatcca gctgaacttt agcggcagtg agtttgtgcg 187800
ggttattacg atcgttaatg tgggtagtaa gacgttgctc aatggaagta agttcatctc 187860
caactaaagc aagctcggct ttatattggt caaacaaagc atccatgtct ttctttacga 187920
acttttcacc ggcggcagta attcgcttaa gcagtaatac ttgaggcgta aacccgtaaa 187980
gttcccacaa cgcatgtagg tgaccgttgg gtttgtaatc atccggttta ccagtaatat 188040
tgttccaatg aatcttccga gtattgttga tcaacccgag tgcttggtta gcgattgctt 188100
taccaagatt acagtaaaca ccaccgacca tctgggcatc aaccctgatc tcatggtgaa 188160
cccgtgggtt cttaatgaca ataactgcaa aagctggaat gccagtcttc ttagtaatct 188220
ctggatgcat ctgagtgcat tggaaatcgt ccttctcttt taacacatag ccacgaccat 188280
cgatcatgtg cagattgtta ttgtagaagt aacctttatc cagaacaatc acccgatatg 188340
gcagaccagc ttgatctgcc aagttgtggt attctccacg cgtgcggtta ttgaaacaag 188400
tgcccgtccc atcgtaggga agagcgtgaa gtaatgggtt catgttgatt cctttagatt 188460
ggtacccaac cttgacctgg gatattcata gaagcgtaaa gaatgtcgta tacaccgttc 188520
catgcaccgt taccagaacc ccatgcctta gtctcgcgaa tgtaatagaa aacaatacta 188580
ttcaaacgca tgttagagaa cggcggtgtt gtagcaacca ttgcgttggc ttgcgcctga 188640
gtgatattga cactgaaaga tgcgaatgca acatcaccac tgccaccttg aggaagaaga 188700
gatagcaggg catcaatgtt agtccagttc cgattgttat cgagaacagc acgattattc 188760
agaacaccac gacctaatcg accaagagga agcttacctt gatcatagtt agtaaaagca 188820
tttgcaggaa tatctttacg atacaactgt agaatttggt tatacgtcat atcctggttt 188880
aaccaaaatc cgaggttaga gttttcaaca acttcatttc tcagatactt ggtattagcc 188940
agagtattta cttcttgctt gctattggta ttcaactgtg cattagtgac gccatgaacg 189000
ttgccacgtg catcgatgtg ggcctgtagt ggatctccac cgatcttatt tacttccgca 189060
gccgaaagct gtggggtaag atagagttcg ttcgatatac ctgctgtagc ctctgcaaga 189120
ctcgctacgc ggtagttttc tacaagacct aaacctacat gttcttttgt gtcgacgtgt 189180
gggttttctt tatcttgaat gtgtagatcg aggcgattat tgaaacgttg taagaaacga 189240
tcatattcag cttttacatc aacacggaac tctgcttctg tattaccaag ttggccagtg 189300
attgcccgag agatattctc aatctcgttg ttaaacggct gatatgtatc caaacgccag 189360
cgtagggcag ctaactcgcc aggaccataa atcggctcag tgccgttata atcaagccat 189420
ttaggaatat agtcagaagg cttagttttc cagaagttta cataatcgtc gatgactgtg 189480
aaactaaatg caacatcgcc gcctaccatc tgcgccgaca tgtaaatctt accggtacga 189540
gtacgatcca agaaaacaat accactggca atatcaaggc catagaactc gctggcttgc 189600
ttatggtaat acgtgacgat ataatcttta tcacgaatta aaggaacgta acgagagtca 189660
tatacacgga ggctattaac atagaaacca ccgtgataca tggttaccat tttaaaaggg 189720
aaccccgaga taggggtaag agttgcttct tcgctaccta ccaggttatt cggatcacgt 189780
ccggtcttat ctaacggtag ttgtacgatt acatcggaca tttaaattct ccaaattgaa 189840
caaaagacgg aaccaccgtg cttttacaca cagtgattcc atccgttgcc agggtaggtt 189900
acaaacgatc gtaagcgtcg ttaaacactt tctctatcgc tttgaagata ttctcctcag 189960
cgtagttgtc tacccgttta ggtgtcatga acgaagagtt attcgttcca cctttagctt 190020
gtgcttgctg tgccggtagc cagtcaggga cattacctaa accaatatct ctaggctcaa 190080
gtccatgaac gttacctttt tcaaggatgt gtgcgttcat acgatcccga gcactacgga 190140
gtaggttgag aatgatgtta ttaaactgac cgatattgcc tttcagctta tcgagttcga 190200
cacgaaatac tgtcatagcc atcttaagtc tccttagggt gcgacaatag tcgtcccatc 190260
attccagatg agagcattgg tcggagaatc accccagaat tcggtataac caagattgtt 190320
tactgtaaca gtgaaacctt taccagcagc cgcactatag aaaggtgctg acccgtaagg 190380
aatttctaac tgtccattct cgttggaacc gaacatagcg atgtctgtat ccatattctc 190440
aaggctagat ggatcacgtc gaatctgaac ggcgtggtgt ccatagttgc cagagataga 190500
actcacatcg gttagggtgt ttgctttgac caaacgatta tctttcgctg accaaacatc 190560
gagagtagaa gtgacttcag tcaatttaaa tgtaggcgta tatgtaatct catacacacg 190620
gattcgacta gcatttccat tagtggtatt accaccttgg aatactagat acttggaacc 190680
aatccggata tcggagattt cccagccgcc agtcaattga gcagcgatta caggcgtagc 190740
agcagaaacc caatcactag cacctattgc tgtataagtc gggtcaccag acggtgggga 190800
cttttcaaca attgccattt gacgagaatc cgcttcttcg gttgctaccc acatttcggt 190860
tacattgtca gactcggcgt acagttgagt tactgtacct ccggcgatct tcatgatctt 190920
accttcatct gcaccgtcac ttggttttag ttgaacatat agagcagttt tagagcccca 190980
catagcaacc atcgcatttg cctggttgaa gccagcacca gcagcccaac cagcaggaat 191040
tgctagttta gcagaaccgg ctgaacggat accatcgccc tgtgaccaag taccggactg 191100
gaagtcacgt atggctggaa ctagatgata gtctgcatcc tgtaggctta accaagacca 191160
agctgcacca cggattggag tgatcggata tgcatcggca cccgctggtt cagagcgata 191220
aactgtatca cctgaaccgt tgaataacgc atatgctgct gcaccggcgt taacaccttg 191280
aatcttactc agacgttctt tatcttgctc gtctggagga gtcgggtcat tgaaactgat 191340
atctgccgaa gaagcaatac cttctccgat cttctcagtc acttctgcca tgatgccatt 191400
aatatcgctg ttgagcggga acttagcttc ccattcctca ggagtttccc caccaaaggt 191460
agtcgcatca ccaccacttc caccagccgc aatcttctga tcaatttcct gtttggtata 191520
tgtaccaatt aaaccagggg tgatattgtg cgggttggta tcagtaaggt gtttattgaa 191580
atcaataatt aattgatcca gacgcgggtc accttgaact gcttggataa gcaaagacac 191640
cgtatatgga gtcatcaagg tactattgtt agtcgggtca actgcctgtt gtggtgttgc 191700
agccggatag ttaggaacgt tacctaaacc aatgtcacgt ggtaccattc catgaacgtt 191760

-continued acccgtggcg gcaatgtgtg cattaagagg cttgagtgcg ttttcttgga tggacaacag 191820
tacaccacga gggttcgtaa acatgtcgtt acgattacca tctttgtgct gttggtctgt 191880
tgccatagag aagttgggca cattaccaag ctggatttgc accttgttaa cacggtgcgg 191940
gttatcatag tttcttaagt gcgactcggt tgtaccggaa gcggtagcct ccatgatatc 192000
accaagacgt tgaagagaag cattaatctc ttcagaaccc acaagactat cgatcggttg 192060
atcatgatcg agtggtggga acgaggcagg gagtacatca atattacccc atgcacgaat 192120
cagcgggttg tactgtcgac gagacagttc cgccagaatg gcttggtcgc taaagcccca 192180
ctgcccaccg atggtccgat aatcaagacg agcttgaccg gcgatagagc gtttcatgaa 192240
gcggatagaa ccagcgatcg gtcgaccaat agaatccatt gcttcgatga aacggtgacc 192300
gatcatgtag tcgacgcctt ctacaaacag agcaccggtc tggttgttcc gtacttttag 192360
agagtcgaca aagaaaggag ccgctttcgg aataatgaaa taataatcgg tagggccggg 192420
tacttgcagg gtttggattt cccctgtgat gaggttagct gggttagtgc catgcaaatc 192480
ctcgtcatat agaccggttg tactaacggt ggacatcgcg ccctccttta aagcgctagc 192540
gcgcggttgt tagcgtaatg atgtgaaatt cacataagat tgtccgatct tttctaacgg 192600
agacatgaca atgtacgtgc ttgtacgttc taggtatcgc cctagtcgcc gaggtggtcg 192660
gtggcaggaa gcggacttta caaatgagct agtaactaca ctagctgcga agtatgggga 192720
tatctatctc tacatccaat atcctggcca aggtgagcct gtaacaagag cactgcactg 192780
ggttaatgtt actaattggc taaacgatgt tggtccaaca gttactgttc aagagtggct 192840
aacctcttta ggtaataaag ctctaccttt tgatgcagaa ctacctaacg aaaaaattcg 192900
tttggtaaag tatgctcaag catggcactg tggttataac tttaccccag ttgctcgtgg 192960
aggccatcct ttagatcaag ggagtgattt ccataaggaa gatctcctta tgactcatcc 193020
aaaacatcag ccttcaaaga tcagagatta ttccatgatc tctgttaatg gttatttcca 193080
tttatgtgac tataccagtg ctggtgtaag gattattgat ggaaatacga cgttacgtaa 193140
atgtaacgat aatcagattg gtgtttacag tttcgaaact attggtaagc ttacttttgt 193200
tcctattgtt gacagtatga ttagcggact taatcccact gctcctttgt gggatggtac 193260
ttatctaacc atgcctgaga atgttgacat cgagaataaa actgtattgc ttgttactgg 193320
cggttatcta aacgttctat ctagtgttta taatcgtgta ggcgaaagaa catggagagt 193380
tcagtttggt aacatgatgt ttttagatcg ttatctagag tcataccacg caatggatct 193440
ctcttctctc ggattaacat tcgataaaga gaacccgact ctattcaatg tagatgaact 193500
caaaaacaat gatgttatcc gaaagtattt aactcttagt cagagtttct ttgtaatcgt 193560
tgattcccaa tcattcttcc aggaatacga agctgtagaa tatctcaatc tacctggacg 193620
ttacttcgat aacaaatacg atagatcgcc tctcgttggt gcgtatggta ggatgctaga 193680
ttatcacaca atcaaagaac ctcaccatga aggtataatc cctcaacatg aaaatatgta 193740
tgtctactgc gctgtattaa accgtaggaa ttcctatgat gctaatacgc gagcatggcc 193800
tgagcaagag atcgttgatg gtggacgtta tccagctcat ccgtttagag acgaaacagc 193860
atattatcga attttagggg ttgaaggtta aagcaacata ttgcccggct caaggccggg 193920
ctttatgtcg ttaacggaag tcagatgtat cttcttcgtc ttccagttca tcctgttcag 193980
cggccgatat tggatcttca agaccctcaa cttgcggctc atcttcggga ttagtttcat 194040
cggtattttc actggacgat tcatccatgt cagtgatatc actatcacca gctggagtat 194100
cacctgtacc accatcaaca ccaaggtcag tatcagaacc atctaaatca gagaaggagt 194160
catctccaga ctcgtcatta ttgtcattgt tccaactgtc accaccacct acatcatcag 194220
ctccatcgat agtagattta tacttagcct caagacgctt cttagcttct tgttgatgct 194280
tagcatagct aaggatagca gagccaacag tttcctgttg tacgttcagc caatccagca 194340
agctgaatgc aggtttatca ccatccattt ctgtaagaac attaagttct ggaaggatgt 194400
tgtgtgttgc cataaactga cgtttaaata cagctttcaa ctgaaccatt atctggtcag 194460
acagaccagg tatggaagta aactcatcag ggaagagttc gctggtgatg tagttttcca 194520
agcccatagt cagaagtcga tcataggcat ccatcgattc tgcttgacgt tcatgttgag 194580
tattatcggg tgccggtaga gaaacctcaa tggcagtgat aaactcatca actacttctt 194640
caactgtcaa ctgtttaagt tcaggcgatg tcaacatgtc aacgttgtct tgaatgattt 194700
tgtacatttg attacgcagg atagaactgt gcgttacaaa tacacgaatg aatttagaca 194760
agtgttgaca gaacgctttc tgtttctctt taacacgtcg agacattaca aggtcattct 194820
gtaccacaga agtagcgaag tctggagaag acatcgggtc tactttctca ggtggtacac 194880
ccatacccga gatgtgcata cggcgaaggc gatcttgtag atcaggattc ccagcattaa 194940
cgttggtatt gtaatcgtcg tattgcacct ttgtctctgc gtagtcagca ccattggtgt 195000
tgatttcaaa gtcaaagcca gaacgaatca gatggtccat cgcttgcgta gggtcaggag 195060
cagccagagg gaaactacgg tgcgccgatt ccatgatatt cgattggata ttactgattg 195120
tttgttccgg atctgtatcg tcgggatcaa gagtaatact tacacgctta cgaccaacag 195180
cattacgcat acccccaata gcttctgcca taagaagagt agaacgcatg gttgcgataa 195240
tcttcgagcg agacagaaga gtttcaccaa tgccattttc gttatagtcg aatgcaatat 195300
aaactaaaag ctctgccggg atgaatacca gttgagtatg tttagctttc caagaacgat 195360
acaacatgat cctctgaatt tcttcagtta gaccgatctc aatttcttga tcatacatgc 195420
cgttacgaag acggttgtta agatcattca caataatcgc gttgtatgtt tgctggattt 195480
catccacttc gaaatcttgt ttagaagtat tagcacccat cgcttcccga gtaaggcgta 195540
gaacttcaga actgttgtcg ttattcttac cacctttcca acctgattga agctcaccat 195600
aaaaatctcg ggttgagtct ttggagagcg ggtaaccatg ttggtcgacc aacaagaaat 195660
agccgatgtg ttcatgtggg cgcccctgta cgaatacggg tacaatggat tccattggaa 195720
gagggagagt caatggatgt ccaaccgaag gccgattcat gtacttagga gctgtgatta 195780
cctgagtatg ttcagtgccg cctagtctat tctgataaag ctgttcgatt tcagcgttac 195840
cgaatttatg aacagcgttt tccatcgaga tctgattacc gcgaagctta cgcgcaatat 195900
tcatttcgcg tacacgttgt gacatcgatg gaactttgag aatgttaaag ttatccgtta 195960
cagtgaggag cttatctcca cgaatacggt tagctgtagc attatcatga tatccctcaa 196020
gagagatatt gttcttatct gggtgaccaa ggaaacccaa gttttcatta gttgtattct 196080
ggacacgatc tctaatagag gagaaagttt ccatagatac ctggcgacgc ccattaataa 196140
ggttatctag aacgttttca gggagaacag ctaagatgga agcaccctta cggaacaagc 196200
aatcccgaag gatcaggtcc agacgctcgt caatcttata gtctcgttta aagtacgttt 196260
caactggctc aagcaaaagc tttgcaatct cgctatcaaa gatagctgga tcaatagcga 196320
atgtgaggtc cgtatccgaa agtgctttag gatcgatgat actaccgacg tatactgttt 196380
ctaccaactc taggtctggt agcaactgca taatagagtc ggagtcaacg atctcttgcg 196440
aagtatcacg cgaaacctta tctaatgtga aacggtttac gttcacacga ggctttgctg 196500

-continued cttcgctgcc aattgcgttc gggtccttac gcaacaggtt gaggagggcg ttagtcggag 196560
ttgctttcga tcctaaacgg agcgtctgca actttgggta cgctacctca ttcgtttgtc 196620
gagccatttg aagctcctcg tttaacaagt gagtaaatta ccatgagtag catgtatttt 196680
ggagtttacc gtgacgatgt catgagactt gcaagatctg tagtaatcaa gttttctgaa 196740
atagctaatc agattaatga acgcctaaaa gaggtcggac atgaagctga tccagcaaga 196800
ccggagactt ggaaatatta tcagaacctt gctggtgagt atcatgaaac agatgtcatg 196860
atgacagttc gttccgcgga tactcttgaa atcatcgatt tcacaaaaga aaatctggcg 196920
cttcaccgcg ctactgcgcg agagtatatt ccgggtagcg ttttatacaa tagccttgta 196980
agacagttcc cagaacaagc aggtttgatt actggaatct tatatccaat tgacatccaa 197040
acggcaatag attcaaatga tggggatatt ttgtactttg atccgaagta tgtagaagat 197100
aatgaatact ctttcttcca tcaacttcag tcgtgggtta atgtatttat tactcgctgg 197160
tataacccgc agtttaattt aactgacgat ctataccttg caaacttcct tggtcattta 197220
tatacccgtt tacctattgc tattatgctt attcgtctgc ggaatgcaaa gactaacgaa 197280
gcgcatagtt atcacgttac ggaatacctc gcatctcacc aagggttgga tgagtttatt 197340
ccctatcttt ctcttgagca acgtttatgg ttatatcgta acattgcgtt tctagaacgc 197400
aatgcgggta agaaggaaat ttggcaacgt cttgttaaga atattcttac acctcgtggc 197460
attccgttga tcagttttac tattgaacaa aacagttcta aaatgcctga gcagcatcga 197520
ccaaccgtcg atatgataaa acacgacgtt aacttccctg tcgtacaaga aggccaagaa 197580
acgacatctg tggcagacgt tcttgaaagg gaagatgacc ttgcaagaga gaaccctctt 197640
gttcgtttcg atgctgagca agatatcacc gataagatga gttccgatca atacagttgg 197700
cttagaacta aagttcttga ctctgaggtg attgaccggt ctaatagttc tgtacgttca 197760
ttaatgagcg tattgctgaa cgaatggtta catttggcct caagtgataa atatagggct 197820
tatgttcaaa tacctaatcc taagactggc gaattcatga ccatgacggt taaagatgcc 197880
ttcattgtga tgatgtatac ctatgccaag gctcgtgata ttccaaccga taacatccct 197940
agtcttgtag catatgaagt actaagagat aagttaccta cctttggtga acttcgacca 198000
gctgttgata aacgtattat ccctgaccgt ctaattactg ctgtgcaaga catggttact 198060
ccaatgggta actatatctc cactgagcag ttctatctgg actgtgtccg tttacacaaa 198120
gaatatctcc tgcaatggga aatgtattct ttccaggagc atcctgctgg tcgtgcttat 198180
tgtgagcaac ttgtaaagtt ccattacatg catcggatgt gtaaactggc tccaccaaat 198240
accaagtttg aagattattt ccgtagagca tctttcgata tcctcaatct aaataagact 198300
gaggcagaac agatgtgtat ggattgcatc aatattgcaa ctggctccaa cttggttcgt 198360
gttattacac taggtgaagt gcaacgtgaa ttgctacggt tgatgggtcg tctatccagt 198420
tatcctcttc aatatcttcg taacgttagc tttaccgatt tccatattct tggtatggta 198480
atgccgcgtg tgggggatat tacagtagat gccgctggta actatatctg caacgtcgct 198540
gttcaaaatg tcaaagcata tagaacgtcg gcagggcata cgtatcgtgt tgttgatgat 198600
tctacttctc cattcgtcga ctacgtttat agtcaacagg atatgttctg gattaatcca 198660
tttgtagaag tgagagacct tagttacgct gacgcccatt attacattcc agtaaatggt 198720
gttaacgtaa gtaatgttgt tatcgaaact aataattcgc cgaatacaac tggcgacttg 198780
gatcaatatc agaattccac tgaccctaac tggccgaaac ttaaggagta atcatgtaca 198840
ttacgagaga ctatttacag tctactcctt ggacatctat aatcgacatg atcaacgatg 198900
cttgttttac ccaattgttt ccgggtagta ctaagcttga acagttcgaa tcactgggtg 198960
gtaccaagac tcgtattgtt ataagtgtaa atcgcagtaa ggcttccggt aacttactac 199020
cggaagtcga actcgatact tatacgtacg atcgattaga tttgacgaca ttttttagac 199080
aaacccaagt gcttgattta tcgaatgtgg atactccata ttccagttta aaggttgtcg 199140
aaaaattatc cgagttaaat aacattgttt ttgatgtaga tgatttcgaa cataccgagt 199200
ataatgtatt caaccaagaa ttcattctcc atgcgaataa aaagtctctt cgttttgtag 199260
gttttcttcg ggttcgtttg attaatacac tacgaaagga attatctact ttcagtaaag 199320
ttgaattccc tgacgtaggt aaacctgaca atgttaaagc taatgatctt tcactgatca 199380
atggtactta ttacatcact ggatatgact ttagtgaaca tagagagtat cttcgtcatc 199440
taacaaaggc tggtacccat ccagatccta agaagatggc cgctattctc gctgaggtga 199500
cgaataaacc ttggacagca tcaaagacac cagcttctca caacatcgct tatactgaag 199560
aaataggggt tctaaagtac aggatcattt ataatggcat tgtactacct cgatttagtg 199620
ggcgtactga tatacaaaat gtacttgtta tcgagttaca taaaacttta tgtcaggatg 199680
tcgttggcga aattagaatt cattataact aaggagtaga gatgcacgtt aaaaacatga 199740
aatctaaact actccaacag tttagtattc agaacaagtt ggatccagct attcgtcctg 199800
aggatgttat ttggactggt attgaaatat ggttgcagaa cggtaataac tcaagagcta 199860
ctattcaggc tgttgggaca agcaagtatt ttaaaggaca gaaacaaata ttctttaatc 199920
gatatcgaat tgaagaagct ctcaatgggg ttgttattcc agggaagaga attgattatt 199980
caactatcca tgatgttatt aaagtactcc gtgataaagt gactgtaccc gtcgatactg 200040
atgaattcct agatggtcct ctaactggta atacggttat tttaaaaccc actactcgtt 200100
ctctagccta cattccaact tcacaagttg aattaagttt cgagaaataa aaaaaataaa 200160
gcatatcgcc ctctcccgaa ggagagggct ttatgttgtt actcatcgct gttcaatcga 200220
ccatactcta tcgatctctt tcatctcgat cattcgtaga gtagccccaa atacaacgac 200280
aatacacaac agcattgtaa ttgaagtaag ggacatctta atgaaatcac gtttgccaat 200340
cttttcaaat ggcacgtaga tgagatacct aaaccgatga tttagataaa gagcaaagaa 200400
agcagcgaga acagctatca ggaaccacat gtgaaattcc tgagtccacg tcaatacata 200460
accgaagaca gacatttaca ccagcgccac gaaagtgcca tctttaaagc caactttacg 200520
tttagcttca tcgtaccata catcaacacc catgcgagcc aggccttcta cgacatattt 200580
atcatagtta cctttaccac gcatgatgga cttcagttga cgagtcagga tggtgtggtt 200640
agtggaaagg aacatacctg gtacgtcaag gtctttaaca cggagattac gcggtagcag 200700
cgactccatg gaaatgttca gaagttccat gcgacggaga tcttcacgca gagcccgaac 200760
attataaacc atggccagtc tgatgtcacc acctttacgg agatgttcct cggtcagatg 200820
tggcagagtt gcggttggat caacaatcac tgctctttca ccaaaacttt gcacgactgg 200880
atcgaggtaa gggttatgta caacatattc cccattaacc caacgataca aatccaaagt 200940
agaagttact ttgtaagttg cctcaggatc accccgcaaa ggaagatcat cgacagtaag 201000
gacatcaata gacatactct ctcctttgcc tttagggagt tcagttggac tataactgct 201060
agcgtccatt atggtttcaa agaaatccat atcatgttct acatcacgaa ttgccttacc 201120
gaacacttca cgatgagacg gaatgaacat ggattttaca gcgttgaaaa cctgattcat 201180
tttgcaattt ccttttgata gagtgtattt atatcacctc tgtgatatag gcgttattta 201240

-continued tctttaaata caggattatc gaaatcatct tcatagagga tatcgatacc tacaatatca 201300
accacctgct cattgtcatt cagttgatat ctaaacccaa ctgtaagagg aagcagatta 201360
taaagggcat tcagatcacg ggccaaggga cctgctgcgg taatatccaa aatcaataca 201420
agtggtgtat tgatggtgtt actatattga atggaccaac tatcaatagt agcacataca 201480
cgatttgcat ctactactag agaacgaaga ataatattct caagtgaaga tacttttact 201540
tggggatgac ctaattcgat tcctgtcaac aggagttcat tcttcttaac aaaagaagaa 201600
ttctcccaca ggtgaagttg actcaaacca aatgcatttt caacgattgc ttctactcgt 201660
tcttcaccga gtacggcaag atcccggcga ataccagcga ccatacgttg gcgcatttca 201720
tcgaaggaaa cggttacccg atatttggca ttcggtagtt tttcgaattt cattactctg 201780
ctcctagagg gacatatagc ccctctaatg aggggctagt tatcaatctg acaatatgtc 201840
gaatgtgata atttctttca atacaccagc cgcattcttg aggccgcgta caccaagtcg 201900
cattggaata tcgttcttga tcatcgcatg catccgatca tgattgggcc cgaatggacg 201960
gatgtatacg ttgaagccaa tgagtttagc tttctcatgt acagggtcga taccgagtac 202020
taaagctgca ccattattgc agttgatgga tgttgctcgt ttgtagtctg tttcaatgtt 202080
acctgtcatc ttaggatgac caaactcaca agcgatcacg ccggaacgaa tatcattgct 202140
aaacttactg acttcataat tcacatgcat gtattttgga agtcgatcta aagcaatgaa 202200
ttctacgcct actccatttt caaatgataa catctcattt tcctatgaaa aggtccctcc 202260
gaagagggac acttatgttt acttcaggcg cttcaacaga accgctttct cggtcagacg 202320
tccacgaata acttccatgt aaacgccatc aacggtgatc aaccgcatac ggacattagc 202380
aaggccagat gccgtagcac gagtgatcat acctttcagc acttcacgaa cagtcgggtg 202440
agttccttca gaaacaagga cggctttctc ggtcagaacg ttcagagtgg ccatctgttc 202500
aagagtccaa cctacctgga agttaacgta ctgatcggca acaccacgga tatcatcaac 202560
ctcagccatc gttaccgaac gagcgataat ttgagctgca cacgctttga tgatttgcag 202620
tacttgcaca cctttcttgt tactgatgta atccagcaga tcaccgatgt catgtgcgaa 202680
atcactgatg gtgatatttt ggatcgacag gctatctgcc atgaagtcat tgatggaatc 202740
ggtcagacga tcattcagga aacggaaata gcggatgctc agttgaccgc gatttaccat 202800
ttctttcagt tcggtagcaa tcccgatcag atcggtatag ttacgcagat tactcagctg 202860
ctcgaaggtt tcatcgctaa catccatgtg atagatgctc atcgatttat attcgtgtgc 202920
aggcagagtg atcgactgcg attcttcgtc gtcaccaatg ttcaggagtt cccgaacagc 202980
agcacgtgct tcagattcgt tttcgagatc gttagcaccc atgaacatct tgttatcaag 203040
aatgatcgga cgcattgccg ccgcttcacc gagttcatta tccttgacga ggctttctac 203100
ttcttcaata cccattgcat ctccaccgat agtagagatg ggagtggtgg aagcatatac 203160
cacaccgtta ggacgatatt cacgacgacg caggtcatca ttcagttcgt gtttcaggta 203220
ttccatttgc gggttccatt caatgaattt ctcttttact acaccatcgg ggaacttgac 203280
gaagaaacgg caatagtgtt ccggatcaac cagaggactg tacggatctt catcaccaac 203340
ggtccgttcc caatcaacca gttgtgccgg tttaatcaga attcccccag ggttatgaat 203400
ctcatcgtaa ggacgagcga tgtttacacg gaaaccagta ggttggtaat acatcggatc 203460
gatcatcacc tgagatacgt cgatcggaac agggagatca gtatcttcca caacgggtgt 203520
attttgcact tgcggttgtt gactgtacat cggttgttgc tcctgttgat gggagtagcc 203580
accgtaaata tcagtactga tctcttcctt cggcatcagg ggagcagatg cagccggagt 203640
atcatcgtaa tacgaactgg tggtgctcga taccgtgttt ggcgctgcgc cataagtacc 203700
agcgggttga gagaaagtag cttgggtggt tgttgcgaac tgtcccatgt tacctgggtt 203760
aatgggaggc aaattacctg ccatctggat accttgcggt tgacccatca ttcccatttg 203820
ctgttgttgg ggacgatagt taccagattt gtacgcttga atctcttgga ggatctgctg 203880
atacatggct tgagcagttt gcagaccttg gaacatatgt tgcggaactg cacccatttg 203940
cacgagagca ggatacgatg caacgcattg accaaggaat gcttcataca tacgctgtgc 204000
agctttcggc ggagcatccg tctgactgta gttcttgcag acacacagga actcaacgaa 204060
atccaccagg tgctgacacc attgttggaa gatctggttt tggaaccagt tcgacgacag 204120
caggttgtac gcgaaaatat gaaggttgct ttttccaacc gacgattgcg caagcccacg 204180
gaacagacca atagccatga gcaccagctg ttggttattc atcaggttct ggctgagttg 204240
gagttgaggt acccggtcat tgccatgagg cagattacca ttaaaggtac tctgatcgac 204300
ttgttggcag gataccggga gttgagcttg ttggttgtac atctgacttt tcctatttga 204360
gaagtttaag agacaaaacg ttgttgagct ttgtcaataa gttcacgatc ttcttcacgt 204420
cgttcaacca atccgtcgta tctaactccg acgaagaggt ttagtcggcc acgaccatcc 204480
gggttgtttt tcggttggtt tttgtattgg cccacctccg cgatcgaagc gtggattaga 204540
cgagagctat caccgattag tgatttgttg tgtgctttag aagtcttcgc gcgatcctgc 204600
ggtacaagga tcgaggttac tttaataacc ttgctatcac caggagacga cagtgtgtcg 204660
agctcaccgt gttcactggt aagtttctta atgcacgtat tgagtttgaa tgaacgtttc 204720
agggcatcgt tgatttcctg tccagtccac tctttatctt tacgaccttg gaacgtatac 204780
gcaaacatgg agacagcata gttaaactct gccatcacat acctaagaat actcaggcgt 204840
ttgtcgtaca tactagtttc atcaatgtca gtggcataca gatggtgtgc catatctgtc 204900
atgatcgcat atagcagttc ccagatggta ttgactttca ctccaactga acgaagttct 204960
tcaatggtca tctcatccag agagttgttg aagctatcca ggtgagattc aatgttctca 205020
gcaattttac cttgatgctc gaagtcacca aagatcatca gaccgagaat gattcgccat 205080
agctgtttat tatccatgta gctcggctcg tagaaccggc ttgggaatgc atctacgacg 205140
taccagaacc ctgcaacgag tcgacggaca aagtctgtct ccttgtcttt gggtagaacc 205200
agaaccatat ctccagttgg atgacgacgt ttcagaaccg cagattcata aacgttccat 205260
tgatcacgcg gatactggga ctcaggaaag tctttcaaat atccaatttg aatatctact 205320
ccagcccaac gcttgaacgt ttcaacgaca ccaaactcac agaagaagta atgtgcaaga 205380
cacgactcga tgtgctgccg gttatccaga tcacgtttag tgcgcttaga catttcgttg 205440
tgaatctgag accagatcac atacatcact tcacgctgac cattacacat gtagtggtgg 205500
tcaacttgct taaacgtcag tttggcacgc cggaatggaa tgaagatact gccattcaat 205560
accgagaagc caacatcagt caacaccgga gagatcgaat aggttgcacc attgagcgta 205620
cagataccac catcacgaac atatggtaat agtacccttc gtgggaacat catttcgcct 205680
ttatagctag tgatcagctc gatcatgtac gtattactct cggcgatatt tgctacacgc 205740
ttagagccat actcacgggt tatctcttcg aaatgaactt cgggtttaca cagacggttt 205800
ccatgatact tgaagtcagc agggaatagc gccgagttga tttcaaacaa cttatcaaca 205860
tatgcacgag ttgcgttcat gcctgtttct gggttgatct ccatcatgtg ctttactgca 205920
agcccattgg ctaaatcttt atttagcttg ggtatgacac catcaatcct actgattacg 205980

-continued tacgggtcca tcacccctcc tatcgctttc ggaatatctt ttcgagcaat gcatctgcct 206040
tggctacttc agctaagaag tccacgacag ttccaactga tatatcccta aacaggatga 206100
tatctctcac agccaaaggt tcgagttctt cgtcgtatag atgtcgatgg aacatatcaa 206160
aacaatccat acgtctctga gcatcttcct ttgacattcc ttttgtactt tcctttacag 206220
cttctctcca ttcacgtaaa ctggaataga tgccatactt cttaaagtct ccaggtttga 206280
taacaatcgc tttcgcatta tcccgtcgtg ctgcaaatgt cacattaccc cttaggttaa 206340
tatgaatacc aacaggcata tctggcatga agacaggctt tacctcaagt agatcgctgc 206400
cgaatggcat aaatacactt tcggttatac gctcatcgtc tacgaaatag gcaacagttg 206460
tagtagtagt ccagatgata tcttcctgac ggtagagttc atcgttcttc gagaagaaac 206520
aatcgcgcgg gaagaatgta gtcttcttcg ctcgatctgt ggaaactact tgaacgttga 206580
gcgcttcgat ccaaagccca taaggatcgg tatcgatgtg gtcaaggtca acaatgaaat 206640
agaaatccag ttcacatggc gtgttggttc ctttgttctt aacagaacct accagttgtt 206700
ccagatattc ttgagtgaga ttaggccaat gtttaatcat tgctccgata ttaagttcta 206760
catcgccacc ccatgtaaag ttgatacaaa taacaagtct attttcaata cggttagtac 206820
ccggtagatc caggacaata cctgttccat cgataatact tatttcatgc gtcgactggt 206880
ttaagtaacg tacacgttta tcgacgagac cttgaccgaa gaaaatgttt tggaaaacag 206940
atgtctgcca tctgtccatg tacgatgtgt caagaggaca ctccagtacg ggatcgtcct 207000
caatatgacc cgcacgggaa cggttgatct ttaccattta aaacaatcct atccaatacc 207060
atttctactt tacgtccttt gggcctactc cgttcttgac taggttcata tcgactcgtt 207120
tgggatgctt tcgaatctct atgatttctg tctccacgtt tcccatgcgc aacacgcgtt 207180
ttacctttac ccttccgcgt gttgcgcgaa cgttgttttt cttcaggggt acctcccgat 207240
tcataacaac ggccattgga tatattaaca tgtcttattt gcttctcgaa gcgattagca 207300
aaatgggaca tattctcatc ctgggtagga tgaatagtag tggtagtttg agaattggtt 207360
tggttagacg tattattact aaccgtagta ttttctttca tgacgacaat gtcgccagga 207420
ttcatttggg aatcagtgag ctcttgctca acatgatgcc cgtgtgtatt ccagaacatt 207480
gtctgatcct ctaattaggg aatgattctt caataccgta atatagattt gaaatatttt 207540
ttaatgacga cataaagcct ctacccgaag gtagaggctg ttatgccagc agtcagctta 207600
acacttccgc tttaccgctc taggcggcgg gccactccgt cttcaagata acgggtagta 207660
ccattttcaa gcttacggaa ggtacccttt ccagttcaac cttttacggc ttcaaccagg 207720
ggcttgttcc actgagactc acccatcact tcttcgaagc cagtaacgtc gaattcgaga 207780
gcgaacggga tgttgttaac gtgcaggttg aacggaatcg cagcgatttc gcgagtaact 207840
tgctggccac cacgggtgat cggcaggtcg gcgattacgg tcgatacgta gtagaattga 207900
ccgaagctga ggatgtcgtt ctcttgcgga gtcttacggg tcggaatcac taccagctta 207960
ccgtcgaaca gttcgttgtt ggtcgatacc aggtcgtatt ccaggtaagc gcccagggta 208020
cgatcgtcgc ccttggtcat caggtagtta gcgatctctt tgtccgagca gaacaggaac 208080
atcggacgct cgtcttggtt accggagatc acgcggaaag ctgcttcgat gttggattca 208140
cggtaagccg ggaacagtac acctttaaca gcgttcagga ttgccgagca gacgtcttcc 208200
caacggtctt gcgacttcag ggtgtcgatc atgtcaggca ggtgcagctt cttgtagcgg 208260
taggtcggac gcattactgc ggacagagca ccttcaacag caccgaactg cggacggtcg 208320
aaaccgttag cggttacttc tttcagctga gccaggtagt tcagcaggcg cttaacagcg 208380
ttgttgctgt tacggatgtt ggtgttgaca gtcagagcct taacaacttc gcccggacct 208440
tcttcgtcca tagtgctcag cggcagggta accggagcat gcatcggaat cgggtgacgg 208500
aattgcaggg cacgagtttg cagcaggtga ccacgctgac ggcggttagt gttggtgaag 208560
cgggtatcga ggtcgaaacc aacgatttcc atttcgccaa tgctgtcggc cagagcttta 208620
ccatcgccag tttccaggtc gatgcgacgc ttgtcttcgt ccaggatgcg atcgatagtt 208680
acttcaccga tggtgaaacg gctatcgcca cggctcaggc tgatgtgacc actgaattgc 208740
atgctcagac gcagaaccca cttacgttgt tccagttctt tcatgccagc agtttgtgca 208800
gcgtcagtag tgcgagttac ggccgaaaca gtcaggtcat ccgaccagaa gtcgatcttg 208860
gcaccgcggg tatcaccaac caggtccggc tggaacactg cgcgcggcag acgttcagtt 208920
tggaacttga tgactttacc ttggaactta acgtacagag ccttcagacg gcccgacgga 208980
tcgatggtat ccgaaatgtc cagcatgcct ttgttgatca gcaggttggc gttcgagtta 209040
cccatcaggt ccagtttaac gcccggcttc agcggagcag tttcgatgga catgttttgt 209100
tcgttgataa cggttaccgg aggcagcaga gccggatcag cgaagtactt caggttagtg 209160
ccagcaggat cgatagccgg gatcagtgca gtgcactcgt cgtccaggat ggacggatca 209220
cgataggctt caaccatgtt gacttcttgg ttgtcgagtt tctgaccgga aacagcgtgg 209280
taaacgtctt tcattaccgc gatgtacgga agaacctgaa caacaccacc ttcaatcggg 209340
ttgataacgg tggtcggata gatacgctca gcgaactcat cctgacggga agcagccagg 209400
ttataaccaa cggtcacaac gcggaaatca cgctgggatt tctcgttgta gttttccaga 209460
ccgacgccag cagcagcttc gaaagtttgg atcgaaccag ccgggccgtc gaaacgatgt 209520
tcaaccgaaa tgacgttctt gtcagtggaa gcaattttct taccaacttg tttcagagcc 209580
ttaacgtact cagtggagtt ggacattgcc agggcagcca tggtggcagc ggacagttgg 209640
ttttcgccta cacggctgtt agcgccttcg aaggattcga agccacactg acgggcaact 209700
ttttgcaggc tagcgtacat accagcagca ctttgagcat cttcgtcgct cagttggccg 209760
aagttttcca gaccgatctt actaatcagt ttgctaccag cggacaggat gctgtcgccg 209820
tagtcttttt ccaggtccag tttaccaagg aaggattcca tggagaaacg agtcagggag 209880
cggtcgccgt tcactttgaa cagagattta aggtctttca tgttttattc ctacgcagga 209940
tgggttttgg atgttacaaa tatcttgtca tcaaagctgg tattttccgg attcagcctt 210000
gtgactccag ataataagtg aagagatttg ttgccattac ttgctcaaat gggcaagctc 210060
tagtcagctc gctaatcata ctatcaaaga aagtgtggtt agccttaatt gtgagccggt 210120
caggatcgct tgaaccagtg tgcagactct tctgcaccgc aacccaaaga tactcatcta 210180
caggataaag gctataaaca ctgatataat cagaatcatt tgccttacgc agagccatat 210240
tggcaatacg ttcctctaca cgattgtgca attcttgcat cttgaattga ttatcgtcgt 210300
cggaggttgc ctttagggcg atcccaacaa ccggactgtc agccttctcg atctgagttc 210360
cctgacagaa ccggaatggg aattcattaa ttgcagcgtc gatctccgca aggtcattta 210420
ccgagcttac ggaagctata tagttggggc agagtagctt agtaaactgc acaccatcag 210480
ctttgtactg atcatagact gcttcgggga ttacaagtaa cttgatcatc ggggtattga 210540
cctattgtgg gaccaaggct attaagtgtc tacataggaa tatatactta aattggtgac 210600
aaattactta agataaaaat gatacacggt acatcatttt aattttacta aaaggatgcg 210660
gttcaaatgt cctccccaaa acagcttctt gtcagttgcg ttaccctgct ttgcttggag 210720
caccgcccag attctccggc ctctccgtct actgaactaa ttgataaaat tgttggttca 210780
cttgaaatta aagagactac tgttgatcat gatcatggtc gacaaacttt tcttgagctt 210840
cgtaaacttg ttcaagatct caataagaaa gttaagcacg aatttccaag tatcgctgaa 210900
gtactacaat ctgtgcaagt gagctgccgt gaagagaact atctttacga agctgtacta 210960
aatggtgtta atgaaaactt cccagatggg atggctatca tgcaccggat taactcttat 211020
cgtcgttcgc ttaatgaata catcaatgat gaaactatta aagcgatcat gaaagagtat 211080
tccactaagc ttctgtttaa ccgtggtggc ggtaatgata tcgctggtat gatcaacgag 211140
atgggagcta agctcgatcc ttatgtaaag gctcgtgctg aaagtcgaca tcccgctgaa 211200
atgggttgcc ttgattttga caacccggaa ggtgtagaag aattcttcga agctgtacaa 211260
actactttgt ctgccgatgg tgctttcaaa ctaggttgga aaggtttcaa ccgtgtattg 211320
ggtagcctag gtgctttccg tcgtggtgag tttattacca ccgcagctct acaacataac 211380
tttaaatcgt atctggttat gttactgttt gtacatgtcg cattgtttaa taagccatgg 211440
atgcgtgata aatcgaagaa gcctcttctt ctatttgcaa cccttgaaaa cgaaatctct 211500
gataaccttc tgactattta caaatacatc cgtgaaaacg aaacgggtga agaagtcatt 211560
gtcaaagata tcgataaacg tgaagctgct gcttatgttt gcgcgcgcct tgaagagaat 211620
ggctttaaag ttaagatggt tcggttcgac cccactgaat ttacaattgg tggtttcact 211680
aactatctag atggtcttca gggacaggga tacgagattc aattcctggt agttgactat 211740
ctgaacatgc tacctaagac aggacttgat gctaaagtag caggtgacga tattcgtctt 211800
ctattccgtc gcatgcgtaa ctacactact cctcgtggta tcactttcat cagccctcat 211860
cagcttggtt ctgatgcact gcaactgatg cgtgaaaata ccgaggactt cgttaaggta 211920
gtagcgaaca aaggttatta cgatggttgt cgtcgtctgg gtcaggaacc tgaccttgag 211980
ctgttccacc acatcatccg ccataaagga aaagcgtatc tcgctattca acgtggtaaa 212040
caccgtaaca ctgtaacggc agaagaagac caatatgttc ttctaccatt tagtaatatc 212100
ggtacgattc catgggacat tgataaagag gaagattatt ctctgaaagt tgttcctggg 212160
tctgtaattg gcggcgatct cgattctgac gcatggtcta tctaacgaca taaatgcctt 212220
cccttcgggg aaggctttat tcacaaattc acaagagtaa atatcatgag ttgtattgac 212280
gcacttatcg ataacctaaa aggttacctt cgtttcaatc tacaacaacg tcacggtact 212340
tctgttctgg tacatgtggc atcccaaaat ctttataagg tccgctttga gatagcaaaa 212400
ctgtttatca atgcattaga aggaatggat gtagacttcc tcaccatgtc ggccaacgag 212460
atcatggaga aaggagagag gtatagagca tctctgttct ttagtcatca tctgcatatc 212520
gacattctcc agaaagctgc accttgccca gatggtgatt ttatatcagt agatgtatct 212580
aactactcta aatatttctt tgatacagat ccatgccagg aaggccaggc gatgttgact 212640
aactatctcg aagaacgtaa gacctaacat actgctccct tcggggagct ttatgccgta 212700
aaaggctcta caacgcgttt atagagatat tagagataaa gcctacatgg tgacacttaa 212760
tattagaaat gtcgtgtaga ggctcctgag aggcaaggcg actgtgttgt ttttaaagct 212820
taattcattt ggtatggcga tgtttgggca tcgcctccgt tagatcccct tcgggtaaaa 212880
gcaggaataa ggattaaaga agtttataat tagaataagg aaataccttc ggtattgttt 212940
attactaaat aaaacccccc tcctccggag gtaccttttc ctcgttctac agattcatta 213000
aacacccaag taaaacttct aaatcaacaa aaaaaaaata aactaagtaa agccctctcc 213060
acaaggaaga gggcaattga ggttaagctg ctctagtaaa caaaagatta ctggagttag 213120

```
acttgatatg atagttcgat gatccgttaa tccatttagc atcggaaagc ttgcttacaa 213180
gctgaccatt gccaatgtaa ccaaggaaca tcttaccatc gtatacagca actttgattt 213240
gctcatttcg cccatagacg atcggcttac cattgaatgc tgttacctct agaccagtca 213300
agtacccgtg gtggggatct ggtctggaac ttgtttcaaa gacttccatt aggagtctcc 213360
tctgcaagtg ggcccatttg ggcaaaaagt caagcttaaa cttgacgaca tatagccctc 213420
ctggttgcac aggagggcta atctttttcag aacgtacggt gttgttataa tactgctagc 213480
gaaaatgccc acgaggggta agtagctaat ccgcagttct cttggacgac acctgctgac 213540
agtgtagtcg cgaatgcact gtttggaacc ccattggttt agcggccaat ggggatttcc 213600
ttttatgccg cttcggactt ctgtttaaca ggtttcttgt acttccactt gtacagttgg 213660
tgcaggatga aactcggaag acccagtgcc agtacaccag cgacggctgt accgacaatc 213720
tcttggggag tgattgcatt gaactcggtg ccgaaaacaa cctgagtaat gataatgatc 213780
atcaaaccga tcagagtggt gatccacaga cgtggatgca aggaacgact cagacgaagc 213840
cctggagcag aaacgcgttc catccgagta gaccaggtgt ggttacggta gtacatcatg 213900
tcagtgaagt aatcactgta gatgtgcaac agttctccac gttgatcacc ggtaccatga 213960
gccaagccat ggtagtagta aataccacca tcttctttgt gggtgtaaag ttcagcgttg 214020
tctttggtat acatcgacat ttttattact ccggcattcc agtgtgcaca agagaattga 214080
aacgaacatc gaacgtatcg tacatatccg atgttagttc ctcgaagact ggactatcca 214140
tgaaggcttc cagtgcgcgg cgagctgcaa gacgcttatc accttcacca ttagctccgg 214200
gataaaccga attaccctcg ccaggcttgg caaagccgtc aaagatatgc gactcgcctt 214260
cacggtcagt cacagttgct ttaacggaat aacccatgta acggagtccc attattcatc 214320
ccatcctttt acttcgtacc agagacaggc actattgtat tcaacaatgt aaccgtcttt 214380
acggaggatt tccgcttgac gattattcat cttcccttca actggcgtgt tctcgttgct 214440
gtaatcgaag tttacctctg aatcaccagc gagcgcccgt tgcttaattt tagcatggat 214500
tgattccata ccagcttctt tataaagaag ttcacgcagc tcttgtaatg tcatgtaact 214560
actcctacaa taaagactcg actgatttca ttgagataag cgagcactag aagaatacct 214620
gtccagatag cgatattcat tgtagtacgc ttctcttcca atccaggatt agtggaatta 214680
actattcgat gacagaaagc accgaataaa ccaagaccca tcaccacgaa gatgatggtg 214740
aaccaaccaa gatagatcat tgctgttgca ccggggtaag ttgtttgagg gcattgatga 214800
tacggtgaac agtatcacgt gccaactcgc gattgtggaa gttattggaa atctgatact 214860
gaagctctac ttcgcccgtt tccgagttcc gatcgaaatc ttttacagtg taactgctat 214920
ccaagatagc ttccaccatt tcgtcgttaa gtttgaactc ggcaatcgtt ggcgaaacta 214980
aacgcccctg gagatttctg atgacctcgt tacggaacgc gatggcgcct tctgcaatct 215040
ccagtcgttc ttcaacagag atgaacgggt tcttccagag ttcggtttcc attgtagggc 215100
gaacagaagc tttctcccat gcgatgcacc aatagaacca acgttcttga atttcttcgt 215160
tggctttatc gaatgcctct attgctttct tattgcggaa acagtccatt gggcgagtat 215220
ctttggggag ccaggtgtca gttttctcgt aataaacgaa acgatctaca cccggagtca 215280
ctgcttggaa ttctttcagt tttttgtcca tgtgaaataa tacctattgg ctgatagtat 215340
gtaaggagat tacgcgttac ttcttattcc tactgctggg ttagtgccca aaacgcgcaa 215400
tgcccgagac gaactctttg gcgaaaagaa atgggattta gcccctaccg gaaggtaggg 215460
```

gctttatgcc gtcaaccgac aataagacct tcgatcgata gggtctcggt atcggcggcg 215520
ggttgggtaa gacgagttac acgaatataa tccgtgtagt catccagatc caaacaacag 215580
ctgcaaccac gtactttgat cttggttgct tcgatttcga aatcatccag cttgatatcg 215640
ctgccgaagt gatcgaccat acgttgaaac aacttaccga acgagaacgt ttcgtactcg 215700
cagtcgatat ggaggacatc aacagtgtcc accggtgggt tataactact gctcatttgc 215760
catctcctta cgtttatttt tagcccagtt cttttcatag ccagaacgaa tgaatttacc 215820
cgatccagca ttgagccaat agcgctcacc tttgagataa cgttcccgtt tagcacgggt 215880
caggcgaaga ggatcgaaca tatcctgttc ctggcacatg aggcgatcac gcaagaagca 215940
gttgtcgttc aggatacgaa ccgaatacaa ttgccccagt cggcagttcg ccagttgggc 216000
tttctcagtg cgcaacttgt gttcatatgc cttagcatct tcgtaacgat tgcgaggatg 216060
tttctttccg agtttacgag acattgtttt tcctattttg ttaatttacg aaaaatctta 216120
tcatggaatg tcattgccaa cacgacacct atggaaccac ctagaccact agatataata 216180
gcgggaagac ccactatcac aaatagacca atggtggtca actcaagggt actgataccc 216240
cacgaggtga agaaagcagc ctttttataa ccatgaaaga tgtttctttg ctgaaaggtt 216300
tttacaaaag cgtagatgaa tgatgtggct gtacttaata gtagtaatac ccagataggt 216360
agatcgtgat taatgttaat cacttccctt gttcccactc ggtaggttca cgtttagtac 216420
gctggatgtt gtggatatct tccagcttat aaccacgacc agtcgccatg tagatatgct 216480
ctttgtcgac atgagtttgg aatgcagtca gtgcttcaac aggagcttcc agagggaagt 216540
attcggtgtt gttgcaatcc caacagaatt cccattcatt atcacgaact tcgtagctgt 216600
tctcgctgag gtaagtaata ttgatcgtgt gcgctgtcgc attctttcca tcgaagtggt 216660
aggaacctac gttggaacga atatcgatgc gcccgccatc gatggtgtct tggtagtaga 216720
acccacgctc atagaaaaac ttcagcatcg atacgaagta gctattcagc actgccttag 216780
cgttagcttc attcactacc catttcccat cgacgatgtt gttcaggtaa tcacggtcgt 216840
gattgatccc gaagtcatca acgatatcgg cgtacagctt gtgatattta gccacctcat 216900
agagacgttc gagagtagcc cagaggaata ccccattggg ctgcaagccg agaatgattc 216960
gacctacggc ccacatccca cttccattca ccttgtagtc ttcatacaga tgccctttga 217020
tattagaacc aggttgcagt tcatccgccg ggtaaccagt acgaagccgg gcacgaataa 217080
cattcagaac agcttcaccg ttattgatgt ccacaaggtt aataccaaag gtagtccagc 217140
taccacggat acgtccctga tatgcaatac gaatggcatt tccaaattca gagatgatcc 217200
aacgatggtc atcgtcgatc acgaaacggc agccgttctt ccacagtgca accaaattat 217260
ctttggccgc caggatacgt tttgtagcat tatcctcggt agcggccgca tcgggtgagg 217320
tacgcagata agacaacaga agcagctcgg cagcttcgtt ggtctgagtg gaaaacatag 217380
cgcggttcag acttgcatta atgatcatgg taatttcctt tttgcggttt atgggtttat 217440
tactaaataa aaaattacga cataaaaaat aaaaaagggg acccgaaggt cccctgttat 217500
cacgcagcta catgagcata ggtcaatgca ttgcatttcg gtttggtcgg agagacctca 217560
ctgaagaaca ttactcgatc gttgatgtac tcacgggcgt gttcttcact ctcgaagaac 217620
atacccatgg ccagtttatc tttcacgttt tcctgagtta ccggaatgcc acgagcttcg 217680
atcaccaccg cccagacacg accatcggta tccattacag ttaccagatg gaagaagatc 217740
ttggtcggat tgggcatggc agcagtagcg ggtttggacc actctgctac agtacccatg 217800
gactggacag tcatgtccgc cgtattgcgc tgatgcatcc aaccttccac agtcggtaca 217860

-continued

```
ccgtttttca ggatgatgat atcataccag tttgcattgt tacgcatgac gcagcgttcg 217920
tatttgccac cggcattgac attacccatg atcagcacat cgtgaagcgg aacttcgatg 217980
tgagtgatct tggaagtata gtcaggaatc agtcgatctt cgacctttac ccagttagct 218040
gcacgggggt gagtcaatgc aacgcgaaca acgcctttga cggcttgttc tttaagggca 218100
gccattacca gaactgcttg aacgacgtcc ataattactc cttaatgcat gttttctatt 218160
ttgacaatat cccactgcga caattcagtg tcacgataga acttttgaag tgcctcttcg 218220
attcccattt gagagggagc ctcccagaca gtaccattgt aacacgtgat tttccagagc 218280
atgcctattc cttattgaaa gttcttagga acgaattatt tgataacaac cgcttccgag 218340
agagtttcca tactgctgat aaccagtttg gatttatctt cgtcgggttc ttccattgct 218400
tcacgcagga gttcaccgat ggttttgggt tgaacgtcat cactgatttc acgagaacat 218460
gccgaatctt catacatgtc agtcatctcg atgtcgtcat ccaaaccaga gtcgtagtac 218520
gagtcttcca tggagtagca cgattcatca gaagaatccg aagactctcc atacatttca 218580
tcgaagtcac gttccatttc tttttcgtac atttcggaca ttgctttgtt atcttcttcc 218640
tgcgccttac gacgagaagt cttgtagaat ggcagcaagc gttgcaggac tttatggaac 218700
ttcttcttgc tgatcaacca gctaccgaaa taacgagaca gttttacttc agctgccttg 218760
atagtcggat cagcatacat cgctgctacc agtttctcca gatcgtacag atgatccttc 218820
gaagggttgg tatatgcagg atgctcttgg agagcgaaca tcacgaacgt acgcatgtca 218880
gtgatgaagt actggttgtg gtgcttgttg atctcgacgt agaccggatc ggtatgacga 218940
tggtagtcga actcctcagc ccaggtcagg ttgcgaacct tagtagggcg aggaccttct 219000
acccaacgaa cagtcggatg tttctcacga atgttccaac catgcgcacg atcgtactca 219060
gtcggttctt ctttgaacca ggtgaagtta ccttcgccac gttcgaggat ctttttacac 219120
cagctaatgt tgatgctgta cttgcgtcct tcgatcaagt tgcagggttt atccagaaca 219180
gcgacatagc tgtcatgacc attggccacg ataccaagaa cggtagcttc gaaggtttca 219240
taacgctgac cgggatacac gcgttcattt tcgtccagga aacggagaga acaggactcg 219300
aagattgcac gggtaccagc agggaaatga gcgcggccga aggggctctc ggctttacgt 219360
tccttgcgac gttcgataac ccattccagt tttctttgg tcagacgggt ggtgggttcg 219420
cgatattgtt tcatggtaat ttcctttta catttgggtt tagttgagta catctcaatg 219480
catcctttcc aagacacatt gagatggggt ctccgaagag acccatctat tattcttggg 219540
tcagttcccc aagacgacct tcagctttca tacggcggat ctccgaaatg gacttaccgt 219600
attttgcagc cagttccttt acggtgcctt caggggcagg tttactcatg ttgcgaaagt 219660
tttgcttggc gatgttgtag ttttgagcct gaagagttct cagctcagaa cgaaccaaag 219720
cattgccaat gcactgagag gtgaaagtga ccatgaaaga cttcagctta tcacggtacg 219780
tattgaccca tgcacaggat tcatccacgt gcgtgcacat gtactcggcg gctttggcat 219840
attccaacaa gccgactgca tctggtccaa catcctggta aaccattttg ttgaaaaggc 219900
ccagtgcgat atcagatgca cgttcagctg taatgaaatc gattgcatca ttaatgatca 219960
acgtttccag atctttgaac ttaaccgcat cgtttttgat caacgccagc atagcgtcaa 220020
cctttacggt caacatcatg tcttcattac gacgattgac cagttcattg gtctgctctt 220080
gggtgaacac atggtccacg ttttggaaga ctttcgacag acgactatcc atttatttat 220140
cctcatttac agtgaatgca aacatagtac atttcggttt agccggatgt tgacaccatt 220200
```

-continued ccttcgaaac cttaccttcg ggtttggtca gttcataata gaactcaccg caagcagcag 220260
cgagtcccat cagaactgca agaaaaccta cacctatttt ggttttcact tagcgatgat 220320
ccgttgtacg aaatgttgga gatttgcaac cagccgatcg aactcttcct cggtcagctg 220380
atcacgatga gattccagaa gtacttctac ctccggaaga acgttcagag cgatgtccag 220440
ctggatacgc gaaatgaact ctgcgacatc cagttcacga tcacgcctga gccgattcac 220500
caacttgcga tgttgatcac tattacggta ggccgagatc ttatcgataa gaatatcgga 220560
gataccgctt tcgatctgtt ccgctacagt tcgcccttct tccttggtgg ttgcttttac 220620
ggcgaggata gcagcaacgg cggttgcact aaccgccaat gcaatgagac cgtatttaac 220680
gtaggtttcc atcctattac ccccaaccca tttcggattt gaattcatcg atgcgtacat 220740
cgaatgcagc tttgtactca ccgtcacgat cacgcatttc aatagccatt ttaatgcgga 220800
gactcaacag gccctgagag aaacgcagac gagcagcggt atcattctcg atcgcagctt 220860
tacgtgcttc ttggatcagt acgtccaacc gcttactgaa atcagcgaaa agaatcttat 220920
cgttcagact cttagccacg atatcagtac cgatcatgac accagcgaca gccagggcaa 220980
cgccaagacc aattgccatt tctttgagga cttgattcat ttgtatattc ctattttcga 221040
atttgaagtg agaatggatt aacgcagttc agcttttggt tttgcagttt cgtccttggt 221100
cttacgacgc tcttccatcc agttgttatg gtaagcagca acgccgacga agccgacaac 221160
ggctacggcg atgagaccca agctgagtgc attttcttta atgaagtcca tgactattac 221220
cctttcagag tggcatccga attgaagacg tcgggaccaa ccgagagact tcccagaaga 221280
tccggagcaa ggtaaacaga gttgagggtt tcgtatacac cagcaacagt gtctacttta 221340
accaggctag aactgcgcag ggatacccat tcaccgttac ggaaggtttc accgaccagt 221400
acacgaacat catctacgtc agtgcgattt ggccatagat ccttaccttc cactatttct 221460
acgttacgcg catggtagac cagtttacca ttcatgcgag caacgatatt cggacggcac 221520
atgttgtcga ttactttaac tgctacggac ttttccattt ttatctcctt atttagttac 221580
gagcatttct tggccattgg gaccgatacg atgaccgaga ataacctcgg attctttttc 221640
aactttcgga gcttcatagg aaccgccgta aacaacagct gcaccgagaa ccataccaac 221700
cagaaccatt acgatagctt tcatgttgag tttccttctc tagatagggg tattatcaca 221760
tttgtaatat acgttttaaa aagacttaaa tgtacattcg aatatgataa aaagaaaggg 221820
ctccgaagag cccttcttat tacagtttac gcaggaactt gacaacctcc tcacgcagtt 221880
cgcgcagagt tgccgtcagc agaatacgtt cttctgcttc atggatcagg cgttctgcca 221940
gatcggacag ttcttcttta cgtttatcga gatcgtaatc cggcgggatt cgatcattgg 222000
cgtcacgcag tttctgcatg acttcttctg ctgtgttctc gtcggtccat gtaatggcga 222060
tcatcgagat tacaccgccg actacaacac aacccagacc ttttacaaaa ttaccgaaca 222120
tgttactttc cttatttgca gatggggtta ttgagcagtt gtttcttcag ccggagcaga 222180
ggtatcctgt tcttgaacag gagattcagc tgcggtatcc gtggatgcat catcgccagt 222240
tggttcgaca acgttgtcgt tcagagtttc atacagctta catgcagctg taccgagagc 222300
gataacggca gccagagcac cagtaacaac cagaatcttt ttcatgatgg agttcccttt 222360
ttaaggtagg tctcgataga tgacctgttt gatataatga tcgacacgcg gttcagcagt 222420
ctttcggatt ggctcgtatt cctgatctag gatctcacga acctcttccc aacatgcttt 222480
acgtagcatc gcgtagcgtc tctctggatc accaaagagg tactgactcc tacggagcaa 222540
gacatggtga tagctttcaa cgaccttacc ggccttagct acgactttat taaccatgtc 222600
tatatgcctt tgcattagat aagctgcacc agcaaaaccg gatacaatta tacctaatgc 222660
aacggcacca acaacatagc gggttttcat gcacccacta cttcatcgta aagagtacca 222720
gcaatattca ttgccaggat accgacagtt acgacaaata cagtttttac gagagtgttc 222780
atgtttattc tccttgagca gcattgaata cttcatcaac tgcccaacag gcagcattaa 222840
caacgatgat gcatgcagcg agttttacac agaagcgtgc gagtcccatg ttgatctcct 222900
tgatctgttg actaatatca cacttgtaat atagccttta aattggtttg aatgtagtct 222960
ttagactacg gacttacgag cgatgcgctg aagcagattc tgatcggtga tgaaatgacc 223020
gagaacacga tcaattacat cgtcggccac atgttcgttg tgattactta cttcattaca 223080
cagaccactc acgagtccag cttgacgaag tttactttcg gtattagcga tcgacttaat 223140
acgatattcg cgaataactt caacaaactg acgttcaccg gctacgaaac tactcttcaa 223200
actagagtac ctgagaatgt tctccatctt accgatcatg ttatccatag ttttcatgtg 223260
ccagcgccag atatccgatt tgatcccttt agctagctca tgttgacggt gcatgtaaat 223320
tgcataagcc atgtaggcca ggaaagcgat tacacttaca gctacaattg cgttgattgc 223380
gatattcatt tttcaatttc cttttgggtt tggtttgaca cgacataaag ccctgatcga 223440
agaccagggc tttttaggtt tgattaagca agggccgcca tccagggcgg tactacgacc 223500
accatctcgt tagggatatg actactgaac ttttctaatg tttgtttaac atcaggccat 223560
ttcagcatgc cgtttccgca accgagcggt ggtactacga tcttccactt agggtcgatc 223620
ccatcttcta catcaatatt gtcgactatc cattggaggc cgtcattgat atagcttaac 223680
tgtgaatcat cttgccaacg atctttcgtt gggaacatca tgtaacgttt accatcatcg 223740
gcaagataga tggttgggtt accgatggtg atgattcgat acttgcaatc atgtttatat 223800
ctttgataca gttcagggaa cttctcacgg aagctttccg ctaaacctgt acccattacg 223860
ccacgggtat taacagttat taggtaaaga tccccaggct ctttaaaaat gtctttacct 223920
atcacgaatt cagccatagt caatggctcc tttgtcctac aaaatctaat ggtcgcgaaa 223980
ccacaactca tcagattgtg caagattagg tgaactcatt cactgccttt tttaccgcta 224040
tagtaagggt aattgcagcg gttattaaag caataccagc ggttgcatat tgcataagtt 224100
cacgattgtg ggcgtactca cgacgactct tttcgttttc ttcgtgaggt ttattatgat 224160
catagaacat ggtttatcct tagaagccgt tgaaaatgat tgttgcaaca agagatataa 224220
cgaacacgat tacaacatgc tctagtttaa cccagctcgg tgggacattg ggatcactct 224280
tattggaacg cgggaacatt tcttccttag cttgttcttg cataaagcac ctaatataac 224340
tggtttattc ccaattgtga tatagggttt aaaatgcttt gaatgcaagg tggacactca 224400
cgaagttcta taatgaacgc ctctatattc ccttcgtcgt tgcaatatgt ctttatagtc 224460
tcgatttcac cttttaagct attaaatgct aatcgatgaa agttatatag ttctttgaaa 224520
ttaccttcaa agaaacttgt atcgattgga tagcgttgta gttccataag gatgtattga 224580
taccctttat tgaactcttt agcgttgtgg ttataaataa agttgtgctg tagtttcaca 224640
tactcagtgg ctaaagagta taagtggttt actacatcta ttgaaagatc gatgaatcct 224700
tttatagatc caataaagtt gtatgaccaa acgtggtcaa tacgaaagaa cacgttctgc 224760
atatggtcct acctaaataa aaacccaccc caattacggg gtgggctcta taccgtcttc 224820
tgttacttcg aagcgattaa tgaaaacgcc caatgtgact ttaccgacgt ggcgattgac 224880
tgtggcccca gcgtcagctg atctacgttg ttcgtttaca cctaataaca cgccgtggta 224940
tgttttcact cggttatcag atattgtctg aaatttaaca ggcatccccg gatagagtaa 225000
atcaggatta ccatgtgtcc attccaattt gatctcttgt ccttgctttc tagccatatc 225060
cgtatattgc ttgaaagggt tagatgtcaa tctatctttt gcccagcgaa cgttattgaa 225120
tcctgtttcc aaatccttca tcttgacttc gaataagtta gtagccctat caactaacat 225180
tttgttgtct ttgtcaattg caaagtcttg gaatacttta cgagcatccc caaatcggaa 225240
agagttacca ttctgaagtt gctcggcgag tccttggtca agtgaagtcg catcgccagt 225300
ggctaacact gtgatatggc gcatcgtgtt tctaaacgtc ttctcggcac cctggtaccg 225360
atcattagga acgttgatca agtttagcac ttttgtattc tttccataac gagttgtatc 225420
gtaaagagga tacaagaata aaacctgatt ttgtatataa cgtccaatac ccgtagaata 225480
gattcctcct tctttatctt ggaagaatcg atgaacgtct ttcaaaggca ttccatctgg 225540
gatgataatc tgattacgtt cttcttgact atatccatct gcgatatcga tggcaagtaa 225600
tctttggcta tccgagcctc ccactaattg cccaaattgc gtccacagtg atttaagagc 225660
attcattgtg gtcgtaactc gatatgtagt gccacaagtt accatcatca gtttatacgt 225720
cagttcatcc acaagttgca tctgtacgct gatcaatccg atctggttca tcgcttctct 225780
ggatttaaga ttagagttct ttcctgacaa ggccgggtta tcgtcaccac taacggaaat 225840
aatccctcgg taacgtttgg taactgcttt ccgttcgacg ttacgtgtag ctactgcttc 225900
cagtagaggt atctcagata catcgacttg taggttatcg cgataaggga cgatatcatg 225960
gacatagtca ccataaccaa ttaagaactg aacctctctg atatcaccaa gttgaccact 226020
cccgtagtct ctattcaaat aaagaaaatc aagacgtaca ggagtaatcc actttttatt 226080
agcaaggatt ttaatctcat tgcggaagtt agaatagctt tcaccaattt cggtaacctg 226140
ttcgacttca cgcattaaaa gcgtactatc gacagacatt attcagcctc cacgatgtaa 226200
cgttcaatct gatctacgat agaaacgtat ggctttaatt taccttcgac ttcactacgt 226260
gcctgcaacc acttattagt ggatgccaag ttacgacgac ggttcattgc cacaagcgag 226320
tcaaatattt gactacgtac gtcttcacgc ggttccagct tttcgctag ttcataaacc 226380
tcaatagcaa gtgcttcgaa aagacgaaga tcttcaatag gtgggaaacc agctggatgt 226440
gcatggaata gagtttgttc tcgccagtca cccagatgtt tctggatgtc agcatagatc 226500
tgcacgcagt ctttatagtt aacgagacct acgctatacc cctcacccat catcattgca 226560
ataccagcgg ctgtttgttg accacgggac atttgcgata cacgttcacg gtcgactagt 226620
cgatctcccg ttacgttgat atggttatta cgtagatagt tagtgctata agctgcaaga 226680
tctggtgtaa caacttcata acgaagatgg aacaaacgcc atgccgcagt atatcgttca 226740
cagagttgca ttggagatta cctcgttgcg tatttaagta gtgctatcag gacagggtga 226800
taataaaatc gttccaaatt gtcccacgaa aggcaacatt tcgtcacttt tcttaattgg 226860
ttcatgtcca taggttgacg attgatcatt tgccaagtta acatttccag tttagtctgg 226920
agcttggcat cttccgtata aaaggcttcg gtaaatacat agaagttatc acgaactacg 226980
ggcgcgatgt cagccgggcg atcccacgct tcatcttgtt ttatgacatc tggatcagca 227040
cgtttaaacc attcgctgtt tcgttcttct tgcgtcttat acggtatttg aggacgacgg 227100
ggttgacctt catggaacgg aattccttct ggtcgagcac ggtcttcacc atcgtattgt 227160
gaatccacgt cagttggtcc ctcgataggg aacacgaacc tagggatacc ggtataacca 227220
attgcctgta gttctggccg ccagcgggag attctagtag ctacgagatg tgcacgttca 227280
gtagaaccgc aaagacgggt agcatcttga cgtaagatag catcccaaat agttggttgc 227340
ttcattacag gttcggacat tacattcagt aacttaacat tcatcatccg tcgatcagtt 227400
ttcatgtcaa ccatcataac catcgcttta gttacaaaat ggtcataggt tttcattaac 227460
tgatctggta ccaggaatgt actatgttca acagagaaga aatcactaat gtatctccga 227520
atgatctctt tacgaagagc agcaaaatct ttttgatctt gttgttcttg ttcagtaaca 227580
aacggaccac aaccactagt aagagaactt gcagaataat agtaagtgat tatagtctta 227640
cgttcaaggt cttctacttg ttgttcatta agtttactca ccatcttcca ttcgatagcg 227700
tatgtggaat cacgcaagaa tgtttcacga cgagccgccg taatagtgaa tagacctagt 227760
acaccatcac caatgttacc aatgaacata tctccaacgt taggaacgag gaacggatat 227820
gtgtgtccgg caccagtaac agagaatgta cgaatacgtt catcttggga aatatctaaa 227880
gactggttaa ccttaagatc cattccttta atgcaacggt attgttgata tggtggttga 227940
cgatggagag ccaggggagt tggttcttga gtttcgtcaa gaatttgtga gaaatacgtt 228000
acgttccagt tagaaccatt tatccatgca agcatcgaac tttttggtac gaactttgta 228060
tcaatggcaa tgccccgata aacctcgggg cgtgctttga cagtaacagg attaacttct 228120
ggactctgag gagcaatttc ttcctcatct acaaaaagag acatcgttaa ctcctaatgt 228180
cagaaataat gtgcgaaaat aatacgttca atggaccgac tttgtgttga tctatataac 228240
caccactggc tccaacttct gcgatgatct tgtcttgctc ttcacgagct ttagcaatat 228300
caccccattt cacgatacca cgcttaaacg tattaggcag gtcagacgtg attggtgtag 228360
taccttcacc tggagcatcg ggatcttctg gacgaggacc acttagaccc agtagttcca 228420
ttttctcgat cgggttacga ccaatactaa cacggaacaa ccggaacaga ctccagcagg 228480
tagttggata acgacgaatc atctcccagt acttatcatg gataccatag aagttcttag 228540
agagactaat ttgaatgtgg tagtacttca aaggatccag tgggatggtt gttctcagaa 228600
gagtagtccc aggatcaatt gtcatcggta cacgtaaccg ctcgttattt tggtacaacc 228660
ggatttcaaa gaaagagcca tctgcgattg cagctgttcc tagagtctgg ataaactcaa 228720
gccaatatgg attgaatgta aatcgaccta ggttcttgaa gtccatcagt gatgtcaggt 228780
catctttact caggcacaac aacccattaa agaatgtgaa gcggtgcggt ggaatttggt 228840
cagtatgcca atcatcgata tctggatgct ggatataagg tagacccata tctcgcatta 228900
agagaaattg atgatctaat gttccacgta aagatgtagt cttccgatca accgcttgat 228960
aattctgata tcgatactcc ggtcggaata ctttaggaat agtacactgg ttcattagga 229020
ttggatagtt aacacgcata tgcgtaggtc gttcataacg acacagatag ctaaaattaa 229080
cagtgtatcc accagcatta tcagacgact tttgtggcgt atctggagat gtactaaagt 229140
caaaccaacc gaccacatca acttgacgtt cgtatataga aagtgtagga tgtgtacttg 229200
ctagggtagc catttcggtt tgaggttggc accaatgttt ctccatccac tcacggaagg 229260
ttagatcggt tggccagttt gacttctgca ttgtatcata cagtcctttc atcaaaccta 229320
aaagagatgg agggacatta tagtgatacg ttagagacat tgtcatctca gcaccgccgg 229380
ctgaacaacg tatccgttga tcgtctaacc agcgttgagc cagtaccacg ttaggtgcct 229440
gatattcaat gtctatcctg aagtcaacaa aacgtcgaat cggtcgaata gtaatatcat 229500
gaacatcatc aacgaataga ggaaagttct cgttgttata aaccgcagtt gaaagagtaa 229560
agttctcttc ggctatttct tcatatgcaa ctgtaatacg ttcttctggg tcaaagtgaa 229620
cagcatcggc tgcatcgcaa cagttaccaa acataccgtc gttcatagga acggtatcga 229680

-continued cacgtccagg taggtaaact cgggtagcac cgggtaactg catcattgta gcaatttgtc 229740
gaatagcatc gactgatacc ttccgcatta cggtttcgta tacgtctggc aaggggataa 229800
ttgcatgggg catggtaacc acctcatggt ttaagatcat aagatccggc ataaagccct 229860
gcctttttag ggcagggcaa tatgttgtta cttacagagc tttacgaaca acactaacaa 229920
taccatctgc cacgtcaaga gcatgctgtg ttacgaactt atacgcatcc acatgcgcgt 229980
aagacacttt cagcattgca ctagccagat catccagctc agcttgttca tcccaacccg 230040
atgcacggga agtagtatcg aactcactgg agccagtgct caatgcacgg ttgcgtgtaa 230100
cgtcgagatt gataatgtca tcgatagctt tagaaccaac ggaatcagca agcttatcag 230160
ccagggcgac gtatgcctta gccatcttaa gcatgttcgc tagatcagct ttggtcacat 230220
cgaaactaac ttggcgatcc tctactttga ccttcttgaa gacaggtacc agagtatatg 230280
ccaaagcctc gatcttacta tcgccaccgc gtgggccttt ctcgtattca atagcccaac 230340
cacccatgag agcgttagcc atgttttccg gatacttggc aggtttgata ttcagagcag 230400
tcttaactag cggaccagtc ttatcgtaac caccttcagt aacagccttg ttgatgacac 230460
ctactacttc ttgcagtgca cgttcagagt ctttaacgcc cttaacagcg atctcggaag 230520
tgacacgaag atcttttgca atagcttgca cgaggttagt ttctttggtg gctatatcgc 230580
tagaaatacc tttaacggtt tcacgcccga tattggactt accaagttta gtcagagcaa 230640
ggtcgacatc tttgttaagt gcttgagaac gcttcttaac tttagtaacg aggggacctt 230700
cccaccattt aatcaacttc tcgttcagtg cacgcttcag accggtaata cgactaagga 230760
aaccgcggaa agactcaaga ctagcagcat agtacttatc gagatcttct ttaccatatt 230820
gctccatcga aggaacggaa ggagcatagt caccaaatgc tttcttgagt tcatcaagtt 230880
taacttgact caggataaga gtttgaacac tatagctttc ttgagagaga ccatatttca 230940
gaatctccat gaagccttct acagactcct tctctttctg aagatcttcg attgtacgac 231000
tggcatcaat cgcttcctct tcatcagcat cggcttcttc ttcggcctca tcggcttctt 231060
ttacggcttc ggctacatcg tcttcagtga catcagtgtc aacgtcctcg atatccagtt 231120
caccttcatc gaagttagct tcaccgtcat catcgatttc tccatcgggt tcgtcttctt 231180
cgatctcttc gaggactggt tcgtcttcag tgacatctgt agtctcatcg gtagactcgg 231240
attgatcttc gacttgttca tctacaacct ccgcttctgt ctcaacagga gtttcctctt 231300
cgttgacgat gtcttcttca ggagtttctt ccacttccgc cggtgtttct tcttcgactt 231360
cagtttcctc gactactggt tcttcctctg ctggaatttc ttccacagta gattcttcag 231420
tttcagtcac ttgttcttca actggagttt cttcagctgg aatatcatca gtggaatctt 231480
cagcgatttc ttcgttgact tcttccgttt cagctacatc ttcagaaact tcttcttcgg 231540
tagtttccgc gatagactct tcgacttcgg gtacggtgac ttcgtcagcg ccttcttcaa 231600
cttcaggggt agaaacacca tccacctgat catttgcttc ggtttgagct tccggttcta 231660
actcaggtag ttcttcatca ccaccctgag tttcaccacc ttctacagtg gccggctcag 231720
tgttgtcgag ttcaggggca gcatcactga catcagctac ttcttcaatc tctgcttccg 231780
aagtctcttc tacttcttca accggggttt ccggttcttc accgatggta tcagcggtag 231840
cagtttcacc accgtcatcg acagtagttt cggtatcaag agattcaaca tcgttagtca 231900
gttcggtttc accagcaccg ccgctattag tgatatctac gttttgttca ccagtagtat 231960
cttcagcagg tacagtgtta ccatttacat ctgtctcgtt ggcttcgatg gcctcagcat 232020
ctgccgcggc tgcttcaaca gtttcctgtt gggttgcttg aatctgttcg gcctgttcag 232080
tgagttcttt cacttcggca gcttgtgctt cttcagcttg agcagcagcg gcctcagccg 232140
cagattcatt ggtagtagcc ataggttctg gaataccaga cggctcttca ctggtttcac 232200
cagcaagagg ttcttctacc gtttccagat caccatcggg ttttacttct tcagtggggg 232260
tagcttgcgc aagttcatcg cctgcttcaa ctacatcgct ttccggttct gcggatgctt 232320
ctacattagt agcatctaca gtttcaacag gcttatcttc aacttcggtg gagctctcag 232380
cgaagtcttc aagactggtg atatatttgt gaatgttctt caacatgttg tttaccttct 232440
gtacagaata cgagtagcgt tattcgtcct aaacgctact catggacgaa acactgtttc 232500
agattattga acgccaaggc ctacttaata ttggaacgac atacattaag aacagcgtta 232560
agattacgcc cggcaagagc caagataccc aagtaaggat tagcaagcca atcaatgtag 232620
cgctcaagta cttcaacaaa ctgacgtaga attgcttcat ctgcgccctc aacttgatca 232680
ttgacaatct gattacgaat acctttgaca atattcaaca ttgatcgaat acgttctttc 232740
cgacgatgac ggatactcat accacttgca cggttaaaca tctcggccat cttctctact 232800
tggcgcaata cagtaatctg tacaggtcca gagaaatgtt gaaatttaat taaatctgga 232860
aggggtaaag gatcacgttc agagttatct agtttaacac tgatacccaa cattcgatct 232920
ataccagttg cttctggcga tttgtcaaga actacgacct gataattacc catcaggtga 232980
agagactcat gccgatatcc acgatgacta taaagtggat tagaagaaac cattttaacc 233040
gggttggata acatgattgt ttcaacgagt ttatttaatt cctcagcggt tgtaatgcgc 233100
tgtgggatat ggaatgctgc acgaataagt tcttcattat tgtaatcaaa gaactgtttc 233160
ccaatttgct caaggttctt taggtttgca atcaatccct gtacttcatt gatggcttta 233220
taacgaacac aaagattttg aattcgagta gtcacatcaa aggtcggttc ctttgaacgg 233280
cgtgcagtag tacgtgttaa cgtattaagt tcttctactc gaagaaggat attgtcaaat 233340
gctagagata aagctagact accatcgaac atatcttcca taattcgatt tagaaatgca 233400
atgactttat caagaatacc tacaacggtt cctttgaaat cttcacaacc gagatctagt 233460
agatgtgatt ctctttcaaa cattggataa ttttcaaaac caccaattag atcaagaata 233520
cgattagcag taacttcatc tttctcaagt agcgcactca gtgccgcagg ggagtcatcg 233580
aatacgacga tttcctcggg tggattagat tccacatcta ggggaatatt ttctgtttcc 233640
attgttaact cctgaacata agacgggact ccgaagagcc ccgtctatgt cttagtcttt 233700
agccggctct ttatgcagct tagcttcttg aatataaaca gaagcgtatg caacaacagt 233760
acgggttaca taccggatga tttcacgaga acgcgggttg gattcacgaa tcagttctag 233820
tgcagtctga gttacttttc gagcagcagc tttagatgca tcgtcgagat cttcattgtt 233880
aagctgatct tcgattttac taactgcttt cttaagggct tcagcacctt ctttgatctt 233940
aacgtgttca tcgcgagctg ctttcagaat ctcgatgata tcgcgaaggc gcttcgtatt 234000
ggtacgcaga gtacttggac tggatacttt aacctcaaat tccgccggtg cttctttggc 234060
agaagtggct ggaccaatac cgtaaacgat accgtctgct tgaagttcaa cacgcatgtt 234120
accagggaag atatcgtagt ttgcaccgta gatgtcatca agaggagcgg tagctttgta 234180
caacttctcc gacatctctt cgccatcacc tttaactacg ttataaccgc taataagttt 234240
agcaaggttc tcgtagtatt tcttaacagc ggccgggtat acgtaagccg agaaatgagc 234300
tagaccactg agaactttgg tatcaccaag tttggattta ccattcgcaa agacaggcgc 234360
cggattgtta agaacaaagg tcttacctgt accggtccag agattaccac cagaagcaag 234420

-continued aatctcttcg agttgagtga caactttatc tgctttggag ataccgttca tcagattatc 234480
gataccacca ataatggcgt caatgatctt ctcgatgatt tctttcagtt tctcaaatgc 234540
cttgttggcg tattctttaa tatcttctac agaaatttct gcacgaagaa tatcagaacg 234600
ttcgccggca ttatagtttt caagtcctgt ggatacctga ttagtaccaa gaacacgttc 234660
agcttgttta ataccaactc gaaggaatgc tgccgtctgc tgagaaatct ccccacgagc 234720
ttgacgcagt agaccggaat acgcttcaag ggcatgttgc gtttcaatca gttcatctgc 234780
acgttgttca aggatttctt tttcaacgtg agcatgcgat acagcatcga tttcaccaac 234840
agcttcagta acgtcaactg gaccttcgat aggagcaaac tcagcaggta cttcaaccgg 234900
ctcggtttct acaacagtat cggtaccaac tgcaccaatt tcgggtacag gtgtcggaac 234960
gggtaattca acaggagcct catcgaccac attggtcggt gcttcgatga cttctacttc 235020
ttgtgtttcc aaaggagctt ctgcaacagc agcaacttct ggagtaatcg gttcttcttt 235080
gaattcttct agagaaccga cgtatttatg aatggatcgt agcattacat tttcctcgga 235140
ggagaatcat cgcgcgatga tgattgttaa taaccataga attggttaag aggtcgcact 235200
gagctctaat tcacacactt tatttcgaat gttagtgata gcattaatac gtgcaacaat 235260
tggaccatag ttcggccgta atttcggaat aagatccatt acaatactag acactcgatc 235320
tagagcatcc cgagatcttt tccatactgt ctcaccacga cgatcttcca atgcaataag 235380
atctttggtt agacatttca tttgctcaag taccttagct tcctctttaa agagttcacc 235440
aaggctattt gtaacgacca gattctgttt aagagtcttt tggatttcca atcgactgcg 235500
cactggatgt tcatatgttt ctggcccgct ggtcatatcc tcatcatgga tgaccattgg 235560
tagaagagat acgtcacgga aatggataac atagttaccc ggtagaacaa catctttgag 235620
cggatgaata atactggcat gcttaccaat gaattccgag ttcgcttcaa atgtcgtgat 235680
atcaccagtt tctacatcgt aactcttaag ggacttacat agccgattaa tattatcgac 235740
aaggtacttc gggtaagtat taatgaagaa cttcattaca gtggtttcag ctttgaaatc 235800
atccaggcag aactcagagc ctgcaaaaag cttggaagct ccattaacag tgatagttgt 235860
accgttgtca tggaattcca tactggcttt cttattgctg ctctgttgag ctaacttaag 235920
aagctcttct gttttctttt cagttgagct gataccagag ataacacgtt gtgcgagtag 235980
tttagcttca tcgattatct tttcgatgag ctcaaggatt tttctaccca cctcttttaa 236040
acgatcaact agtgactctt gtgaaatagt tggatcagta agaagtgctt caattgatac 236100
acgttcttgt ttaccaagaa tacggtctat atgctcaaga ccaatagcca tgaacttacg 236160
agtttgtaaa cttaggccat ctcgacctgc atcagttaat tgatcaagat aagcttcaat 236220
agcgatatgg gcttcaaaca aatctttgaa ttcttgttca tgatcattga cgatcatatc 236280
cggaagttct tcctgaggac tatcttttaa ttgcgggcga tttgctggat tctgacgagt 236340 gtccatttttg atttctcgtt atgttaaaca tagaatttgg catagcagtc ataaagccct 236400
ccatagggag ggcatttatg ttagtactta gttagctcgt gtttagcgat agctagtttc 236460
gcaaaaacag aggtaacaat ctgacgttca acttgagcaa gaacatcgag agaacggatc 236520
ttagtgatta gacttgtgat ggcaccaaat acagctgggt catccagctc agtcactagt 236580
tttgcaccga gggagtccga tagctgttga agttcaccat tgtgccgatt tacagatgca 236640
tcatcggtca tgacagctag aacagtttca cattcctgag caaatttagt gatagcactt 236700
gctggacgga gatcaacctc aataggtcca ttcgagtcag taccctgaat aatcttaaag 236760
cctaggtttt ccatatccca cgaaagacgg atactaccgg gtaggaaatc ttgaccgata 236820
gaggcttgaa caacttttgt catttcactg tgggtgtgat ctagaacact ttcaatatat 236880
tcagaagcat cgcctttacc aacattatct ttggcaaatt tcatcacgga cattagtgct 236940
ttgggaagac gatcgtagag gaatacagcg taagcctttt cagttgcgat ggtgtcgtat 237000
gtgttctctc catcggcaac aatgttagtg gtatcttcaa tacgaatctt cttagattct 237060
tcgtcgatat cacctttacg ctctttaatc tcagcagctt tcttcttaag atcttccgaa 237120
acattttctg gaacagagcc acgcatctta ccgccaggat aagcagggaa ggcacgagaa 237180
gcagcaatta gttgttgtgc tgccttttgt gttttaactt taggaccagc cagtttttgg 237240
taaatcgcct tcgctcgttc aatcagccta gcaatgaact ctacaatgcg cttaccaagc 237300
tctttaacgc gctctttaac atcttccatg gaaacagtag tggtttgtag tccatcgcgc 237360
atagtgcacg ttttaaagcc ttccaggcta agtgcttctc gtttgatatt gagccgcgca 237420
tcaatctgtt tcatgccaat tcgcatcatt gcagcagatt gtttagtgat acctttgtca 237480
ccagcttgtt taaggagttg agagtaagct tctagagatt cagcgacacc ttcgaggtct 237540
tcggattcta caacttcttg ttcagctaca tcgttttgga aatcagatac gtcttcaatc 237600
tctacctgga tatcttccgc tggttcgatg attgtttcag caggttctgt atttacagta 237660
cagggcattt cagtgtcaag catgttagcc tcgaaataga attagtttac atagcataaa 237720
gggagccgaa gctccccatg ctttaacggg tggaagcatc catccagttg attagaccgc 237780
ggatgtaagt gaaatagaat tcccactgac caccgccttc tttgaagaat gtggcttcgc 237840
catcatcagc gaattcagca atcttactgg caagcttaac acaccatttc tggtcttcac 237900
ctttagtgta cgtagcaatg ttacggataa catccgtgta cttaccggaa ccttccatgt 237960
gcgctggaat aaatcgacca aatagaccgt actcattctc aacgttgaaa gtatcccacc 238020
actctttgcc catagatgtt ttccaatagc cagtgatata atcaatagct ttaatgatct 238080
catctgcggc tgaggctacc tgttctggag tcattgcagg aagagtaacg tctacgtaag 238140
aatgtgccat accactgtta tatttaacag gtttgaactt attcttatca aagcttggca 238200
tgccgtcgta cattttctga gtcttctcag gatggttacg atattccatc ttgatcagga 238260
agtcagtata tggcttaacg gagttagcag ctcgggtaaa cacagctgcg ttaccacggg 238320
ccgcctggtt aagttgacca actgccttag cgattacttg tttgaagtta tccccaagag 238380
aaggatctcc tttgaactta atatcgcctt caatgaaacg acgattcttc agccaattcg 238440
gatcaccaaa cgttttagag atcttgctct taaccgcatt gtactgctct ggcttaagat 238500
cttctttacg cccatgaatc atagcgttga agaagtgacc gatttcggta aagaggcctt 238560
cattagagaa tacgaacgga tcgtgagact ccatgccagc accttgcact ttaaggttct 238620
caaggcatgc ttcaagatac atggctttac cagaagacgt ataagtaaca agagcagtta 238680
ccatctggag attcatctct ttgatcatat ctgctacagc tgtaacgtaa agttgttgta 238740
gctcttgaac ataacgttca tcaccaccag tacgtgcagc tttaattgct tcttgtgact 238800
tagtacgagc agaatctaca attcgagaaa tacggtcaga cttacctgca ttctgataga 238860
acttctgaag tgacttcaaa gctttctcga tatcagtacg agaaagagca tctagttctt 238920
cacctgcatg ttcatcttca ccacgctcaa gaataagggc atggccttct cgaatgattt 238980
taccaccacc tggaagatct ttctcaacgt gatcacggtt ctgactcaga cgtgtttcaa 239040
taacatttct gaactcgttc acaccatcac tagtcgcttc catcttagca agttgttgac 239100
caaggaatac aacgttagac tgcattgcca tggcagcaga tacagctaga tcaataacag 239160

```
ctacttctgc acttgtatca gtgccaacga atttaccgcc agcatagaag aacttagctt 239220
tcgatacttt aatcttttcg ttttcaggaa tcgcgttgcg cggtacatca ctgatctgag 239280
aaagcagctt gtctacttta gcttcagatt gtttacgctt tagatcaaag ttcttaatgt 239340
attcgatcag cttggcgaga agttcttgaa tctttttgta gactgcccca ccgatctgct 239400
tcattcgtcc agtgatagtc tcatcatcaa tatcgacaga ttccattgcc gaacgaggag 239460
tagtatcgaa tgcctcaagt cctgttgctt tgaccttgag attaaaagtc cgatcaatat 239520
gaacaagacc tttatgaagt actgcggcag attgcttaga tacacgacca gtcttaacga 239580
catcgtgata agcttctaga gcagtctgtg ctgtatgcaa ctgatcgata ctattcgcca 239640
cttgaccgat gcgatcatgt gccaacatag tttcttcaca catacccaca tcagaaggtt 239700
ccattacttc aacaggctta tcttcttcaa cgggatgagc tagaggttcc ccgtcaacgt 239760
tttctgtcga gggtttctct tcttcctggg tctcgctttc ctcaatctct tcgatggggt 239820
tagctgctgc ttcatgggct tctacctgtt catgtacggt gggttcaacc actgactcac 239880
tctcggcttc cgtttcagaa gtagcttctt ccatagtctc actaggagag gctggattaa 239940
cgataggttc aggagtagcg ttttcttcaa ctacttcttc aacttgttca gtttcactta 240000
caacctgttc cgtggactca ttggtaccct caggagtgat tgcaggttca tcactatttt 240060
ctcggacaac ttcagattct gctctctgtg tttcgatatt aggtttctca ccagtaccat 240120
cccacagagg ttcatgcgca tcgccaaaat cttcgtggcc ataaatacct tgacgcgtga 240180
cccattcacc tttaacgaat acccagtcaa caccgttaac gtgataaaca gcaccttctt 240240
ctggattttc tggtagatct ttggtagtgg tcaaggcttt tacagaagta tcaactgtat 240300
caactggtac ttcgcgagct acgccatcag caatagcttc gtttgaggag gtggctttac 240360
caccaccaag atgtttgttc agattgtgaa tagtcatttc gattctctga catgtgaata 240420
gataacatag cataaagggg aaccgtgtgg ttccccaata tgtcatcaac ccaaacgctt 240480
ctgttcttct tccgtaggtt tgcgaagagg agcctgatac gccttaagtt caaggtcggc 240540
taccatagcc aaacctgcaa ttaagcgaat cataccagcg agagtgttgt tatagtcaat 240600
gatcatccgc atgacattat taaggatcat tgttagatcg ttaacgacat tagatacgga 240660
tggccgggct tcatctcttt cctcagcgcc aggtttttta cgaccttgac tttggcgaag 240720
ttgtccagct tttactctaa tcttttcagc ggattgttca agtttacgaa gttgagcaga 240780
gatcttttgg tcatagcctt tgcgcgattg taagcgttta gctaatccaa gtagtactcc 240840
taaacgctga cgaacagcgt ttatattcga cacttcaact ttgttatctt gctcatttaa 240900
tggtttctgt tctggtacag tgtaatactt aaaacggaag tcccgaatgg agtttaccat 240960
aaactgccaa tctttaagtt gctcagtctt agtttcactc ggaccagaga aataaagagc 241020
cttattaccc tgagttaact cagaacggaa caaagtagca ttgactctaa acctgtcgtc 241080
ttggtcgact tcaatagccc ccttcatcca acgtttcgca ttgaatattt caaaccgaat 241140
agtggagtca tctgtccact cttgatcaag ggtaagatta ttgaatgttt tgtcgatcgc 241200
agtgagataa ggcatgaaca ccttatcata gaaatcaatg gtgttttgtg tttgttccag 241260
aacaggtcga atatccaatg gtttaaactc gccattgata ttaaacttct ttgcctttct 241320
cagttcaatc tccgatttaa atggtttagt tccatttaag ttcgaagcca tctcataaag 241380
catagtgatt cgttctacag tacgatctat accagccatc agtactttag cgtagccata 241440
taggtcacta ttcgctctct ttatttctaa cttagtacgt tcccaaacct gcctgctcga 241500
atcactaatg tcttctgtag agacaacgtc agtgagaccg aatttctcaa cagcataagc 241560
```

taacatctca ggactggctg tgtcatagtt agactggata aatgtatcga gtcgctctat 241620
ggtttccatc cccatcatta acttatcaag tttttcagca caagcatcga actcgttgaa 241680
ttcatcttca atcgagacgg acagatcgac gggtgttacc ccgtcgactg cgttaggttg 241740
ggaatggtta actgagtcaa ccatggaccc ctccttactt attgattttt tcaggtacac 241800
taccaaacaa catgttcatt gtgtacatga gatcatcgaa gccacctttc ttcttgagcc 241860
attcctgaag catgtcgttc tcgttcggag aaagattgta gcttaggaaa agttcagcga 241920
tatcccgacg atcttcgatt agttgaacac ccgctggcgg ttctgctgta agtagcattg 241980
gccatgcatg gatattcact cgacgtttac ctgtggcaat aaaccgtaca gtatcttgca 242040
ggaatgcgta attgtgatca gcaatcatgg cattattatc ttgacggata aaccagttat 242100
agttacccga gaatttaata agagcgagat caattacacg tttacggaat tcccaataca 242160
cagcgcggcg aggaaagttg gtatattcaa ccataagttc aacaacacgc ggatcacctt 242220
ggcgcatagt gaaacgttgt tgagctttag cttgaccgcc agaatactca cgattagcat 242280
cgaaaggttt gactgcatta gtaggcattg tcaactcctt attgtacgcc agcgcgttct 242340
tcgatcttat tgatctcgta ttcatacgcg gagatacgac gctcgtaagc ttcgatctgt 242400
ttttgcagaa cagggctggt cggttcttta gccagaagtg cacgtagttc ttccaaccga 242460
agttgaagac catagtactc ttcttgtgcc acgttatatc gctcagcctg catctctgca 242520
atcagcttac cgatgatcaa gaagggattc tgacgaggag agaaaccagc catacccaga 242580
ggatcagttt tggtaagtcc aagattctgc tgtgcaactt ggaaagtcga ttcgtcaact 242640
gtagcattag aagcagcatt aagcttttgc ttcagtgctt gaggttgaag agtcatcgcc 242700
ggatacagtg cagcgaactg ttccatgttg gtatcgatcc aatcggattc agccgacgtc 242760
catgcagcgc gggtagcctt cccatgtagg gcagcttctt gggcaacaag gaacagcaga 242820
tatttacgac caaatcgaat atagaaagcc agaccttcga tgaacttgag catgttagct 242880
cgatcgaatg tcaggtttgt attagtgaat tggatcgaga atagactacg gatttcttta 242940
cgaataactt cgaagttacc acgaatgtta tcgagagaac ccagcatcag atcgatagcc 243000
ggctggttaa aagtaatacc acgacgaaga acgttttcca ttcgtttggc gaggttagac 243060
ttcagcggga taccttggaa agcttcccga acatcagaaa caatcggggc aagggtatcg 243120
tcatattcgg tctggagttg atccagaacg ttcagcagtt gacggcgctc cattacaggt 243180
gcaagctgct ggacatagtt aagaatactc attggtcatg tccttggtta aatgttggtt 243240
tgcatctgtt tgctgaacat cttaaagatt tcagtgatgt cttgaccttt agatttctca 243300
gccatcttca cttcatcgat gcggaagcta gatgcaatat ccacaccacg gtgataaata 243360
gtaacacgct gccaacgttc atcaacaacg atcaacatga gtagatagct attatcgaag 243420
atcttacgac gggtattcgg atcttctagt ttaccgtaaa gagcattggc agttgttttc 243480
atcgtggtag acgaaacgac agcaatgtta gaagcatctg ccatagaaac acggccagtc 243540
tgaacagact tgctcaggtt attacgacga cgatcagtga tctctttgta aactccggac 243600
ttatcggaaa tcagagctgc aaagtgtgca tcaatcatat cctgtccaag aacgaagtcg 243660
cgccagaaac gaatctgtcc agttttaacc aggaacagac gatggctcca agtatcacgg 243720
ccgccggcac taaagatatg agtaagagtc tgcgacggaa ctgctgccgg aatgagacgg 243780
atgagtacag gcagtttagc cttagcatca ccatcggtaa tttcaacgtt cagtagttta 243840
cccacagcga ggttttcggt ttcgtatact ttctgagtat cacccgaaga catccgtggt 243900
gcagcttctt tcttttccct atcacccttc ttacgatcat cgtcttttga ttgctcatac 243960
gcttcttgag agtattcagc aatcagttca ggacggatct tttggttgaa cgcttcgagg 244020
gacgggaaac cgttcatgta attttctttc gagaagacag cgccactaac atcagcacca 244080
atagaacggt acgggttcag gctatcgaat actttgagag tatcgatttt acctacacca 244140
agaaccatat taacagcttg cagataatat ccggcgaatt ggctaagtgc tattttaagg 244200
atatcttgca tgtaaggttg gtcgaccaga acgctatcaa taatagcaag tggttcaact 244260
cgacatgggc gagtcaaatc tgcaagggag ttaatctcca tgctattttt ggtcgcatta 244320
aggactgtgg tcataagacc tttaaaagct tggctaccgg cagcagcgcc tgctgcgcca 244380
gccatagcac tagctacgat tggtagtggc atcgttctct tccttcattt gttcacagag 244440
atttgaaaaa tggcattaag tgattatcta acgcaaatta cacaaaacat tgggatgtcg 244500
ccgcgtgatc gttccattga agattcattc aaaggcctga acatcacagg tcgtaacaat 244560
gcgatttcgt taaatacaga aaaccatggt tatactttct ttacccgtcc attactgaac 244620
ctggctgaag ataactgcat ggtggacagg cgactgtcca tgatcctgaa tcctaaccca 244680
cagagtatcg agcgtatggt tagggcatat ttggatccga gagcacatag tgaaggtggc 244740
acagcatggt gcggtggagt agatcctctt aacccgttta tccccccttct tagtaacaac 244800 ttgattagtc ttactggttg ggaagatttt actattaatc tcggtaccac aacacccggt 244860
gtttaccgtg acgtaatgtc ctatgtggac gacgtgccat atcagtacaa cacctacgat 244920
ttacaggcga cattccgcaa tattgctgga gatcctataa catggatgtt caagatctgg 244980
ctagtctata tgggacttaa tagagaaggt cgtatcctac cctatcccga tttattgatg 245040
cttaatgaat acgatgccaa cacgcgtatc tatcgcctgg taatggactc cactaaaaca 245100
tttgtaaccc gtattgctgc atgtggtgct gctttaccaa tgaatgctcc aactggtcaa 245160
attattaact ttactggtga tggagcagag acaccgttcc aaactgcaag tgatcaactc 245220
aactttagtt tccgttgcat gggaatgaca atttacgatc atatcttgat ctatgagttt 245280
aatgatcttg ttgaaacatt taacccgctg atgcgagata acaaccgtgg gcgtttgaca 245340
caaaagttac gacagcatga aaagaaatgg tttaacttcc aggcctaccc gtacattaat 245400
agtgcgaata tggaattaga atggcacgta cctaagtcta tctacgacca aatggccggc 245460
ggtaacctaa cacgcggata caatccaagt tgaggaaatt ttaatgagtc agtttaaaga 245520
acggatgtat agtgctcgac gtaatccagc gttgatgcaa accatcgctc ttaatgaact 245580
ggatacacaa atgaacggct ctagtaatgg agccgtcatt gctgatattc cagatgcatc 245640
tatccctttt gtattctcgc ttgagatcgg ttccatggaa accgcgatgg caattggtga 245700
aatggaggca ttgggacgtc agctgtatcc acgtctttcg ctgggtagtg aagagctcta 245760
taaacacatg tcagatgatg actatattgg acgctttgct tctcctgcta gaacaacctt 245820
caatttcttg attgcctacg atgaagttat tgctaaagca gtggccgtcg gagatacagg 245880
tatcaagaaa ctagttatac cgcgcttaac ggaatttgat gcagctggta ttaaattcac 245940
gatgcagtac ccaattgaaa ttcgggttat gcgtcacggt ggtattacta tcgaatatgt 246000
cctcgataaa aagtcacctg tggaaaccct atcgacgaac attgtaccat ggtctatgct 246060
cgtcattgat cgacgtaagg ttatttctct tagcatcccg gtctatcagt tcgcagtaaa 246120
gacacatacc gaatctctta acccatctag tcttttccaa gagtcgtata cattcaccga 246180
tcagttcttc tatgcgcggg cgtacatcag ccgtactgaa gatgataatt gggtggaact 246240
taaaacgact cactcggctt tggtctatga cccaatggaa ctgaccgttg tgtttaaagt 246300
tattggtaat aaactccaag tgagtattcc aactatctat acaaacacac gaatggcgca 246360
gggtgatatc cgtatcgata tctatactac ccaaggaaag atggatcgcg acctgggtgc 246420
ttataaagca aaccagttta agttctatct gaactctatt gatgacgata gctcgtatgt 246480
gtctccgttg acaacgttta acctcattca atctctggcc cgtggtcgag tagaaggagg 246540
tgcgaattcg gttgatttta acgtactccg taatcaggtt attaataata cactcggtgc 246600
aaaccaagta cctattacta acgttcaaat tactgacgct gttaatcggc gtggttatac 246660
actcgtatcc aatatcgata acattacgaa tagacagttc ctcgcttcaa ggcgtctagg 246720
agctccgagg tcgcttgatg ttatttctgg tgctggtgta gccatgtcgc aacttaaagt 246780
cgatatggag tctttggcgg gctctataca tgtagcggac aatggtgatc gattaacgat 246840
caaacctagt atgctctaca cgttcaataa tggtcgtgtt aacaccgttg ctgatgctga 246900
gattgctcgt ctaaaaggca gcaccgccga acagattgca cgtgaggtga acaatggccg 246960
ttacgtgtat tctccgttcc ataacgtact agatgcgtcg cgtgagaatt ttgaggttcg 247020
tccctactat ttagacaatc caacaatcac cgaaaagatt tttgttggtg agaacgacac 247080
agccaattta caagctgcta tcgatgtctt tgatatagtt aaaacggatg aaggttatcg 247140
aattacagtt cgtttagaat ctggcgagca gttcaagaaa ctagctgatg aacaagttgt 247200
acttcaaatt ggctatcagc cagctggtga agtacgctgg gcttctgtta atggtaagtt 247260
cattggtatc gaagacggtg agcgcgtatt tacttttgat atcaaaacta accatgacat 247320
caattccaag aacgagctct acacgactaa catgtcgatg ttctccgagg tgcaaaacaa 247380
tttcgcgagt actctaaata acatgtttga tatcactatc cttgttgtta atacgagtac 247440
acctggttat caacctaacc agatcgatga aatggttcaa gcccacctat tgccacaaca 247500
attcatggtt gtcaaccgtg aacgtctagt tacaacactt ggttatgaca tgaccaaaat 247560
gtggcgacgt agtcgtactg tacttggtga tgagtcttat cagcactggg aacatgatgt 247620
aatgtggttc tatgaggaaa acgaatataa acgcgatgaa gcaggtaaca tcattgtaac 247680
gattaaacct gatggtactc tcgattatga gatacttcat cgtaaaggtg atccggtatt 247740
ggatgcacaa ggtaatcagg ttcgcaagca ccagaaaggc gatgtaatgt tagactcaaa 247800
cggtaaacct attttggttg caccgcgtaa gcgtctacgt gaaattactt taatgatggt 247860
tgatggacta ttctactttg ccaatgaaaa atcggcactt gactacaaag tcgaaattcc 247920
gatggaattc gttacatggc ttgagaatga catcagtatc ctcgatgcac agttacttga 247980
aatgtgtgag atgtatctct atccgactac cacttatggt gatactactg ttaccgtacg 248040
tgaaggtcag aaagctacca tctccgtcga tcaagcattc actcttagtt tctatctgaa 248100
accagctgaa tataccaata ctacaattcg acctagcctt atggctaacg gtaagtctgt 248160
acttaatgaa tacatcagtc gtaagactgt atcgatgtct gatacagttg ctcaacttga 248220
agcgacgtct ggtgacgggg tacaggcact tgaggtattc ggtttgggtg gcactaataa 248280
ctacgccatt cttacagttg aagatgatgc tgttcgcctc gcgattcgta agaagcttgt 248340
tgttcttgct aaccaagagt taactgtaga agacgacgtt caattcaact tccttaaaca 248400
cgaagtactg aataactaaa cgacataaag cccggcattg agccgggctt tatgttgtca 248460
aataccaagc tcacgtttga tatcttcaaa acgcttaatc agtttatccc aggcgacatt 248520
agctacgtca cttgcgacat gaacatagaa atcctcacga acgatgtcgt gcgccttgat 248580
gaagaagttg gcatatgttg caccagcttt gtactgataa agaggaatac ggctgaatac 248640
cttaaccatg tcattcagtg cttcaatacc agcgttaacg ttggcaataa cagcctgaag 248700
tttaggaagt ggtacaacag attcttctag atcaaatcga ttcactttac gcagttcgtc 248760
tgcacattta ccatagagct catagatgaa cttatatgta attggctcac gctttaacat 248820
gcgtttagta tcttcaaaga aacgaatacc aactcgtttg tgtttgatat agaagttagg 248880
atcgtcagac tgactatcca tgttcttcag cgtttctgcc agagactgta gtcgtggtcc 248940
aatatgagat tcaaagccaa gttctaaacg agagcggtcc attacttgac gaagctgtcg 249000
aatttgctcc agcagttgtg caccaaattt ttgtgcttct tgttggatat ttcggattcg 249060
acgaagatca tcatctacac caaaagccaa caggccgata tcggagcggg gtagcttagg 249120
atcaagtaga accacttcgg cagcttcgta atacttacga tcaagattac gattacccaa 249180
acggttcaaa gcttgcatct ctttccagtt ggattctaat ttaacgattt tttcgttaat 249240
agaaacgatc ctaccttgga tcacttcgtc attcatctca actgacttaa cccaacggat 249300
tgtctttaca ataaagtcaa ccagtacatg gaaccattct ttaatggtag ccataatagc 249360
cgaaccaata gcttcattag aaacctttag attcaagcta gtacgtgtgg gcgtgaatag 249420
agcgttatag ttttccagag atggtagtac tggcacattc aaaccaatag cttccatgga 249480
actatggata ccacgaagag ctgtgatatc atgcgaacta acaccttcgg cacggatagt 249540
agaacgtaga tcgtctagcg tgctaatata ctccaatgca gcatgtagct tttcttgcag 249600
atttggatcg agctgaactc cacggacggg agctgcttca agctcttcac ctaactgtcg 249660
ttgtccttca ataagaacgt catcgtgttc atgcattttc attaccttta gaatgctcgt 249720
aaagcttgtc acgtaagagg tacaattcta aacgaataat ttcttcaatt gcttttcgcc 249780
tggctactac aactccacgc ttagaatcaa atgctgcttt attcgctaca attgcatcgg 249840
tgacaatccg atggccatta cgtaatttag taatgcagac tgtcaccaac atttcagggt 249900
cagagatgat cttctctttt acgattaatg actttgcgta tgcttttgta atacgcgggt 249960
gaactaagtc atcatgggta tggtcgatca tgacgacccc tccctgaatt agccttctac 250020
ttcaagctga cgcagaacac tggctatagc attttgactc ttagcgaaat caaaacgact 250080
ggcaagcatg ttagcggtag cggtttcatc gattgtctga taatcttctg ctgtaacgga 250140
tttcattgca gcttcaatga tagctgggtc gctaacacag ttaatcagtt ccaatcggat 250200
acggatgact tgtttaaaga gttcacgagt cagattcagg tcgagagcaa tattctcgtt 250260
aacctgacca gctaccttct tcaacatagg catgtgtgca tcaatcaact cttcacaaga 250320
aagagatgga tcaagctgga caaagaaacc aacagcgtta gctacaaaca tggcgcgagc 250380
ttgacgatca ttgttggtcg gggatttaat ttctttcagg atacgggcaa tttcaaaacc 250440
agtacgcatt tcggtctacc ttgtttattg agttaagcgg aaagcttgta agaacaaatc 250500
attgttcagc aatgtctcaa gattctcttc agtttgttta tactgagttt ctttacgacg 250560
agctggacgg aagaattcta ggacggtatc gaacaaatta cggttattag aaaagtctcg 250620
aataatgtca tcgatagctt taacatcatc actcatcgaa gctttatctt taactgtatc 250680
agttctacgt agttgagcaa taagatctcg acggactttc atgattcgtt cacgtgggtc 250740
atcgtaacgt gcagagaaat tgaattcatc tacttcgcta tttgtaagaa taaccaacat 250800
gactaatggt gagaaccaaa gcatggccaa ggcatggata atcaacatga tgtacccaga 250860
ctcttggtac tccattccgt agtatttatc gaacttatgg aggcatgtcg ctagatcacg 250920
accataaccc aaacgagagg caaacatatc tgccatctgc tcttcacgtc gcattgctgt 250980
aacagggtta ttcatcaaat ggtgtcgtgg tgccttttta taagcagata gaatagcacg 251040
gcgaacgtta ccgatatcag agcggtcatt aatgtaggcc tggtattctt cttctttaag 251100
gttttccttc aaccatttat cggtgagaac ctcaagcttg aatacgttgt ttttcttacc 251160
ttgtagaatt tcaattccat ctgtaagata atagttaagc catacgtagt cgcccatgta 251220
cataaagacg ttaaaggtgt gtcctatttc gtgaacaaga gcagcagtta cttcacgaat 251280
ggtgaaacct agtttctcac taatgaaccc aagagagata tacatcttaa acttcagttc 251340
atcggcgaga ccacctttaa cacgaacgtt cttaacatcg ataatggttt caagtttccg 251400
cggatcgtta tagctgttct ctgctcgaag ccacttatgt gcattatacc aagtaccgct 251460
atgacccaac gccatcattt ctaggctaac gccggcgtct aatccggagt caccactgac 251520
agtaaactcg taattaatac cggtttcaac ttttaattct tttgcaaaat cagtaaacaa 251580
actaacggga atgatcttgt ccttttttata cgcttctctg ataagagtaa cgtatttttc 251640
agtgatcggt ccaatgttgg atttagctcc aactactaac atctcttgag agatagtgta 251700
tcggttatac atgagagtgg cctactcgtc agttttatta atcataaagt aaagctcgaa 251760
tgagagatta ctctggtgat taatactacg tgatttaagt tttaaaaagg aagctcaaaa 251820
atgagtgata atatttcttt cagtaaagaa gatgtaatcg gtgtcgaggc taaacatatt 251880
acatacgtca ccgataggaa tcaccgtaag catgacttac atgttgttaa agaagtcgtg 251940
catcttaaag ataaacgcag gattccacga ctgaggttta ttgaggatta tgaacggcca 252000
tggtggctgg atcctgaagc aaataaaaaa gaaagccagc gtacttatca tgagaagaaa 252060
gactatgagt acgctagtaa gcttattaaa cgtaagtcta cccagattaa catgccgcat 252120
gcgattgcta aagctctggg tgattacagc atgggaccta accctaggct tcgtcaactg 252180
agtcgaagtc cttacctgta tggtgcggac gttagttctg tatgctgctt gaagaacgat 252240
tatcgaactg ctgcacctga tctcatttct cgtaacacgg tagcaggtgg tgatattgag 252300
accaacgttt acgaagatgg aaaagacgga cagattatct gtatgtccgt aagccataaa 252360
gaaaacgttt atcttgccta tcttaaacat tgggttagtg atcttaaaga ccccgtgaaa 252420
gaaacgttcg aggaactaga acgtattcct gaattggttg cacttcgtaa tggccgtaat 252480
cttaaaatag aaatcgaagt ggttgatcaa ccagttcaca ttgtcattaa ctgtattaag 252540
cggctacacg aatggaaacc agacttcttc tctttctgga acatcagctt cgacatgagt 252600
cgaatcttga agaccctgga agatgcagga gttgatccgg cacttgtatt tagcgatccg 252660
tctgttccta ataattacaa gtatttccat ttccgccaag accaggcgat gacaactacc 252720
gcttctggtg ttactaaatc taagggacct gaagatcagt ggcattggat tacatgtcct 252780
gcctctttcc aacccattga tgcgatgtct acgtatcggg taactcgtct tgctaaaggt 252840
aaagagcctt cgtatgctct cgactatatt cttaagaagg agctaaacgt tgatgaagaa 252900
acagagattc ttggtgaaga agatctgatt aaattcaaga agagtcttga taaacttctg 252960
gtagaacgtc ctggtagtta tccgtatctg tttgttaact atagcggtaa agaggatgat 253020
tggacaccgg tagagcattt cacttggggt gaaactgtac acctaggtaa ccatgttcgt 253080
tacacaatga actttggtaa acttaagttt gctgaaactg atcaccttgg tggtatcgaa 253140
tggcacattg agatgcagaa gaaccacaag gttcgttatg gtctttacaa catcattgac 253200
tccattcgtc tggaacaact ggatgaaaag atcaacgacc ttgctagttc gattactctg 253260
ttctctaagt cttctgacta taagaacttc agctctaacc cgaagcgtct ctgtgatgac 253320
atgcacttct ggtatctgaa ccgtcctgag ccatgcgtaa ttggcactag ctccgaccag 253380
atggttcacg agctagatca atacgttgta ggtcatgata gctggattgt tacactgccg 253440
tcctatatgg ctggtccaaa tgggttgaag tgtgttaagg acttacctga ttacaagact 253500
ttgatcttta gtcacgtagc tgaccttgac atcgtttcga cttatccgaa cgttagtcag 253560
attctcaata tcgctcggga aacaactgtc atggaattct ccatgatgaa agatatctcc 253620
gaacatcatc gtcgagaagt aggtgtgaac ttgacaggtg gacgtgttaa tgccattgag 253680
atctgtcaga aaatcatgaa ggctccgaag ctggatgaga tgctgaagct ttatttggat 253740
aagaaggcta actccccaaa gtgatatatc gatggaaacg tcgcggagga tacgaatgtt 253800
cctccgttgg cgataaaagg ttctccgcct taaatgctgt aatgcccgat ggccgaacta 253860
ttgagatgca ctaccaatgc gatgttaaag gttatgatgt tggtggtact aattggaagc 253920
tcggtaaagg caagcctccg ttgagtccta taaactcatg ggatgcatat ttagctctat 253980
gggaaacatg ggcaaaggcg agtcctgacc tgatgaaaga acttcgtaaa ggagctgaag 254040
caaacgaagg atatctttct gatgtctttg catcgactaa tatctcacaa gcacgcgctt 254100
tagcagaact cttgaataaa gggtattgac aacatattgc ccaccatta ggtggggctt 254160
tatgccgtta agctttacca atcaactcta gaacaggacg ccaacccata tgtgcacccg 254220
tattggtggg tacgttaata ttcaactggg acatgttact ataaccgata ccggcatatg 254280
ctgttttacc atcgactaag ccagtttcct gaccccagct ataactaccg gctccttgtc 254340
cacctacccc gagatcagcg ttggttaagt tttcccatgc ctttgtaccg gttacagttc 254400
catggacgtt atacattaga tcacgccatt ctcttcctgg agcagcgtta ttggttatac 254460
ctgtatcggt agcgccaata tacatcaatc gacactggta tacgttgtca ccgatagtga 254520
ttcgtttacc cctaccattc aatccagcac ttgccagaga attccatgtc atgttgtttt 254580
tgagtggttt ttgtgggata taaagaatgg tacttctgtg agagaactta aaccagtccg 254640
gtgcctcatt aagaacagtc ccctcgctca aaccaactaa ggtagctaac gcagatgctg 254700
taattaattc actagatggg acacgaccaa agtaacctat atcgtcatta ccggctataa 254760
gtgattcagt accaggtcct ttcgatggaa taatgtccgg gtcaatccaa attagaattg 254820
gacgccatcc gtagttattc atatttgaac cagctacttc tctacccaca tagctgattg 254880
aattaaaacc acgatagaag cctttaccta cgtcagtacc agtagtttgg acttcacgta 254940
cccaattagc ccccaccggta ctagctaaac caaagtcact tgttgagaat gactcaaatg 255000
ccgctgcacc agattgtctg ggtattacca tcgaataaac caaacggtta tattcgccgc 255060
caccagttgc actggcacca gggttatcaa tacccgtcat aacacgacat aggaacttat 255120
gtctaccgat ctgtatttcc ttaccatcga tgagtccatg gttctctata atcgatctag 255180
cagcgcctcg tctaaaaggt gttttcggta aataaataag tctgttattc tctttgtatt 255240
taaaccaagt tgtttcacta gtgtgtaatg taccctctgt gaaaccaact agattagaga 255300
atgcttcagg ttgtggtagg cctgctttaa acccaccgaa ataactaaag taatcactac 255360
cagcaattgg aatttgtgat cctggtggaa atgtatcatc gtacttatta agaactgcta 255420
ataatgattc gaacatatgt aatcctgttc tttcttaaaa cctataccat tgccggcata 255480
aagccctccc tgaagggagg gcgttatgtt tactgtactt gttggaagta ctgaagcagg 255540
agaggttgac gcttagtcgg gaagagggat accagactag gaacatcgta ctgggtccgc 255600
gcttctttgt tctcatcggc gaagatgaag aacagagtca ggatctgaat gtgcgattct 255660
tgtacaccac cttgaacact caaaccatca gtgaaacgga atgcatggct atcatcgaac 255720
aggccaggag acttacggtt ttcggtgatg aatttccgaa taatttccat accgttctta 255780
aagccaactg gatcttcgag attgataaca taacgaataa cgttatccag ttgtttctgc 255840
gccatgacac cagtttgcgg agtcagtggt ttacccggag cacaaatttc tttgtatttc 255900
ttgagagttt cttcaatgta agtttggttc acttcggtaa gtccttcgta ggagagttgg 255960
atacgaacag cttcgacatc tactttcgga gcagccgcag tcggaatagt tccggtcaaa 256020
tgggtagtct gagttgtctg tccggtttga gctttataag ccaggatgac atcttcagga 256080
gcattgctct tactaaccaa catcaaacgt tctttcagtt caacggccag tgcgggttca 256140
ctggtagaac cctctgggcg aatctcacca agagcccagc tttcaagttc ttgtgtggtc 256200
cattgagttg ctttacgtgc aaaacgagtg atgtcggatt tccaagcacc tttagaagtt 256260
ttgtcaggaa caataccact gacaaggaac tctttacatt gctgtggatt ccaggctaga 256320
tcaagagtag cttcacggcg ttgatgttca acaatagctt ccttcagaac attgtaacga 256380
acatcttcaa caagctcgcc tttgatatac agttcgagtt cttctttagt ccaacccgat 256440
acaggagtat caacgagagg cttgacttcc tcaactactt caggttcaga aatagctgcg 256500
gtagcttctt ctcgaagcag atcgaccaga gcgggggtag gttctggatc agccagctct 256560
tcttcggttt caccttccgg aggaagatca gtagtctctt cgagatcact ttcttcttct 256620
cctttagggt caccactgtc ttcagcttca gattcaacat cggtatcgaa tttatcaaca 256680
acttcaccgc aagtcagcat ccgaccatcg tcatcataga acgcatcacg atggagtgca 256740
gctagaacag gagctacgag tgctgctact tcgttgtcat catgaccttc gaaagcagct 256800
tgtagttctt caaaagaaag gggaccgtat tcaaccggtg actcttgggg agtttccgga 256860
ataacaggag taacaggttc taccggttta gctacggtag gaatagagaa accacgattt 256920
cgatttttag ccatggggat ttcctagttt gtgaatagtc aaagaattag gggaattggt 256980
aagattcccc tttgtcttaa gaaagacgac ggaccgggtc ccatttaaca gtcttcagag 257040
tagcactgtg catcttcgac atgaagatac tcaagaagcg tccacccaca ccagctgccg 257100
cagcaggaat accgttgggg ttctcagcaa gagctttacc cgcacaagta gcacagatat 257160
tcttatctcg tccaaggata cccttttcaa tgtcacgtcc agacttacac gtcattggac 257220
cacgtacatc gataatttga cccataagtc catcaatgtt ttcagaggta ataagaatgg 257280
attctccatc cttaaccata gtgtaaccaa cgagttcttt agcattaaac ttatctactc 257340
gcgttggaac accaatatgt gttttacagt ctggttctat aattcggact gtaccgacca 257400
ttcgataaat agtcttggtg gactcgccac ccaatgcagt ctgagcacca cggttataag 257460
aaccataacg aagagagttg ttcatcacag gcatgtgatc tgtatcaatg ccttcttcaa 257520
gtgacttaga gataagttca accgacgtac catccgagaa cggagattca ccaccaaata 257580
gatagtgaac tttcttacga acaccaccga atagcttagc atgttttgca tcatagaact 257640
catacgactc atcgtcagat agatactctt catccatctt aataagttcg ttacctattt 257700
ttgcaacaat agctgggtca gttaattgat ctttatattg ttccaaaaga gctgcacgta 257760
ctttatctct gtctgggtga gcagtcatcg atttacgtgt aacagaagta acaaggctat 257820
ctgcgtaagc gggaatagct agacaatgat ccgcaaacat tagatattgc caaacgtaga 257880
tcttaccatc cggtgctcgt tcagtgacgt taccatcttc acggtcgtca atcagtctat 257940
ctagcagctc attctcaatt ttagcaggtg agaaatatcc tgtctgaaat gggaagatat 258000
ccccgaacgg aaggactaga cagaggtagt taacgaatac attgccatac gtagtacgta 258060
acggttcagt acctttgtag ttttctattt cacccggttg taaaatgaat tcatcacgga 258120
agtgtaaagg agctcgacct tcgatgtaat cgtcgatgaa aattttctca tcgccattcg 258180
gcatgtagaa ccacattcgg ccttcaccaa aatgtggctt ataaggcatg ttaggaatat 258240
catcgttatt ataaacgatg ttgaacagac tgttcatcca agcacgtttt ttacatagac 258300
cagctttaat tcctaaaagg aaataatcac gcagtttcat agagctttcc cattttacgc 258360
ttgatctcgt cgatcacccg ttccatgata ttacgttcca tctcgttctc tgtgtattca 258420
tcgatagaaa ctttaacagt gctatagata ctatcgaggt gaagattaga gaagaatgca 258480
agacctacca tttcataagc cgcatcttga gcgttcttat tgtccaggct ttcaagacta 258540
ttagaaagga gttctaacca gtcatgtccg actcgcatac cagaattaga cagttcgaga 258600
accatactaa acttatctcg acctatggta ttcatcaatc gattaagaac acggatacgg 258660
gatacaggag cgatgtattc gtcgatgtga ccacgcgtca tcatagtgtc ttgcaccatc 258720
gcttttaaag catcgatgaa agaaacagat acttcattaa ttaaaggcca cacttcgtcg 258780
aaagaaaggc gttcaaacat aggtaccaga tgagcaagaa tttcctcatt atcgaaatcg 258840
ccttgtagaa tcaactcaat ctggtcagga agaatataat ttggcaaacc taaaatagta 258900
cggacaattg caagccgttg ctcttgtgtc gcctcatccg atactttaac ttcgtgtgca 258960
gctagaacct gatcatgggc cacacggata atatcgtcga tacggccaag caacatcata 259020
gtgtctgcat tgtcatcagc aatagagcaa acggtatgca gttcatcaag agctgccgag 259080
taatccattt cctctaggga agctacgcat tcaagcatga tttcttttcg ttcttccatc 259140
actaggggag tgaggatact atctagcatt tctttcattg gaattatcct gtataaatga 259200
atatctaaca tacggttatg ttgcaggtat gtcttcgtaa tatgtgaaaa gttacgtttc 259260
ctgtaacatc tatgttacta cactattcca ttaggagctt caatgagtaa gtttagtgag 259320
ctgccgttta atttgatgga tacaatacac catccaaaac caactcctga agatgaaaaa 259380
cggctctctg aagcccttga taaaatattc ccccataatc caaaattgga gcacaatcaa 259440
atgaccgcac tgtccccgaa agaacaactg gaccaagctg tagaagcttc tgctgtagca 259500
gcacaacaac tcattaaaga agatggctgg gccattcttc gcgaattgta tcgcactaca 259560
gctgctgctc ttaatgctac ttccattgtt atcattccgg cgctggagcg tcgtgaagaa 259620
attctgagta aactcagtga tcctgaaggt ttctctaaag atctgcaaaa ctgcatgtct 259680
gatattgaac agatgatcag tgctctggaa gctcttagta ttcttcacgt aaacaaaact 259740
ggtacacctg atctggctga tctcgatcaa atcggtaagc tgactttggg ttacgcaaat 259800
ctccaacata aagtagaaac agctgttcaa ccactgctga tgggtctcat tgctaagatg 259860
caagaagctg gtgttgatac tgtttccttc gtgaaataag gtaatacaaa atgcaagagc 259920
ttgatatgga taaagaagac aattatcctg ctgagggtaa ttgggaacag caagctgatg 259980
cagaagtaga acaggggccc acgggtccca ctctaccgga cgcacctgcg gaagaagtat 260040
cttcttcgcc tgctgttgaa ctacctcctc tggtaattga ccagaaacca gttaacttca 260100
ctgagacacg ttcttgttct agtgaagcta ttcctggtat gacctctttg atgagtttca 260160
ttctagaaaa ccccaagacc tttaaccagg tattggaacg tcactcggcg ctattgaatg 260220
gaatgcacca aggtgatctc actactacta gcagtgaccg agattggttg atttctctag 260280
tagctggtat gaaccatact aaccttgacc ccactcctat cggtgggacg gaacgtgaag 260340
gttctgtatg gcaacaaggt attactggtc atgataacgg taaccttatt cgaccaggtc 260400
gcccttctca aaagatcgat cgtaataaac gacacagtaa agaagaactg ttggcatacc 260460
tctccaagaa atctggtctt ggtgcgacat acgaaacgtt tatgcctcgt tcgggtatct 260520
ggcttcgcct gcgtgctccg acacttactg aagtagtcgc attgcaaaca gaaatgcagc 260580
agatcaagct acggctggga atgcaaacca aaggtatgtc gttctctaac gctggttccg 260640
taatgatgaa cgcgatgact gacctggctc tgtcttgtgt tattgcatca aacaagtcct 260700
tcattactcc aagtgacctg gaacatgaac tatcgatctt tgatgaagct atcctgcatc 260760
atgccctagc ttctacaatg tacattgatg gattcaacta cgacgttcca tgtattgcag 260820
acccggacaa ctgtacggct cgtatcactg caaaacttaa catgtcgtct atcgtttggt 260880
ttgacaacac tgtattcagt aatgatcagc gtaaatttat cgctaagaaa tttgcacctg 260940
ctacggatga agacttcaaa gcttaccgtg aaggtttcgg tattggcggt aagaaagtat 261000
tctggtttgg tgatattggt gttcgtcttg ctatcccgac tatcgctcaa cgtaagatgg 261060
ctgcttctca gtggtctcag acattgatcg aaatgtctca aggtacattt aacgaaccgc 261120
cacatggtgt tcaacgttca gcgtacattg ataaactgag taaagctact atcgccatgc 261180
agtatgctca ttgggtagat ggtatctatg aaaaggacga cgatgtagaa gacttcgaag 261240
atcaactgct ttccgacgat caggaaatca ttagtgatta tctggcgaac actctgagtg 261300
atccgcagta cgcggagcag ttctttgata ccgtacatga gtatactaac tcttgtgtac 261360
tggctgtggt agctcttcca tcgcataact gcaaagaatg taaaggtcct cagggccaag 261420
cattcaacga acgtttcccg caccttgtac cgctagacat gatggcaata tttttcacgt 261480
tggcgggcca gaaagccaag cacctggagt aatcaacgag gacccccggc atagtcgtct 261540
aacaattaat ttggaggacg acaacgggca cgttacaatg aactctttcg gtcgcaagac 261600
tgttaatggt aagagtgcat tcgatgaact cgtgcgaacg ctagatgccg taaggccagc 261660
tattgccgaa atgttgacca ggaaggccta ccataaagac tacggtattt tcgatcatga 261720
ttcaccagag gctgatcctt tagatctggt tagaatgcat cctaaggaaa acgtcgtaga 261780
aggtggacct gaaagaactt ggatacggaa gtttgtcaat tacaagatca atgacattta 261840
tggtttatct ttactagagt tctttgaact accctttaat gattgtttgt tcatgattga 261900
acttgcagag tcgaaggcta ttcaaagtac atcgcaagct agacaaatcg agaaagatct 261960
tggattaaaa taaaaaaaaa taaagcatag ctcctacccg aaggtaggag ctttatgccg 262020
tcttacactt gtgcttcaat catcatgaaa agaccaccca agaagagagt gatcagcgct 262080
acgatagcag ctccccatat gagagcagtg caaatcatat taatgcggtc gagcatgatg 262140
atatctttct ttggtaaacg agttcgacga acatcatcgt tatcttttac cagttttgct 262200
acgaacaggg acccagcgat aatcgaaata gagatccacc agatcagcat gatggtttcc 262260
atgattaact ccttgttagt tcatgagcgt ccacggcggt aactggagag gggtatacac 262320
gctaaccagg gccgtaatga tcattactag ataaatcgca aagctaattg cccaactgac 262380
gcagaggaac atgcagaggt acttccaatt aggaagccac ttgcatacac ccattacgaa 262440
caaccacgat acagcatagc cagtcatgat caatagtcca ggaaagctaa gtgtcccgta 262500
aataaacgct attgggttag taaacatcaa atccatgtta actcctattt tggaagcatg 262560
tcgaataaat gatatccact atagccggtg atagcaataa taactacgcc aaatagaacc 262620
atagagattc tatctgaaaa ggttttactg ctagttacca agccatagaa agtcattaca 262680
cctccaaccg taagagaagc gaagaaggtg agtatcagta caatccatcc catggtatca 262740
actcagaaag atgttataaa aggttgccat gatcaagtat acggcaagaa ggattgctgc 262800
caaaggacca gatgcattga aagctttagc cagtttaatc ggcaggtggt tcgttttgac 262860

-continued acccatgacc gcaagtccct gtttcaggaa aaagacgatg aacagagtga tgatagcgaa 262920
agcaaataca ttggtgataa tagccattac attgtccttt atgtgggtgt atattcacag 262980
ttgtaatata ggctttaaat gaacttaaat gcatatttga gattagctgc tgcgaacata 263040
gcaacagtga agaacccaaa tccagcgatt agataataac gatactctct ccagtgttta 263100
ggtgtatcgt aggcatttgg atcaactagt gcattaccga tacctaaaac acaggtacat 263160
gcagctagta cacctgttga aatagccagt gcagcataag gtagatagat gtatgccaca 263220
acgggaattg ctataacaat taccagaagg aggaacatta ggttggggaa agggagagca 263280
gagggagatg ttttcatttg tatttcctta gatgtgggat gcagcgatta cgaacatggt 263340
cagcgtaaag taagctaata ccaagtaaca tttctttacg aacgtatgga tcaatcgggt 263400
caatgcaatc tcagaatact ctatagactg ctttattaac ttcggtttga tgttctgtcc 263460
ggctaaacgt aacaagtgtt tatagtgcgc cgttctgtac tcctcacgga gcttcagttc 263520
caatacatac atcacgacgg ttaatatcgg tgaaacaata agtaggatca caggtgacat 263580
ttctattcct cttaacggta taaagcccac ccgaaggtgg gctgttatta gtgcatggct 263640
atccgtctga gtaccattga aagagtttta ccggcgaaat gctcactttt attccgagca 263700
tatctcacgt ggtgcggtat gttttcacac actaggtagg tcaacctagg taccacatct 263760
tggaagtctt tcagtttacg gagacgaccc agaatttgaa tgttatcttt cttggaatcg 263820
gtagcttgta acaatactac ctcacgaaga ttagggatgt ctacacctgt accagatgac 263880
ttaatagtgg acaccgtaat gtcgttctta agtaactgtt cataactgca acctgagaca 263940
tgtccgttaa ccacaaggtc agggaactta gtcttcagat atttaaccag tttttcaata 264000
aaggcgaccg ttgcacaaag gaggagtagt ttctgaccag gtaaccgatc tttcacatac 264060
acgccctcag caatacgacc gaccatcctg aaatagtcat ccatccgttt aggatctttc 264120
atcattaccg tttcgtaacg cgcatggtta tacgtattct taaacggtgt aagataatcc 264180
ttcggtttga tctttggttc agtgtagagt agccccatgc agttgatgta gacatcgtag 264240
ttgggcaggc gacacatggt ctctgctggc aacatcttgt caatcatctt cgtcacgtag 264300
gcgttccctg tgtagggagt agccgacaaa tagatctgct tattaatgtt agagtaaata 264360
tcgatacgga aggttagtcc tggatcttct tgaatctcgt cgttaatttg cagtcctgct 264420
tgtattgctt cgtggaaccg gggtggaggt acattgtatc cgagctcatg gagtcggtta 264480
ccatacttct caaagttatc tagatatgcc cggtaggtag tagaagagat tacaataacg 264540
tcaatccctt caagatcgtt ttcgacgccg cgatctatta gtttttggag ttctgcggaa 264600
cccgagatgg taatgtatct ctgggcaatg tccttgtaag tgttctgaag agcctcaatc 264660
caaataccaa aatacttggg aggaaccatc acaacacatc ttacccccat cgaagccaag 264720
gacgctaggc tcgtgagggt tttccctttc ccgtttgcaa gtctacccgt gcagaatgta 264780
accaatcacg caaaatatct tcacggatga tttcctgata atcccggagt acgtatttct 264840
cgtacatttc gtaaacagca gttgctgctt tagggacagg gatatcctca atctcgactc 264900
gttctcttgg gatacctttg ttctccagat aaccgatcag gtcttctagt gaatttcggt 264960
ggatataagt ctctgataga tcttcgaaac aaccatagta ctttttcttg agttccatga 265020
tgattcgatt accagggatt ttcttaggtt ctttcaaaga aagcccttca agaaacccct 265080
gcatcttagc gaacgtttcc cgagtatacc cagatagtcg gacaccatgc gtatagcgct 265140
cagccttgag tatcggtagc ataaaaaatt aacgagggga aagggagagc caaagccctc 265200
cctacctcga cctccatctt agagcagctt acctcccatg accgcaagat cgtagggatg 265260
gtcattcctc agtgtgtaga ggaaactgcc aggattgttc aacggctcat gttgcttctc 265320
aaacgacatc gcaccagcaa gagaacggga catcatcagt ttgttgtatt tttcaaactg 265380
acccgtaata cccggcttag gcagacgata atcgcgttca gcgatagagc gcaccatcat 265440
agcataaacc agaacctcac agtgaacggc attcaaagag aacttctcat tcaacagcga 265500
cacagtggct gccaaagcat caactgggtc tttgtagttc ttaagataag tcttgctagt 265560
aaaacctacc ttatctgagc tcagtttaga cccttcagta tcactaccag agtgcaggaa 265620
tgactgaata cgcttcatca cttcgtacat gtttacgtgc ttattaggca acgtcaggaa 265680
cggcagggca aagtcaaacc cggccatatc gatcacgata ttatcacgag cgtcaagttc 265740
ccaacgtaca cgtttgatat gttgcagcat ttcagtcgat agactagctc gacggttata 265800
cagcgacacc gtcaatacat cgccttcgtc tactccatca accgtccgta ccaaaccaat 265860
acgggtcagt tcagaagcac tcggtgctgg atatgcacta aggtcatcga tcatcagaat 265920
atcagccagg ttctgggctt cgttacgacc gatcatcaag cggaaacctt tacccgagag 265980
ttctttcttc agataaagag tttcagccgc agatccagtt cgcaggtact tagcttcgac 266040
gccaccaatc tgatactgtt ctacagccga ggttgcatca gtgtgttttg tcgacaatac 266100
cgcagaagtg attttgtcac ccatggatac agccgatacc tgaccaatga cagttccttt 266160
tggaatagag aaacttagtc gcccataaca ccgcgaacat acaccctgag gatccggatg 266220
cacacatccc aaaatagaac gcatcttaat ctttttaccg ataagatgtt tctcatcccc 266280
tttcagccag tccagttgac ctgtctgttc gttcagatag tacttgccac gaagagcttt 266340
caacgtaccc tgcattacag ggaagtcgat caagtgacca ttacaatcac cagtgtgtag 266400
gttctgtaca tactgagcaa tcaactgaga cttccggttg aaatactcgg ttacacgcag 266460
tagctctttg ttatacaaca gagctttggt acccgatcgg gattcgatca tgttttcata 266520
caaaccccaa ataccatcaa tgtaaccagt ggtacacggc tcactgaaaa tatcagagtt 266580
aatgtctgtc gggaaaccac gtggtccgta tgcctgaagc aattgctcca ttttctgcgt 266640
acccgagcgc aggccctcaa tgatgctgtt accacggaac tgtgtttcgt cgttgaatgc 266700
ttctttgatc atcccgtaag aaatgttttc aatcccgtac gtagtaggtt gtacatcttg 266760
gttagccttt ctaactgccg ggtgattgta cacttccata atgtcaaaga tcgacagggt 266820
tgcaatgtaa gcactcagtc gagtcgtggt ttcattataa agccaattct ttccttcaat 266880
agccagttta gccaaaacct ctggatcgat ctgttcacca ctccatgcat gaataccccca 266940
aataactttg ttcaggtatt tcacaagaga tttagaggta acccgagtag atgccagatg 267000
gtaatctttc agaaccgggg catcagggaa agctttcagt ggataccaga gcagaaccga 267060
cagcttggtg atccgatctt ttgcatagag tttctctccg tcatcaaaga tgatctcatg 267120
ccattcactt ggaatcgccc agagttcatc gtaactcata ttgagaagat cacgtgcttt 267180
atactgattc attatttacc tcttggcgtg cagcccggtt aaacaccggg cgcgtacttg 267240
aactgcaatc cacggcattc caacaagtgc gacagaagtc caactggtcg ggagttaccg 267300
aatgggattt tggaacgatc aactgctttc tcaatgttgg acggtttatc cgcagtgagg 267360
atagagttga tcacagcaat gtgtgcttcg gggttattgg tttgatccaa cagttctacc 267420
gtgggtagtg caccgaccgt acagttgtaa gatcgagtct cagattcacc aaacgaacga 267480
atagcgcttt ctcgaccagg tgtactggac cgatcggagt tattcagttt cgatggtaga 267540
ccaaactgtt gagtcttcac cgatgctacg gccgaccagt cttcaccgat cttttcgagc 267600
agcatcatgt atagcgggcc aagcaacatt gggtcttttg tcgttacttc tttacctgtt 267660
tgatctcgat atgtcaccgg tgcatatgtt ggacagaagc gagaattaag gatttggtta 267720
cttgctgtcg gcaaatgtac ggggtcatca accggggaat acaagtacgc aaaaccatct 267780
ctcaatacat gcgatacatg ttgaatcgga ttcgggtgat ccttaaccat tccatgcatt 267840
gtcggagtaa cgattgcata gaaatcaagc agctcattaa aggcatactt gataaagtca 267900
ggattgtttc tgatatggtt tacaacgtcg tcaagttcat aggaaccatg acgctctagc 267960
ccacattcaa ctcggagacg ttgagccaga tcgcgagatg ctgcaccgaa accatgttca 268020
tagatacgac catagttaga acgacgcata gtcgagccgc caaagataac aacatctgca 268080
acgttaccat tcacgtcacg aggcatatct gctcgcttca tgatcttaca aacgacacct 268140
ttgccgccat ggaaatcagt ggctttatat gcaccgcccg gttctttaat cgattcatag 268200
gtgatttcaa cacgccattc atcaagttga tccagtcgat acatacgggt cagcttacgt 268260
tgaccttcgg cttgaggcag atagatcatc gcttctacta caagttgacg aaactcctcg 268320
gtcatatgga ggcgatcttt acggcgggca gacagacctt tatatacctt gatgatctca 268380
cggtaatacg acgccagtgc gtcatagtac ttccgcagtt gtccatccat accactcgga 268440
gtataagatg gattttgacg atcatcccaa tacactttga tgtctttaat gattgcgccc 268500
ggatcaccaa ttacggcacg gtcgaacgta cgatcgagag tgcgcaatgc acgtggagtc 268560
atttcagctg gcgagagatc gtcatcaagg tctcgaacag cgaagataac accatcatca 268620
cgaatacgtt caccgatatc agggaagagc ttgatgtttt tatcgtcacc gtacatattg 268680
aggaagaatg ctttcttacc agctccgcca gtagcggttg tataagtacg aggagccatc 268740
ttctcccgaa ggaactcatc gcagaatacg aaaccatcct caatagtacc aggcatagaa 268800
ccgaacatca cggtggcgtt aacgcccatg cccagaagac cattttcttt tacagttgtg 268860
gattgtgcaa taaccgtatc tttggcaaac atctcgccaa cggcaaggtt attccataca 268920
tctttctgct tctcaagttt gaatccaaag tcctggtgaa agcttaggta ctctggtaca 268980
tggataacac cgattcgttt aaactcgtcg taatactcct catacacgat cgtagttacg 269040
gggttatgtc gaatagatcc acgacccaca ccagtgggat acttacggat aatattcaga 269100
acaacgcaat ccgttgggaa acgaatatcg aaggtatgtt cagcataacg catttcgata 269160
cccgccatta cccgacgtgg ctcgttccct tccactactg gcgattgtcc aatatgtgac 269220
agcaacatgg caccgcgtgc cgcggaggtt gttccgtaat atggatcaat tgccgcgtga 269280
ccgagcaaac gcaggttaat ttcacggatg gcatttggta gactttgcat ctataactcc 269340
tgttgatcgt tggtgcagaa tgattatata gatgtgaaaa ttattttttt gtaggattcc 269400
tctatggcat ttacaattat ggaacaaacc ggtgacggtg gagcatcaat gttttatgat 269460
ccagctttcc gtttaattgt cgaaacacat atcaacattc tccgtaatat caactcggtt 269520
agagtagaga ttccgaatga gttgtactgg caatacgaag gaaactttta tgggtattta 269580
acagagatcg gtattgagcc tgaactccat tggatttatt tgcgtgttaa tggcatggaa 269640
aatccaaacc agtttgcagc agatgtccgt aaccctttag acaaagtgta caacaatatc 269700
ttgatcaagc catctaacaa cgagatcggt gcattacaac agttctacac tagtcgaaaa 269760
ttttaaagca atagcagggg accctaaggc cccctgcttt atgccatctt acaccaatcc 269820
aagaccattg gtttgacgca tgccagccac agcctgcatg tacgggttag ccggttgacc 269880
attacccatc atcatcatgc cctgttgttg gccacccatc cacgcgggaa tgggtgcgtt 269940
cgcttggata ccctggggct gcatgttacc catttgcata ggttgcatca tcccacccat 270000
gccattcatc tgcatcatgc cattgcctgg catcatcatg ccgttattca tcggcatcat 270060
cattcccatt tgctgctgca tcatctgcgg ttggggattc tgtgcggcca tgaattcgct 270120
catggagaca gtatcttttt ctacaggttt gctaacaact gcggcgggac gagtcagctg 270180
aggagtactg gcttgtggag cagtaacgct cggtgcttgt tgctgggttt gtacagcttc 270240
ggcagtttcc ggagtatcct catcacgacc accgaggttg ccattcagcg gagggataag 270300
gttatagatc ttcgggaact cgtcgatcag atccagatca aacacaggaa taagattgac 270360
ggggatttgc agtgggatcg cgtaccggtt aatcagctga ttgagcatca cgattacttt 270420
gtgatacgct gtcagaagac tggtgtaata aggtgcaaca cggctggtag taccaaaggc 270480
atactcttcc ggattgtcac caaacggaac gatcagtttg aacagcgcag tgagaacctt 270540
acgttgtttc ttcgccatct tgataccaag aacatcatca gtttcagcct gaagatcttc 270600
caggatcggg aagcgaatga tcgccatacg gtttactttc ttaccatcga aagtaccgcc 270660
attcttcaag taaactgcaa ccagtcggtt cttcttagta gcagcaggca tcagtttctc 270720
gaacagaccg acagttgctt tatccgcatc tgccagtttc ttcaggaagt cagttgcatc 270780
cggcggcagg tccttgtggg acgacttgtc cgctgcgatg gtcagaagtt gttcggccat 270840
tttgtggacg acgaaactaa tgtgtgcttt tgctgcgcgt tgcagatact gaatcaccgg 270900
ggaagtaccc cggcgactca atgcttcact cagcgggtgg aacggctgga agtcttcacc 270960
gaatcccttg cgaaggaact tatcggttgg gattacaaga cgtttaccgt ctacggtcga 271020
aggagaagca gtacctaccg gattacggag gctgatataa ccttcttcat cgaactcgca 271080
ggcgaacgag gggagtacag acttatacga gtccaagatc aacgacattg cttgctcctt 271140
ggttaatagc gttaggcatc atgatgggtg cagctaccgg atgttggtaa ccgacagact 271200
gaagagcctg atgttgagtc ggattgggaa ttacttcttg taccagccac agcatatcac 271260
cagacaggtt agtcgggtgt tgctcgttac gggtaatcat cggggagaac agactatccg 271320
taaaggtcgg tgcaatgaaa cgagtcagtg actgaccacc gatggcaata tcgatgatcg 271380
agtcaccagc caagtccgaa tgcatcgaga tacggaacgg cagctggtta ccacgggtga 271440
tgttgttcag gatatcgata gccaggcggc gttcgaattc cagaatgtat tgacgcatgt 271500
ccaggttatc aatgatagcc ttagagttct gcggatggaa ctcgaacgaa tagttattcg 271560
gaccagtgcc attagttaca gcaaacgagc aagtgcggag gaaggtatcc atcatgatcg 271620
acggaatggt ctgtgccaac agacttgcac caatggaggt atagtctgca ccgctccaaa 271680
cttcggagtc ttctgcctga gaaatacgac ggattgaacg gccatcgttc atggagaact 271740
gagtaacctg ttgggtgccg cattcaggga agagccgctt gagatcacgg aaagtgatat 271800
agccattctc catatacccg gcatgatctt taagaacagc caagaaggtg ttagtatgga 271860
tctgctggtt cctgcactgg gcagcagctt caccaaacat tacatcttta tcaggagccc 271920
cgaacagatc atctccttgg ttctccattg cattctcttt gacagcatgt tggtatgcgc 271980
caagagtatt cgacagataa cgagttggag aggtatctcg acgttggcta tacttgtatg 272040
ctcctccttc accaaccatc gtgcgatggt cgatggaccg attgatcatt ccgtcaaaca 272100
aaccagagct ttgcagtttc tgtgccacat gcgctgtttg accaatacta aagatatctt 272160
caggacggat caggtgagca gttgcacgag agaacattcc attcattcca cccatcatgt 272220
caacaggaga aacgatctgg ttggaaccta cgatcgacgc aacgtgttgg ggaccatgaa 272280
tggtttgttg aatagcttga gcaatgatag tttcggagtt gaagtagata cgcatgtcat 272340
ccggcagata attctgagat gcgtcagcgt ggtcactata gccaaagaag atacgttgag 272400
tcagcgttcc cgcaatgaat ggatgttgct cattcacttt catcaagaag cggaaccggc 272460
gagaacgcca gccatgtgca ataccgacac taccttctac cgatgcttgg ggagtgataa 272520
ccgaagaagc tacttcttgt acagcactta cccgaaggtt catgccacca tttgtagctt 272580
gttccagttg acgagctact tcttggttag cattaatcga gaaaggtcga atgtgctgtt 272640
cttgataggt gccggtttcc accagaacaa agttctgtac ggacagcttc gagttgacag 272700
ctgcaccagc ggaaatgccc atgttgattc cgtgcatgta atttacctct tgaattttac 272760
tggttgatct gagcgaggtg tagaaccact tcggtgatcg tgtgcttgat atttggaggt 272820
ggaatcagaa tgttgttctg agcaatctga ccagaaagct tgaacagctc aggtggacca 272880
tgatagatcc aagtagagga gcggatggac tggttacagt tattcactgc aatacccgcc 272940
atgttatctg gcttaggaat ctctcccgat tgggggacct tagcgagttt catatgcgga 273000
tagagttcat cgagctgtgc cttatacttc tgagcaattc tcgaaccact tcgggtatta 273060
ctaagctgat tagtcgatcc atgttcaccg tgataaacag gttcgacttg taggaacaca 273120
gctacatcaa ggtaacccca atgccacagt agagcctggg tagttgccaa cagtgtattg 273180
actggcagtt tggagatatg atagaaagca cgcgccggga aagcttttgc cattacccat 273240
tgtgccagta gtacttggtg aggacggatc tcaaagttcg cgacctgact cacgcaacta 273300
atacattttc tcagtttctc catgtcgata gtaggatcta ccgtttgtgc cagtagctca 273360
taatccatcg catcgatgtt gtatgcctca atgtcacctg ggctaactcg acctttcgtc 273420
ttgtgtgcct caataaacga agttttatct tcgtcgtcac caccgccgcc ttctggacgc 273480
ttttcattaa cgcgatcagt tggactacgc tcggcaggat tgagattgct acgtacgtaa 273540
cggaacgtgt tagctacgat agagtgggac attggatcgt tcagaggaac gattgtcagt 273600
cggcgaacca gaaccttcga acgaagatgt actggaattt caactgaact cataccacgc 273660
caaaggctac ccaaagtagt cggttcatct tcaacgcaga atttgacgta cccttccagt 273720
ttgtcaaatg cagcatctac atcttcaccc acttcatctt tttcaagtag cggccagtta 273780
gcaatttcac aacggctaat caaaccaaca acttcgtttt ctttgtggag ttcttgatcc 273840
gtaccagaat caatgtattc tccccaaatc ggaaccatcg gtcgaagacc aagtgccaca 273900
gtagcgaggt tgatgtagtc atgttgaaga taagtctgct cacgcttggt gtagcgcgat 273960
tcatcagtga tcgttttctg gatctctggt ggaatatgca gattaccaat agtcaacagc 274020
caacgacgga gtttgttcat tggcagagct gagtacagtt catggatgta atggatcagc 274080
gtactggaga tgtgcgctgg ttcgaagtcc atcttgaaca gatcgttgat tttgacatag 274140
ctgttccaga tacgatcttg atcagcctca tcgcagcttt ctaggtaatc attaaattcc 274200
ttgaaaacac gagttggatc attgagtttt actttgctat aagcccttgt actccacttg 274260
atttcgtttc ctttatggct agtggttact tccacaaagc cgttgccttg taccccagta 274320
acgtcgatgc gcatttatac ctctttagtt ctggtgatgc acagttgtaa tatagatctg 274380
agatattttt taatgtcagg aaatagaggg catacagcat ctctcggtgt ttaccaaaga 274440
gatgctgtag atttatttag aagtcaggaa tggaatcgtc aaagccattg tcctggaaac 274500
caccggagga cggacgattg taaccttgag gagcaccacc gctattacca ccacggttgc 274560
cgccattata gccaccttga cgttgaccac cgccgccacc gttaccaaag ttagctgggt 274620
tggctacgtt cttagcgttc tggtcaaaac tgcttaccat catctggtaa atgattgcag 274680
tggccggttc caggaaaccg gtagcgtaag cttcggacat ctctttcgga gagatgggag 274740
aaccatcacc attcaggatg gtgtgatatt tcgacggacc gaagaagaac cggatacgcg 274800
ggcgctgttg ctgagaagag ataagagcaa tgtaaatacg accagagttc tgttcgcggc 274860
cgattaccag tgtggtgatc ggaatgatct tatcgatctt tttaccgcca acaaagtcat 274920
cttggtgaac aaacttacgt tcttgaggaa catctttacc atcgacaaga tcccgtgcat 274980
acttcattgc agctgcaaaa gtagccaggt cagttttgaa ttcaatctta ccgttattca 275040
gatcaccttg aacgttagta cgtacggtca ggcgaggtac gttaccaaag acaccgaaac 275100
gcaggttagg acgtttctga gaaccttcta ccggatcagc atgtagccaa gtggacatta 275160
cagagaacgg agagagggca gggccttggg attgttgaga catgatgtgt tagctccaat 275220
tggattaatt ttttacactt cgcgaaagtg tttctacgta ctatatcgat gaagagtatt 275280
ctttctaatc agcgtaatag cgcgtaacat tctttaagtt ctttactgcc atgagttgta 275340
atgtcatgat agattttgtc ttgtgtagtt acgggcgacc aacgtctcga agcagctaac 275400
tgtttcagtt gggccttaat agcttttggt tgtgcatcga aaacaacgct atcgccaaac 275460
acttgtagag tgaatttagt gaatgggatg ggcgtatcct cttttatgcc gttaagcttg 275520
gtgtaccaca agttgtacgg ttttattttc ccagtgtggg attccaacaa aagaagacga 275580
tcgaaatatt gtttccacaa tagctcatgt ggaaaatggg taaccaaagc gatcgtacct 275640
tgggtcctta ctggagcttt atcgatctcc atcacttcta ttcctgcatc tttcatttga 275700
tgcagaagtt caattgccgc gtaacgttcg tatacttcat atgccatttg ttttggcgtt 275760
ttggcttctt tataaatagc cttggggtat tcccacttga ccgcgtcttt agatgcgata 275820
taccaacgca ccttgacttt cgatccatgt tgccccagtg caaccggaat tgtctgtatt 275880
tcctgcatta ggattgtaac agcatcagct ggattaatgc catggacttt atccgtagct 275940
acagctgaat taagattacg ggccaatgtt cgaagattga cccatatctc ttttaccgat 276000
ttaacgtcaa tcggatgctt aggttgattc gggtgaattc ctaagaatcc ctcaaaggca 276060
agagaagtac cgatactaac tggaagctgt ccgacatctc tttcaatgag ttccatattt 276120
aattcctaac gaactgtgcc aacctttcaa gacaacggac ttgtatggtc tgatcatcag 276180
tgacttttga aatctcttct ttaagaagat cactaattgt ctctggtgta atagcgataa 276240
acttagacat gtcaaattct tttagacttg tcgctacact attctttttc ttagtagctt 276300
tttccaccaa gacagaccat tcgtagttag gatactcaac tcgaaatgtt tcgatatcgc 276360
cgttagctac gtccattggg tcacaacgca gtcgtatagc agaatacttg ggtagttctg 276420
ctaaggtttc ttttacttta ttaagaagtt gtttagtatc ataaccgtga acttctaaag 276480
taacatactt cttagcattc ttgttcttta taaatgtcgc cgtgaaatta ccatcctcac 276540
gaacgataaa atgaaacaac cctttatcga tctcatcgcc atgacagatt cgatcgaaag 276600
aaccagctgc gtaaattcta tcattaatag tcatgttgtg gacatgacca attaagatct 276660
gatgttttac taaagctaag tattcttctt catcgtgagt tggttcttct acaatggaag 276720
gtagctgata actaaatgca ccatgcataa tagcaaagtc aaccttctct atgcccagtg 276780
aagccatctg ttcttttacc tgcgataaag taacagctgt tgatggatgc catttatctg 276840
ggacataaag aaaatgtgca tcgagcttct caatatactc aattgacagt gtcttagagt 276900
aatggagatc gactggaata tttacgttta ctttttgctc tacaaagaac tgggtttgtt 276960
ccctatcatg gctaggtgta ccttcaacta ttctgagcat cacgttattt gcagcgcagc 277020
gcatcatgaa cgttgttgcc caacggttta tctgatgtac agattcatca ccgtagttaa 277080
gctgtcggtc gaataggtca ccagtaataa tgaccatatc gagttccttt aacatcttat 277140
ctgtaataac tttatctaag tttaacagaa tatgagaggt aggagttgtc cgatgaccta 277200
ggtgaatatc acctaggctt atatatcgaa atgtaccggg gaactttgtt ttatcagtct 277260
tcataatcgt cgtcaaatga gcttgtatca gcctgttgac gtacactacc attagaccct 277320
ttaacgggaa cacccccggc gagggtgtac aatggattcc cactttcatc ttcgaaagtg 277380
cggttgtaca tcgccaggat gttagctaaa ggaatgagaa cacttttgtc cacggttgta 277440
gtaatagata cactacttaa gaattccgtg atatacggtt caagatcttg cagagaccgt 277500
tcacgttcaa tagcaatgta atctactaca tgtgaaatag atgcagttgt agcatcggct 277560
gcccatgagg tagctggcct gggatacaaa gctggtacag taaaaagaat cttcggctct 277620
gcttcattag aagctacacg cagaggattt gtcaattcta gtacgtattt ccgataacgg 277680
gttaagttat cagtatccca tggtcttact agtaggggta agacctcttt cacaaacctg 277740
tcttccagga taatgggcaa ctgcatctcg tcgtttgcga tgattgtatt cagacaatca 277800
tcgattccac gcgttacatg acgtgcgcgg atttcttcag ctgtatcagt ttgatactgg 277860
ctcattcaat tctccttgta ctttttcaag tgcatcttta gaagcaagga tattaatgac 277920
gattgcattc tgaccttcaa acagttcatc atgttgcttc aggtattgaa cgaatggttc 277980
ggttccatgg ttttggattt gatcgggggt attaatagat gcgaaatcaa taccaccatc 278040
ttctcgtttg gttgcaatta cactattctc gtgtgccgtt acgttaacac catcaacaac 278100
ttcaatagta aaaccataac gacgtgtgga tacttcttga gtcatatgct caagactttc 278160
acgaaggcta ttattcaacc caccaaagaa actagagaga atcttaatga cacggagttc 278220
atgtagatct tccgattggg tcagtgcttc caaaatttgt ttaatagcct tttcagaaac 278280
atgaagcctt tcgctcagcc gttctaccgt gcgattaaga tgttccactc gttgaatgag 278340
tgcatctgtt tcattaaggt caggagcaga tttaacatct gattccccat cgaccagtac 278400
ctgtgcttct tccatttgag aatcaagatt cgacatatat ttacccgttg ttgatattag 278460
caatattcac aatgtgtgaa ttttggaatt gaaccagttt acccactgta tactctttag 278520
taccatcagt gactatacct gtaaactgaa tggagaatgc atccggatta tctggactcg 278580
ctggaacaat actaaccaaa gcctgagctg attcaccaaa cacggttcgt agtttatttg 278640
ttagtacatc acgaagctga atttccagat taaggatatc gttagcatat tccttcagta 278700
gatattgaag cgaagtattt tgtgtcctat gtaacgttga catggaccta tttgttgtaa 278760
ggaaagtaga gatgatgtag tctgctttgg attccattga ggtaatccaa ccatcagtac 278820
ctagtgttgg gagagagact gtcatggcaa ctccaaaaaa aataatagga aagtatgcgg 278880
agtcctaaga ctccgctaac tacatcattg gactcaatcg gactccacga aaaggaagtc 278940
taagaaagga tgtccgaatg gcaactcaat cctttttcgg gtatagccgc caccgatagc 279000
gttgattgct tcccaaatac gaccatcatg aatttccacg aaatgtactt tatcattagg 279060
gtcattggaa atctgtaatt gaatcgtatc tgggaatcca gggggaccca tgacaattat 279120
ttcatttttg tcaattactt cgacgccatc acgttcaata caacaatacc atttattacc 279180
gtcgcgatgt atcttaacca tcttatcggg gttattggca cagtaagtta ctacattcat 279240
acgccctttt tgagcttgta ttttttgagc gtaactatcg agaatagggc gacgtgcttt 279300
attaggatcg gccttaaacg acaccggttc gatcatacta aattccttat atcctcgtta 279360
taaaggagtc ccctaaggga ctccgtttat gttgttaacc caacaagttc cctacaggac 279420
tggttggatc catttcgttt tcatctagag caacattcac aagattccat gaacggagaa 279480
tatcaacctt ctcgtagaga gaaagctctt tatcaccttc tgggatttct tcgtagaact 279540
gcttgactac ggtgtggtca tcattgacaa ccagtacttc gtccatcaca cgacgataat 279600
cgtaatggcg ttcgccaaca cgatcaccat gatggtttac atacgaatca gcataacctt 279660
caaccatgtt gttcagatac ataccacgca ggcgttcttg tgccatgatg tatcgttgca 279720
tgatcggatt tgcggtttgc aattgctcta acgtgtacag tccatgaatg ttgttagaca 279780
tccaactgtt atccgtttta gcaacaatgt tccgcatcgc ctgtaccgct gtgctggtac 279840
tgatcatctg gtaaagattt tgtgcttgat cgaagaacga agttgccatc gaactcaggt 279900
tactacgaag tgtctgagaa cgttcaccca accagttcgt ggtattttga tccagatggc 279960
caccagcgac gatgtccatc agatcgacgc cgtatgcctg ttgtaacatg gattactcct 280020
cttggatcgt taagctgctt tcgccaacca ttcttccaag gacggaagat agtcctcgtg 280080
agcatagttg atgatggtct ctactaccgg accttgtagt tccaagttac ccgagatctc 280140
gtgcggatca tcaggactca gtacccaagt atgcggagcg attcgttcag ttgcatcagc 280200
cagatagtta tcgggcatca acgtcaaatt caactgatcg ccgtcgaaat cggccgttat 280260
gttcagataa gttcgtaaag cttatcccgt ctctcaatag tagacagctg catgtcgcca 280320
tgcagaccag actatatcat caccttcacc ctaagtggtc aggtgcctcc catttcgagc 280380
cacttggccc tactctactc ggttcacttt cgtgcctttc gatagtcgtt gaacgttcct 280440
tacatttctg taaggcttcg ctgctgattg tctcagagag agttcccagc aattagagag 280500
gttattcgac atggatttct ccatgaagga actatgtagt taaactttac ccaagctttc 280560
tttacaacac aactgcttta tttaaagaca gttctattat ttccggattg ggtataagtt 280620
aaccctctta taaaagagca actcttaact acttttattc ggagctttaa gacagaggac 280680
cgacatgctg attgagttat cgcgaatgtc attcttgata acggtgatga agaactgttg 280740
agtcgaacca cgttgcagag tcgggttgcg gtggaataca caaggaagac ccttatactt 280800
cgattccgcg atgatctctt tgaacagttg atcgatgact tcgttgtact tcagaacgtt 280860
ctcgtaaatg aacgagttcg cttggcgagt cgtcatacgg aatttgcgtt tgagcttgtt 280920
gatcagatga tacttcaaca gctgacaacc gacaccccac ggaatgtgaa gttcatcgta 280980
atcatgcgga tcactgatag aagtaattac tgcacgtgca gtcaggttaa gacgaccacc 281040
tagtacatgt cgacgaacca aaccgggttt ctgtgcaatt cgttgtttgt cgtagttctc 281100
gtggaagata gctagaagct tcagtgcacg agctacacgg ttttgtacag tgattggttt 281160
cagcggaatt gccgaactac cgatactact aatagtcagt accgcatcga ttgctgcgcc 281220
gatcggctta tcgatgtaaa cacccgaggt cgtagactct acaacgaagc agagtttagt 281280
tgggatcgga atgttcttcg ggaacagatg ttctttattc tggttaacga atgcagccat 281340
ctcacctttg ttggtattga tgatactgct atcgagcaag aactggaaga tcgtatcgaa 281400
gttctgaacg aagttgttca gtccacgcgg gaactggcga gccagcaact tgtcaagttt 281460
ccgttttgtt tccttcgaac tgatcgtatc gtaatcgtac tgatactggg tgttggtcag 281520
atactccagg aagtcgaatt ctttcatcga catataacct gaaagcataa tccacaactc 281580
gggactcacc agacgatcca cccctccgg tgcccgaatc cacatcgatg ggacgatggg 281640
tcggttgctc gtgcttacta ctggtgtacc gcagttatcg cagattaccc caagcttgta 281700
tgcttctgtg atatgctcac agtcacacga agctgagttc tcgatcgcat ctgcatcctg 281760
ataatgggag aacagataac gttggaattc ctccttttgt tcagcattgc tggtattaaa 281820

-continued gtcattagcg aatactactt tacctctttg gttagcgagc atctcgtcat gattgacaac 281880
ctgagcatat agacccatac ctacttccta ttatgtctcg acaaaaaaag gagatagaag 281940
cggctcccga aggagccgcc ttatctacta tcgatggacc accaacggag cctggcacga 282000
tcctagcatc gtctacaaag cttaacctcc gctcttctct gtagcacttt gacactagga 282060
ccttttacca tccatcgttg tttgatcaca cgttacccaa gagtaactcc tttcggttaa 282120
gtgatcactc acggcccgtg tagcgagagg tcgacctaga ctttacgtcc actagtcgat 282180
tacttcgcgg aacctactcc taaccgttat caccgaagtg aaccagggtc gcagtatttg 282240
aatcgggatg ccagccttct gacaccccta tcaaccgggg gagttgtttc ttagtacaga 282300
gtaccaaccg aacctaccat gttcatctgg tagccgccac caacgcccat gccgttgaca 282360
acctgtgcgg tagaaccgac agcgaagtct tggatcatgg tgttgccaac gaagcgctga 282420
gcaccgaaga cctgtgcaac gttgtccatt gctacagtca gaccagcagc agcaatcgcc 282480
ttatccagac cctcgatgaa cttcgggttg aagataccac gatgtgcacg agtggtgtag 282540
gttacagcac ccaggaacgc acggtcgtag ttcttggatt gcttgttacg cagttccgga 282600
tggatgttcg ggttgcattg agtaccgtac caggacatcc actcttgttg gttgccctca 282660
gcagcgttca gtgcacccag tgcatccagg tcacgacggt cacgtttctc gtcgccatcc 282720
cagtagtagc ccttgttcac ttcagtgcca gtcgatgcaa tgatcggctg agtgttgaag 282780
tcgaagaagc gctcgaagcc accaccaacc aggttctgta cagcgcgaat gatcgcggca 282840
gtagctttct gttggttcgg gccacccatg gcatccagga agattacgtc cagtgctgcg 282900
ttgtcgccca tgcgatccag atcgatcagg aaggacgggt tcggacgaac catgctcagc 282960
atcagatcag cgaagttctg atcggtgaag gtatcggact tggtatcgat cttcttaccc 283020
aggttggaca gccaacccag agcaccgatg tcacccaggt ctttaacttt accaacttga 283080
ggcaggaact tacgagccca agcctggcca gcggttacac ggaaggcgtt cgacagagcg 283140
aagaggtaca gttccagagt gtttgccttg atccagttgg cctgacgaat gtcggttacc 283200
aggatcgccg gggagaacgg cggcagcggt tgggtctgtt gaccgaacat ctgggcttgc 283260
ggagtggggg tgtactccag ggttacttgt accgacacct ggttcagcat ggtgtctgct 283320
tcgtagaact cgttctcttg ctgaccttgt ttcttggtac ggttcaggct gatcacgata 283380
tcggacttga tcgggttacc gacgctgtcc attaccggac gaccggagaa gtccatcttg 283440
gcagccaggg tttcatcttg gccgcgcagc attgcgatct ggaacggagt ctcgccagct 283500
ttcttagcca gaacgtcgtc acacaggttg acggaacgga tcagaatgtc tttcagcagg 283560
acttcgtctt tcaaatcgaa ttcagccggg atcggcagcg ggccagccgg gtgtacttca 283620
gccttcggac gaccggtggt ctgacgaacg aattcgcaga tgcggttcca gtactgaacg 283680
gtgaatacgt cttgtacttc gacgtctaca tcgaagcgat cgtggctcat gccgttctga 283740
atggtaacct gacgcggagg cagggtgatt gccgggttcg gcatgatcag cggacgaact 283800
acgatgatac cgttaccacc agcagcgtgc ttgacgatca gcagcgcgga gtagccaaca 283860
cggttggcat cacggtcgaa acgcagaatc tggaaatcgt tttccaggtc ttgatggtcg 283920
atggcatctt tgccaacgcg ggtcattact tgcagcgctt cgctcgcacg ggcgtcgccg 283980
ccatcagtac gaccggaacg tttgaacatg ttcggcaggc cggaaatacc gccttgcaga 284040
gcttgaggtg cagcttgttg catacgagga gcttcctgtt gtgcgcgcgg agcagcttga 284100
gccggagcgt tgttggcttg agcttgagtg ttttgagttt cggtatcacg aatcatgatt 284160
tgttcctatg tttgtaacgt ttcttgatca agaatgagat ccaacagtgt attggattca 284220
aaactgttat atagatctca gattttttt aatgcaatat agaccggagg acccgctata 284280
aaagcaaggt catttgagga cattcagtct tcacatactg tattacatat ttgtttcctt 284340
aagattcaaa cttcagtatg cagtgatctg gggcatagct caaatagcag gtcaggacct 284400
cacggtcatt tcctgtatta aataactagc cccagtattt cttttcttat ttctcgtcag 284460
acaagaggtc ttcaagatca tccaagtggt ctttcaactt actgtagatt tccttcgcac 284520
tcttaatgtt cacaacttta ctgagttgat cagcgtattg cgcaatcgcc gaagaatact 284580
ctttcatgtg agtgagcatc gtgtcatcaa aacgattgtc atcttcaata aaggaagaat 284640
gcaaattgcg aagaccttga atggccgtca ctggatcgat ggtgttgttt ttaacacaat 284700
cccgaacatg cgccttgacg atagagaata cccagtctcg ttccttctta tctttgatag 284760
aagagaaaac aatagtcagc ggagaacgga aatactcacc ccggcgaata ctatctgccg 284820
aaagtgccgc aatcttcatc gattttacat tgcctccttc cttattaatt ttatttgcgg 284880
tttcactaat acgctgagcc tcttcaacaa gaagttgtgc aatagaagga ccagaaaatt 284940
cacgatggat agcagcacgc gcttcttcct ctggggaaag tttaccactc gtgaaagcag 285000
tagagatccg atcaagtgta tgcgtattct cttctacatg tttgtcatta tcgttattat 285060
cactctctgc atagtagaga tcagtgagac ctgggttttg caggtatgac gaacttttca 285120
ctgtttcatg ttcgaaccca gtattgatcc gattaccacc acggaaaata gaaggcacgg 285180
aacgaaggcg agtttcagca atgaaatcat caccgagttg gttcgttttc tgggagggcg 285240
cgtaactaat cggacctttc gaagtatact gaccaacgat gtacgggtta tcgtgtttga 285300
tttccttttt ctccattcga ccagtagaga tcaaccaatc ttcaaacagc atcccattca 285360
tctggccggc ttcacagcaa cgtttataga agttaatata tttcccataa acgatagctc 285420
gttcatcgag agctttgcta taattggaat taaggaagtt cagtacttcc ccaacagttg 285480
ggatcttgtc cgaaggcagg tttcgaatat ccagatcaat agctacttta actgccagtt 285540
ctttaacgaa cttgccgttg tacccaatga aatccatgcg atgttctgta ggtataacgc 285600
tggcgatgaa gtcagtaatg gcttcggcaa gattaatgtc aatattcttg tctttggatt 285660
gcatctcact attctccact ttgtcaataa gttcgtcgta tttaccggac tgagccaaca 285720
tgataccttc gcgttgtctc tcgtaatacc agtcttcaaa aagaatacca gtattacttt 285780
tctgatatgt ttctttaaat atactgaaat tttcagacat cgctttaacg cgatcagaaa 285840
cagtattaag gaactgaata cggatgtgat tattaataac gtccgtgggt gcatgaaaat 285900
ccggaagggt tttcaaaatc tcatcgaaca tggctttaac aaatttcggg ttatgtatca 285960
cgaaaagatc cgtgttaatt cgacccatcg tttcctcgaa gaaacgtctg agcgaattat 286020
tgacaacagc aagtttataa gaagacgtgc tgttcaatgc tttatttatc attacaattt 286080
ccttttcttt gattagggtg aatatatcaa aactatgata tagatttgaa ataatttcta 286140
atggacgaaa accatgtaca tgctattccg ggacgcccca gcgcggcgct tagggcaagc 286200
agttgaccca aagatcgtct atctccgtag gacgtatcgg gaactgatca atgatgtaaa 286260
aacgtattac cgtcgagccc ccaaagcggt tggctcggct aatattttcg ccaacatgat 286320
tcaacatttt atcatcgact ggaagattga tgatgccgct tgggcaaaga aggttgaaga 286380
tcaggctaaa ggtttatcac gcgtatttgg tcttacctca gctattaata gagggaagat 286440
tcatgagaag ggggattacac taggtcccaa ctgtgaagaa gtcgctatag ccagttatga 286500
gaagttcgag aaggagggtc tcggaaagcg ctggagagat ctgactccag ttaaatatct 286560

-continued

```
ttatcatacc cggacagacg tgaatcttcc aatgatgaat aatactacag ctggtaaagg 286620
ttacggtgtt atcacagtta acattccaat gctgttagtt caatatcgct attggttacg 286680
ttggcaacaa caacgtggtg tagaacaact agagaatgcc tatcgcttcg ttgggagtat 286740
cgtcctcccc aacatggtag agagctattt agatgttgct tacttcaata ggttatctcg 286800
acaagcacag ggtatcaaat gtttgaattt ccctgtatct catcctttct atctaaccga 286860
tatgactcca cgggttgata agctcgtaga gaatgtaaac tttgagaact ctattaaagg 286920
catagagctg gaaggtctag cttggattac tcctgctatt gttaagacta atcttttcga 286980
agttatggag attcctcggg aacctatcac gtatcaaaac gaatgggctt acactttagc 287040
acgtctaccg tacattaagt atctagtaac catgcttaag aagaacccag gttacgaccg 287100
ttcccagatg aacgaagtat taatcgatct gattgacgct accaacgacc aagtcttcaa 287160
aaccgctggt aataccgaaa tggttaaagc gctacgtcgt gatgtagcta tcctaattga 287220
agaaatgaaa aaaacataat aaacagcccc tacccgaagg taggggcttt atgtcgttat 287280
ttgaattgtt ccaagagttt atcgtagaac tcttgattct tcttcttagt tgcctcagcg 287340
cgaagaccga tcagttcttt cttcagtaca ttagccttga ggaactgata accagaatac 287400
caattgatat ctttagatgg aacgtcttca cactcagcat atacatccga caacaaacga 287460
atgtaacgct gattacgaat actgttcttt acagtttcgg cttttatgtt agggtactta 287520
gcgatcagct tatcccatac atctttcttt atcgaaatag agatgtgttg tgggtcgatc 287580
tgccgtctaa ctgatacagc tagtgcagcc ataccagtca caacgaagtc attagaagat 287640
aaattgtaat gactcttaac cctgagtagt ggaccatgaa cttttgggtt atggatcata 287700
ttaacctcga cataaagccc agcttaagct gggcgtttaa gttaaacctg ttcaccgtcc 287760
tgtacagaga cttcctcaac aggtttcagg ggtttactat cagcacgctc ttggaactta 287820
tccaggagac gtttctgata ctcagggata gcctcgccgg aaacagtttc aacgaaagaa 287880
ctcaaggtat ggttcttgag gatctcacgt ttaataccat cttgggtctg agtttgaatc 287940
tgactcagct tagccaaaat agatccaccc atcaaagctt tcaccatacc ggacttacag 288000
ttggtgatat gcttggaacg cttggcacct ttctttttct tacggcgggt gcgcatgcgg 288060
gattcgatcg aatcgatttc ggtcggctca gcttcaacag tttccatttt gctcaggtgt 288120
tgttccagaa ggtcagtaga catttcagat tcagtatcag tagattccaa catgatgttg 288180
ttatgtccta gttcacgaag tttattgtac atgtagagac ggctattcgt tttgggaatg 288240
tcgtccaata caggagagga aatgatttgg agttcgcccg gtttgaaacc cttggtgaaa 288300
acgtcgttta tactcaacca ttcaggagga gtaacgatac catcgaactt tggcatttca 288360
ttacattcgg tatcgtaggt gggtatcttt ttcataagta cctcatgtcg tgtaccaggt 288420
agttcaccgt ttttgctgat caggttattg tactgggtcc atagtctttg gctttgcgaa 288480
gttgtcgatc ttgtaccatg caatacccag ctacgacgaa ccagggtcat accagcccaa 288540
agagtttcta gttgatcctt agagagttct tcatgttctt tcatgaagtt agcgataaga 288600
tcatctaatt cttggagttc atccggtaga tatcctgcaa gtgtataacc cgagtaagaa 288660
tctgtaatca gtttgccttc cggagcgaat gcctgacgta gagcaacatc aaaatggcag 288720
tacatgttgt aatccaacag taatgcttgt tccatatagg ggtagtctaa gccaagtgta 288780
cagatctttg cgaaacggct agctccaggt tgagcaatct caccacatag attaccatcc 288840
agtacattgt aagtaccgaa aggaaaagat acaacttctt tattttgcgt tggattggaa 288900
ttatacatca tattttctca tctgtggatt tacgacataa aggagtcccg aaggactcct 288960
```

-continued ctggtttaaa gttttccgat gtaatcaata atgatcggtc ccttgaactc aataccacta 289020
cggactatgc ggtcgttaca tggttgcttg gctgtaacga taaccacatc tttattaaac 289080
gtgaatttac gcatacgttc atagatcatt ttcaattcag gatcgctcat tattcacctc 289140
ttaatagaaa tcggaaatca aacgagtgtt acctttatcg atcaggaaga tacccaaaga 289200
ttcaaagatc agatagaaga cacccatcgt gttggagatg atcgtacgaa catccgctac 289260
acgtgtgatc tcatctggga taccacggtt ttctacaaca gacattggaa catggaagtt 289320
ggtaatacca gtcttcttat tttccatagc ccagcgtttt agacgcatgg ccaagccttt 289380
atcttcgatg gattcaaccc attcgttaaa acgggttctg ttgtccaccg ttacagaaat 289440
ctttacgaaa ctataaggtg gttcttcaat ctcaccaaag gatggactgc atacttcttt 289500
ccagaaagta tgtttggcat aagtggcatt atcttcagat ttgtatgcat ctattttctt 289560
acacttacca gtggtaagat attcagcttt accagaacgt acagatgcga taatgtctct 289620
ttccagatct gctacttctt tcaacattgc tggtagatct aaaggtgttt cagctttaat 289680
ggatttaata atatcatcca tcattcgctt agcggtcttg ttaatcttcg gtggaacttt 289740
agaatctcga aggccgacac ctttaacttc catacgtgct ttagcaaaca taacaccctc 289800
ttgtgcatct tgagacgcgt aatagtgttt tgaacgtgtg gtcagggaaa gtaccgcgaa 289860
gtaatattcg ttcttcatag cgagcaggcg gagcttctct ttcgatacgc ccatgttagc 289920
cgattgaatc gctagaatgt gtgctacaac acacgacacc aagaatacca acgcaaacac 289980
tagacgcttg gcttcgtcag tgaaagtgat cttaccaaag aactcttcta cccaatactg 290040
catcgtgaac atggtcgagt ctgtatcgga aataacagct gcacgacgat aagcagttgg 290100
gaaagcatga atgctggaag gaacgttctt ggtcagcaat agtgcatcaa taagacgctt 290160
gtatttccac agcgtatcag agatgttctt acctgttgca tagatcttgt cgaatacttc 290220
aggagactct ttactcagct tgtcgtagtt acgaccttta accaagtcaa agcagatgaa 290280
gttagccaac agttggaggt caccatcgta agtgttgtaa acttctttgg taacctttttg 290340
ttcatcggta cctactttag caagctcagt caggaaaccg cgaatcaaag ttttgttatg 290400
tttgtaagta tgatacagat cacctacgta cataacagca gcacgttgta gtggtgtgaa 290460
gccagtaacc aacatccgaa tctgttcggt gtagtcacgg ttctgccaat agtgcgcagt 290520
cgaatacaga accatctcaa ccacttcttc cggagtcgga tagtgcatgt tgaaatgttc 290580
gatgcaatct ttcagcttct tcatgtcggt gttgttagca atcgacagaa gattagcctt 290640
ggtgatttcc ggactataat agtgacggtt accggtgatg aacttctcgt tgttagcgtt 290700
agcatacgag gttgctgtac ggcaggtcga tgtcaaactg gagtgagtcg acttgtaata 290760
cagaattgtt gcagctgata cggttgctcc actataggag ttattgttaa ttttgaagtt 290820
ctcttgttcg cctttacgaa cctgggcaag ttctgctgct tcaggagtac cttcaccttc 290880
cagccgcatt tgttctttct ttacacgttt acggttagca acaccttcag caatatactg 290940
cgagtgtgta gactgtcgct gtgattctgg gagatacaca gtcatactcg gcgacagcaa 291000
aagattctgt ttttctacgc gtccaagaaa acccataaaa gtggtttctt taagactacg 291060
gtcaccatgg gggtttttat caaccaccag ggtttttgga ttattcaagg caaattgacc 291120
ttgaggacga gattgttctt ttacaaactc cagacaggtt tcaaaatcat ctcccgtcat 291180
tgccgagata taaagagcct gatcattgag gtatccttca atgatgttca agtcacgggc 291240
atattcatcg accgggagaa tgaacgggtt aggcatactg cactggttca tatttcctct 291300

```
cttaaaattt gatctttcaa gagatggcta cgctaaaacg gaaaaaaatt aggacaccca 291360
atggatgtcc aaagattgag cggtagcaca tcaaattact ttcacatatt gatgtgccac 291420
aaggtaaaag ttcgcgacga catatatgcc ctccgagtgg agggcactat gtttattcca 291480
agacaactga atctggaact tcgttattca tcttgcaagc ttcgatgatt cgttccaaac 291540
gtcgttgatc gatattctgg aatactaagg tagctttctg accgttgttg acgaccacgc 291600
ttccttcacg aatccatgga ataccaatat actggtgctg cccgccttca aattcaacgc 291660
gtacataact gtactgcgat ggatcgtttg gtgtacccgc tgggagagtc ggatacacgt 291720
tttggtgagc ggcgattaaa tcgaaaccca ggatacgtac aagatttgcg tctaggaatg 291780
cggccagtgt tacattctta aagttgtttc cgtattgtgc agacggataa acttcaaaac 291840
tgattttctg gccaattgct acgtcacgaa tggatggcat gattgactcc gttgaactga 291900
ttgttaagca ctcataggtt tgcgcgaaac cacgaatgca aacgatccat tcatatcaat 291960
cggccacatt gacagaacgt ctaataacgg gttattcagt gtaaactctt taaagacttt 292020
atacatctca accacgttga tatcatcgtc gtctaacaga tcgtccgtag cgccggctga 292080
ttcgagaata tgtatcccga aattgttcat tacttctcgt tgaaaataga acagaacgcg 292140
cttacggatt tgatcaaccg gcaacttaat atctttacct acagttgcag ctaattcgtc 292200
ttccagggaa tcatctactt ccttttttatc ccgctcgtcc atccaacgat cctgatagaa 292260
ccgcaatccg aatctctctg catactgagc tcctgcaatt gtaccagcta tgacaagatc 292320
atgtatcatc gttcaatccc aacccgattt gttctttagt tacgctaagg ggtgaattaa 292380
ttgtacgcaa atatgactca cgatcctctg gcggcagcat tgcaagctgt agctcctgtt 292440
cacgttcaag acaagcttgt tcgcgatacg gattgtcatt aggattgtaa ggttcacgta 292500
catgtggacc atcggccgga tcatctgtgt atggagcgtc aggattgtca ccgaccagaa 292560
cataatagct gtcgtactga ccaacagcaa agttctctat cttatcgatt aaacaaccat 292620
tattttccaa atcagcgatc gctggttgaa gacattctcc gagcattccc gttgtctctg 292680
caaacttagc ttcaagataa agcatagttg tagagtcatt aataagatca ttcttaatgc 292740
tcgggaaata ttcttctacg tagtgtacaa aacctacgtt ttccttagct ggggcagtta 292800
ggatatattc gacgtgtttg ttaacacagt cttgcatgag tgcaataaca gaatcttctt 292860
ctgctacatg atcgtcttcg ttttttggta catgtgtctg taacatcttg ttccggacaa 292920
catctgtcat ctgaacaatc tgacgatcaa tcactttaga gttgatcatg atcccgcaag 292980
tacggggacc agcagattct tggatatgtg ttggggtgat gtactgggtg cgattagcta 293040
ctgccataat atcgacagtg ccatccggat tgaagatgtc gggtatcgct cgatgcattt 293100
cttggacatt catttagggg cctccatgga gatcaccatt attgagagtt tgtatttgtc 293160
ataacctact atgttcacag tagaaattat ctctgatttt gactggaacg aacgtagggt 293220
agataccata tcgtccttat aggcatttac acagacatcc atcaattctc gaaaacggag 293280
gcgccaatcg acagcttcac catcgtcgtt aattgtcttt atgatgtcct gaccatcaaa 293340
atcttcacta ataagagata aataagaatc ctccagatag agctcataat agccatccca 293400
gctcggtagg tttaagtgcc cgacgtactg ccgaacacag tcggcaaagt aagccagcac 293460
acgcttaact agaagcgcgt ttcttccttt taccaactgg tcggttaaag tcttcgattc 293520
gaaaaccagt aacgatcgca tgctgttgcc acttactccc atagtactct agcagaaatc 293580
tagcagctgt tcctttaaac attatcggga atatactaac aattcctcgt ggtaatgctt 293640
tcagaaatat gatcgcgtgc tctagaaaca actcctgata tcgttccgct agtttaccat 293700
```

tataactaaa atttggtatg gtaacatcct ttggtattac ctctggattt tcatttaacg 293760
ccttagatac gctaagtacc caagttataa cgtcatccca tactcctcct ggaccgtagc 293820
ccttgaactc tttcttcttg tagatcactc gatgtaatct ttcaagctcg ttgtaattag 293880
ggaagaatat tcccaggtcc attgagaaga ctagggacgc gggtggcgat aacatacact 293940
gcatctccat aagttcttaa gtaacgaagt tcaatggtgt cggttggaag gtatgatatt 294000
atctctttta tttgtcgtcg gattgtccta acgatacatt taccaatatc tgaatccata 294060
aaaacttcag tgataattgc atcgtcatcg agatcagttc cgtgacctat atcagcctca 294120
gccatcaata tagctaatga gttgatatcg gataccgtga agccaaccaa atctgcccat 294180
gcttctattt gccaactacg aggtccataa agaacatcca tggatagcct cacgaatatc 294240
gtctcacgca acgtaatacc ccacgattaa gtagactgta tctgatttct cgtctaagta 294300
aacttttcta tttgcgtagt caagatggat acaatctggg ataagatatc ccagtgcctt 294360
aaccctattc atgacgaact caatgagtat cttgtcatga gtgtctttgg gtttagattt 294420
atttgactct ttcttgtatc cgcagattaa aagaactgat ttctcaaaga gctcaatatg 294480
ttcttcatta tcaaagtcaa gctgccagca aatagatgtg gcaattagat cgacaagacc 294540
ttctcgtccg atattacgca ttacatcgta atatttatca tcgaccatac cgatgaaatc 294600
cgacgccttg aatgttatca ataattgttc tttcacattt atctctccgg cataaagcct 294660
cctttcggag gccctatgtt agttattttc caaataccaa cgttctgcaa tagcccgttg 294720
ttctggggga agataatcgt tacgaaggaa cgatgcaaca agctccatca tttctttctc 294780
cgtacgactg atccctttca tttcgtatat ggcgagaatg tgactagaac tgtattcaag 294840
cgtgtatttc ttatcccgtt taacatacga cgagaagtaa ctcaggccga aagccgtgat 294900
aactttacgc acgtaatttt gtttgaattc ctccatgtta gcaataccaa caagtgcgaa 294960
caaatcatcg ttcacttgag gacaaatggg atcaagggtt atcattggat acatagttgt 295020
cagtgtatct aagaacactg ctgccatggc cctgttggga ttattcagga aatcaattac 295080
tttctgaact cgttcaggtg tacgatgttt acccatcatt gcaattgcac gggtcaacgt 295140
atttggatct cgcattacgg ctccaaatgt acgcatgaat tcaccatgta gatacgacac 295200
tagagaagtg cagttcaatg caatctcggc atggctgtca tcattatgct gatcggtcag 295260
gcgatagtat tcctggattc tatgatcttc accttcagca agcccaataa ggttaccaat 295320
gcagactggt ttccattcgg tataggtgcg tcgatcaatg tggtgttcca attgattatc 295380
gatttcaatc gtaacgcctt cccagataac atcactagca aagatcttat aaacctccag 295440
ttgtttttca tctaatgtgc ctggaggtga attaaatagg gcacctgctt tatgtacctc 295500
gtagtcaatc tctgtttcga atgcacttcg actagtcaag atttctttga ctgtaaggaa 295560
caccagttga atcgcggtgt tacgagtcgg gcgcggtaga cccagatgcg gattgctttt 295620
ggtaaagtgt tcgagatatg tatacaggac atctacctgt gggttaatct caagcactac 295680
aaaccgtttg gacgacattg cattgctcca tttattaatt gataggtatt gctaagtaga 295740
taacagaacc aatacgtctg taaccaacat gcatcccgga agcttccact ggaagattga 295800
gagtgtcgta aagtaatgaa cgcgcctcat tatgaaatgc catccattcc agttcggcct 295860
gcgtgttacg atatggtgcg taacccatta caaaacaaca ttgaaacgaa tttattgcgt 295920
tctggatgaa atcatctatt aactgttcct tagcttttac caggagtcct gagaagtcag 295980
tagtatccat gtcaaccgat tcaattgctt tagatttaac taaagccatg aagggtggtt 296040
gagtaatggc ctttatgact ccagccaact cgaaggcatg aagttgaact tgtctttgag 296100
gaatcatagt tagtattccg gaaatcactc agagctatga tatagatttg aaatctttta 296160
aaatcgtcac agaacccccg ttgtatatga taccccacct gggtattatc tccatgggtg 296220
ttcgttcgct ggcgagcttc ctaggggcgt ttaaacatga atgctattca atatgcactt 296280
cgagatttac ctttccgaat tccccgtcag attctagagt ctgttttcat tggacaagaa 296340
gctgcatcta atgcagctat ttgcggtgaa gtcatttctc ttgaaactag aattcgagag 296400
gcggtattag aaccacgtgt ctttgcagac atgaacttga tcggtggaac taaaacttat 296460
attccactgg actttcctgt taagtctgaa tatgtcgatc cgtacactgt tatttactat 296520
atcccggatg aatacaccca acagcgtccc atcgtccagg tatttagtat tcacttcggt 296580
atcctaggtt atcagaactc tggatatgca atgcactata atgaatcgac tattggtgct 296640
gaatcacgta aagtattaga ctctgcgcga agactacctg ttgcacagac tgcatacatt 296700
aacttgatta accataacac tgtaatggtt agatttattt acttgccttc acatgctgcg 296760
tatttatcgt gtcgcttggg caatgatgac gagttactta atattcgtcc tcaggctatc 296820
cctgtattct ctaaactagt tgaatatgct gttaaagcct actgctataa tgaactttac 296880
atcaatatgg gtgaagctca gttatccggc ggtcaagagc ttggtgtatt ccgtgacaaa 296940
gtttacgaat ggtctgaagc gaacgatctc tatgatgagc aactgaagaa gtggcggaag 297000
gtatcccgga acttcaatga ccctgaaggt aaccgacacc atatccgtac tatcatggcg 297060
gcgccgtaag ggcgtaggtg tttatatgtt cgagtcttta ctcgctacat tagtcagaac 297120
taatcttgga tggcaaggaa tccctgtaca gggtcctaac atgcctgtta ctagggtagg 297180
tgcacctgca accctactca atggtaaagt atatattgct ggtggcggca cgcaaggtgg 297240
aacaaatggt gtatccactt cgacgttaat gacgtatgat cttgccactg gtgtgtatga 297300
tcaaaacttc agtactgttc cgtcgtctgt atatttctct ggtatcgtta acgatggaac 297360
atatctgtac cacctcggcg gcgctacatt tccaggtaat gctgttaata gcacttttgt 297420
taggattgat ccattaacaa aagaaaaact ggttttgaaa tccccacctg tggctcgtta 297480
cgatttccac atgttctatg agtcgggctt tatttatact tacggtggca cgccgtcaaa 297540
cgacgtgtta atgaaatata atatcgctac cgacacttgg gaaactgtaa cccaaccaac 297600
acttcgcccg ccagctagaa catcgtctgc tagtgtttat ctaaatggta aattctattt 297660
aatcggtggc gttagcaatc gtaatgattt ctgggaatat actttatcca caaatacgtg 297720
ggtacagcta agtaatttcc caattactac ttgggttggt agtggcttca ccatggatgg 297780
tcggatattc ctgatgcctg gtgcaccctt aatcaataac aacgcgaata aaaatatcta 297840
cgaatattta cccgatgaaa ataaatgggt attgttcaag aatatagcta atatcgtatt 297900
caattcgagt attgtatccg atggaaaacg gttgtattgt ttcggtggtt ctggtaacag 297960
ttcagtcaac gctgctagta ataccatgta ttatctaaaa taaaaaaaaa taagcatagc 298020
ccctacccga aggtaggggc tttatgccat tatgacaaac gctccaagca ttccagaacg 298080
tcatcaggat cacatttcat gcaaaccaaa tcaggtttcg atgccgatgc ttcagcaaca 298140
agctctagat tactatcatt aatgatgacc ttatcttcct gaacgaagac atcccaatcc 298200
ccataagtcc aacggccctg aggattagtt tcgacaacac gtttggcttc agcttggatc 298260
ttatcaaaga aagcttgcat aatcaatctc cttacacgtt attaagaata gacaggatca 298320
ttgctttcgg agtaacgcca acaccggcac aataacgacg gaaagattcg catggctgtg 298380
tagctttacg ttcaactaca ttcaagttaa agcacatgtt accacgtgca tcaagaatgg 298440
ttacaaattt actattgctg gttactcggt aatcacgacc gagaaccttt acggttttgt 298500
acgcatggct attcatgtcg tgatacctct aaggtttatt atcacgtttg taatatagcc 298560
tttaaattgg tttgaatgta aaaaagaaaa acaaaataaa cccaccccga agggtgggcc 298620
tgtatctaaa tgtttactaa aagagcttta tccaacagaa agataaccca gaaagaaaat 298680
aagtatgctt caacagcagc aggcttatat ttctgtttta catcttccat taagttgaat 298740
acatgtatcg aatatagttt acctataata gcaattatcg ctacaagcgt aacaataccc 298800
gcaccaatcc acatgctatc aacattctta ttaaggaagc caaccgtcac gcttgccatg 298860
aatacaacaa ccgtggttat caaccaatta gctaactgat taacacgtag ctccagttca 298920
ggatgacggt tattgttatc gtctctatat ttctttttat ctatcgcaat gatagtaaag 298980
gaaataccaa gaccgatgaa gaaagacaaa aatatcgcaa acagacttat cattttatct 299040
caccaataac gtctaaggaa tacatcgaga tcttgtacag cacgatgatc cttagctcgt 299100
actttagggt ctctcgattc tatcttctca agggcttcaa acgtttcttt caggtgaagg 299160
ggatggagaa cttggacctc gtaactatta acaagttgtc cttgttgctc ctttgtcatt 299220
ttgcgcaaac gggtgaaatc atagaagaca atgaacttac cttgatcgtc ttctgtctct 299280
tcgttaccag cttcaatcca gcgattgtat tgagcaggtg tcagaaagat atcaatggta 299340
ttcacttctt tacgcagatt gtaaataacc attgcactga gatgacctag ggccatttct 299400
tcaggtgggc acttattggt agtagcccaa gttttcatga tctcgatgat gtgttcacgt 299460
tgcgacatgc taagtactct ataatgatta catatcagta gttttggagt gtctttccaa 299520
tacaaaactg tgccgtactg atccactgac ggacttcacc ttgcgtggac gagagttcaa 299580
tttcatcacc cgtcaaagtg gcagtgagat attcctttgt atgtccgcga ctacgactag 299640
aaaaggtaat tacattaccc ttctttttga cagcaagacg agtatagcta tcaccagcta 299700
cgcaggtttc atcgagttca agttcgatcc attctcggat catttctttg agttgctcat 299760
ttggactttg cattaacttt ctccatcgct tcaattgcta gcatgatacc agcacgggta 299820
gggataggtt cttcagtaga gtaatcaaac gtcacggtct tttctgaaag attgacctct 299880
acgggccatt gacgccatct ggcggcagtg tgacggatcc acagtatatc tttgtcgata 299940
ggagaactgt agaactctag gttattatgc acgctatcat tccacgcttg acgtggaagt 300000
ttagacaccc gatctacgac tgtcttttca aacgatcgat gaacgataaa ttggagagtg 300060
ttataaatta actcatgggc actatcctga tcttcagccc aaagacagtt gatacgatca 300120
agccgtttcg agagaggatc aagttcaaat acaacatcgg gacacaaccg cttatttgga 300180
tccgtccctt gcatcaggat agaattttta tttggcgcat accacaattg aacatggcgt 300240
ttggtattag ggtcgataca tgcagaacgc tgacggccga gaagtctcca gatctggatc 300300
agggtagcta tatcgttaaa catttctatc tcccatggac ataagctctc ccatctaagg 300360
gagagcattt atgccacttt ttctttacat gtttcggtta atgttacacc ccatccggga 300420
tgactctttc tgttaaataa caatggctta ctacgtataa acggagcatc ctctgtaaaa 300480
acggtgaatg tacaatgacc ggggttgtca tcaatcttga aatagaaatt ttcttttagg 300540
tcatctactt tagtaatgtt caatggaatt aacattccac ccccatgaac ataccaacgt 300600
ttgtaaatcc ttttagcaag cctatcctcg accattggat tagactggaa ccgagctatc 300660
ctcaaacgca ttccattgac ttcagaccac gcatcaactt tgtcgtaaca tgtgactcca 300720
ttcttgtcat atacaaacac aaagccttca agaacgccga ctaaggtgac ggcatggtgt 300780
aacatcgctg tgtaattgga gagttcgagg ttaagctcag ctgccattag ctcatcgagc 300840
tttttcgctg ctgtcttagc catcattcct ccttagaggt ttaatcaggt ttcattattg 300900
attccttact gttgttaatt gatacaaaag attggacggt tattaaggct tcatataacc 300960
ttgataacgt tctatagctc gttcacctac ggctttacga tgttcatgca tttcaacagc 301020
atcgcgcctg gcatacgtag cccaaatgcg ggcactgtcc attatatccc tttgataaag 301080
gtcagttcca ctcagagctt gaataaactc atcgtccggt agatcttcct gtttgtagaa 301140
agtatcctct gcttggatat aataaaacag tacttggagt gcagcccttg tctcggagtc 301200
agagagcaaa gctttcaatg cactgcgcat tgtgttatta cagacgtcgc agttaatagc 301260
gagttcacca atggtaatac ggtcattctg tgccacagtt cgcatcaata cttcagtgca 301320
atcaacggcc agtttgataa gacgttcagg tgtaagcttt atcatttctt ctccttacaa 301380
acaaagataa tcttcgttgt tcgatttgta ttgatgacat ggagttcact gttatcgcca 301440
cggtggtaac tgatattcca attattccgg gtatacaaag aactgtgttg atcgatgatg 301500
gctctacaca cctcaatgga agacacagaa acttcttctt ctttaactac aggtaattcg 301560
ccaatagctc cggtagagac aatggtagct aagatccaac tcatgaaacc tccagacgga 301620
ataaaagggg agccgaagct ccccttttat ttagaggacg aaaccatcat cagaacggtt 301680
gtcatcgata tcaacgatcg cagctcgttg ggtgtaacga acttgctgac gatgatgttc 301740
ctgtttttga tccaggagag acttaatccg ctcttggata ccaaccgagt tgataacgaa 301800
gtgcagttgc tcagacagag cgtcttcgtc gtcaggggat gcgataccta cagtccgaac 301860
aaacggatta ccataagcta cttctttgga agcatctgtg tacagggatg cgacagaaat 301920
catctcaggg acagaagctg cttcttgacg agaagtatgg atatgcagtt cacacagttg 301980
cggttgaatg taactatgct tactagtgaa gcgtgcccag tgatccagat ccagtacatc 302040
aagacgttca tgtttctgat tagacaggta aatcagagca tggacagcaa ataccgcatc 302100
tttgtcgatt tcggaatacg gaacgccgtt cacgttttcg atcggacaga tgttgatcgg 302160
ggtgttggtt gcagcagcga taccttccag agtcttcatg gtatcgatat cgttttgcag 302220
aacctcagtg gattcaatac cactgacaac gaccggaatt acagtttcac cagctttagc 302280
cagagccgat acaatcagcg gaccaagaac agaaccagaa ccaccgccca tagaaaacag 302340
gacgatattg aaatcgccag ctggatatcg ttcaaggaaa ggtgcaatct gatggcgaac 302400
cttaggcatg atgaatgcac ggttcttacc tgccccacga gtaccctcgg tcaaaaagac 302460
acgatcgata tcatgactag aacttacgtt cttatcgcag gtgtcaatgt ataccagatc 302520
cggatgccat tgaaggttta caccaatatt cagaccagca ccaccacagc agtatacacg 302580
agtttttact ttagtcattt ccacgtttcc tcttgattaa ccttcttgaa ttgtaactag 302640
cgtgtcgcgt tcttgttcat tgagcacagt cttgctgttc atcccaaaat gaatactacc 302700
aaacgctcca ttgtcacaca tattaaccgt aactccggta tttgttagct aagaactagc 302760
tcttggtctt tgaacgaatt gagatagact ttaacctgaa catcgactcc aagatagtaa 302820
cctaccatca aggttaccgt acagttatcg tgaaccatgg tgttaacaat ggatacacta 302880
tccagattag caaaattcct gattgtcggc gttatccgat aaatcttcgg aattgactcg 302940
aagtcaaact cgtgtcgttc actaaccttc agtgtattca gatccaagaa cgtgattgtc 303000
tttggacgac agtattcatc aacttcgaca tgtttaatcg cagatgacgt attctcagga 303060
actagaagct gatatactcg atcattactg tagaaagtaa tacgaccgat ttcctgtttg 303120
atccactcac tgggtttata ataactaacc gaatgaacac cggtatcgaa gctccaagaa 303180
ctttggacat cgaagaattt atatccttca gcaatcatca gttcaataag cttctgataa 303240
tgttctccca attgatgaac tgtattacgt tgaccaatta cactgaagaa cgaacctaga 303300
ttctgtttag tgatttcaat atttgtctca ctaggtttgt aagtcagttc gaagtcttcc 303360
tgtgttacgt tccattccga tactttcaga aagatatcgt tggtaactgg gttaactgca 303420
ccaaaggtga tttcatctac gttttcaata accaggaagt tcttgaagat atctttgatg 303480
gctggaagtg cttcgccaat agatttcatt tcgattcctc tttaggaagg accaagaaag 303540
taaacccgtt accacttgca tggataacca gttccaattt gccaccgttg tcgatagcat 303600
gttgcatcag gcggttgtaa ttgatagcgc tcatttgtac ttcctcaggt tagaatttca 303660
gaaatgggta ccacacgaat aatcagggtc gttggagatt gatactcttt actaaccgtt 303720
gccattatca ctgacggata agaacagaga atcgtcttag gggagaccat gtcgactttg 303780
aacttaatgt acatctgttt gatcaactca tggacatctt cgtcgttgtt aaccaagaac 303840
aaagaatcag ggatcaatgt tttcattttc ggttttttcc agttttacga gttaatattc 303900
aactaggtaa tatagatttg aaataatttt tactactggg tggatggggc tttgtagccc 303960
cacgacaccc tcttccaagt tttgcgacat agtcgttttt gtttccctac cccgtactaa 304020
agaataagga aattatatat gggacccccc ca 304052

<210> SEQ ID NO 6
<211> LENGTH: 259
<212> TYPE: PRT
<213> ORGANISM: Artificial Sequence
<220> FEATURE:
<223> OTHER INFORMATION: synthetic_Endolysin LNT102

<400> SEQUENCE: 6

Met Gly Thr Val Leu Lys Arg Gly Asp Arg Gly Ser Ala Val Glu Asp
1 5 10 15

Leu Gln Met Lys Leu Asn Val Ala Gly Tyr Asn Leu Ser Ala Asp Gly
20 25 30

Ile Phe Gly Gly Asp Thr Glu Lys Ala Val Arg Asp Val Gln Ala Gly
35 40 45

Ala Gly Leu Val Val Asp Gly Lys Val Gly Pro Lys Thr Leu Tyr Ala
50 55 60

Ile Ala Lys Ser Ala Thr Val Pro Ala Lys Trp Glu Ala Ile Pro Phe
65 70 75 80

Pro Thr Ala Asn Lys Ser Arg Ser Ala Ala Met Pro Thr Leu Asn Ala
85 90 95

Val Gly Ala Met Thr Gly Val Asp Ser Arg Leu Leu Ala Thr Phe Ala
100 105 110

Ser Ile Glu Ser Ala Phe Asp Tyr Thr Val Lys Ala Lys Thr Ser Ser
115 120 125

Ala Thr Gly Trp Phe Gln Phe Leu Asp Ala Thr Trp Asp Asp Met Ile
130 135 140

Lys Ala Tyr Gly Ser Lys Tyr Gly Ile Pro Lys Asp Pro Thr Arg Ala
145 150 155 160

Leu Arg Lys Asp Pro Arg Ala Asn Ala Leu Met Gly Ala Glu Phe Ile
165 170 175

Lys Gly Asn Ala Ala Val Leu Arg Pro Val Ile Asn Arg Glu Pro Ser
180 185 190

Asp Thr Asp Leu Tyr Leu Ala His Phe Leu Gly Ala Gly Gly Ala Lys
195 200 205

```
Lys Phe Leu Ser Ala Asp Gln Lys Thr Leu Gly Glu Val Leu Phe Pro
    210                 215                 220

Lys Pro Ala Lys Ala Asn Pro Ser Ile Phe Ser Asn Lys Gly Val Pro
225                 230                 235                 240

Arg Thr Leu Ala Glu Ile Tyr Lys Leu Phe Glu Asp Lys Val Ser Lys
                245                 250                 255

His Arg Ala


<210> SEQ ID NO 7
<211> LENGTH: 777
<212> TYPE: DNA
<213> ORGANISM: Artificial Sequence
<220> FEATURE:
<223> OTHER INFORMATION: synthetic_Endolysin LNT102 coding gene

<400> SEQUENCE: 7

atgggtactg tactcaaacg tggcgaccgc ggctctgctg tggaagatct acaaatgaaa      60

cttaacgtcg caggatacaa cctgagcgct gacggaatct tcggtggaga tacagagaaa     120

gctgttcgtg atgtgcaagc tggcgcgggc ttggtggttg acggaaaagt tggacctaaa     180

actctatatg cgattgccaa atccgctact gttcctgcta aatgggaagc tatccctttc     240

ccaacagcta ataaatctcg gtcggctgca atgcccactc tgaatgcggt tggagcaatg     300

actggtgtgg attctcggtt actcgctaca ttcgcttcca ttgagtctgc ttttgattac     360

actgtcaaag caaaaacatc ttcggctact ggttggttcc agttccttga tgctacatgg     420

gatgacatga tcaaagcata tggttccaaa tacgggatac ctaaagatcc cactagggca     480

ctccgtaaag acccacgtgc aaatgcatta atgggtgcag aattcattaa aggaaatgca     540

gctgtattac gtccagtaat caatcgcgaa ccgagtgata cagacttgta tttggcacat     600

ttccttggtg ctggcggcgc taagaaattc ctatccgcag atcagaaaac tctcggtgaa     660

gttctattcc cgaaacctgc taaagcaaac ccgtcgatct ttagcaataa aggtgtacca     720

cgtacccttg cagagatcta caagctgttc gaagataaag tttcgaaaca tcgggca        777


<210> SEQ ID NO 8
<211> LENGTH: 37
<212> TYPE: PRT
<213> ORGANISM: Artificial Sequence
<220> FEATURE:
<223> OTHER INFORMATION: synthetic_Cecropin A

<400> SEQUENCE: 8

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35


<210> SEQ ID NO 9
<211> LENGTH: 111
<212> TYPE: DNA
<213> ORGANISM: Artificial Sequence
<220> FEATURE:
<223> OTHER INFORMATION: synthetic_Cecropin A coding gene

<400> SEQUENCE: 9

aaatggaaac tgtttaaaaa aattgaaaaa gtgggccaga acattcgcga tggcattatt      60
```

```
aaagcgggcc cggcggtggc ggtggtgggc caggcgaccc agattgcgaa a            111


<210> SEQ ID NO 10
<211> LENGTH: 303
<212> TYPE: PRT
<213> ORGANISM: Artificial Sequence
<220> FEATURE:
<223> OTHER INFORMATION: synthetic_Endolysin LNT103

<400> SEQUENCE: 10

Met Lys Trp Lys Leu Phe Lys Lys Ile Glu Lys Val Gly Gln Asn Ile
1               5                   10                  15

Arg Asp Gly Ile Ile Lys Ala Gly Pro Ala Val Ala Val Val Gly Gln
            20                  25                  30

Ala Thr Gln Ile Ala Lys Gly Ser Gly Ser Gly Ser Met Gly Thr Val
        35                  40                  45

Leu Lys Arg Gly Asp Arg Gly Ser Ala Val Glu Asp Leu Gln Met Lys
    50                  55                  60

Leu Asn Val Ala Gly Tyr Asn Leu Ser Ala Asp Gly Ile Phe Gly Gly
65                  70                  75                  80

Asp Thr Glu Lys Ala Val Arg Asp Val Gln Ala Gly Ala Gly Leu Val
                85                  90                  95

Val Asp Gly Lys Val Gly Pro Lys Thr Leu Tyr Ala Ile Ala Lys Ser
            100                 105                 110

Ala Thr Val Pro Ala Lys Trp Glu Ala Ile Pro Phe Pro Thr Ala Asn
        115                 120                 125

Lys Ser Arg Ser Ala Ala Met Pro Thr Leu Asn Ala Val Gly Ala Met
    130                 135                 140

Thr Gly Val Asp Ser Arg Leu Leu Ala Thr Phe Ala Ser Ile Glu Ser
145                 150                 155                 160

Ala Phe Asp Tyr Thr Val Lys Ala Lys Thr Ser Ser Ala Thr Gly Trp
                165                 170                 175

Phe Gln Phe Leu Asp Ala Thr Trp Asp Asp Met Ile Lys Ala Tyr Gly
            180                 185                 190

Ser Lys Tyr Gly Ile Pro Lys Asp Pro Thr Arg Ala Leu Arg Lys Asp
        195                 200                 205

Pro Arg Ala Asn Ala Leu Met Gly Ala Glu Phe Ile Lys Gly Asn Ala
    210                 215                 220

Ala Val Leu Arg Pro Val Ile Asn Arg Glu Pro Ser Asp Thr Asp Leu
225                 230                 235                 240

Tyr Leu Ala His Phe Leu Gly Ala Gly Gly Ala Lys Lys Phe Leu Ser
                245                 250                 255

Ala Asp Gln Lys Thr Leu Gly Glu Val Leu Phe Pro Lys Pro Ala Lys
            260                 265                 270

Ala Asn Pro Ser Ile Phe Ser Asn Lys Gly Val Pro Arg Thr Leu Ala
        275                 280                 285

Glu Ile Tyr Lys Leu Phe Glu Asp Lys Val Ser Lys His Arg Ala
    290                 295                 300


<210> SEQ ID NO 11
<211> LENGTH: 912
<212> TYPE: DNA
<213> ORGANISM: Artificial Sequence
<220> FEATURE:
<223> OTHER INFORMATION: synthetic_Endolysin LNT103 coding gene

<400> SEQUENCE: 11
```

-continued

```
atgaaatgga aactgtttaa aaaaattgaa aaagtgggcc agaacattcg cgatggcatt     60
attaaagcgg gcccggcggt ggcggtggtg ggccaggcga cccagattgc gaaaggcagc    120
ggctcgggta gtatgggtac tgtactcaaa cgtggcgacc gcggctctgc tgtggaagat    180
ctacaaatga aacttaacgt cgcaggatac aacctgagcg ctgacggaat cttcggtgga    240
gatacagaga aagctgttcg tgatgtgcaa gctggcgcgg gcttggtggt tgacggaaaa    300
gttggaccta aaactctata tgcgattgcc aaatccgcta ctgttcctgc taaatgggaa    360
gctatccctt tcccaacagc taataaatct cggtcggctg caatgcccac tctgaatgcg    420
gttggagcaa tgactggtgt ggattctcgg ttactcgcta cattcgcttc cattgagtct    480
gcttttgatt acactgtcaa agcaaaaaca tcttcggcta ctggttggtt ccagttcctt    540
gatgctacat gggatgacat gatcaaagca tatggttcca aatacgggat acctaaagat    600
cccactaggg cactccgtaa agacccacgt gcaaatgcat taatgggtgc agaattcatt    660
aaaggaaatg cagctgtatt acgtccagta atcaatcgcg aaccgagtga tacagacttg    720
tatttggcac atttccttgg tgctggcggc gctaagaaat tcctatccgc agatcagaaa    780
actctcggtg aagttctatt cccgaaacct gctaaagcaa acccgtcgat ctttagcaat    840
aaaggtgtac cacgtaccct tgcagagatc tacaagctgt tcgaagataa agtttcgaaa    900
catcgggcat ag                                                         912

<210> SEQ ID NO 12
<211> LENGTH: 6
<212> TYPE: PRT
<213> ORGANISM: Artificial Sequence
<220> FEATURE:
<223> OTHER INFORMATION: synthetic_linker

<400> SEQUENCE: 12

Gly Ser Gly Ser Gly Ser
1               5


<210> SEQ ID NO 13
<211> LENGTH: 303
<212> TYPE: PRT
<213> ORGANISM: Artificial Sequence
<220> FEATURE:
<223> OTHER INFORMATION: synthetic_Fusion Polypeptide CecA-LNT101

<400> SEQUENCE: 13

Met Lys Trp Lys Leu Phe Lys Lys Ile Glu Lys Val Gly Gln Asn Ile
1               5                   10                  15

Arg Asp Gly Ile Ile Lys Ala Gly Pro Ala Val Ala Val Val Gly Gln
            20                  25                  30

Ala Thr Gln Ile Ala Lys Gly Ser Gly Ser Gly Ser Met Gly Thr Val
        35                  40                  45

Leu Lys Arg Gly Asp Arg Gly Ser Ala Val Glu Asp Leu Gln Met Lys
    50                  55                  60

Leu Arg Val Ala Gly Tyr Ala Val Ser Ala Asp Gly Ile Phe Gly Gly
65                  70                  75                  80

Asp Thr Glu Lys Ala Val Arg Asp Phe Gln Ala Ser Lys Ala Leu Val
                85                  90                  95

Val Asp Gly Lys Val Gly Pro Ala Thr Leu Ala Glu Leu Ala Lys Ser
            100                 105                 110

Ala Thr Val Pro Ala Lys Trp Glu Ala Ile Pro Phe Pro Thr Ala Asn
        115                 120                 125
```

```
Lys Ser Arg Ser Ala Ala Met Pro Thr Leu Asn Ala Val Gly Ala Met
    130                 135                 140

Thr Gly Thr Asp Ser Arg Leu Leu Ala Thr Phe Ala Ser Ile Glu Ser
145                 150                 155                 160

Ala Phe Asp Tyr Thr Val Lys Ala Ser Thr Ser Ser Ala Thr Gly Trp
                165                 170                 175

Phe Gln Phe Leu Asp Ala Thr Trp Asp Asp Met Ile Lys Ala His Gly
            180                 185                 190

Ser Lys Tyr Gly Ile Pro Lys Asp Pro Thr Arg Ala Leu Arg Lys Asp
        195                 200                 205

Pro Arg Ala Asn Ala Leu Met Gly Ala Glu Phe Leu Lys Gly Asn Ala
    210                 215                 220

Ala Val Leu Arg Pro Val Ile Asn Arg Glu Pro Ser Asp Thr Asp Leu
225                 230                 235                 240

Tyr Leu Ala His Phe Leu Gly Ala Gly Gly Ala Lys Lys Phe Leu Ser
                245                 250                 255

Ala Asp Gln Lys Thr Leu Gly Glu Val Leu Phe Pro Lys Pro Ala Lys
            260                 265                 270

Ala Asn Pro Ser Ile Phe Ser Asn Lys Gly Val Pro Arg Thr Leu Ala
        275                 280                 285

Glu Ile Tyr Lys Leu Phe Glu Asp Lys Val Ser Lys His Arg Ala
    290                 295                 300
```

<210> SEQ ID NO 14
<211> LENGTH: 912
<212> TYPE: DNA
<213> ORGANISM: Artificial Sequence
<220> FEATURE:
<223> OTHER INFORMATION: synthetic_Fusion Polypeptide CecA-LNT101 coding gene

<400> SEQUENCE: 14

```
atgaaatgga aactgtttaa aaaaattgaa aaagtgggcc agaacattcg cgatggcatt     60

attaaagcgg gcccggcggt ggcggtggtg ggccaggcga cccagattgc gaaaggcagc    120

ggctcgggta gtatgggtac tgtactcaaa cgtggcgacc gcggctctgc tgtggaagat    180

ctacaaatga aacttcgagt cgcaggatac gcagttagcg ctgacggaat cttcggtgga    240

gatacagaga aagctgttcg tgatttccaa gcttctaaag ctttggtggt tgacggaaaa    300

gttggacctg ctactctagc tgaactagcc aaatccgcta ctgttcctgc taaatgggaa    360

gctatccctt tcccaacagc taataaatct cggtcggctg caatgcccac tctgaatgcg    420

gttggagcaa tgactggtac cgattctcgg ttactcgcta cattcgcttc cattgagtct    480

gcttttgatt acactgtcaa agcatccaca tcttcggcta ctggttggtt ccagttcctt    540

gatgctacat gggatgacat gatcaaagca catggttcca aatacgggat acctaaagat    600

cccactaggg cactccgtaa agacccacgt gcaaatgcat taatgggtgc agaattcctt    660

aaaggaaatg cagctgtatt acgtccagta atcaatcgcg aaccgagtga tacagacttg    720

tatttggcac atttccttgg tgctggcggc gctaagaaat tcctatccgc agatcagaaa    780

actctcggtg aagttctatt cccgaaacct gctaaagcaa acccgtcgat ctttagcaat    840

aaaggtgtac cacgtaccct tgcagagatc tacaagctgt tcgaagataa agtttcgaaa    900

catcgggcat ag                                                        912
```

<210> SEQ ID NO 15
<211> LENGTH: 313

<212> TYPE: PRT
<213> ORGANISM: Artificial Sequence
<220> FEATURE:
<223> OTHER INFORMATION: synthetic_Fusion Polypeptide LNT103 with MAS, His tag, and extra sequence

<400> SEQUENCE: 15

```
Met Ala Ser Lys Trp Lys Leu Phe Lys Lys Ile Glu Lys Val Gly Gln
1               5                   10                  15

Asn Ile Arg Asp Gly Ile Ile Lys Ala Gly Pro Ala Val Ala Val Val
            20                  25                  30

Gly Gln Ala Thr Gln Ile Ala Lys Gly Ser Gly Ser Gly Ser Met Gly
        35                  40                  45

Thr Val Leu Lys Arg Gly Asp Arg Gly Ser Ala Val Glu Asp Leu Gln
    50                  55                  60

Met Lys Leu Asn Val Ala Gly Tyr Asn Leu Ser Ala Asp Gly Ile Phe
65                  70                  75                  80

Gly Gly Asp Thr Glu Lys Ala Val Arg Asp Val Gln Ala Gly Ala Gly
                85                  90                  95

Leu Val Val Asp Gly Lys Val Gly Pro Lys Thr Leu Tyr Ala Ile Ala
            100                 105                 110

Lys Ser Ala Thr Val Pro Ala Lys Trp Glu Ala Ile Pro Phe Pro Thr
        115                 120                 125

Ala Asn Lys Ser Arg Ser Ala Ala Met Pro Thr Leu Asn Ala Val Gly
    130                 135                 140

Ala Met Thr Gly Val Asp Ser Arg Leu Leu Ala Thr Phe Ala Ser Ile
145                 150                 155                 160

Glu Ser Ala Phe Asp Tyr Thr Val Lys Ala Lys Thr Ser Ser Ala Thr
                165                 170                 175

Gly Trp Phe Gln Phe Leu Asp Ala Thr Trp Asp Asp Met Ile Lys Ala
            180                 185                 190

Tyr Gly Ser Lys Tyr Gly Ile Pro Lys Asp Pro Thr Arg Ala Leu Arg
        195                 200                 205

Lys Asp Pro Arg Ala Asn Ala Leu Met Gly Ala Glu Phe Ile Lys Gly
    210                 215                 220

Asn Ala Ala Val Leu Arg Pro Val Ile Asn Arg Glu Pro Ser Asp Thr
225                 230                 235                 240

Asp Leu Tyr Leu Ala His Phe Leu Gly Ala Gly Gly Ala Lys Lys Phe
                245                 250                 255

Leu Ser Ala Asp Gln Lys Thr Leu Gly Glu Val Leu Phe Pro Lys Pro
            260                 265                 270

Ala Lys Ala Asn Pro Ser Ile Phe Ser Asn Lys Gly Val Pro Arg Thr
        275                 280                 285

Leu Ala Glu Ile Tyr Lys Leu Phe Glu Asp Lys Val Ser Lys His Arg
    290                 295                 300

Ala Leu Glu His His His His His His
305                 310
```

<210> SEQ ID NO 16
<211> LENGTH: 313
<212> TYPE: PRT
<213> ORGANISM: Artificial Sequence
<220> FEATURE:
<223> OTHER INFORMATION: synthetic_Fusion Polypeptide CecA-LNT101 with MAS, His tag, and extra sequence

<400> SEQUENCE: 16

-continued

```
Met Ala Ser Lys Trp Lys Leu Phe Lys Lys Ile Glu Lys Val Gly Gln
1               5                   10                  15

Asn Ile Arg Asp Gly Ile Ile Lys Ala Gly Pro Ala Val Ala Val Val
            20                  25                  30

Gly Gln Ala Thr Gln Ile Ala Lys Gly Ser Gly Ser Gly Ser Met Gly
        35                  40                  45

Thr Val Leu Lys Arg Gly Asp Arg Gly Ser Ala Val Glu Asp Leu Gln
    50                  55                  60

Met Lys Leu Arg Val Ala Gly Tyr Ala Val Ser Ala Asp Gly Ile Phe
65                  70                  75                  80

Gly Gly Asp Thr Glu Lys Ala Val Arg Asp Phe Gln Ala Ser Lys Ala
                85                  90                  95

Leu Val Val Asp Gly Lys Val Gly Pro Ala Thr Leu Ala Glu Leu Ala
            100                 105                 110

Lys Ser Ala Thr Val Pro Ala Lys Trp Glu Ala Ile Pro Phe Pro Thr
        115                 120                 125

Ala Asn Lys Ser Arg Ser Ala Ala Met Pro Thr Leu Asn Ala Val Gly
    130                 135                 140

Ala Met Thr Gly Thr Asp Ser Arg Leu Leu Ala Thr Phe Ala Ser Ile
145                 150                 155                 160

Glu Ser Ala Phe Asp Tyr Thr Val Lys Ala Ser Thr Ser Ser Ala Thr
                165                 170                 175

Gly Trp Phe Gln Phe Leu Asp Ala Thr Trp Asp Asp Met Ile Lys Ala
            180                 185                 190

His Gly Ser Lys Tyr Gly Ile Pro Lys Asp Pro Thr Arg Ala Leu Arg
        195                 200                 205

Lys Asp Pro Arg Ala Asn Ala Leu Met Gly Ala Glu Phe Leu Lys Gly
    210                 215                 220

Asn Ala Ala Val Leu Arg Pro Val Ile Asn Arg Glu Pro Ser Asp Thr
225                 230                 235                 240

Asp Leu Tyr Leu Ala His Phe Leu Gly Ala Gly Gly Ala Lys Lys Phe
                245                 250                 255

Leu Ser Ala Asp Gln Lys Thr Leu Gly Glu Val Leu Phe Pro Lys Pro
            260                 265                 270

Ala Lys Ala Asn Pro Ser Ile Phe Ser Asn Lys Gly Val Pro Arg Thr
        275                 280                 285

Leu Ala Glu Ile Tyr Lys Leu Phe Glu Asp Lys Val Ser Lys His Arg
    290                 295                 300

Ala Leu Glu His His His His His His
305                 310
```

POLYPEPTIDE, FUSION POLYPEPTIDE, AND ANTIBIOTIC AGAINST GRAM-NEGATIVE BACTERIA COMPRISING SAME

GOVERNMENT SUPPORT

This invention was made with government support under Ref No: 1415184431 awarded by the Korea Evaluation Institute of Industrial Technology, Ministry of Trade, Industry and Energy.

TECHNICAL FIELD

In the present description, a novel polypeptide, a fusion polypeptide comprising the polypeptide and a use as an antibiotic thereof are provided. More specifically, a novel polypeptide derived from a bacteriophage, a fusion polypeptide comprising the polypeptide and Cecropin A, and an antibiotic against gram negative bacterium comprising the polypeptide and/or fusion protein.

BACKGROUND ART

Bacteriophage refers to a bacterium-specific virus that infects specific bacterium and inhibits and hinders the growth of the infected bacterium. The bacteriophage has the ability to kill bacterium in the way of proliferating inside bacterial cells after infection to their host bacterium, and destroy the cell wall of the host bacterium using endolysin, a protein of bacteriophage when progeny bacteriophages come out of the bacterium after proliferation. Therefore, a substance having endolysin activity of a bacteriophage can be usefully applied as an antibiotic candidate.

Recently, antibiotic-resistant bacterium is rapidly increasing, and multidrug-resistant bacterium that cannot be treated with any antibiotic are also increasing. In particular, *Pseudomonas aeruginosa*, one of gram negative bacteria, is one of ESKAPE (*Enterococcus faecium, Staphylococcus aureus, Klebsiella pneumoniae, Acinetobacter baumannii, Pseudomonas aeruginosa*, and *Enterobacter* species) bacteria that urgently need development of new treatment methods worldwide, and *E. coli* (*Escherichia coli*) is a bacterium involved in various infections. Therefore, it is required to develop a treatment method that is differentiated from the conventional antibiotics.

DISCLOSURE

Technical Problem

One example provides a novel polypeptide. The polypeptide may comprise the amino acid sequence of SEQ ID NO: 1 or SEQ ID NO: 6. The polypeptide may be derived from a bacteriophage or a variant thereof. The polypeptide may have endolysin activity.

Another example provides a polynucleotide encoding the polypeptide. The polynucleotide may comprise the nucleic acid sequence of SEQ ID NO: 2 or SEQ ID NO: 7.

Other example provides a recombinant vector comprising the polynucleotide. The recombinant vector may be used as an expression vector.

Other example provides a recombinant cell comprising the polynucleotide or a recombinant vector comprising the same. The recombinant cell may be for expression of the polynucleotide.

Other example provides a bacteriophage comprising the polypeptide of SEQ ID NO: 1, a polynucleotide encoding the same (for example, SEQ ID NO: 2), or a combination thereof. The genome of the bacteriophage may comprise the nucleic acid sequence of SEQ ID NO: 5.

Other example provides a novel fusion polypeptide. The fusion polypeptide may comprise Cecropin A and endolysin. The Cecropin A may be represented, for example, by the amino acid sequence of SEQ ID NO: 8. The endolysin may be derived from a bacteriophage or a variant thereof, and for example, it may be represented by the amino acid sequence of SEQ ID NO: 1 or SEQ ID NO: 6. In the fusion polypeptide, the Cecropin A (e.g., SEQ ID NO: 8) and endolysin (for example, SEQ ID NO: 1 or SEQ ID NO: 6) may be linked through a linker in any order or directly linked without a linker. In one example, the fusion polypeptide may be represented by the amino acid sequence of SEQ ID NO: 10 or SEQ ID NO: 13.

Other example provides a polynucleotide encoding the fusion polypeptide. The polynucleotide may comprise the nucleic acid sequence of SEQ ID NO: 11 or SEQ ID NO: 14.

Other example provides a recombinant vector comprising the polynucleotide. The recombinant vector may be used as an expression vector.

Other example provides a recombinant cell comprising the polynucleotide or a recombinant vector comprising the same. The recombinant cell may be for expression of the polynucleotide.

Other example, provides an antibiotic, comprising one or more kinds selected from the group consisting of (1) one or more polypeptide selected from SEQ ID NO: 1 and SEQ ID NO: 6, (2) a fusion polypeptide comprising the polypeptide and Cecropin A (for example, SEQ ID NO: 10 or SEQ ID NO: 13), or a combination thereof, (3) a polynucleotide encoding the (1) polypeptide, (4) a polynucleotide encoding the (2) fusion polypeptide, (5) a recombinant vector comprising the (3) polynucleotide, the (4) polynucleotide, or a combination thereof, (6) a recombinant cell comprising the (3) polynucleotide, the (4) polynucleotide, or a combination thereof or a recombinant vector comprising the polynucleotide, and (7) a bacteriophage comprising the polypeptide of SEQ ID NO: 1, a polynucleotide encoding the same, or a combination thereof.

The antibiotic may have antibiotic effect against gram negative bacterium.

The antibiotic (the first antibiotic) provide in the present description has an advantage to exhibit a synergy effect by the antibiotic effect itself and an excellent antibiotic effect as the second antibiotic at a low concentration, as used in combination with another antibiotic (the second antibiotic). For this reason, side effects such as toxicity (for example, kidney toxicity, liver toxicity, etc.) by use of an antibiotic at a high concentration may be reduced. In addition, it can inhibit emergence of antibiotic-resistant bacterium through combination of antibiotics of different mechanisms.

Accordingly, one example, provides a combination antibiotic comprising (a) one or more selected from the group consisting of (1) one or more polypeptide selected from SEQ ID NO: 1 and SEQ ID NO: 6, (2) a fusion polypeptide comprising the polypeptide and Cecropin A (for example, SEQ ID NO: 10 or SEQ ID NO: 13), or a combination thereof, (3) a polynucleotide encoding the (1) polypeptide, (4) a polynucleotide encoding the (2) fusion polypeptide, (5) a recombinant vector comprising the (3) polynucleotide, the (4) polynucleotide, or a combination thereof, (6) a recombinant cell comprising the (3) polynucleotide, the (4) polynucleotide, or a combination thereof or a recombinant vector comprising the polynucleotide, and (7) a bacteriophage comprising the polypeptide of SEQ ID NO: 1, a polynucleotide encoding the same, or a combination thereof; and (b) an antibiotic (for example, a polymyxin-based antibiotic such as polymyxin B and/or Colistin, etc.).

Other example provides a pharmaceutical composition for preventing and/or treating infection of *Pseudomonas* sp. bacterium or disease caused by *Pseudomonas* sp. bacterium comprising the antibiotic or combination antibiotic as an active ingredient. Other example provides a method for preventing or treating infection of *Pseudomonas* sp. bacterium or disease caused by *Pseudomonas* sp. bacterium, comprising administering a pharmaceutically effective dose of the antibiotic or combination antibiotic into a subject in need of preventing and/or treating infection of *Pseudomonas* sp. bacterium or disease caused by *Pseudomonas* sp. bacterium.

Other example provides a feed additive comprising the antibiotic or combination antibiotic as an active ingredient.

Other example provides a disinfectant comprising the antibiotic or combination antibiotic as an active ingredient.

Other example provides a method for disinfection, comprising applying the antibiotic or combination antibiotic into a subject in need of disinfection.

Other example provides a detergent comprising the antibiotic or combination antibiotic as an active ingredient.

Other example provides a method for cleaning, comprising applying the antibiotic or combination antibiotic into a subject in need of cleaning.

Technical Solution

When a bacteriophage that can be used as a natural antibiotic by proliferating bacterium as a host penetrates the bacterium and finishes proliferation inside, the completed phage particles are released to the outside of the bacterium, and then, an enzyme that attacks and decomposes the cell wall of bacterium and creates a pathway for release to the outside is endolysin. All bacteriophages have this endolysin gene in their genome and use the endolysin protein expressed during proliferation. Bacteriophages that proliferate bacterium as a host and endolysin derived from bacteriophages having a property of decomposing the cell wall can be used as natural antibiotics.

In case of gram positive bacterium, as the cell wall is located on the outermost wall, when endolysin is added from the outside, the cell wall is immediately attacked and decomposed. On the other hand, in case of gram negative bacterium, the outer cell membrane is present at the outermost part and the cell wall is located inside it, and therefore, even if endolysin is added from the outside, it must first pass through the outer cell membrane to meet the cell wall. Thus, it has been known that basically endolysin has no effect on gram negative bacterium. The polypeptide having endolysin activity provided in the present description is characterized by having an effect of killing gram negative bacterium.

On the other hand, the Cecropin A is a peptide having antibacterial activity which has action of lysing the bacterial membrane.

In the present description, a novel polypeptide or a fusion polypeptide in which Cecropin A is fused to the novel polypeptide demonstrates a superior antibiotic effect than conventional endolysin, and thereby, a polypeptide having endolysin activity, and an antibiotic thereof and/or a use related thereto are provided.

Hereinafter, the present invention will be described in more detail:

Definition of Terms

In the present description, that a polynucleotide (may be used interchangeably with "gene") or a polypeptide (may be used interchangeably with "protein" "comprises a specific nucleic acid sequence or amino acid sequence" or "consists of a specific nucleic acid sequence or amino acid sequence" may mean that the polynucleotide or polypeptide essentially includes the specific nucleic acid sequence or amino acids sequence, and it may be interpreted as including a "substantially equivalent sequence" in which a mutation (deletion, substitution, modification and/or addition) is added to the specific nucleic acid sequence or amino acid sequence within a range of maintaining the original function and/or desired function of the polynucleotide or polypeptide (or not excluding the mutation).

In one example, that a polynucleotide or polypeptide "comprises a specific nucleic acid sequence or amino acid sequence" or "consists of or is represented by a specific nucleic acid sequence or amino acid sequence" may mean that the polynucleotide or polypeptide (i) essentially comprises the specific nucleic acid sequence or amino acid sequence, or (ii) consists of or an amino acid sequence having identity of 96% or more, 96.5% or more, 97% or more, 97.5% or more, 98% or more, 98.5% or more, 99% or more, 99.5% or more, or 99.9% or more to the specific nucleic acid sequence or amino acid sequence or essentially comprises that, and maintains the original function and/or desired function. In the present description, the original function may be endolysin enzymatic function (for example, peptidoglycan hydrolytic activity), Cecropin A activity (for example, cell membrane lytic activity), and/or antibiotic action (in case of amino acid sequence), or endolysin enzymatic function, or function encoding protein having Cecropin A activity and/or antibiotic action (in case of nucleic acid sequence), and the desired function may mean antibiotic activity against gram negative bacterium, for example, *Pseudomonas* sp. bacterium, for example, *Pseudomonas aeruginosa*.

In the present description, the term, "identity" means a degree of correspondence with a given nucleic acid sequence or amino acid sequence and may be represented by a percentage (%). In case of identity for a nucleic acid sequence, for example, it may be determined by using algorithm BLAST by a document (reference: Karlin and Altschul, Pro. Natl. Acad. Sci. USA, 90, 5873, 1993) or FASTA by Pearson (reference: Methods Enzymol., 183, 63, 1990). Based on this algorithm BLAST, programs called BLASTN or BLASTX have been developed.

The protein or polypeptide provided in the present description may be separated and/or purified from the nature, or be recombinantly or chemically synthesized. When the amino acid sequence of the protein or polypeptide provided in the present description comprises a methionine (Met, M) or Met-Ala-Ser (MAS) sequence as the first amino acid residue from the N-terminus, the protein or polypeptide may be recombinantly produced, and the methionine at the first amino acid position from the N-terminus may be encoded by an initiation codon. Therefore, when the amino acid sequence of the protein or polypeptide provided in the present description comprises methionine by recombinant production at the N-terminus, and when the protein or polypeptide is obtained by other method (for example, chemical synthesis or separation from the nature), it may be interpreted as comprising an amino acid sequence starting from the second amino acid residue excluding the methionine at the first position from the N-terminus by the recombinant production or an amino acid sequence starting from the amino acid residue following the MAS sequence (for example, the 4th amino acid residue).

Novel Polypeptide and Polynucleotide Encoding the Same

One example provides a novel polypeptide. The polypeptide may comprise the amino acid sequence of SEQ ID NO: 1. The polypeptide may be derived from a bacteriophage. The polypeptide may have endolysin activity derived from a bacteriophage. The polypeptide may have a molecular weight of about 28 kDa (28 kDa±2).

In another example, the polypeptide may comprise the amino acid sequence of SEQ ID NO: 6. The polypeptide may be an endolysin variant derived from a bacteriophage, and may have excellent endolysin activity and/or antibiotic activity compared to endolysin derived from a bacteriophage. The polypeptide may have a molecular weight of about 28 kDa (28 kDa±2). The polypeptide may be prepared recombinantly or synthetically (for example, chemical synthesis).

Other example provides a polynucleotide encoding the polypeptide. The polynucleotide may comprise the nucleic acid sequence of SEQ ID NO: 2 or SEQ ID NO: 7.

Endolysin refers to a peptidoglycan hydrolase encoded by a bacteriophage. Endolysin is synthesized during late gene expression in the lytic cycle of bacteriophage proliferation and mediates the release of progeny virions from infected cells through degradation of bacterial peptidoglycan. In respect of enzymatic activity, endolysin may commonly have one or more activities selected from the group consisting of glucosaminidase, muramidase (one kind of lysozyme), transglycosylase, amidase, endopeptidase, and the like.

In the present description, unless otherwise described, the polypeptide having endolysin activity as a polypeptide 'comprising the amino acid sequence of SEQ ID NO: 1 or SEQ ID NO: 6' or 'consisting of the amino acid sequence of SEQ ID NO: 1 or SEQ ID NO: 6', may refer to (1) a polypeptide consisting of the amino acid sequence of SEQ ID NO: 1 or SEQ ID NO: 6 or essentially comprising the same, and/or (2) a polypeptide which consists of an amino acid sequence having identity of 96% or more, 96.5% or more, 97% or more, 97.5% or more, 98% or more, 98.5% or more, 99% or more, 99.5% or more, or 99.9% or more to the amino acid sequence of SEQ ID NO: 1 or SEQ ID NO: 6 (for example, an amino acid sequence having identity of 99.3% or more, 99.4% or more, 99.5% or more, 99.6% or more, 99.7% or more, 99.8% or more, or 99.9% or more to the amino acid sequence of SEQ ID NO: 1, or an amino acid sequence having identity of 96% or more, 96.5% or more, 97% or more, 97.5% or more, 98% or more, 98.5% or more, 99% or more, 99.5% or more, or 99.9% or more to the amino acid sequence to the amino acid sequence of SEQ ID NO: 6) or essentially comprises the same, and has (maintains) endolysin enzymatic function (for example, peptidoglycan hydrolytic activity) and/or antibiotic activity against *Pseudomonas* sp. bacterium, for example, *Pseudomonas aeruginosa*.

In addition, in the present description, unless otherwise described, a polynucleotide encoding a polypeptide 'comprising the amino acid sequence of 'SEQ ID NO: 1 or SEQ ID NO: 6' or 'consisting of the amino acid sequence of SEQ ID NO: 1 or SEQ ID NO: 6', may refer to (a) a polynucleotide encoding a polypeptide consisting of the amino acid sequence of SEQ ID NO: 1 or SEQ ID NO: 6, or essentially comprising the same. and/or (b) a polypeptide which consists of an amino acid sequence having identity of 96% or more, 96.5% or more, 97% or more, 97.5% or more, 98% or more, 98.5% or more, 99% or more, 99.5% or more, or 99.9% or more to the amino acid sequence of SEQ ID NO: 1 or SEQ ID NO: 6 (for example, an amino acid sequence having identity of 99.3% or more, 99.4% or more, 99.5% or more, 99.6% or more, 99.7% or more, 99.8% or more, or 99.9% or more to the amino acid sequence of SEQ ID NO: 1, or an amino acid sequence having identity of 96% or more, 96.5% or more, 97% or more, 97.5% or more, 98% or more, 98.5% or more, 99% or more, 99.5% or more, or 99.9% or more to the amino acid sequence of SEQ ID NO: 6), or essentially comprises the same, and has (maintains) endolysin enzymatic function (for example, peptidoglycan hydrolytic activity) and/or antibiotic activity against *Pseudomonas* sp. bacterium, for example, *Pseudomonas aeruginosa*, and/or (c) a polynucleotide 'comprising the nucleic acid sequence of SEQ ID NO: 2 or SEQ ID NO: 7' or 'consisting of the nucleic acid sequence of SEQ ID NO: 2 or SEQ ID NO: 7', and the polynucleotide 'comprising the nucleic acid sequence of SEQ ID NO: 2 or SEQ ID NO: 7' or 'consisting of the nucleic acid sequence of SEQ ID NO: 2 or SEQ ID NO: 7', may refer to (d) a polynucleotide consisting of the nucleic acid sequence of SEQ ID NO: 2 or SEQ ID NO: 7, or essentially comprising the same, or (e) a polynucleotide which consists of a nucleic acid sequence having identity of 96% or more, 96.5% or more, 97% or more, 97.5% or more, 98% or more, 98.5% or more, 99% or more, 99.5% or more, or 99.9% or more to the nucleic acid sequence of SEQ ID NO: 2 or SEQ ID NO: 7 (for example, a nucleic acid sequence having identity of 99.7% or more, 99.8% or more, or 99.9% or more to the nucleic acid sequence of SEQ ID NO: 2, or a nucleic acid sequence having identity of 96% or more, 96.5% or more, 97% or more, 97.5% or more, 98% or more, 98.5% or more, 99% or more, 99.5% or more, or 99.9% or more to the nucleic acid sequence of SEQ ID NO: 7) or essentially comprises the same, and has (maintains) endolysin enzymatic function (for example, peptidoglycan hydrolytic activity) and/or antibiotic activity against *Pseudomonas* sp. bacterium, for example, *Pseudomonas aeruginosa*.

Fusion Polypeptide and Polynucleotide Encoding the Same

Other example provides a novel fusion polypeptide. The fusion polypeptide may comprise Cecropin A and endolysin.

The Cecropin A may be derived from a moth (*Hyalophora cecropia*), and for example, may be represented by the amino acid sequence of SEQ ID NO: 8. The endolysin may be derived from a bacteriophage or a variant thereof, and for example, it may be represented by the amino acid sequence of SEQ ID NO: 1 or SEQ ID NO: 6.

In the fusion polypeptide, the Cecropin A (for example, SEQ ID NO: 8) and endolysin (for example, SEQ ID NO: 1 or SEQ ID NO: 6) may be linked in any order. In other words, in the fusion polypeptide, the Cecropin A and endolysin may be linked in the order of Cecropin A and endolysin or the order of endolysin and Cecropin A, and for example, it may be linked in the order of Cecropin A and endolysin.

In addition, the Cecropin A (for example, SEQ ID NO: 8) and endolysin (for example, SEQ ID NO: 1 or SEQ ID NO: 6) may be linked through a linker or directly linked without a linker.

In one example, the fusion polypeptide may be represented by the amino acid sequence of SEQ ID NO: 10 or SEQ ID NO: 13.

The fusion polypeptide may have excellent antibiotic activity and/or excellent outer membrane permeabilization against gram negative bacterium, compared to endolysin or Cecropin A. The fusion polypeptide may have a molecular weight of about 34 kDa (for example, 34 kDa±3). The fusion polypeptide or endolysin and Cecropin A may be prepared recombinantly or synthetically (for example, chemical synthesis).

Other example provides a polynucleotide encoding the fusion polypeptide. The polynucleotide may comprise the nucleic acid sequence of SEQ ID NO: 11 or SEQ ID NO: 14.

The novel polypeptide provided in the present description (for example, SEQ ID NO: 1 or SEQ ID NO: 6) has endolysin activity. Endolysin means peptidoglycan hydrolase encoding a bacteriophage. Endolysin is synthesized during later gene expression in a lytic cycle of bacteriophage proliferation and mediates the release of progeny virions from infected cells through degradation of bacterial peptidoglycan. In respect of enzymatic activity, endolysin may commonly have one or more activities selected from the group consisting of glucosaminidase, muramidase (one kind of lysozyme), transglycosylase, amidase, endopeptidase, and the like.

In the present description, unless otherwise described, the fusion polypeptide, may comprise (1) a polypeptide which consists of an amino acid sequence having identity of 96% or more, 96.5% or more, 97% or more, 97.5% or more, 98% or more, 98.5% or more, 99% or more, 99.5% or more, or 99.9% or more to the amino acid sequence of SEQ ID NO: 8 or SEQ ID NO: 8 or essentially comprises the same, and has (maintains) Cecropin A activity; and (2) a polypeptide which consists of SEQ ID NO: 1, SEQ ID NO: 6, or an amino acid sequence having identity of 96% or more, 96.5% or more, 97% or more, 97.5% or more, 98% or more, 98.5% or more, 99% or more, 99.5% or more, or 99.9% or more to these amino acids sequences (for example, an amino acid sequence having identity of 99.3% or more, 99.4% or more, 99.5% or more, 99.6% or more, 99.7% or more, 99.8% or more, or 99.9% or more to the amino acid sequence of SEQ ID NO: 1, or an amino acid sequence having identity of 96% or more, 96.5% or more, 97% or more, 97.5% or more, 98% or more, 98.5% or more, 99% or more, 99.5% or more, or 99.9% or more to the amino acid sequence of SEQ ID NO: 6) or essentially comprises the same, and has (maintains) endolysin activity in any order (for example, in order from the N-terminus).

In one example, the fusion polypeptide, may mean a polypeptide essentially comprising the amino acid sequence of SEQ ID NO: 10 or SEQ ID NO: 13, and/or a polypeptide which consists of the amino acid sequence having identity of 96% or more, 96.5% or more, 97% or more, 97.5% or more, 98% or more, 98.5% or more, 99% or more, 99.5% or more, or 99.9% or more to the amino acid sequence of SEQ ID NO: 10 or SEQ ID NO: 13 or essentially comprises the same, and has (maintains) antibiotic activity against gram negative bacterium.

In addition, in the present description, unless otherwise described, a polynucleotide encoding a polypeptide comprising the amino acid sequence of SEQ ID NO: 10, may mean (a) a polynucleotide encoding a polypeptide consisting of the amino acid sequence of SEQ ID NO: 10 or SEQ ID NO: 13 or a polypeptide essentially comprising the same, and/or (b) a polynucleotide which consists of the amino acid sequence having identity of 96% or more, 96.5% or more, 97% or more, 97.5% or more, 98% or more, 98.5% or more, 99% or more, 99.5% or more, or 99.9% or more to the amino acid sequence of SEQ ID NO: 10 or SEQ ID NO: 13 or essentially comprises the same, and has (maintains) antibiotic activity against gram negative bacterium, and/or (c) a polynucleotide comprising the nucleic acid sequence of SEQ ID NO: 11 or SEQ ID NO: 14, and the polypeptide comprising the nucleic acid sequence of SEQ ID NO: 11 or SEQ ID NO: 14 may mean (d) a polynucleotide consisting of the nucleic acid sequence of SEQ ID NO: 11 or SEQ ID NO: 14 or essentially comprising the same, and/or (e) a polynucleotide which consists of the nucleic acid sequence having identity of 96% or more, 96.5% or more, 97% or more, 97.5% or more, 98% or more, 98.5% or more, 99% or more, 99.5% or more, or 99.9% or more to the nucleic acid sequence of SEQ ID NO: 11 or SEQ ID NO: 14 or essentially comprising the same, and has (maintains) antibiotic activity against gram negative bacterium.

In the fusion polypeptide provided in the present description, Cecropin A and endolysin may be linked through a peptide linker or directly linked without a peptide linker. The peptide linker may be a polypeptide consisting of any amino acids of 1 to 100, 2 to 50, 1 to 30, 2 to 20 or 2 to 10, and the kind of the amino acids comprised therein has no limitation. The peptide linker may comprise one or more kinds of amino acid residues selected from the group consisting of for example, Gly, Ser, Leu, Gln, Asn, Thr and Ala, respectively. The amino acid sequence suitable for the peptide linker is known in the art. On the other hand, the length of the linker may be variously determined within a limit that does not affect the structure and/or function of the fusion protein. For example, the peptide linker may be composed as including a total of 1 to 100, 2 to 50, 1 to 30, 2 to 20 or 2 to 10 of one or more kinds selected from the group consisting of Gly, Ser, Leu, Gln, Asn, Thr and Ala. In one example, the peptide linker may be represented by GSGSGS (SEQ ID NO: 12).

Recombinant Vector, and Recombinant Cell

Other example provides a recombinant vector comprising the aforementioned polypeptide (a polypeptide comprising the amino acid sequence of SEQ ID NO: 1 or SEQ ID NO:

6) or a polynucleotide encoding the aforementioned fusion polypeptide (for example, SEQ ID NO: 10 or SEQ ID NO: 13). The recombinant vector may be used as an expression vector.

Other example provides a method for preparation of the polypeptide or the fusion polypeptide, comprising expression the polypeptide or fusion polypeptide in an appropriate host cell. The expression the polypeptide or the fusion polypeptide in an appropriate host cell may be performed by culturing the polynucleotide or recombinant vector comprising the same in a recombinant cell. The method for preparation of endolysin, may further comprise separating and/or purifying expressed endolysin, after the expression.

Introduction of the polynucleotide or vector into a host cell may be performed by appropriately selecting a transformation method. In the present description, the term "transformation" refers to introducing a vector comprising a polynucleotide encoding the polypeptide into a host cell so that the polypeptide encoding the polynucleotide can be expressed. The transformed polynucleotide may include all, whether inserted and located in the chromosome of the host cell or located extrachromosomally, as long as they can be expressed in the host cell. The type of the polynucleotide to be introduced is not limited, as long as it is introduced into the host cell and expressed. For example, the polynucleotide may be introduced into a host cell in a form of expression cassette which is a gene structure comprising all elements required for self-expression. The expression cassette may commonly comprise expression regulatory elements such as a promoter operably linked to the polynucleotide, a transcription termination signal, a ribosome binding site and/or a translation termination signal, and the like. The expression cassette may be in a form of expression vector capable of self replication. In addition, the polynucleotide may be introduced into a host cell in its own form and be operably linked to a sequence required for expression in a host cell. In the above, the term "operably linked" may mean that an expression regulatory element (e.g., promoter) and a polynucleotide are functionally linked to perform transcriptional regulation (e.g., transcription initiation) of the polynucleotide. Operable linking may be performed using a genetic recombinant technique known in the art.

The method for transforming the polynucleotide into a host cell may be performed by any method for introducing a nucleic acid into a cell (microorganism), and may be performed by appropriately selecting a transformation technique known in the art depending on the host cell. As the known transformation method, electroporation, calcium phosphate ($CaPO_4$) precipitation, calcium chloride ($CaCl_2$) precipitation, microinjection, polyethylene glycol (PEG) precipitation (polyethylene glycol-mediated uptake), DEAE-dextran method, cation liposome method, lipofection, lithium acetate-DMSO method, and the like may be exemplified, but not limited thereto.

In the present description, the term "vector" refers to a DNA structure containing a nucleotide sequence of a polynucleotide operably linked to an appropriate regulatory sequence so as to express a target protein in a suitable host. The regulatory sequence may comprise a promoter capable of initiating transcription, any operator sequence for regulating transcription, a sequence encoding an appropriate mRNA ribosome binding site, and/or a sequence regulating termination of transcription and/or translation. The vector may be expressed regardless of genome of a host cell or interpreted in the genome of the host cell, after transformed into a proper host cell.

The vector available in the present description is not particularly limited as long as it can be replicated in a host cell, and may be selected from all commonly used vectors. The example of the commonly used vectors may include a natural or recombinant plasmid, cosmid, virus, bacteriophage, or the like. For example, as the vector, pWE15, M13, MBL3, MBL4, IXII, ASHII, APII, t10, t11, Charon4A, and Charon21A and the like may be used as the phage vector or cosmid vector, and pBR-based, pUC-based, pBluescriptII-based, pGEM-based, pTZ-based, pCL-based and pET-based, and the like may be used as the plasmid vector. Specifically, pDZ, pACYC177, pACYC184, pCL, pECCG117, pUC19, pBR322, pMW118, pCC1BAC vectors, and the like may be exemplified, but not limited thereto.

The vector may further comprise a selection marker for confirming whether inserted in the chromosome or not. The selection marker is for selecting transformed cells with a vector, that is, confirming insertion of the polynucleotide, and genes that confer selectable phenotypes such as drug resistance, auxotrophy, resistance to cytotoxic agents or expression of surface proteins may be selected and used. In an environment treated with a selective agent, only cells expressing a selection marker survive or exhibit other expression traits and therefore, transformed cells may be selected.

The polypeptide provided in the present description may be not naturally derived, and may be synthesized recombinantly or chemically. When the polypeptide is recombinantly produced, it may be in a form in which a common signal peptide, a cleavage site, a tag, and the like are combined for purification. Therefore, in one non-limitative example, the polypeptide provided in the present description may be in a form further comprising one or more selected from the group consisting of a signal peptide, a cleavage site, a tag (for example, His tag, GST (glutathione-s-transferase) tag, MBP (maltose binding protein) tag, etc.), and the like, which can be commonly used in the process of recombinant production of a protein, or may be in a purified form in which they are removed.

Antibiotics

Other example, provides an antibiotic, comprising one or more kinds selected from the group consisting of (1) one or more polypeptides selected from SEQ ID NO: 1 and SEQ ID NO: 6, (2) a fusion polypeptide comprising the polypeptide and Cecropin A (for example, SEQ ID NO: 10), or a combination thereof, (3) a polynucleotide encoding the (1) polypeptide, (4) a polynucleotide encoding the (2) fusion polypeptide, (5) a recombinant vector comprising the (3) polynucleotide, the (4) polynucleotide, or a combination thereof, (6) a recombinant cell comprising a recombinant vector comprising the (3) polynucleotide, the (4) polynucleotide, or a combination thereof or the polynucleotide, and (7) a bacteriophage comprising the polypeptide of SEQ ID NO: 1, a polynucleotide encoding the same, or a combination thereof.

The antibiotic may have an antibiotic effect against gram negative bacterium. The gram negative bacterium may be one or more kinds (for example, 1 kind, 2 kinds, 3 kinds, 4 kinds or 5 kinds) selected from the group consisting of *Pseudomonas* sp. bacterium, *Acinetobacter* sp. bacterium, *Escherichia* sp. bacterium, *Enterobacter* sp. bacterium,

*Klebsiella* sp. bacterium, and the like. For example, the *Pseudomonas* sp. bacterium may be *Pseudomonas aeruginosa*, and the *Acinetobacter* sp. bacterium may be *Acinetobacter baumannii*, and the *Escherichia* sp. bacterium may be *Escherichia coli*, and the *Enterobacter* sp. bacterium may be *Enterobacter aerogenes*, and the *Klebsiella* sp. bacterium may be *Klebsiella pneumoniae*, but not limited thereto.

The antibiotic provided in the present description may further comprise another antibiotic (the second antibiotic), in addition to one or more kinds selected from the group consisting of the aforementioned polypeptide (polypeptide comprising the amino acid sequence of SEQ ID NO: 1 or SEQ ID NO: 6) or the fusion polypeptide, a polynucleotide encoding the polypeptide or the fusion polypeptide, a recombinant vector comprising the polynucleotide, and a recombinant cell comprising the polynucleotide or a recombinant vector comprising the same (hereinafter, the first antibiotic).

The second antibiotic may be one or more kinds selected from commonly used antibiotics, for example, antibiotics having antibiotic activity against gram negative bacterium. In one specific example, the second antibiotic may be a polymyxin-based antibiotic, and for example, it may be polymyxin B, Colistin, or a combination thereof, but not limited thereto.

As such, by using the antibiotic (the first antibiotic) with other antibiotic (the second antibiotic) in combination, it has an advantage of exhibiting a synergy effect by the antibiotic effect of the first antibiotic itself and an excellent antibiotic effect as the second antibiotic at a low concentration. Due to this, side effects such as toxicity (for example, kidney toxicity, liver toxicity, etc.) by use of an antibiotic at a high concentration may be reduced. In addition, emergence of antibiotic-resistant bacterium through use in combination of an antibiotic of other mechanism may be inhibited.

Accordingly, one example, provides a combination antibiotic comprising (a) one or more kinds selected from the group consisting of (1) one or more polypeptides selected from SEQ ID NO: 1 and SEQ ID NO: 6, (2) a fusion polypeptide comprising the polypeptide and Cecropin A (for example, SEQ ID NO: 10), or a combination thereof, (3) a polynucleotide encoding the (1) polypeptide, (4) a polynucleotide encoding the (2) fusion polypeptide, (5) a recombinant vector comprising the (3) polynucleotide, the (4) polynucleotide or a combination thereof, (6) a recombinant cell comprising the (3) polynucleotide, the (4) polynucleotide or a combination thereof or a recombinant vector comprising the polynucleotide, and (7) a bacteriophage comprising the polypeptide of SEQ ID NO: 1, a polynucleotide encoding the same or a combination thereof; and (b) an antibiotic (for example, a polymyxin-based antibiotic such as polymyxin B, Colistin or a combination thereof, or the like).

In the present description, the term "antibiotic" encompasses all the types of agents having growth inhibitory ability and/or killing ability against gram negative bacterium, and unless otherwise mentioned, it may be interchangeably used with antibacterial agent, preservative, disinfectant, or the like.

Pharmaceutical Composition

Other example provides a pharmaceutical composition for preventing and/or treating infection of gram negative bacterium or disease caused by gram negative bacterium comprising the antibiotic or combination antibiotic.

Other example provides a method for preventing or treating infection of gram negative bacterium or disease caused by gram negative bacterium, administering a pharmaceutically effective dose of the antibiotic or combination antibiotic into a subject in need of preventing and/or treating infection of gram negative bacterium or disease caused by gram negative bacterium. The method for preventing or treating, may further comprise confirming a subject in need of preventing and/or treating infection of gram negative bacterium or disease caused by gram negative bacterium, before the administering. The gram negative bacterium is same as described above.

The disease caused by gram negative bacterium may be selected from all diseases caused by infection of gram negative bacterium, and for example, it may be selected from the group consisting of disease caused by *Pseudomonas* sp. bacterium such as skin infection, bedsore, pneumonia, bacteremia, septicemia, endocarditis, meningitis, otitis externa, otitis media, keratitis, osteomyelitis, enteritis, peritonitis or cystic fibrosis; disease caused by *Acinetobacter* sp. bacterium such as skin infection, pneumonia, bacteremia or septicemia; disease caused by *Escherichia* sp. bacterium such as enteritis, Crohn's disease, ulcerative colitis, bacillary dysentery, urinary tract infection, skin infection, bacteremia or septicemia, and the like, but not limited thereto.

As used in the present description, the pharmaceutically effective dose refers to a contained amount or dosage of an active ingredient capable of obtaining a desired effect. The contained amount or dosage of an active ingredient in the pharmaceutical composition may be variously prescribed by factors such as preparation method, administration method, patient's age, body weight, gender, morbidity, food, administration time, administration interval, administration route, excretion rate and reaction sensitivity. For example, when the active ingredient is a polypeptide, a single dose may be in a range of 0.001 to 1000 mg/kg, 0.01 to 100 mg/kg, 0.01 to 50 mg/kg, 0.01 to 20 mg/kg, 0.01 to 10 mg/kg, 0.01 to 5 mg/kg, 0.1 to 100 mg/kg, 0.1 to 50 mg/kg, 0.1 to 20 mg/kg, 0.1 to 10 mg/kg, 0.1 to 5 mg/kg, 1 to 100 mg/kg, 1 to 50 mg/kg, 1 to 20 mg/kg, 1 to 10 mg/kg, or 1 to 5 mg/kg, but not limited thereto.

In other example, the content of the active ingredient in the pharmaceutical composition may be 0.01% by weight to 99.9% by weight, 0.01% by weight to 90% by weight, 0.01% by weight to 80% by weight, 0.01% by weight to 70% by weight, 0.01% by weight to 60% by weight, 0.01% by weight to 50% by weight, 0.01% by weight to 40% by weight, 0.01% by weight to 30% by weight, 1% by weight to 99.9% by weight, 1% by weight to 90% by weight, 1% by weight to 80% by weight, 1% by weight to 70% by weight, 1% by weight to 60% by weight, 1% by weight to 50% by weight, 1% by weight to 40% by weight, 1% by weight to 30% by weight, 5% by weight to 99.9% by weight, 5% by weight to 90% by weight, 5% by weight to 80% by weight, 5% by weight to 70% by weight, 5% by weight to 60% by weight, 5% by weight to 50% by weight, 5% by weight to 40% by weight, 5% by weight to 30% by weight, 10% by weight to 99.9% by weight, 10% by weight to 90% by weight, 10% by weight to 80% by weight, 10% by weight to 70% by weight, 10% by weight to 60% by weight, 10% by weight to 50% by weight, 10% by weight to 40% by weight, or 10% by weight to 30% by weight, based on the total weight of the pharmaceutical composition, but not limited thereto.

In addition, the pharmaceutical composition may further comprise a pharmaceutically acceptable carrier, in addition to the active ingredient. The pharmaceutically acceptable carrier may refer to a carrier which is commonly used in preparation of a drug comprising a protein, nucleic acid or cell, and does not stimulate an organism and does not inhibit the biological activity and/or properties of an active ingredient. In one example, the carrier may be one or more kinds selected from the group consisting of lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methylhydroxybenzoate, propylhydroxybenzoate, talc, magnesium stearate, mineral oil, and the like, but not limited thereto. The pharmaceutical composition may further comprise one or more kinds selected from the group consisting of a diluent, an excipient, a lubricant, a wetting agent, a sweetener, a flavoring agent, an emulsifying agent, a suspending agent, a preservative and the like, which are commonly used in preparation of a pharmaceutical composition.

The administration subject of the pharmaceutical composition may be one or more kinds selected from a mammal including primates such as human and monkeys, rodents such as mice and rats, livestock such as dogs, cats, pigs, cattle, horses, sheep and goats, poultry such as chickens, ducks, geese, pheasants, quails and turkeys, and the like, or a cell, tissue or culture thereof derived therefrom.

The pharmaceutical composition may be administered by oral administration or parenteral administration, or be administered by contacting to a cell, tissue or body fluid. Specifically, in case of parenteral administration, it may be administered by subcutaneous injection, intramuscular injection, intravenous injection, intraperitoneal injection, endothelial administration, local administration, intranasal administration, intrapulmonary administration and intrarectal administration, and the like. In case of oral administration, as a protein or peptide is digested, the oral composition should be formulated to coat an active agent or to protect it from degradation in stomach. In case of intranasal administration, the pharmaceutical composition may be administered through nasal spray to dilute it and to be absorbed into nasal cavity through a sprayer or spray system, and a nasal sprayer or a respiratory formulation for the nasal spray may include an aerosol.

In addition, the pharmaceutical composition may be formulated in a form of solution in an oil or aqueous medium, injection, suspension, syrup, emulsion, ointment, patch, extract, powder, powder, granule, tablet, capsule, aerosol, or the like, and it may further comprise a dispersant or a stabilizer for formulation.

Other example provides a feed additive comprising the antibiotic or combination antibiotic as an active ingredient.

Other example provides a feed comprising the composition for the feed additive.

For the feed, the antibiotic or combination antibiotic may be prepared separately in a form of feed additive and mixed to the feed, or it may be prepared by directly adding it during feed preparation.

The antibiotic or combination antibiotic in the feed may be in liquid or dried form, and for example, it may be a dried powder form. The antibiotic may be comprised in an amount of 0.005 to 10% by weight, 0.05 to 10% by weight, 0.1 to 10% by weight, 0.005 to 5% by weight, 0.05 to 5% by weight, 0.1 to 5% by weight, 0.005 to 2% by weight, 0.05 to 2% by weight, or 0.1 to 2% by weight of the total feed weight, but not limited thereto. In addition, the feed may further comprise common additives which can increase preservability of the feed in addition to the antibiotic or combination antibiotic.

In the present description, the feed in which the antibiotic or combination antibiotic may be selected from the group consisting of commercially available feed, or grains, root fruits, food processing by-products, algae, fibers, pharmaceutical by-products, oils and fats, starches, gourds, grain by-products, proteins, inorganic matters, oils and fats, minerals, single cell proteins, zooplankton, leftover food, and the like, but not limited thereto.

Other example provides a food additive or drinking water additive comprising the antibiotic or combination antibiotic as an active ingredient. By mixing the antibiotic or combination antibiotic in drinking water and providing it, the number of gram negative bacterium in drinking water may be reduced. The gram negative bacterium is same as described above.

Other example provides a disinfectant comprising the antibiotic or combination antibiotic as an active ingredient. Other example provides a method for disinfection, comprising applying the antibiotic or combination antibiotic to a subject in need of disinfection. The disinfectant is a generic term for agents to prevent pathogen infection, and may be used for disinfection of general life disinfectants, disinfectants for food and cooking places and facilities, and various kinds of growth and development supplies such as buildings such as poultry farm and pen, livestock bodies, drinking water, litter, egg tray, transport vehicles, tableware, and the like.

Other example provides a detergent comprising the antibiotic or combination antibiotic as an active ingredient. Other example provides a method for cleaning, comprising applying the antibiotic or combination antibiotic into a subject in need of cleaning. As the antibiotic has the antibiotic effect against gram negative bacterium, it may be applied for cleaning (washing) the skin surface or body parts of individuals exposed or likely to be exposed to gram negative bacterium. The gram negative bacterium is same as described above.

Advantageous Effects

The novel polypeptide, variant of the polypeptide or novel fusion polypeptide provided in the present description can be usefully used as an antibiotic against gram negative bacterium, by exhibiting excellent outer membrane permeabilization and killing activity against various gram negative bacterium.

BRIEF DESCRIPTION OF THE DRAWINGS

FIG. 1 is a cleavage map of the expression vector which expresses the endolysin (LNT101) gene of bacteriophage PBPA90 infecting *Pseudomonas aeruginosa*.

FIG. 2 shows the process of purifying endolysin (LNT101) derived from bacteriophage PBPA90.

FIG. 3 is a graph showing the antibiotic effect against *Pseudomonas aeruginosa* in vitro of endolysin (LNT101) derived from bacteriophage PBPA90.

FIG. 4 is a graph showing the antibiotic effect against *Pseudomonas aeruginosa* in vivo of endolysin (LNT101) derived from bacteriophage PBPA90.

FIG. 5 shows the amino acid sequences of endolysin (LNT102) (SEQ ID NO: 6) and endolysin (LNT101) (SEQ ID NO: 1) according to one example in comparison.

FIG. 6 is a cleavage map of the expression vector pBT7-LNT102 for expression of endolysin (LNT102).

FIG. 7 shows the result of SDS-PAGE of reactants obtained in the process of purification of endolysin (LNT102).

FIG. 8 is a graph showing the killing ability against various gram negative bacterium of endolysin (LNT102) and endolysin (LNT101).

FIGS. 9 and 10 are graphs showing the killing ability against gram negative bacterium depending on the concentration and treatment time of endolysin (LNT102).

FIG. 11 is a schematic diagram of the fusion polypeptide (LNT103) according to one example.

FIG. 12 is an image showing the result of SDS-PAGE of the reactants obtained in the process of purification of the fusion polypeptide (LNT103) according to one example.

FIG. 13 is a graph showing the outer membrane permeabilization activity against various gram negative bacterium of the endolysin (LNT101), endolysin variant (LNT102) and fusion polypeptide (LNT103).

FIG. 14 is a graph showing the killing ability against various gram negative bacterium of the endolysin (LNT101), endolysin variant (LNT102) and fusion polypeptide (LNT103).

FIG. 15 is a graph showing the killing ability against various gram negative bacterium of the fusion polypeptides LNT103 and CecA-LNT101.

FIG. 16 is a graph showing the killing ability against gram negative bacterium of the fusion polypeptide (LNT103) according to one example and Cecropin A in comparison.

FIG. 17 is a graph showing the killing ability against gram negative bacterium depending on the concentration and treatment time of the fusion polypeptide according to one example (LNT103).

FIGS. 18 and 19 are graphs showing the evaluation result of cytotoxicity and hemolysis assay of the fusion polypeptide according to one example (LNT103).

FIG. 20 is a graph showing the viability when treating the fusion polypeptide LNT103 in an *Acinetobacter baumannii* systemic infection mouse model compared to treatment of colistin.

MODE FOR INVENTION

The novel endolysin and/or bacteriophage expressing the same provided in the present description exhibit excellent growth inhibitory ability and killing ability against *Pseudomonas* sp. bacterium, for example, *Pseudomonas aeruginosa*, and thereby, they can be usefully used as an antibiotic against *Pseudomonas* sp. bacterium, for example, *Pseudomonas aeruginosa.*

Example 1: Preparation of LNT101 Endolysin and Antibiotic Activity Test

1.1. Separation of Bacteriophage Capable of Killing *Pseudomonas aeruginosa*

1.1.1. Culture Condition of Strain

*Pseudomonas aeruginosa* (PR01957) was used as a host, and cultured with shaking in a LB (Luria-Bertani) medium under the condition of 37° C.

1.1.2. Separation of Bacteriophage

In order to select a bacteriophage infected by *Pseudomonas aeruginosa*, samples were collected from Gwacheon sewage treatment plant, Gwacheon-si, Gyeonggi-do, Korea. The collected samples and *Pseudomonas aeruginosa* were cultured at 37° C. for 3 hours, and then centrifuged at 500 rpm for 20 minutes and the supernatant was collected. Subsequently, the supernatant was filtered with a 0.45 μm filter, and then double agar layer plaque assay was performed.

Briefly describing the analysis method, the culture solution of the host bacterium, *Pseudomonas aeruginosa* and bacteriophage was mixed by 0.1 M.O.I. to the top agar 5 ml, and poured to an agar plate, and cultured at 37° C. for 24 hours to obtain a plaque. Through repeated performance of the process, the purified pure bacteriophage was obtained, and this bacteriophage was named bacteriophage PBPA90.

1.2: Separation and Analysis of Genome of Bacteriophage PBPA90

Sequencing for genome of the bacteriophage PBPA90 obtained in the Example 1.1 was conducted. After culturing *Pseudomonas aeruginosa* in a LB medium of 200 ml to $OD_{600}$=0.5, here, it was lysed by infection with the filtered bacteriophage $10^9$ pfu/ml or 0.1 M.O.I. After that, sodium chloride was added so that the final concentration was 1 M here, and then it was left at 4° C. for 1 hour. Subsequently, after centrifuging at 11,000× g for 10 minutes, PEG (Polyethylene glycol 8000) was added to precipitates by 10% (w/v), and it was left at 4° C. for 1 hour. In succession, after centrifuging at 11,000× g for 10 minutes, the supernatant was removed, and the precipitates were suspended with SM buffer solution [100 mM NaCl, 10 mM $MgSO_4$ (heptahydrate), 50 mM Tris-HCl, pH 7.5]. Chloroform was added at a ratio of 1:1 here, and voltexing was conducted, and then it was centrifuged at 3,000× g for 15 minutes to obtain the supernatant.

40% (w/v) glycerol 3 ml was added to a polycarbonate test tube, and then, 5% (w/v) glycerol 4 ml was added so as not to be mixed. Subsequently, the supernatant was removed, and then precipitates were resuspended with SM buffer solution to obtain bacteriophage genome DNA. The bacteriophage genome DNA was separated using a phage DNA isolation kit (Norgen biotek corp.) according to the manufacturer's manual. The sequence for genome was analyzed using the genome sample separated as above (LAS, Illumina MiSeq platform).

The finally analyzed bacteriophage PBPA90 genome had the total nucleic acid sequence length of 304,052 bp, and had a 44% GC content. The full-length nucleic acid sequence of the bacteriophage PBPA90 genome was represented in SEQ ID NO: 5. The similarity with the conventionally known bacteriophage genome sequence was investigated using BLAST on Web based on the genome nucleic acid sequence information. As the result of BLAST investigation, it was confirmed that the genome sequence of the bacteriophage PBPA90 had low sequence similarity to *Pseudomonas* bacteriophage KTN4 (GenBank accession No.: KU521356.1) (query coverage: 4%, identity: 97.34%). Based on this fact, it was confirmed that the bacteriophage PBPA90 is a new bacteriophage which is not conventionally known.

1.3: Cloning and Purification of LNT101 Endolysin

Through ORF search for the genomic sequence of the analyzed bacteriophage PBPA90 (SEQ ID NO: 5), the ORF of 780 bp at positions 180,029-180,806 (SEQ ID NO: 2) was estimated to be an endolysin gene, and the bacteriophage PBPA90-derived endolysin and a gene encoding this were named LNT101 endolysin and LNT101 gene, respectively.

Using Primer (F: 5'-aaggatccatgggtactgtactcaaacgtggc-3' (SEQ ID NO: 3), R: 5'-aactcgagtgcccgatgtttcgaaactttatcttc-3' (SEQ ID NO: 4)), for the genome of the bacteriophage PBPA90, PCR (polymerase chain reaction) was performed to obtain LNT101 gene (nucleic acid sequence with a 780 bp length at positions 180,029-180,806 in SEQ ID NO: 5). The amino acid sequence of LNT101 endolysin encoded by the LNT101 gene was represented in SEQ ID NO: 1 (259 aa). The PCR was performed under the following condition: step 1: 94° C., 5 minutes; step 2: 94° C., 30 seconds; step 3: 52° C., 45 seconds; step 4: 72° C., 1 minute; step 5: repeating steps 2-4 30 times; step 6: 72° C., 10 minutes. The obtained PCT products were cloned with BamHI/XhoI site of pET-21a vector (Novagen) having N-terminal 6× His-tag, to prepare an expression vector for LNT101 endolysin expression (pET-LNT101 plasmid). The prepared expression vector pET-LNT101 was schematically shown in FIG. 1.

The prepared pET-LNT101 plasmid was transformed in *E. coli* BL21-pLysS strain (Novagen), and then was cultured in LB broth (1% Tryptone, 0.5% (w/v) Yeast extract, 0.5% (w/v) NaCl) to $OD_{600}$=0.5. After that, 1 mM IPTG (Isopropyl β-d-1-thiogalactopyranosid) was added, and then was cultured with shaking at 37° C. for 4 hours. After cell harvest, it was resuspended with lysis buffer (50 mM $NaH_2PO_4$, 300 mM NaCl, 10 mM imidazole), and 1 mM PMSF and 1 mg/ml lysozyme were added, and it was left on ice for 30 minutes. Cells were lysed by sonication, and centrifuged at 13,000 rpm for 40 minutes to obtain the supernatant. This was passed through a column in which Ni-NTA agarose resin (Qiagen) was packed. After that, it was washed with wash buffer (50 mM $NaH_2PO_4$, 300 mM NaCl, 30 mM imidazole), and then it was eluted with elution buffer (50 mM $NaH_2PO_4$, 300 mM NaCl, 300 mM imidazole), to purify LNT101 protein (including 6× His tag).

The purity of the LNT101 protein was confirmed by 15% SDS-PAGE and the concentration of the LNT101 protein was measured by Bradford assay. The result of confirming each reactant obtained in the purification process by SDS-PAGE was shown in FIG. 2. The molecular weight of the purified LNT101 protein confirmed by SDS-PAGE was about 28 kDa. The amino acid sequence of the LNT101 protein was shown in SEQ ID NO: 1.

1.4. Target Bacteria Spectrum Investigation of Bacteriophage PBPA90 and Endolysin LNT101 Derived Therefrom In the present example, in order to investigate a target bacteria spectrum of the bacteriophage PBPA90 selected in the Examples 1.1 and 1.2 and endolysin LNT101 separated and purifying in the Example 1.3, the antibacterial activity against gram negative bacterium such as *Pseudomonas aeruginosa* ATCC13388, ATCC9027, ATCC10145, ATCC15692, ATCC15522, ATCC25619, ATCC27853, CCARM2134, CCARM2200, CCARM2029, CCARM2144, CCARM2298, CCARM2326, PR01957, *E. coli* ATCC8739, *Enterobacter cloacae* CCARM0252, *Klebsiella pneumoniae* KCTC2261, *Klebsiella aerogenes* CCARM16006, *Campylobacter jejuni* KCTC5327, *Cronobacter sakazakii* KCTC2949, *Salmonella typhimurium* ATCC14028, *Salmonella enteritidis* ATCC13076 was tested.

The target bacteria spectrum of the bacteriophage PBPA90 and endolysin LNT101 was confirmed by a spot test. For the spot test, bacterium sterilized in 4 ml top agar (1% Tryptone, 0.5% Yeast extract, 0.5% NaCl, 0.7% agar) of $1\times10^{11}$ CFU/200 μl were added and poured to a LB plate. After hardening the top agar, the bacteriophage PBPA90 10 μl ($1\times10^{8}$ PFU/ml) or LNT101 10 μl (2 mg/ml) was spotted, and it was incubated at 37° C. for 18 hours.

Production of the halo zone formed as the result of the incubation was confirmed, and the result was shown in Table 1 below:

TABLE 1

| Host | | LNT101 |
|---|---|---|
| *P. aeruginosa* | ATCC 13388 | ○ |
| | ATCC 9027 | ○ |
| | ATCC 10145 | ○ |
| | ATCC 15692 | ○ |
| | ATCC 15522 | ○ |
| | ATCC 25619 | ○ |
| | ATCC 27853 | ○ |
| | CCARM 2134 | ○ |
| | CCARM 2200 | ○ |
| | PR1957 | ○ |
| | CCARM 2029 | ○ |
| | CCARM 2144 | ○ |
| | CCARM 2298 | ○ |
| | CCARM 2326 | ○ |
| *E. coli* | ATCC 8739 | ○ |
| *E. cloacae* | CCARM 0252 | ○ |
| *K. pneumoniae* | KCTC 2261 | ○ |
| *K. aerugenes* | CCARM 16006 | ○ |
| *C. jejuni* | KCTC 5327 | ○ |
| *C. sakazakii* | KCTC 2949 | ○ |
| *S. typhimurium* | ATCC 14028 | ○ |
| *S. enteritidis* | ATCC 13076 | ○ |

(In the Table 1, '○' means production of the halo zone)

As shown in Table 1, the endolysin LNT101 formed the halo zone in all the tested gram negative bacterium, which were *Pseudomonas aeruginosa, E, coli, Enterobacter cloacae, Klebsiella pneumoniae, Campylobacter, Cronobacter*, and *Salmonella* strains. This result shows that the endolysin LNT101 has the degradation ability for peptidoglycans of various gram negative bacterium as aforementioned and has a broad target bacterium spectrum.

1.5. Investigation of Killing Ability Against *Pseudomonas aeruginosa* of Endolysin LNT101

In the present example, for *Pseudomonas aeruginosa* (ATCC 13388) confirmed against which the bacteriophage PBPA90 and endolysin LNT101 had the antibacterial activity in the Example 1.4, the bacterium killing ability of endolysin LNT101 was tested.

In Vitro Test

For this, the endolysin LNT101 at a concentration of 0.1, 0.5, 1.0 μM and *Pseudomonas aeruginosa* (ATCC 13388) $1\Delta10^{6}$ CFU were added so that the final volume was 200 μl to reaction buffer (20 mM Tris-Cl, pH 7.5) and they were left at 37° C. for 1 hour. In 30 minutes, 1 hour and 2 hours, the number of colonies of *Pseudomonas aeruginosa* was confirmed, and the result was shown in FIG. 3. As shown in FIG. 3, it was confirmed that the endolysin LNT101 had the killing ability against *Pseudomonas aeruginosa* in all the tested treatment dose and time, and it was shown that this *Pseudomonas aeruginosa* killing ability was dependent on the treatment time and dose.

In addition, that the LNT101 endolysin had the antibacterial ability in various gram negative bacterium was confirmed by a CFU reduction test, and the result was shown in Table 2 below.

TABLE 2

| Host | | LNT101 |
|---|---|---|
| *P. aeruginosa* | ATCC 13388 | ○ |
| | ATCC 15522 | ○ |
| | CCARM 2092 | ○ |
| | CCARM 2134 | ○ |
| | CCARM 2144 | ○ |
| | CCARM 2326 | ○ |
| | F141 | ○ |
| | PAO1 | ○ |
| *A. baumannii* | ATCC 2508 | ○ |
| | F4 | ○ |
| | F15 | ○ |
| *E. cloacae* | CCARM 0252 | ○ |
| *K. aerugenes* | CCARM 16006 | ○ |

(In the Table 2, '○' means reduction of 0.5 log CFU or more through the CFU reduction assay)

As shown in Table 2, it was confirmed that it had the bacterium killing effect in a dose dependent manner in all the test gram negative bacterium of 8 kinds of *Pseudomonas aeruginosa,* 3 kinds of *Acinetobacter baumannii,* 1 kind of *Enterobacter cloacae*, and 1 kind of *Klebsiella aerogenes*, including antibiotic-resistant bacterium.

In Vivo Test

The *Pseudomonas aeruginosa* killing ability of the endolysin LNT101 was also confirmed in vivo. As an animal model for the in vivo effectivity evaluation, Galleria mellonella was used. The Galleria mellonella model was divided into the healthy group (non-infection group), *Pseudomonas aeruginosa* infected group (drug non-administration group), 2 LNT101 administration groups in which LNT101 was administered into the infection model, Colistin administration group in which colistin was administered into the *Pseudomonas aeruginosa* infected model, and combination administration group in which LNT101 and colistin were administered in combination into the *Pseudomonas aeruginosa* infected model to progress an experiment, and 10 of Galleria mellonella per each group was used.

The *Pseudomonas aeruginosa* infected model was prepared by infecting *Pseudomonas aeruginosa* PA01 at the LD80 concentration, 50 CFU/larva, and LNT101 was administered at 0.6 μg/larva (3 mg/Kg) and 6 μg/larva (30 mg/Kg), respectively. Colistin was administered at 0.5 μg/larva (2.5 mg/Kg), and for administration in combination, Colistin at 0.5 μg/larva (2.5 mg/Kg) and LNT101 at 6 μg/larva (30 mg/Kg) were administered. As the result of observation for 72 hours, the viability of Galleria mellonella was shown in FIG. 4. As shown in FIG. 4, it was confirmed that the infection group was dead 100%, but in the LNT101 and colistin administration groups, the viability was increased. In particular, in the LNT101 6 μg/larva (30 mg/Kg) administration group, the viability of 30% was confirmed.

1.6. Synergy Effect of *Pseudomonas aeruginosa* Killing Ability of Endolysin LTN101 and Polymyxin Antibiotic The synergy effect by treatment in combination of the polymyxin-based antibiotic having a mechanism acting on the cell membrane of bacterium and endolysin LNT101 was confirmed. Specifically, polymyxin B (32 μg/ml-0.03 μg/ml) and colistin (128 μg/ml-0.1 μg/ml) were diluted by ½ per well in a microplate, and then a LNT101 endolysin 1 μM combination treatment group and the same amount of PBS treatment group was made. In all wells, *P. aeruginosa* $1\times10^5$ CFU/ml was treated by total 100 μl. After that, they were cultured at 37° C. for 18 hours. MIC (Minimum Inhibitory Concentration) means the concentration value of the minimum polymyxin-based antibiotic of the well where bacterium did not grow, and the MIC test was performed by broth microdilution technique.

The MIC change of the polymyxin-based antibiotic by combination treatment of the polymyxin-based antibiotic (polymyxin B, Colistin) and LNT101 endolysin at various concentrations was confirmed, and shown in Table 3 below.

TABLE 3

| | Polymyxin B | Polymyxin B + LNT101 | Colistin | Colistin + LNT101 |
|---|---|---|---|---|
| MIC of antibiotics | 4 μg/ml | 2.7 μg/ml | 8 μg/ml | 4 μg/ml |

As shown in Table 3, it was confirmed that the MIC of the polymyxin-based antibiotics, polymyxin B and Colistin was reduced by 50%, in case of use in combination of the LNT101 endolysin.

Example 2. Production of LNT102 Endolysin and Antibiotic Activity Test 2.1. Discovery of a Novel Polypeptide Having Endolysin Activity The endolysin LNT101 separated and purified in the Example 1.3 (SEQ ID NO: 1) was composed of PG_binding_1 domain (10-65 amino acid) and transglycosylase SLT domain (95-179 amino acid).

Eleven amino acids were substituted for LNT101 endolysin and other amino acid sites with the dominant amino acid sequence of the comparative protein, by comparing the amino acid sequence of endolysin LNT101 PG_binding_1 domain with glycoside hydrolase family 25 of Thermoanaerobacterium phage THSA-485A (accession no. YP_006546280.1), peptidoglycan binding protein of Serratia phage phiMAM1 (accession no. YP_007349105.1), Serratia phage 2050H1 peptidoglycan binding protein (accession no. ASZ78903.1), putative peptidoglycan binding protein of Serratia phage vB_SmaA_3M (accession no. AYP28388.1), putative peptidoglycan binding protein of Enwinia phage vB_EamM-Bue1 (accession no. AV022912.1), putative peptidoglycan binding protein of *Pseudomonas* phage Noxifer (accession no. YP_009609055.1), endolysin of *Salmonella* phage Mutine (accession no. AUG88272.1) and peptidoglycan binding protein of *Salmonella* phage bering (accession no. QIQ61961.1), which have a similar amino acid sequence, by BLASTp analysis.

Four amino acids were substituted for LNT101 endolysin and other amino acid sites with the dominant amino acid sequence of the comparative protein, by comparing the amino acid sequence of LNT101 endolysin transglycosylase SLT domain with tail fiber protein of *Pseudomonas* phage Noxifer (accession no. YP_009609112.1), hypothetical protein SL2_199 of *Pseudomonas* phage SL2 (accession no. YP_009619739.1), putative endolysin of *Pseudomonas* phage KTN4 (accession no. ANM44938.1), PHIKZ144 of *Pseudomonas* phage phiKZ (accession no. NP_803710.1), tail fiber protein of *Pseudomonas* phage Psa21 (accession no. QBJ02724.1) and hypothetical protein of *Pseudomonas* phage vB_PaeM_PS119XW (accession no. QEM41943.1), which have a similar amino acid sequence, by BLASTp analysis.

15 substituted amino acid sequence parts were modified in the LNT101 gene sequence part in consideration of codon usage (SEQ ID NO: 7), and this was named LNT102 (SEQ ID NO: 6). The comparison of the sequences of LNT101 and LNT102 was shown in FIG. 5. The LNT102 was cloned to gene synthesis and C-terminal 6× histidine tag-attached pBT7-C-His vector (Bioneer). The expression vector pBT7-LNT102 of LNT102 prepared as such was schematically shown in FIG. 6.

The sequences of the described LNT102 and LNT101 were summarized in Table 4 below:

TABLE 4

| | Amino acid sequence (N→C) or nucleic acid sequence (5'→3') | SEQ ID NO: |
|---|---|---|
| Endolysin LNT102 | MGTVLKRGDRGSAVEDLQMKLNVAGYNLSADGIFGGDTEKAVRDVQAGAGLVVDGKVG<br>PKTLYAIAKSATVPAKWEAIPFPTANKSRSAAMPTLNAVGAMTGVDSRLLATFASIES<br>AFDYTVKAKTSSATGWFQFLDATWDDMIKAYGSKYGIPKDPTRALRKDPRANALMGAE<br>FIKGNAAVLRPVINREPSDTDLYLAHFLGAGGAKKFLSADQKTLGEVLFPKPAKANPS<br>IFSNKGVPRTLAEIYKLFEDKVSKHRA | 6 |
| Endolysin LNT102 coding gene | ATGGGTACTGTACTCAAACGTGGCGACCGCGGCTCTGCTGTGGAAGATCTACAAATGA<br>AACTTAACGTCGCAGGATACAACCTGAGCGCTGACGGAATCTTCGGTGGAGATACAGA<br>GAAAGCTGTTCGTGATGTGCAAGCTGGCGCGGGCTTGGTGGTTGACGGAAAAGTTGGA<br>CCTAAAACTCTATATGCGATTGCCAAATCCGCTACTGTTCCTGCTAAATGGGAAGCTA<br>TCCCTTTCCCAACAGCTAATAAATCTCGGTCGGCTGCAATGCCCACTCTGAATGCGGT<br>TGGAGCAATGACTGGTGTGGATTCTCGGTTACTCGCTACATTCGCTTCCATTGAGTCT<br>GCTTTTGATTACACTGTCAAAGCAAAAACATCTTCGGCTACTGGTTGGTTCCAGTTCC<br>TTGATGCTACATGGGATGACATGATCAAAGCATATGGTTCCAAATACGGGATACCTAA<br>AGATCCCACTAGGGCACTCCGTAAAGACCCACGTGCAAATGCATTAATGGGTGCAGAA<br>TTCATTAAAGGAAATGCAGCTGTATTACGTCCAGTAATCAATCGCGAACCGAGTGATA<br>CAGACTTGTATTTGGCACATTTCCTTGGTGCTGGCGGCGCTAAGAAATTCCTATCCGC<br>AGATCAGAAAACTCTCGGTGAAGTTCTATTCCCGAAACCTGCTAAAGCAAACCCGTCG<br>ATCTTTAGCAATAAAGGTGTACCACGTACCCTTGCAGAGATCTACAAGCTGTTCGAAG<br>ATAAAGTTTCGAAACATCGGGCA | 7 |
| Endolysin LNT101 | MGTVLKRGDRGSAVEDLQMKLRVAGYAVSADGIFGGDTEKAVRDFQASKALVVDGKVG<br>PATLAELAKSATVPAKWEAIPFPTANKSRSAAMPTLNAVGAMTGTDSRLLATFASIES<br>AFDYTVKASTSSATGWFQFLDATWDDMIKAHGSKYGIPKDPTRALRKDPRANALMGAE<br>FLKGNAAVLRPVINREPSDTDLYLAHFLGAGGAKKFLSADQKTLGEVLFPKPAKANPS<br>IFSNKGVPRTLAEIYKLFEDKVSKHRA | 1 |

2.2. Purification of LNT102 Endolysin

After transforming the prepared pBT7-LNT102 plasmid into the *E. coli* BL21-Star(DE3) strain (Invitrogen), it was cultured in LB broth (1% Tryptone, 0.5% (w/v) Yeast extract, 0.5% (w/v) NaCl) by $OD_{600}$=0.5. After that, 1 mM IPTG (Isopropyl β-d-1-thiogalactopyranosid) was added and then cultured with shaking at 37° C. for 4 hours. After cell harvest, it was resuspending with lysis buffer (50 mM $NaH_2PO_4$, 300 mM NaCl, 10 mM imidazole), and 1 mM PMSF and 1 mg/ml lysozyme were added and it was left on ice for 30 minutes. Cells were lysed by sonication, and they were centrifuged at 13,000 rpm for 40 minutes to obtain the supernatant. This was passed through a column in which Ni-NTA agarose resin (Qiagen) was packed. Then, after washing with wash buffer (50 mM $NaH_2PO_4$, 300 mM NaCl, 30 mM imidazole), it was eluted with elution buffer (50 mM $NaH_2PO_4$, 300 mM NaCl, 300 mM imidazole), to purify LNT102 protein (including 6× His tag).

The purity of the LNT102 protein was confirmed by 15% SDS-PAGE and the concentration of the LNT102 protein was measured by Bradford assay. The result of confirming each reactant obtained in the process of purification by SDS-PAGE was shown in FIG. 7. The molecular weight of the purified LNT102 protein confirmed by SDS-PAGE was about 28 kDa.

2.3. Investigation of Killing Ability Against Gram Negative Bacterium of Endolysin LNT102

In the present example, the bacterium killing ability and target bacterium spectrum of the endolysin LNT102 purified in Example 2.2 for various gram negative bacterium were confirmed.

In Vitro Test

For this, Endolysin LNT101 and LNT102 at a concentration of 2 μM and each $1\times10^6$ CFU of *Pseudomonas aeruginosa* (PA01; ATCC 15692), *Acinetobacter baumannii* (ATCC 17978), *Escherichia coli* (ATCC 8739), *Klebsiella pneumoniae* (ATCC 13883), *Enterobacter aerogenes* (CCARM 16006), and *Salmonella enteritidis* (ATCC 13076) was added in reaction buffer (20 mM Tris-Cl, pH 7.5) so that the final volume was 200 μl, and it was left at 37° C. for 2 hours. In 2 hours, the number of colonies of each gram negative bacterium was confirmed, and the result was shown in FIG. 8 (in FIG. 8, PA90 represents endolysin LNT101 and mtPA90 represents endolysin LNT102, respectively). As shown in FIG. 8, it was confirmed that all the endolysin LNT101 and LNT102 had the excellent killing ability compared to the control group against all the tested gram negative bacterium, and in particular, LNT102 showed the more excellent killing ability against gram negative bacterium in the same dose-, compared to LNT101.

The endolysin LNT102 at a concentration of 0.1, 0.5, 2.5 μM, and each $1\times10^6$ CFU of *Pseudomonas aeruginosa, Acinetobacter baumannii*, and *Escherichia coli* was added in reaction buffer (20 mM Tris-Cl, pH 7.5) so that the final volume was 200 μl, and it was left at 37° C. for 2 hours. In 30 minutes, 1 hour and 2 hours, and the result was shown in FIGS. 9 and 10. As shown in FIGS. 9 and 10, it was confirmed that endolysin LNT102 had the killing ability against gram negative bacterium in all the tested treatment doses and time, and it was shown that this killing ability against gram negative bacterium was dependent on the treatment time and dose.

2.4. Synergy Effect of Killing Ability Against Gram Negative Bacteria in Case of Use in Combination of Endolysin LTN102 and Antibiotics A synergy effect by combination treatment of a polymyxin-based antibiotic having a mechanism acting on the cell membrane of bacterium and endolysin LNT102 purified in Example 2.2 was confirmed. Specifically, after treating 4 μg/ml Polymyxin B to the 96 well microplate row A, serial dilution was performed by ½ in rows B-G. Polymyxin was not treated to the row H. After treating 8 μg/ml Colistin to the 96 well microplate row A, a combination treatment group in which LNT102 endolysin 1 μM was further treated and a PBS treatment group in the same amount were made. All wells were treated with *Pseudomonas aeruginosa* and *Escherichia coli* in an amount of $1\times10^5$ CFU/ml, total 100 μl, respectively. After that, they were cultured at 37° C. for 18 hours. MIC (Minimum Inhibitory Concentration) means a concentration value of a minimum polymyxin-based antibiotic of a well in which bacterium do not grow, and the MIC test was performed by broth microdilution technique according to the standard test method of CLSI (Clinical and Laboratory Standards Institute) (Clinical and Laboratory Standards Institute. Methods for dilution antimicrobial susceptibility tests for bacterium that grow aerobically; approved standard. 11th ed. Document M07. Wayne, PA: CLSI; 2018).

The MIC change of the polymyxin-based antibiotics by combination treatment of the polymyxin-base antibiotics (polymyxin B, Colistin) at various concentrations and LNT102 endolysin was measured and shown in Table 5 below.

TABLE 5

| | Polymyxin B + PBS | Polymyxin B + LNT102 | Colistin + PBS | Colistin + LNT102 |
|---|---|---|---|---|
| *P. aeruginosa* (ATCC 27853) | 0.5 μg/ml | <0.06 μg/ml | 2 μg/ml | 0.5 μg/ml |
| *A. baumannii* (ATCC 19606) | 0.5 μg/ml | 0.03 μg/ml | 2 μg/ml | 0.25 μg/ml |
| *E. coli*(ATCC 8739) | 0.5 μg/ml | 0.06 μg/ml | 2 μg/ml | 1 μg/ml |

As shown in Table 5, it was confirmed that the MIC of the polymyxin-based antibiotics, polymyxin B and Colistin was reduced by 1/16 times at maximum, in case of use in combination of the LNT102 endolysin. This result shows that a significantly increased antibiotic effect can be obtained when a conventional antibiotic, for example, a polymyxin-based antibiotic and LNT102 endolysin are treated in combination.

Example 3: Preparation of Fusion Polypeptide 3.1. Preparation of Polypeptide (LNT101 and LNT102 Endolysin)

Endolysin LNT101 (SEQ ID NO: 1) is composed of PG_binding_1 domain (10-65 amino acid) and transglycosylase SLT domain(95-179 amino acid). The endolysin LNT101 variant of SEQ ID NO: 6 (hereinafter, named endolysin LNT102) was prepared by adding 15 amino acid mutations in the endolysin LNT101 (SEQ ID NO: 1).

The coding gene of the endolysin LNT102 (SEQ ID NO: 7) was inserted to pBT7 plasmid to prepare pBT7-LNT102 plasmid for endolysin LNT102 expression. The prepared pBT7-LNT102 plasmid was transformed into *E. coli* BL21-Star(DE3) strain (Invitrogen), it was cultured in LB broth (1% Tryptone, 0.5% (w/v) Yeast extract, 0.5% (w/v) NaCl) by $OD_{600}$=0.5. After that, 1 mM IPTG (Isopropyl β-d-1-thiogalactopyranosid) was added, and then it was cultured with shaking at 37° C. for 4 hours. After cell harvest, it was resuspended with lysis buffer (50 mM $NaH_2PO_4$, 300 mM NaCl, 10 mM imidazole), and 1 mM PMSF and 1 mg/ml lysozyme were added and it was left on ice for 30 minutes. Cells were lysed by sonication, and it was centrifuged at 13,000 rpm for 40 minutes to obtain the supernatant. This was passed through a column in which Ni-NTA agarose resin (Qiagen) was packed. Then, after washing with wash buffer (50 mM $NaH_2PO_4$, 300 mM NaCl, 30 mM imidazole), it was eluted with elution buffer (50 mM $NaH_2PO_4$, 300 mM NaCl, 300 mM imidazole), to purify the LNT102 protein (including 6Δ His tag).

The purity of the LNT102 protein was confirmed by 15% SDS-PAGE, and the concentration of the LNT102 protein was measured by Bradford assay. As the result of confirming each reactant obtained during the process of purification by SDS-PAGE, the molecular weight of the purified LNT102 protein was about 31 kDa.

3.2. Preparation of Fusion Polypeptide

A fusion polypeptide in which Cecropin A was fused in the prepared LNT102 protein was prepared. Specifically, a polynucleotide (SEQ ID NO: 11) encoding a fusion polypeptide (named LNT103) (SEQ ID NO: 10) comprising [Cecropin A (SEQ ID NO: 8)]-[linker (GSGSGS) (SEQ ID NO: 12)]-[endolysin (named LNT102) (SEQ ID NO: 6)] from the N-terminus in order was inserted into pET 21a (Novagen) plasmid to prepare plasmid pET-LNT103 for LNT103 expression. After transforming the prepared pET-LNT103 plasmid into *E. coli* BL21-Star(DE3) strain (Invitrogen), it was cultured in LB broth (1% (w/v) Tryptone, 0.5% (w/v) Yeast extract, 0.5% (w/v) NaCl) by $OD_{600}$=0.5.

After that, after adding 1 mM IPTG (isopropyl β-D-1-thiogalactopyranoside), it was cultured with shaking at 25° C. for 6 hours. After cell harvest, it was resuspended with lysis buffer (50 mM $NaH_2PO_4$, 300 mM NaCl, 10 mM imidazole), and 1 mM PMSF (phenylmethylsulfonyl fluoride) and 1 mg/ml lysozyme were added, and it was left on ice for 30 minutes. Cells were lysed by sonication, and it was centrifuged at 13,000 rpm for 40 minutes to obtain the supernatant. The obtained supernatant was passed through a column in which Ni-NTA agarose resin (Qiagen) was packed. Then, after washing with wash buffer (50 mM $NaH_2PO_4$, 300 mM NaCl, 30 mM imidazole), it was eluted with elution buffer (50 mM $NaH_2PO_4$, 300 mM NaCl, 300 mM imidazole). It was purified/confirmed by 15% SDS-PAGE and the concentration was measured by Bradford assay.

The obtained SDS-PAGE result was shown in FIG. 12. As confirmed in FIG. 12, it was confirmed that the molecular weight of the purified fusion polypeptide LNT103 (SEQ ID NO: 10) was 34 kDa.

In addition, by the same method as the above method, a fusion polypeptide in which Cecropin A was fused to endolysin LNT101 (SEQ ID NO: 1) (CecA-LNT101; SEQ ID NO: 13) was produced. For the produced CecA-LNT101, SDS-PAGE was performed by the aforementioned method, to confirm that the molecular weight of CecA-LNT101 was 34 kDa.

On the other hand, for convenience of the test, the first amino acid M of the purified fusion polypeptide LNT103 (SEQ ID NO: 10) and CecA-LNT101(SEQ ID NO: 13) was substituted with MAS (Met-Ala-Ser), and it was produced in a form in which an extra sequence and a His tag were added to the C-terminus (SEQ ID NO: 15 or SEQ ID NO: 16), and in the following test, SEQ ID NO: 15 was used as LNT103, and SEQ ID NO: 16 was used as CecA-LNT101, respectively.

The amino acid sequences and nucleic acid sequences of the polypeptide and their coding genes described in the present example were summarized in Table 6 below:

TABLE 6

| | Amino acid sequence (N→C) or nucleic acid sequence (5'→3') | SEQ ID NO: |
|---|---|---|
| Cecropin A | KWKLFKKIEKVGQNIRDGIIKAGPAVAVVGQATQIAK | 8 |
| Cecropin A coding gene | AAATGGAAACTGTTTAAAAAAATTGAAAAAGTGGGCCAGAACATTCGCGATGGCA<br>TTATTAAAGCGGGCCCGGCGGTGGCGGTGGTGGGCCAGGCGACCCAGATTGCGAA<br>A | 9 |
| linker | GSGSGS | 12 |
| Endolysin LNT102 | MGTVLKRGDRGSAVEDLQMKLNVAGYNLSADGIFGGDTEKAVRDVQAGAGLVVDG<br>KVGPKTLYAIAKSATVPAKWEAIPFPTANKSRSAAMPTLNAVGAMTGVDSRLLAT<br>FASIESAFDYTVKAKTSSATGWFQFLDATWDDMIKAYGSKYGIPKDPTRALRKDP<br>RANALMGAEFIKGNAAVLRPVINREPSDTDLYLAHFLGAGGAKKFLSADQKTLGE<br>VLFPKPAKANPSIFSNKGVPRTLAEIYKLFEDKVSKHRA | 6 |
| Endolysin LNT102 coding gene | ATGGGTACTGTACTCAAACGTGGCGACCGCGGCTCTGCTGTGGAAGATCTACAAA<br>TGAAACTTAACGTCGCAGGATACAACCTGAGCGCTGACGGAATCTTCGGTGGAGA<br>TACAGAGAAAGCTGTTCGTGATGTGCAAGCTGGCGCGGGCTTGGTGGTTGACGGA<br>AAAGTTGGACCTAAAACTCTATATGCGATTGCCAAATCCGCTACTGTTCCTGCTA<br>AATGGGAAGCTATCCCTTTCCCAACAGCTAATAAATCTCGGTCGGCTGCAATGCC<br>CACTCTGAATGCGGTTGGAGCAATGACTGGTGTGGATTCTCGGTTACTCGCTACA<br>TTCGCTTCCATTGAGTCTGCTTTTGATTACACTGTCAAAGCAAAAACATCTTCGG<br>CTACTGGTTGGTTCCAGTTCCTTGATGCTACATGGGATGACATGATCAAAGCATA<br>TGGTTCCAAATACGGGATACCTAAAGATCCCACTAGGGCACTCCGTAAAGACCCA<br>CGTGCAAATGCATTAATGGGTGCAGAATTCATTAAAGGAAATGCAGCTGTATTAC<br>GTCCAGTAATCAATCGCGAACCGAGTGATACAGACTTGTATTTGGCACATTTCCT<br>TGGTGCTGGCGGCGCTAAGAAATTCCTATCCGCAGATCAGAAAACTCTCGGTGAA<br>GTTCTATTCCCGAAACCTGCTAAAGCAAACCCGTCGATCTTTAGCAATAAAGGTG<br>TACCACGTACCCTTGCAGAGATCTACAAGCTGTTCGAAGATAAAGTTTCGAAACA<br>TCGGGCATAG | 7 |
| Fusion Polypeptide LNT103 | MKWKLFKKIEKVGQNIRDGIIKAGPAVAVVGQATQIAKGSGSGSMGTVLKRGDRG<br>SAVEDLQMKLNVAGYNLSADGIFGGDTEKAVRDVQAGAGLVVDGKVGPKTLYAIA<br>KSATVPAKWEAIPFPTANKSRSAAMPTLNAVGAMTGVDSRLLATFASIESAFDYT<br>VKAKTSSATGWFQFLDATWDDMIKAYGSKYGIPKDPTRALRKDPRANALMGAEFI<br>KGNAAVLRPVINREPSDTDLYLAHFLGAGGAKKFLSADQKTLGEVLFPKPAKANP<br>SIFSNKGVPRTLAEIYKLFEDKVSKHRA | 10 |
| Fusion Polypeptide LNT103 coding gene | ATGAAATGGAAACTGTTTAAAAAAATTGAAAAAGTGGGCCAGAACATTCGCGATG<br>GCATTATTAAAGCGGGCCCGGCGGTGGCGGTGGTGGGCCAGGCGACCCAGATTGC<br>GAAAGGCAGCGGCTCGGGTAGTATGGGTACTGTACTCAAACGTGGCGACCGCGGC<br>TCTGCTGTGGAAGATCTACAAATGAAACTTAACGTCGCAGGATACAACCTGAGCG<br>CTGACGGAATCTTCGGTGGAGATACAGAGAAAGCTGTTCGTGATGTGCAAGCTGG<br>CGCGGGCTTGGTGGTTGACGGAAAAGTTGGACCTAAAACTCTATATGCGATTGCC<br>AAATCCGCTACTGTTCCTGCTAAATGGGAAGCTATCCCTTTCCCAACAGCTAATA<br>AATCTCGGTCGGCTGCAATGCCCACTCTGAATGCGGTTGGAGCAATGACTGGTGT<br>GGATTCTCGGTTACTCGCTACATTCGCTTCCATTGAGTCTGCTTTTGATTACACT<br>GTCAAAGCAAAAACATCTTCGGCTACTGGTTGGTTCCAGTTCCTTGATGCTACAT<br>GGGATGACATGATCAAAGCATATGGTTCCAAATACGGGATACCTAAAGATCCCAC<br>TAGGGCACTCCGTAAAGACCCACGTGCAAATGCATTAATGGGTGCAGAATTCATT<br>AAAGGAAATGCAGCTGTATTACGTCCAGTAATCAATCGCGAACCGAGTGATACAG<br>ACTTGTATTTGGCACATTTCCTTGGTGCTGGCGGCGCTAAGAAATTCCTATCCGC<br>AGATCAGAAAACTCTCGGTGAAGTTCTATTCCCGAAACCTGCTAAAGCAAACCCG<br>TCGATCTTTAGCAATAAAGGTGTACCACGTACCCTTGCAGAGATCTACAAGCTGT<br>TCGAAGATAAAGTTTCGAAACATCGGGCATAG | 11 |
| Endolysin LNT101 | MGTVLKRGDRGSAVEDLQMKLRVAGYAVSADGIFGGDTEKAVRDFQASKALVVDG<br>KVGPATLAELAKSATVPAKWEAIPFPTANKSRSAAMPTLNAVGAMTGTDSRLLAT<br>FASIESAFDYTVKASTSSATGWFQFLDATWDDMIKAHGSKYGIPKDPTRALRKDP<br>RANALMGAEFLKGNAAVLRPVINREPSDTDLYLAHFLGAGGAKKFLSADQKTLGE<br>VLFPKPAKANPSIFSNKGVPRTLAEIYKLFEDKVSKHRA | 1 |
| Endolysin LNT101 coding gene | ATGGGTACTGTACTCAAACGTGGCGACCGCGGCTCTGCTGTGGAAGATCTACAAA<br>TGAAACTTCGAGTCGCAGGATACGCAGTTAGCGCTGACGGAATCTTCGGTGGAGA<br>TACAGAGAAAGCTGTTCGTGATTTCCAAGCTTCTAAAGCTTTGGTGGTTGACGGA<br>AAAGTTGGACCTGCTACTCTAGCTGAACTAGCCAAATCCGCTACTGTTCCTGCTA<br>AATGGGAAGCTATCCCTTTCCCAACAGCTAATAAATCTCGGTCGGCTGCAATGCC<br>CACTCTGAATGCGGTTGGAGCAATGACTGGTACCGATTCTCGGTTACTCGCTACA<br>TTCGCTTCCATTGAGTCTGCTTTTGATTACACTGTCAAAGCATCCACATCTTCGG<br>CTACTGGTTGGTTCCAGTTCCTTGATGCTACATGGGATGACATGATCAAAGCACA<br>TGGTTCCAAATACGGGATACCTAAAGATCCCACTAGGGCACTCCGTAAAGACCCA<br>CGTGCAAATGCATTAATGGGTGCAGAATTCCTTAAAGGAAATGCAGCTGTATTAC<br>GTCCAGTAATCAATCGCGAACCGAGTGATACAGACTTGTATTTGGCACATTTCCT<br>TGGTGCTGGCGGCGCTAAGAAATTCCTATCCGCAGATCAGAAAACTCTCGGTGAA | 2 |

TABLE 6-continued

| | Amino acid sequence (N→C) or nucleic acid sequence (5'→3') | SEQ ID NO: |
|---|---|---|
| | GTTCTATTCCCGAAACCTGCTAAAGCAAACCCGTCGATCTTTAGCAATAAAGGTG<br>TACCACGTACCCTTGCAGAGATCTACAAGCTGTTCGAAGATAAAGTTTCGAAACA<br>TCGGGCATAG | |
| Fusion Polypeptide CecA-LNT101 | MKWKLFKKIEKVGQNIRDGIIKAGPAVAVVGQATQIAKGSGSGSMGTVLKRGDRG<br>SAVEDLQMKLRVAGYAVSADGIFGGDTEKAVRDFQASKALVVDGKVGPATLAELA<br>KSATVPAKWEAIPFPTANKSRSAAMPTLNAVGAMTGTDSRLLATFASIESAFDYT<br>VKASTSSATGWFQFLDATWDDMIKAHGSKYGIPKDPTRALRKDPRANALMGAEFL<br>KGNAAVLRPVINREPSDTDLYLAHFLGAGGAKKFLSADQKTLGEVLFPKPAKANP<br>SIFSNKGVPRTLAEIYKLFEDKVSKHRA | 13 |
| Fusion Polypeptide CecA-LNT101 coding gene | ATGAAATGGAAACTGTTTAAAAAAATTGAAAAAGTGGGCCAGAACATTCGCGATG<br>GCATTATTAAAGCGGGCCCGGCGGTGGCGGTGGTGGGCCAGGCGACCCAGATTGC<br>GAAAGGCAGCGGCTCGGGTAGTATGGGTACTGTACTCAAACGTGGCGACCGCGGC<br>TCTGCTGTGGAAGATCTACAAATGAAACTTCGAGTCGCAGGATACGCAGTTAGCG<br>CTGACGGAATCTTCGGTGGAGATACAGAGAAAGCTGTTCGTGATTTCCAAGCTTC<br>TAAAGCTTTGGTGGTTGACGGAAAAGTTGGACCTGCTACTCTAGCTGAACTAGCC<br>AAATCCGCTACTGTTCCTGCTAAATGGGAAGCTATCCCTTTCCCAACAGCTAATA<br>AATCTCGGTCGGCTGCAATGCCCACTCTGAATGCGGTTGGAGCAATGACTGGTAC<br>CGATTCTCGGTTACTCGCTACATTCGCTTCCATTGAGTCTGCTTTTGATTACACT<br>GTCAAAGCATCCACATCTTCGGCTACTGGTTGGTTCCAGTTCCTTGATGCTACAT<br>GGGATGACATGATCAAAGCACATGGTTCCAAATACGGGATACCTAAAGATCCCAC<br>TAGGGCACTCCGTAAAGACCCACGTGCAAATGCATTAATGGGTGCAGAATTCCTT<br>AAAGGAAATGCAGCTGTATTACGTCCAGTAATCAATCGCGAACCGAGTGATACAG<br>ACTTGTATTTGGCACATTTCCTTGGTGCTGGCGGCGCTAAGAAATTCCTATCCGC<br>AGATCAGAAAACTCTCGGTGAAGTTCTATTCCCGAAACCTGCTAAAGCAAACCCG<br>TCGATCTTTAGCAATAAAGGTGTACCACGTACCCTTGCAGAGATCTACAAGCTGT<br>TCGAAGATAAAGTTTCGAAACATCGGGCATAG | 14 |
| Fusion Polypeptide LNT103 with MAS, His tag, and extra sequence | **MAS**KWKLFKKIEKVGQNIRDGIIKAGPAVAVVGQATQIAKGSGSGSMGTVLKRGD<br>RGSAVEDLQMKLNVAGYNLSADGIFGGDTEKAVRDVQAGAGLVVDGKVGPKTLYA<br>IAKSATVPAKWEAIPFPTANKSRSAAMPTLNAVGAMTGVDSRLLATFASIESAFD<br>YTVKAKTSSATGWFQFLDATWDDMIKAYGSKYGIPKDPTRALRKDPRANALMGAE<br>FIKGNAAVLRPVINREPSDTDLYLAHFLGAGGAKKFLSADQKTLGEVLFPKPAKA<br>NPSIFSNKGVPRTLAEIYKLFEDKVSKHRALEHHHHHH | 15 |
| Fusion Polypeptide CecA-LNT101 with MAS, His tag, and extra sequence | **MAS**KWKLFKKIEKVGQNIRDGIIKAGPAVAVVGQATQIAKGSGSGSMGTVLKRGD<br>RGSAVEDLQMKLRVAGYAVSADGIFGGDTEKAVRDFQASKALVVDGKVGPATLAE<br>LAKSATVPAKWEAIPFPTANKSRSAAMPTLNAVGAMTGTDSRLLATFASIESAFD<br>YTVKASTSSATGWFQFLDATWDDMIKAHGSKYGIPKDPTRALRKDPRANALMGAE<br>FLKGNAAVLRPVINREPSDTDLYLAHFLGAGGAKKFLSADQKTLGEVLFPKPAKA<br>NPSIFSNKGVPRTLAEIYKLFEDKVSKHRALEHHHHHH | 16 |

3.3. Evaluation of Outer Membrane Permeabilization Activity of Fusion Polypeptide LNT103

In order to evaluate the outer membrane permeabilization activity of the gram negative bacterium of the fusion polypeptide prepared in the Example 3.2, NPN uptake assay was performed. As representative gram negative bacterium, *Pseudomonas aeruginosa* and *Acinetobacter baumannii* were used for the test.

*Pseudomonas aeruginosa* (PA01; ATCC 15692) or *Acinetobacter baumannii* (ATCC 19606) was cultured by $OD_{600}$=0.3 and centrifuged at 1,000 g for 10 minutes, and then it was resuspended with a ½ volume of 5 mM HEPES (Hydroxyethyl piperazine Ethane Sulfonic acid) (pH 7.2). 40 μM NPN (1-N-phenylnaphthylamine) solution (40 μM NPN in 5 mM HEPES, pH7.2) 50 μl, the test substance (LNT101, LNT102 or LNT103) 50 μl, and strain suspension solution 100 μl (total 200 μl) were added to a microplate and reacted at 37° C. for 1 hour. Then, fluorescence was measured under the condition of excitation 350 nm and emission 420 nm with a microplate reader (Infinite M200 Pro, TECAN). As a positive control group, Cecropin A (SEQ ID NO: 8), EDTA, or polymyxin B was used, and as a negative control group, 10 μM NPN solution was used. All the experiments were performed in 3 sets.

The obtained result was shown in FIG. 13. In order to compare the outer membrane permeability activity of the LNT101, LNT102 and LNT103 against gram negative bacterium (*Pseudomonas aeruginosa* (PA01; ATCC 15692) and *Acinetobacter baumannii* (ATCC 19606)), the concentration of 2 μM which was the same concentration was treated, and 2 μM of Cecropin A and polymyxin B and 1 mM of EDTA were treated. The obtained result was shown in A and B of FIG. 13 as a fold change over control. As shown in A and B of FIG. 13, it was confirmed that the fusion polypeptide LNT103 had higher outer membrane permeabilization activity against gram negative bacterium than the polypeptides LNT101 and LNT102 at the same concentration, and it was confirmed that it was higher even than the positive control groups, cecropin A, EDTA and polymyxin B.

On the other hand, in order to confirm the difference in the outer membrane permeabilization activity against gram negative bacterium (*Pseudomonas aeruginosa* (PA01; ATCC 15692) and *Acinetobacter baumannii* (ATCC 19606)) according to the concentration of LNT103, LNT103 was treated in an amount of 0.29 μM, 0.88 μM, or (2.65 μM), and 2 μM of cecropin A and polymyxin B, and 1 mM of EDTA were treated. The obtained result was shown in C and D of FIG. 13 as a fold change over negative control. As shown in C and D of FIG. 13, it was confirmed that LNT103 had excellent outer membrane permeabilization activity against gram negative bacterium compared to the LNT101, LNT102, cecropin A and polymyxin B, and the outer membrane permeabilization activity against gram negative bacterium was increased in a concentration-dependent manner.

3.4. Investigation of Killing Ability Against Gram Negative Bacteria of Fusion Polypeptide LNT103

In order to confirm the killing ability against gram negative bacterium of the fusion polypeptide LNT103 prepared in Example 3.2, CFU reduction evaluation was performed for various gram negative bacterium. In order to perform the CFU reduction evaluation, 2 μM of each of LNT101, LNT102, and LNT103 prepared in Example 3, and $1\times10^6$ CFU of each of *Pseudomonas aeruginosa* (PA01; ATCC 15692), *Acinetobacter baumannii* (ATCC 17978), *Escherichia coli* (ATCC 8739), *Klebsiella pneumoniae* (ATCC 13883), and *Enterobacter aerogenes* (CCARM 16006) were added to reaction buffer (20 mM Tris-Cl, pH7.5) so that the final volume was 200 μl, and it was left at 37° C. for 2 hours. After that, the number of the colonies of each gram negative bacterium was confirmed to compare and evaluate the antibiotic effect of each polypeptide. As a control group, the PBS treatment group (treating PBS in the same volume as the fusion polypeptide) was used.

The obtained result was shown in FIG. 14. As shown in FIG. 14, it was confirmed that the fusion polypeptide LNT103 showed the CFU reduction effect of 1.5~5.5 log CFU/ml compared to LNT101 and LNT102. In particular, the CFU Counting result (log CFU/ml) against *Acinetobacter baumannii* (ATCC 19606, ATCC 17978), *E. coli* (ATCC 8739), *Klebsiella pneumoniae* (ATCC 2208) of the fusion polypeptide LNT103 killed all bacterium treated as 0.

In addition, the same test was performed by using the fusion polypeptide LNT103, and CecA-LNT101 at a concentration of 2 μM, and the result was shown in FIG. 15. For comparison, the same test was performed for groups treated with LNT102 or PBS. As shown in FIG. 15, all the groups treated with the fusion polypeptide LNT103, and CecA-LNT101 had excellent antibiotic activity than the groups treated with LNT102 or PBS, and in particular, the counting result (log CFU/ml) for all the tested bacterium was shown as 0 in case of treating LNT103, and CecA-LNT101 in an amount of 2 μM, respectively, and therefore, it was confirmed that they killed all the bacterium.

On the other hand, in order to compare the antibacterial activity in case that a protein other than endolysin (LNT102 or LNT101) was fused to Cecropin A, the killing ability against gram negative bacterium of the fusion polypeptide LNT103 and cecropin A-EGFP fusion protein (a protein in which EGFP (GenBank Accession No. AAB02572.1) having no endolysin activity by replacing LNT102 in LNT103) was evaluated. For this, the proteins were treated in an amount of 0.2 μM or 2 μM, respectively, to perform the CFU reduction test. The obtained result was shown in FIG. 16. As shown in FIG. 16, it was confirmed that the Cecropin A-EGFP fusion protein had no antibacterial activity, while the fusion polypeptide LNT103 had excellent antibacterial activity. In particular, it could be confirmed that the CFU Counting result for all the tested gram negative bacterium killed all bacterium treated with 0, when LNT103 2 μM was treated.

Furthermore, the killing ability against gram negative bacterium according to the concentration and/or treatment time of the fusion polypeptide LNT103 was tested. Specifically, the fusion polypeptide LNT103 at a concentration of 0.1, 0.3, 0.9, or 2.7 μM and $1\times10^6$ CFU of *Pseudomonas aeruginosa* (PA01; ATCC 15692) or *Acinetobacter baumannii* (ATCC 19606) were added to reaction buffer (20 mM Tris-Cl, pH7.5) so that the final volume was 200 μl, and it was left at 37° C. for 2 hours, and then the number of the colonies was confirmed, and the result was shown in A of FIG. 17.

In addition, the fusion polypeptide LNT103 at a concentration of 2 μM and $1\times10^6$ CFU of *Pseudomonas aeruginosa* (PA01; ATCC 15692) were added to reaction buffer (20 mM pH7.5) so that the final volume was 200 μl, and in 0, 20 minutes, 40 minutes and 60 minutes at 37° C., the number of the colonies was confirmed, and the result was shown in B of FIG. 17.

Moreover, the fusion polypeptide LNT103 at a concentration of 1 μM and $1\times10^6$ CFU of *Acinetobacter baumannii* (ATCC 19606) were added to reaction buffer (20 mM pH7.5) so that the final volume was 200 μl, and in 0, 1 minute, 3 minutes, 5 minutes and 10 minutes at 37° C., the number of the colonies was confirmed, and the result was shown in C of FIG. 17.

As shown in A, B and C of FIG. 17, it was confirmed that the fusion polypeptide LNT103 had the killing ability against gram negative bacterium in a concentration and time-dependent manner (in A, B and C of FIG. 17, the part where the bar graph is not represented means that the log CFU/ml value is 0, meaning that all treated bacteria are killed).

In addition, MIC (Minimal Inhibitory Concentration) and MBC (Minimal Bactericidal Concentration) of the fusion polypeptide LNT103 were measured. The MIC and MBC were performed by broth microdilution technique according to the standard test method of CLSI (Clinical and Laboratory Standards Institute), and in the corresponding test method, it was performed by using CAA media (Casamino acid 5 g/L, K2HPO4 5.2 mM, MgSO4 1 mM) instead of MH broth (Casein acid hydrolysate 17.5 g/L, Beef extract 3.0 g/L, Starch 1.5 g/L. pH 7.3) (Clinical and Laboratory Standards Institute. Methods for dilution antimicrobial susceptibility tests for bacterium that grow aerobically; approved standard. 11$^{th}$ ed. Document M07. Wayne, PA: CLSI; 2018). Specifically, the LNT103 was treated at a concentration of 64 μg/ml to a 96 well microplate row A, and the LNT103 was treated at a concentration where serial dilution was performed by ½ in rows B-G. To the row H, LNT103 was not treated. After that, the corresponding bacterium strain (type or QC, CCARM and clinical separation strain; See Tables 2-4) was treated in an amount of $5\times10^5$ CFU/ml, total 100 μl in all wells. Then, it was cultured at 37° C. for 18 hours. MIC was determined to be the lowest concentration at which no colonies were identified by confirming the number of the colonies in each well. The obtained result was shown in Table 7 to Table 9 below:

TABLE 7

| Species | Strain | MIC (μg/ml) | MBC (μg/ml) |
|---|---|---|---|
| *A. baumannii* | ATCC 17978 | 8 | 8 |
| | ATCT 19606 | 8 | 8 |
| | KACC 13090 | 8 | 8 |
| | KACC 14233 | 8 | 8 |

TABLE 7-continued

| Species | Strain | MIC (μg/ml) | MBC (μg/ml) |
|---|---|---|---|
| | CCARM 12001 | 8 | 8 |
| | CCARM 12015 | 16 | 16 |
| | CCARM 12026 | 8 | 8 |
| | CCARM 12035 | 8 | 8 |
| | CCARM 12202 | 8 | 8 |
| | F4 | 16 | 16 |
| | F15 | 8 | 8 |
| | F65 | 4 | 4 |
| | F66 | 4 | 4 |
| | F67 | 8 | 8 |
| | F68 | 4 | 4 |
| | F69 | 8 | 8 |
| | F70 | 16 | 16 |
| | F71 | 8 | 8 |
| | 3680(Gyeongsang National University) | 8 | 8 |
| | 643(Kyungpook National University) | 8 | 16 |

TABLE 8

| Species | Strain | MIC (μg/ml) | MBC (μg/ml) |
|---|---|---|---|
| *P. aeruginosa* | ATCT 13388 | 8 | 16 |
| | ATCC 9027 | 16 | 16 |
| | ATCC 10145 | 16 | 32 |
| | PAO1(ATCC 15692) | 8 | 16 |
| | ATCC 15522 | 16 | 16 |
| | CCARM 2134 | 8 | 16 |
| | CCARM 2144 | 32 | 32 |
| | F102 | 8 | 8 |
| | F141 | 8 | 8 |
| | F341 | 8 | 8 |
| | F388 | 8 | 8 |
| | F265 | 16 | 16 |

TABLE 9

| Species | Strain | MIC (μg/ml) | MBC (μg/ml) |
|---|---|---|---|
| *E. coli* | ATCC 8739 | 8 | 8 |
| | CCARM 1460 | 4 | 4 |
| | CCARM 1A746 | 8 | 8 |
| | CCARM 1B684 | 4 | 8 |
| | CCARM 1G448 | 4 | 4 |
| | FORC81 | 4 | 4 |
| | F340 | 16 | 16 |
| | F481 | 8 | 8 |
| | F485 | 4 | 8 |
| | F524 | 16 | 16 |
| | F716 | 16 | 32 |
| | F852 | 16 | 32 |
| | F859 | 32 | 32 |
| | F862 | 4 | 4 |
| | UPEC 3042 | 32 | 32 |
| | UPEC 3181 | 8 | 8 |

3.5. Synergy Effect of Killing Ability Against Gram Negative Bacteria According to Use in Combination of Fusion Polypeptide LNT103 and Polymyxin Antibiotic The synergy effect of killing ability against gram negative bacterium by combination treatment of a polymyxin-based antibiotic having a mechanism acting on the cell membrane of bacterium and the fusion polypeptide LNT103 was confirmed. Specifically, colistin (polymyxin E) of 16 μl/ml was treated to a 96 well microplate column 1, and it was treated at a concentration where serial dilution was performed by ½ in columns 2-11. The LNT103 of 16 μg/ml was treated to row A, and it was treated at a concentration where serial dilution was performed by ½ in rows B-G. After that, *Acinetobacter baumannii* (ATCC 19606) was treated in an amount of $5\times10^5$ CFU/ml, total 100 μl in all wells. Then, it was cultured at 37° C. for 18 hours, and the FIC (Fractional Inhibitory Concentration) index value was calculated by the following equation:

$$\text{FIC index}=FIC_A+FIC_B=(C_A/MIC_A)+(C_B/MIC_B)$$

($C_A$ and $C_B$ are each concentration of substances treated in combination (polymyxin E and LNT103), and $MIC_A$ and $MIC_B$ are MIC of single drug, FIC value: synergy effect <0.5; antagonism >4; additive 0.5-4)

As the result of the test, the FIC index value was shown as 0.375, and it was confirmed that there was a synergy effect between the two substances.

3.6. In Vitro Toxicity Evaluation of Fusion Polypeptide LNT103

In vitro toxicity of the fusion polypeptide LNT103 was evaluated by cell cytotoxicity assay (WST assay) using Huh-7 cell line and hemolysis assay using sheep blood (MB cell).

The process of progressing the cell cytotoxicity assay was as follows. The Huh07 cell culture solution was prepared and aliquoted in an amount of $1\times10^9$ cells/well per well in a 96 well plate, and it was cultured in a $CO_2$ incubator for 24 hours. Then, PBS as a negative control and 1% (w/v) triton X-100 as a positive control were treated, and as an experimental group, the fusion polypeptide LNT103 was treated at a concentration of 0.25, 0.5, or 1 mg/ml, and then it was left in a $CO_2$ incubator for 24 hours and 48 hours. Then, the cell viability was measured using D-Plus™ CCK cell viability assay kit (Dongin LS), and the result was shown in FIG. 18. As shown in FIG. 18, when the fusion polypeptide LNT103 was treated at a concentration of 0.25 mg/ml, 0.5 mg/ml, or 1 mg/ml for 24 hours, compared to the negative control (PBS), the cell viability of 93%, 90%, 78% was shown, respectively, and when it was treated for 48 hours, compared to the negative control, the cell viability of 108%, 105%, 86% was shown, respectively. In other words, it was confirmed that it showed the cell viability of about 80% or more compared to the control group (PBS) in case of treating the fusion polypeptide LNT103, and thereby, it could be confirmed that the cytotoxicity was relatively low. By this result, it was confirmed that the IC50 of LNT103 was >1 mg/ml.

The process of progressing the hemolysis assay was as follows. After mixing 3 ml sheep blood and 14 ml PBS (pH 7.2), it was centrifuged at 1000 g, 4° C. for 5 minutes to remove the supernatant. After that, PBS was filled again as much as the removed volume and the above washing was progressed 4 times in total. Hemoglobin lysed through washing was removed, and after the last centrifugation, 400 μl of sunken RBC (red blood cell) was dissolved in 9.6 ml PBS to make 4% (v/v) blood solution. After mixing 50 μl of the sample and 50 μl of 4% (v/v) blood solution in a 96 well microplate, it was reacted at 37° C. for 1 hour. For an experimental group, the fusion polypeptide LNT103 was treated from 128 μg/ml to 2 μg/ml in a 2-fold dilution range (PBS, pH 7.2), and for a positive control group, 0.1% (w/v) Triton X-100 and for a negative control group, PBS were treated. After reacting for 1 hour, the microplate was centrifuged at 1000 g, 4° C. for 5 minutes, and 50 μl of the supernatant was collected and it was transferred to a new microplate and the absorbance was measured at 570 nm (Infinite M200 Pro, TECAN). The obtained result was shown in FIG. 19. As shown in FIG. 19, it was confirmed that the fusion polypeptide LNT103 did not show hemolytic activity at all the tested concentrations. By this result, it was confirmed that the MHC (Minimal hemolytic concentration) of LNT103 was >128 μg/ml.

3.7. In Vitro Effectivity Evaluation of Fusion Polypeptide LNT103

For in vivo effectivity evaluation of the fusion polypeptide LNT103, the viability was confirmed in an *Acinetobacter baumannii* ATCC 19606 systemic infection mouse model was confirmed.

The process of progressing an animal experiment was as follows. Mice were used when ICR male 4-week-old mice were purchased and a one-week adaptation period was passed, and the weight was 20~21 g at 5-6 weeks of age. The *Acinetobacter* bacteria were mixed with 10% mucin at 1:1, and 0.5 ml of $2\times10^8$ CFU/ml (5% mucin) of the bacterial solution was inoculated intraperitoneally into mice. In 1 hour and 4 hours after infection, LNT103 20 mpk and LNT103 100 mpk, and colistin 20 mpk as a comparative group were administered, respectively, through a subcutaneous injection. After that, the viability for 96 hours was confirmed, and the result was shown in FIG. 20. As confirmed in FIG. 20, the group in which the LNT103 was administered into the systemic infection mouse model showed higher viability compared to the non-administration group (control) and comparative group (colistin administration group), and the LNT103 showed high viability in a concentration-dependent manner, and therefore, it was confirmed that there was the effect in the corresponding mouse model.

From the above description, those skilled in the art to which the present application pertains will be able to understand that the present application may be executed in other specific forms without changing the technical spirit or essential characteristics thereof. In this regard, it should be understood that Examples described above are illustrative and not restrictive in all respects. The scope of the present application should be construed as that all changed or modified forms derived from the meaning and scope of claims to be described below and equivalent concepts rather than the detailed description are included in the scope of the present application.

The invention claimed is:

1. A polypeptide, comprising the amino acid of SEQ ID NO: 6.

2. The polypeptide according to claim 1, wherein the polypeptide has endolysin activity.

3. A fusion polypeptide, comprising Cecropin A at N-terminus or C-terminus of the polypeptide of SEQ ID NO: 1 or SEQ ID NO: 6.

4. The fusion polypeptide according to claim 3, wherein Cecropin A is represented by the amino acid sequence of SEQ ID NO: 8.

5. The fusion polypeptide according to claim 3, wherein the Cecropin A is linked to the N-terminus of polypeptide of SEQ ID NO: 1 or SEQ ID NO: 6.

6. The fusion polypeptide according to claim 3, wherein the Cecropin A and polypeptide of SEQ ID NO: 1 or SEQ ID NO: 6 are linked by a peptide linker.

7. The fusion polypeptide according to claim 3, represented by the amino acid sequence of SEQ ID NO: 10 or SEQ ID NO: 13.

8. A polynucleotide encoding the polypeptide according to claim 1, or a fusion polypeptide comprising Cecropin A at N-terminus or C-terminus of the polypeptide of SEQ ID NO: 1 or SEQ ID NO: 6.

9. The polynucleotide according to claim 8, represented by the nucleic acid sequence of SEQ ID NO: 7, SEQ ID NO: 11 or SEQ ID NO: 14.

10. A method for preventing or treating infection of Gram negative bacterium or disease caused by Gram negative bacterium, administering a pharmaceutically effective dose of (i) the polypeptide of claim 1, or (ii) a fusion polypeptide comprising Cecropin A at N-terminus or C-terminus of the polypeptide of SEQ ID NO: 1 or SEQ ID NO: 6, into a subject in need of preventing or treating infection of Gram negative bacterium or disease caused by Gram negative bacterium.

11. The method according to claim 10, further administering a pharmaceutically effective dose of a polymyxin-based antibiotic.

12. The method according to claim 11, wherein the polymyxin-based antibiotic is polymyxin B, colistin, or a combination thereof.

13. The method according to claim 10, wherein the Gram negative bacterium is one or more kinds selected from the group consisting of *Pseudomonas* sp. bacterium, *Acinetobacter* sp. bacterium, *Escherichia* sp. bacterium, *Enterobacter* sp. bacterium, and *Klebsiella* sp. bacterium.

14. The method according to claim 10, wherein the Gram negative bacterium is one or more kinds selected from the group consisting of *Pseudomonas aeruginosa, Acinetobacter baumannii, Escherichia coli, Enterobacter aerogenes*, and *Klebsiella pneumoniae.*

15. The method according to claim 10, wherein the Gram negative bacterium is *Pseudomonas* sp. bacterium, and the disease caused by *Pseudomonas* sp. bacterium is skin infection, bedsore, pneumonia, bacteremia, septicemia, endocarditis, meningitis, otitis externa, otitis media, keratitis, osteomyelitis, enteritis, or peritonitis.

16. The method according to claim 10, wherein the Gram negative bacterium is *Acinetobacter* sp. bacterium, and the disease caused by *Acinetobacter* sp. bacterium is skin infection, pneumonia, bacteremia or septicemia.

17. The method according to claim 10, wherein the Gram negative bacterium is *Escherichia* sp. bacterium, and the disease caused by *Escherichia* sp. bacterium is enteritis, Crohn's disease, ulcerative colitis, bacillary dysentery, urinary tract infection, skin infection, bacteremia or septicemia.

18. A method for inhibiting growth of Gram negative bacterium or killing Gram negative bacterium, comprising applying to a subject in need of disinfection an effective amount of (i) the polypeptide of claim 1, or (ii) a fusion polypeptide comprising Cecropin A at N-terminus or C-terminus of the polypeptide of SEQ ID NO: 1 or SEQ ID NO: 6.

19. The method according to claim 18, further comprising applying an effective amount of a polymyxin-based antibiotic.

20. The method according to claim 19, wherein the polymyxin-based antibiotic is polymyxin B, colistin, or a combination thereof.

* * * * *